United States Patent
Desai

(10) Patent No.: US 10,962,553 B2
(45) Date of Patent: Mar. 30, 2021

(54) COMPOSITIONS AND METHODS FOR DETECTING PROTEINOPATHIES

(71) Applicant: BOARD OF SUPERVISORS OF LOUISIANA STATE UNIVERSITY AND AGRICULTURAL AND MECHANICAL COLLEGE, Baton Rouge, LA (US)

(72) Inventor: Shyamal D. Desai, Metairie, LA (US)

(73) Assignee: Board of Supervisors of Louisiana State University and Agricultural and Mechanical College, Baton Rouge, LA (US)

(*) Notice: Subject to any disclaimer, the term of this patent is extended or adjusted under 35 U.S.C. 154(b) by 0 days.

(21) Appl. No.: 15/816,998

(22) Filed: Nov. 17, 2017

(65) Prior Publication Data

US 2018/0120334 A1 May 3, 2018

Related U.S. Application Data

(60) Continuation-in-part of application No. 15/464,473, filed on Mar. 21, 2017, now abandoned, which is a division of application No. 13/688,384, filed on Nov. 29, 2012, now Pat. No. 9,599,626.

(60) Provisional application No. 62/519,423, filed on Jun. 14, 2017, provisional application No. 62/484,621, filed on Apr. 12, 2017, provisional application No. 61/706,863, filed on Sep. 28, 2012, provisional application No. 61/565,715, filed on Dec. 1, 2011.

(51) Int. Cl.
| | | |
|---|---|---|
| G01N 33/68 | (2006.01) | |
| A61K 31/52 | (2006.01) | |
| A61K 31/713 | (2006.01) | |
| A61P 25/00 | (2006.01) | |

(52) U.S. Cl.
CPC ......... *G01N 33/6896* (2013.01); *A61K 31/52* (2013.01); *A61K 31/713* (2013.01); *A61P 25/00* (2018.01); *G01N 2333/56* (2013.01); *G01N 2500/00* (2013.01); *G01N 2800/2835* (2013.01); *G01N 2800/52* (2013.01); *G01N 2800/7047* (2013.01)

(58) Field of Classification Search
CPC .......... G01N 33/6896; G01N 2500/00; G01N 2800/28; G01N 2800/2835; G01N 2800/52; G01N 2800/50; A61K 31/505; A61K 31/52; A61K 31/713; A61K 48/00; A61K 48/0066; A61P 25/28; A61P 25/00; A61P 25/14
See application file for complete search history.

(56) References Cited

U.S. PATENT DOCUMENTS

| | | | |
|---|---|---|---|
| 2004/0185558 A1 | 9/2004 | Griguer et al. | |
| 2005/0019847 A1* | 1/2005 | Zhang ............... | G01N 33/68 435/7.93 |
| 2008/0261226 A1 | 10/2008 | Wang et al. | |
| 2008/0317834 A1 | 12/2008 | Green et al. | |
| 2010/0111874 A1 | 5/2010 | Liu et al. | |

OTHER PUBLICATIONS

Cummings JL and Zhong K. Treatments for behavioural disorders in neurodegenerative diseases: drug development strategies. Nat. Rev. Drug Discovery, 5:64-74. (Year: 2006).*
Golde TE and Miller VM. Proteinopathy-induced neuronal senescence: a hypothesis for brain failure in Alzheimer's and other neurodegenerative diseases. Alzheimer's Res. Therapy, 1:5 (12 pages). (Year: 2009).*
Lehman NL. The ubiquitin proteasome system in neuropathology. Acta Neuropathol. 118:329-347. (Year: 2009).*
Pallardo FV et al. Mitochondrial dysfunction in some oxidative stress-related genetic diseases: Ataxia-telangiectasia, Down syndrome, Fanconi anaemia and Werner syndrome. Biogerontology, 11:401-419. (Year: 2010).*
Siddoo-Atwal et al. Elevation of interferon beta-inducible proteins in Ataxia Telangiectasia cells. Cancer Res. 56:443-447. (Year: 1996).*
Stray-Pedersen A et al. Alpha fetoprotein is increasing with age in ataxia-telangiectasia. Eur. J. Paediatric Neurol. 11:375-380. (Year: 2007).*
Wood LM et al. A novel role for ATM in regulating proteasome-mediated protein degradation through suppression of the ISG15 conjugation pathway. PLoS One, Jan. 2011, 6(1):e16422. (Year: 2011).*
Zhang et al. Interferon-stimulated gene 15 and the protein ISGylation system. J. Interferon & Cytokine Res. 31(1):119-130. (Year: 2011).*
Lou Z et al. Telomere length regulates ISG15 expression in human cells. Aging, 2009, 1(7), 608-621. (Year: 2009).*
Sasaki S et al. Autophagy in spinal cord motor neurons in sporadic amyotrophic lateral sclerosis. J. Neuropathol Exp Neurol. May 2011, 70(5), 349-359. (Year: 2011).*
Siddoo-Atwal C et al. Elevation of interferon beta-inducible proteins in Ataxia Telangiectasia cells. Cancer Research, 56, 443-447. (Year: 1996).*
Stray-Pedersen A et al. Alpha fetoprotein is increasing with age in ataxia-telangiectasia. Eur. J. Paediatric Neurol. 2007, 11, 375-380. (Year: 2007).*
Wang R et al. Activation of interferon signaling pathways in spinal cord astrocytes from an ALS mouse model. Glia, Jun. 2011, 59(6), 946-958. (Year: 2011).*
Anderson JB et al. Stage-associated overexpression of the ubiquitin-like protein, ISG15, in bladder cancer. British J. Cancer, 2006, 94, 1465-1471. (Year: 2006).*

(Continued)

*Primary Examiner* — Kimberly Ballard
(74) *Attorney, Agent, or Firm* — Baker Donelson

(57) ABSTRACT

This invention is directed to compositions and methods for detecting proteinopathies.

11 Claims, 52 Drawing Sheets

(14 of 52 Drawing Sheet(s) Filed in Color)

(56) References Cited

OTHER PUBLICATIONS

Dastur A et al. Herc5, an interferon-induced HECT E3 enzyme, is required for conjugation of ISG15 in human cells. J. Biol. Chem. 2006, 281(7), 4334-4338. (Year: 2006).*
D'Cunha J et al. In vitro and in vivo secretion of human ISG15, an IFN-induced immunomodulatory cytokine. J. Immunol. 1996, 157, 4100-4108. (Year: 1996).*
Giannakopoulos NV et al. Proteomic identification of proteins conjugated to ISG15 in mouse and human cells. Biochem. Biophys. Res. Comm. 2005, 336, 496-506. (Year: 2005).*
Jeon YJ et al. ISG15 and immune diseases. Biochimica et Biophysica Acta, 2010, 1802, 485-496. (Year: 2010).*
Okumura, A. et al., "Innate antiviral response targets HIV-1 release by the induction of ubiquitin-like protein ISG15," Proc Natl Acad Sci US A, vol. 103, pp. 1440-1445 (2006).
Okumura, A. et al., "ISG15 inhibits Ebola VP40 VLP budding in an L-domain-dependent manner by blockinq Nedd4 liqase activity," Proc. Natl. Acad. Sci. US A, vol. 105, pp. 3974-3979 (2008).
Pandey, U. B. et al., "HDAC6 at the intersection of autophagy, the ubiquitin-proteasome system and neurodegeneration," Autophaqy, vol. 3, pp. 643-645 (2007).
Pandey, U. B. et al., "HDAC6 rescues neurodegeneration and provides an essential link between autophaqy and the UPS," Nature, vol. 447, pp. 859-863 (2007).
Pear, W. S. et al., "Production of high-titer helper-free retroviruses by transient transfection," Proc. Natl. Acad. Sci.US A vol. 90 pp. 8392-8396 (1993).
Ritchie et al, Role of ISG15 protease UBP43 (USP18) in innate immunity to viral infection, 2004, Nature Medicine, vol. 10, 12:1374-1378.
Rolig, R. L. et al., "Linking DNA damage and neurodegeneration," Trends Neurosci., vol. 23, pp. 417-424 (2000).
Ross, C. A. et al., "The ubiquitin-proteasome pathway in Parkinson's disease and other neurodeqenerative diseases," Trends Cell Biol., vol. 14, pp. 703-711 (2004).
Rubinsztein, D. C., "Autophagy induction rescues toxicity mediated by proteasome inhibition," Neuron, vol. 54, pp. 854-856 (2007).
Sakaguchi, A. et al., "Functional compatibility between isoform alpha and beta of type II DNA topoisomerase," J Cell Sci, vol. 117, pp. 1047-1054 (2004).
Savitsky, K. et al., "A single ataxia telangiectasia gene with a product similar to PI-3 kinase," Science, vol. 268, DD. 1749-1753 (1995).
Schmitt, H. P., "Protein ubiquitination, degradation and the proteasome in neuro-degenerative disorders: no clear evidence for a significant pathogenetic role of proteasome failure in Alzheimer disease and related disorders," Med. Hypotheses, vol. 67, pp. 311-317 (2006).
Seglen, P. 0. et al., "3-Methyladenine: specific inhibitor of autophagic/lysosomal protein degradation in isolated rat hepatocvtes," Proc. Natl. Acad. Sci.US A, vol. 79, pp. 1889-1892 (1982).
Sharma, A. et al., "Ultraviolet radiation stress triggers the down-regulation of essential replication factor Mcm10," J. Biol. Chem., vol. 285, pp. 8352-8362 (2010).
Shiloh, Y. et al., "Ataxia-telangiectasia and the ATM gene: linking neurodegeneration, immunodeficiency, and cancer to cell cycle checkpoints," J. Clin. Immunol., vol. 16, pp. 254-260 (1996).
Sun, X. et al., "Early diagnosis of ataxia-telangiectasia using radiosensitivity testing," J. Pediatr., vol. 140, pp. 724-731 (2002).
Takeuchi, T. et al., "ISG15 modification of Ubc13 suppresses its ubiquitin-conjugating activity," Biochem. Biophvs. Res. Commun., vol. 336, DD. 9-13 (2005).
Takeuchi, T. et al., "Link between the Ubiquitin Conjugation System and the ISG15 Conjugation System: ISG15 Conjugation to the UbcH6 Ubiquitin E2 Enzyme," J Biochem (Tokyo), vol. 138, pp. 711-719 (2005).
Tanida, I. et al., "LC3 conjugation system in mammalian autophagy," Int. J. Biochem. Cell Biol., vol. 36 pp. 2503-2518 (2004).

Taylor, A. M. et al., "Ataxia telangiectasia: a human mutation with abnormal radiation sensitivity," Nature, vol. 258, DD. 427-429 (1975).
Thomson, T. M. et al., "Ubiquitin and SUMO signaling in DNA repair," Biochem. Soc. Trans., vol. 38, pp. 116-131 (2010).
Valentin-Vega, Y. A. et al., "Mitochondrial dysfunction in ataxia-telangiectasia," Blood, vol. 119, DD. 1490-1500 (2012).
Wang, R. et al., "Activation of interferon signaling pathways in spinal cord astrocytes from an ALS mouse model," Glia, vol. 59, pp. 946-958 (2011).
WO 2005/116204, Dec. 2005. Because of the extreme length of document only front page and translation of relevant portion of a document (search result) are provided. 2 pages.
Wood, L.M. et al., "A novel role for ATM in regulating proteasome-mediated protein degradation through suppression of the ISG15 conjugation pathway," PLoS ONE, vol. 6, No. 1, pp. 1-12 (published Jan. 26, 2011).
Wu, W. K., et al., "Induction of autophagy by proteasome inhibitor is associated with proliferative arrest in colon cancer cells," Biochem. Biophys. Res. Commun., vol. 374, pp. 258-263 (2008).
Wu, X. et al., "ATM phosphorylation of Nijmegen breakage syndrome protein is required in a DNA damage response," Nature, vol. 405, pp. 477-482 (2000).
Wu, X. et al., Interactions of the Nijmegen breakage syndrome protein with ATM and BRCA 1. Cold Sprinq Harb. SvmP. Quant. Biol., vol. 65, pp. 535-545 (2000).
Yamamoto, A. et al., "Bafilomycin A 1 prevents maturation of autophagic vacuoles by inhibiting fusion between autophagosomes and lysosomes in rat hepatoma cell line, H-4-II-E cells," Cell Struct. Funct., vol. 23, DD. 33-42 (1998).
Zhang, D. et al., Interferon-stimulated gene 15 and the protein ISGylation system. J Interferon Cytokine Res., vol. 31, pp. 119-130 (2011).
Zou, W. et al., "ISG15 modification of ubiquitin E2 Ubc13 disrupts its ability to form thioester bond with ubiquitin," Biochem. Biophys. Res. Commun., vol. 336, pp. 61-68 (2005).
Zou, W. et al., "Negative regulation of ISG15 E3 ligase EFP through its autoISGylation," Biochem. Biophys. Res. Commun., vol. 354, pp. 321-327 (2007).
Agamanolis, D. P. et al., "Ataxia-telangiectasia. Report of a case with Lewy bodies and vascular abnormalities within cerebral tissue," J. Neuropathol. Exp. Neural. 38, 475-489 (1979).
Ambrose, M. et al., "Intrinsic mitochondrial dysfunction in ATM-deficient lymphoblastoid cells," Hum Mal Genet,, vol. 16, pp. 2154-2164 (2007).
Bader, E., "Ataxia-telangiectasia: an overview," Kroc Found. Ser. vol. 19, pp. 1-63 (1985).
Barlow, C. et al., "ATM is a cytoplasmic protein in mouse brain required to prevent lysosomal accumulation," Proc. Natl, Acad. Sci. US A, vol. 97, pp. 871-876 (2000).
Biton, S. et al., "The neurological phenotype of ataxia-telangiectasia: solving a persistent puzzle," DNA Repair (Arnst), vol. 7, pp. 1028-1038 (2008).
Bregman, D. B. et al., "UV-induced ubiquitination of RNA polymerase II: a novel modification deficient in Cockayne syndrome cells," Proc. Natl. Acad. Sci.US A vol. 93, pp. 11586-11590 (1996).
Browne, S. E. et al., "Oxidative damage and mitochondrial dysfunction in neurodegenerative diseases," Biochem Soc Trans, vol. 22: DD.1002-1006 (1994).
Chen et al, ISG15, a ubiquitin-like interferon-stimulated gene, promotes hepatitis C virus production in vitro: Implications for chronic infection and response to treatment, 2010, Journal of General Virology, 91: 382-388.
Cherra, S. J. et al., "Autophagy in neuroprotection and neurodegeneration: A question of balance," Future Neural., vol. 3, pp. 309-323 (2008).
Chu, C. T., "Autophagic stress in neuronal injury and disease," J. Neuropathol. Exp. Neural., vol. 65, pp. 423-432 (2006).
Chun, H. H. et al., "Ataxia-telangiectasia, an evolving phenotype," DNA Repair (Arnst), vol. 3, pp. 1187-1196 (2004).
Ciechanover, A.,"Early work on the ubiquitin proteasome system, an interview with Aaron Ciechanover. Interview bv COD" Cell Death Differ vol. 12 DD. 1167-1177 (2005).

(56) References Cited

OTHER PUBLICATIONS

Desai, S. D. et al., "Elevated expression of ISG15 in tumor cells interferes with the ubiquitin/26S proteasome pathway," Cancer Res., vol. 66, pp. 921-928 (2006).
Desai, S. D. et al., "ISG15 as a novel tumor biomarker for drug sensitivity," Mal. Cancer Ther., vol. 7, pp. 1430-1439 (2008).
Desai, S. D. et al., "ISG15 disrupts cytoskeletal architecture and promotes motility in human breast cancer cells," Exp. Biol. Med. (Maywood), vol. 237, pp. 38-49 (2012).
Desai, S. D. et al., "Ubiquitin-dependent destruction of topoisomerase I is stimulated by the antitumor drug camptothecin," J. Biol. Chem., vol. 272, pp. 24159-24164 (1997).
Desai, S. D. et al., "Ubiquitin/26S proteasome-mediated degradation of topoisomerase I as a resistance mechanism to camptothecin in tumor cells," Cancer Res., vol. 61, pp. 5926-5932 (2001).
Desai, S. D. et al., "Transcription-dependent degradation of topoisomerase I-DNA covalent complexes," Mal. Cell Biol., vol. 23, pp. 2341-2350 (2003).
Desai, S.D. et al., "Rethinking neurodegeneration in Ataxia Telangiectasia: Role of proteinopathy," an abstract submitted for the 14th International Workshop on Ataxia-Telangiectasia and ATM (Feb. 7-11, 2012).
Easton, D. F., "Cancer risks in A-T heterozygotes," Int. J. Radiat. Biol., vol. 66, pp. S177-182 (1994).
Eilam, R. et al., "Late degeneration of nigro-striatal neurons in ATM-/- mice," Neuroscience 121, 83-98 (2003).
Figueiredo-Pereira, M. E. et al., "The ubiquitin/proteasome pathway: friend or foe in zinc-, cadmium-, and H2O2-Induced neuronal oxidative stress," Mal. Biol. Rep., vol. 26, pp. 65-69 (1999).
Frappart, P. 0. et al., "Ataxia-telangiectasia and related diseases," Neuromolecular Med., vol. 8, pp. 495-511 (2006).
Ge, P. F. et al., "Inhibition of autophagy induced by proteasome inhibition increases cell death in human SHG-44 qlioma cells," Acta Pharmacol. Sin., vol. 30, pp. 1046-1052 (2009).
Haas, A. L. et al., "Interferon induces a 15-kilodalton protein exhibiting marked homology to ubiquitin," J. Biol. Chem. vol. 262 pp. 11315-11323 (1987).
Herzog, K.H. et al., "Requirement for Atm in ionizing radiation-induced cell death in the developing central nervous system," Science, vol. 280: pp. 1089-1091 (1998).
Ikeda, F. et al., "Atypical ubiquitin chains: new molecular signals. 'Protein Modifications: Beyond the Usual Suspects' review series," EMBO Rep, vol. 9: DD. 536-542 (2008).
Johri, A. et al., "Mitochondrial dysfunction in neurodegenerative diseases," J Pharmacol Exp Ther, vol. 342 pp. 619-630 (2012).
Kabeya, Y et al., LC3, a mammalian homologue of yeast Apg8p, is localized in autophagosome membranes after processing. EMBO J., vol. 19, pp. 5720-5728 (2000).
Katyal, S. et al., "DNA strand breaks, neurodegeneration and aging in the brain," Mech. Ageing Dev., vol. 129, pp. 483-491 (2008).
Klionsky, D. J. et al., "Autophagy as a regulated pathway of cellular degradation," Science, vol. 290, DD. 1717-1721 (2000).

Klionsky, D. J. et al., "Guidelines for the use and interpretation of assays for monitoring autophagy in hiqher eukaryotes," Autophaqy, vol. 4, pp. 151-175 (2008).
Komatsu, M. et al., "Physiological significance of selective degradation of p62 by autophagy," FESS Lett., vol. 584, DD. 1374-1378 (2010).
Lavin, M. F. et al., ATM signaling and genomic stability in response to DNA damage. Mutat. Res., vol. 569, pp. 123-132 (2005).
Lavin, M. F. et al., "ATM: the protein encoded by the gene mutated in the radiosensitive syndrome ataxia-telanqiectasia," Int. J. Radiat. Biol., vol. 75, pp. 1201-1214 (1999).
Lavin, M. F. et al., "Functional consequences of sequence alterations in the ATM gene," DNA Repair (Arnst), vol. 3, pp. 1197-1205 (2004).
Lehman, N. L., "The ubiquitin proteasome system in neuropathology," Acta Neuropathol., vol. 118, pp. 329-347 (2009).
Lin, M. T. et al., "Mitochondrial dysfunction and oxidative stress in neurodegenerative diseases," Nature, vol. 443 DD. 787-795 (2006).
Liu, L. F., DNA topoisomerase poisons as antitumor drugs. Annu. Rev. Biochem., vol. 58, pp. 351-375 (1989).
Loeb, K. R. et al., "The interferon-inducible 15-kDa ubiquitin homolog conjugates to intracellular Droteins " J. Biol. Chem. vol. 267 DD. 7806-7813 (1992).
Lu, F. et al., "ISG15 enhances the innate antiviral response by inhibition of IRF-3 degradation," Cell Mal Biol (Noisv-le-qrand), vol. 52, pp. 29-41 (2006).
Malakhova, 0. A. et al., "ISG15 inhibits Nedd4 ubiquitin E3 activity and enhances the innate antiviral response," J. Biol. Chem., vol. 283, pp. 8783-8787 (2008).
Maragakis, N. J. et al., "Mechanisms of Disease: astrocytes in neurodegenerative disease," Nat. Clin. Pract. Neural., vol. 2, pp. 679-689 (2006).
Matsuoka, S. et al., "ATM and ATR substrate analysis reveals extensive protein networks responsive to DNA damage," Science, vol. 316, pp. 1160-1166 plus online supporting material (2007).
Menendez-Benito V. et al., Endoplasmic reticulum stress compromises the ubiquitin-proteasome system. Hum Mal Genet, vol. 14, pp. 2787-2799 (2005).
Metcalf, D. J. et al., "Autophagy and misfolded proteins in neurodegeneration," Exp Neural., vol. 238, pp. 22-28 (2012).
Mizushima, N.,"Autophaqv: process and function," Genes Dev., vol. 21, DD. 2861-2873 (2007).
Mu et al, A Proteomic Analysis of Ataxia Telangiectasia-mutated (ATM)/ATM-Rad3-related (ATR) Substrates Identifies the Ubiquitin-Proteasome System as a Regulator for DNA Damage Checkpoints, 2007, Journal of Biological Chemistry, vol. 282, 24: 17330-1 7334.
Narasimhan, J. et al., "Conjugation of the 15-kDa interferon-induced ubiquitin homolog is distinct from that of ubiquitin," J. Biol. Chem., vol. 271, pp. 324-330 (1996).
Nedelsky, N. B. et al., "Autophagy and the ubiquitin-proteasome system: collaborators in neuroprotection," Biochim. Biophvs. Acta., vol. 1782, DD. 691-699 (2008).

* cited by examiner

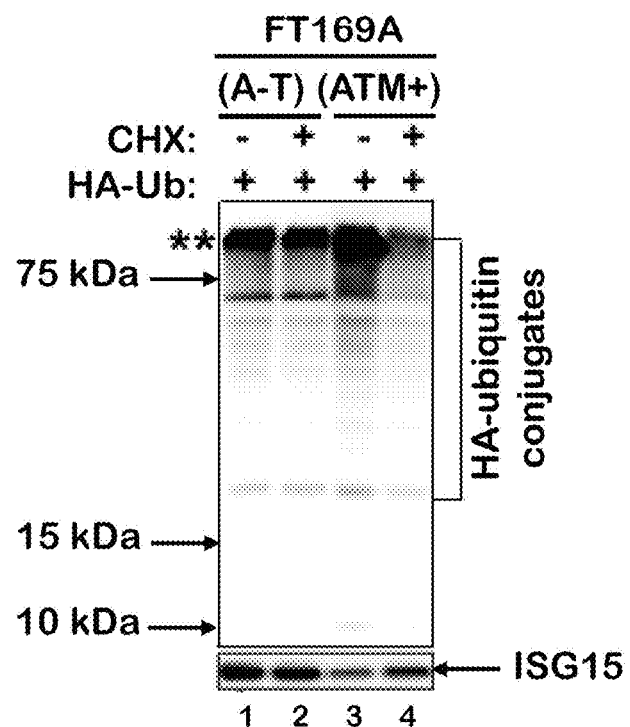
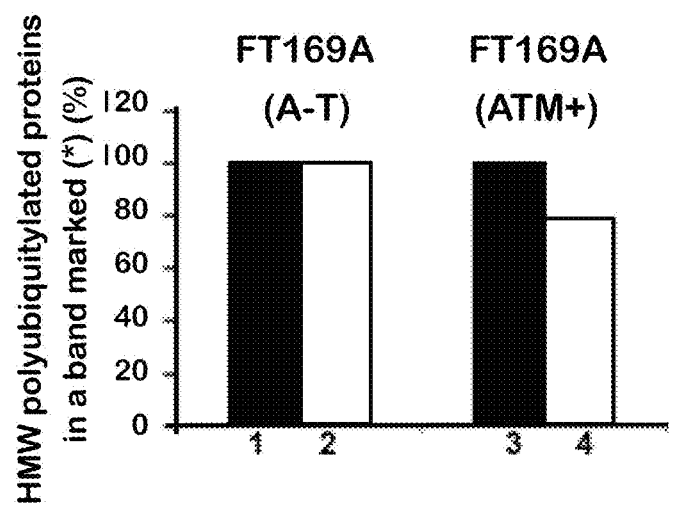
Fig. 1B

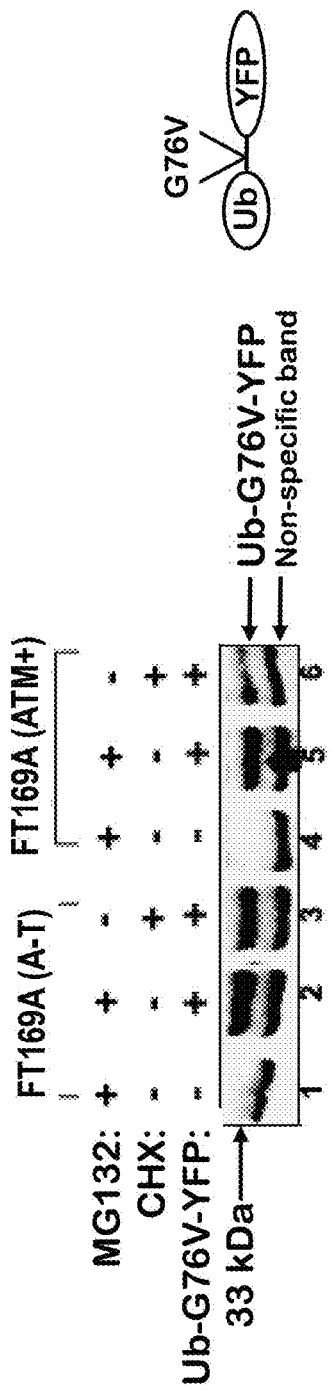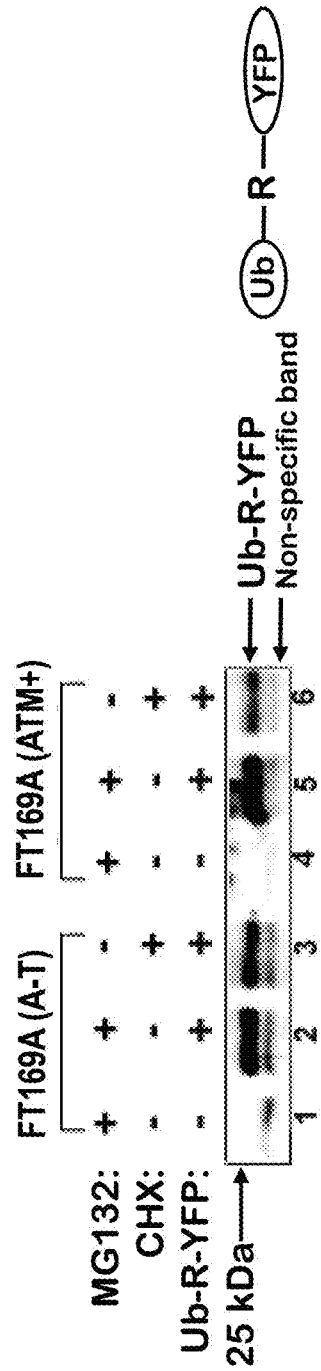
Fig. 2A
Fig. 2B

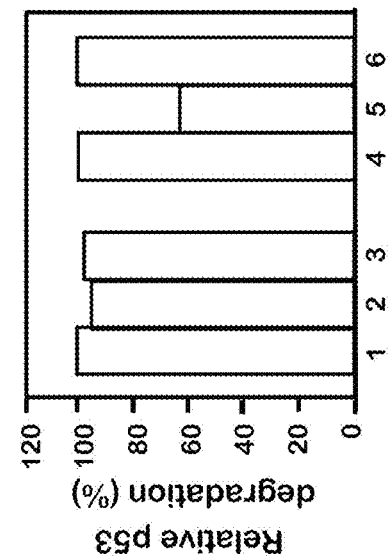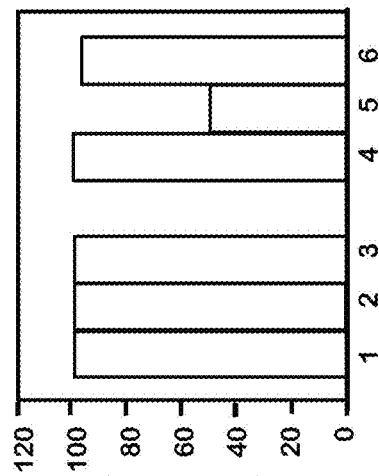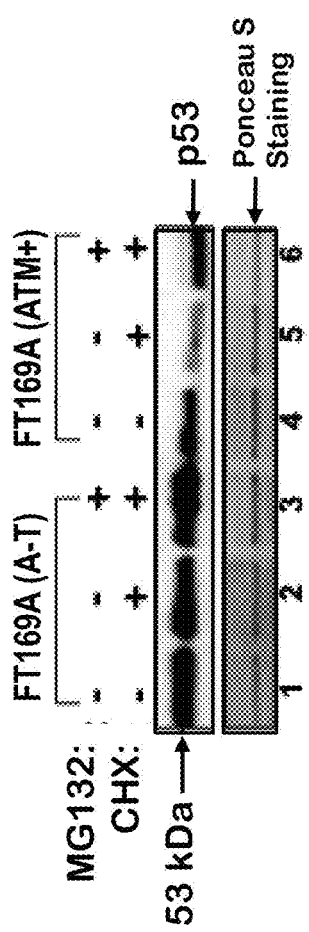
Fig. 2C
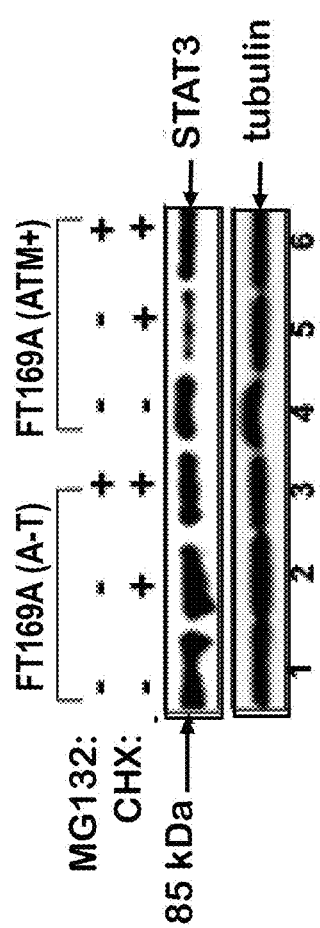
Fig. 2D

Fig. 18A
ATM+ cells in Culture
(staining with the autophagy dye)
No treatment        + UV
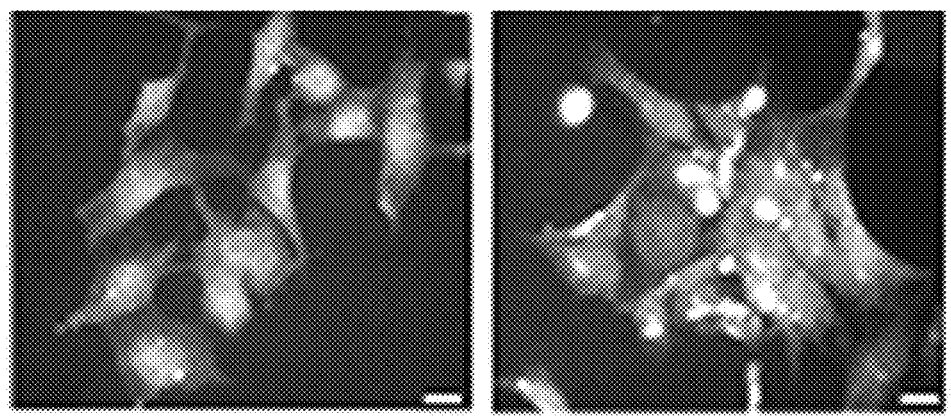
Fig. 18B
ATM+/- Organotypic brain tissue culture
(staining with LC3)
No treatment        + UV (150 mJ)
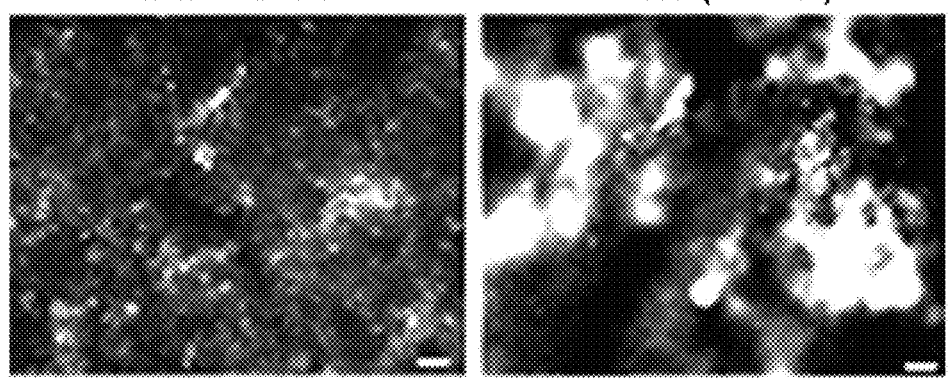
Fig. 18C
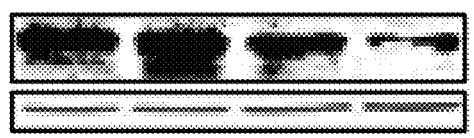
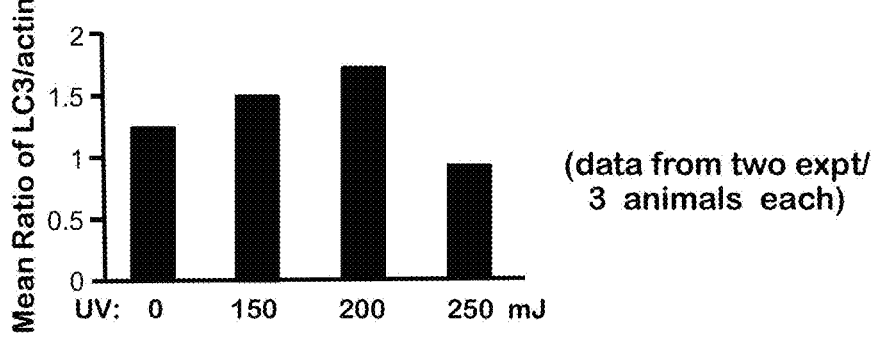
(data from two expt/
3 animals each)

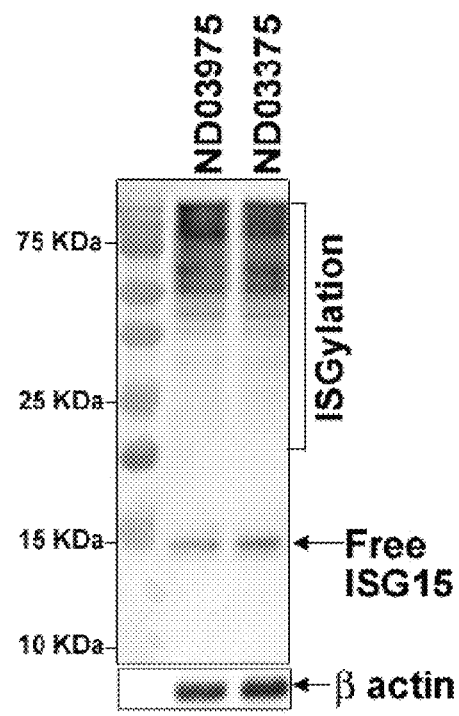
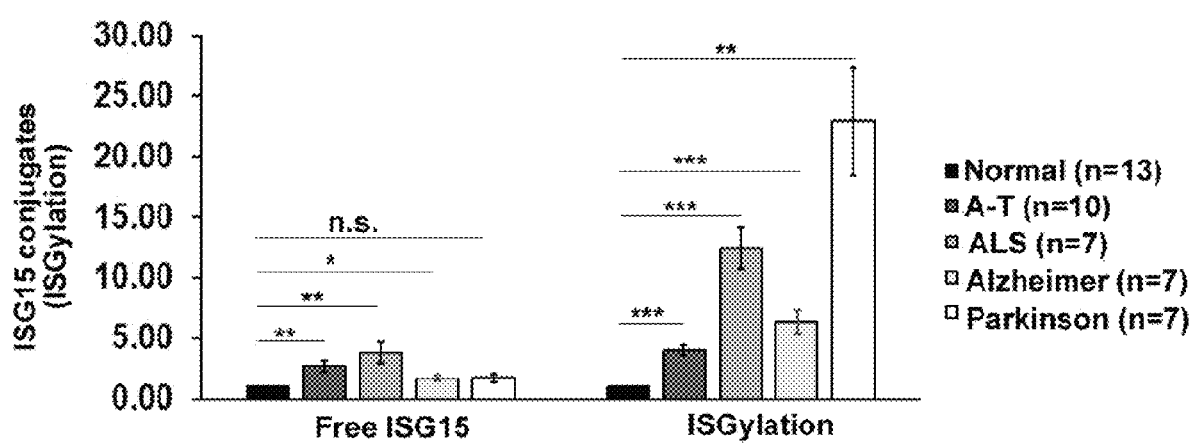
FIG. 22

| Diseases | Sample size |
|---|---|
| * Alzheimer | 100 |
| * Parkinson | 100 |
| * ALS | 100 |
| A-T | 20 |
| Friedreich Ataxia | 20 |
| Huntington | 20 |
| *Normal | 100 |

* Available free of cost

FIG. 23

COMPOSITIONS AND METHODS FOR DETECTING PROTEINOPATHIES

This application claims priority from U.S. Provisional Patent Application Ser. No. 62/484,621, filed on Apr. 12, 2017 and U.S. Provisional application Ser. No. 62/519,423, filed on Jun. 14, 2017; and is a continuation-in-part application of U.S. patent application Ser. No. 15/464,473, filed Mar. 21, 2017, which is a divisional of U.S. patent application Ser. No. 13/688,384, filed Nov. 29, 2012, now U.S. Pat. No. 9,599,626, which claims priority under 35 U.S.C. § 119(e) both from U.S. Provisional Application Ser. No. 61/565,715, filed Dec. 1, 2011, and from U.S. Provisional Application Ser. No. 61/706,863, filed Sep. 28, 2012, the entire disclosures of each which are incorporated by reference in their entireties.

GOVERNMENT INTERESTS

This invention was made with government support under grant number R21NS060960 awarded by the National Institutes of Health. The government has certain rights in the invention.

FIELD OF THE INVENTION

The invention is directed to compositions, methods, and kits for detecting proteinopathies.

BACKGROUND OF THE INVENTION

Neurodegenerative diseases, rare and common, place an enormous burden on patients and caregivers globally. Over 6 million people in the United States alone suffer from neurodegenerative diseases, all of which are chronic, incurable, and with causes unknown. Identifying a common molecular mechanism underpinning neurodegenerative disease pathology is urgently needed to aid in the design of effective therapies to ease suffering for patients, reduce economic cost, and improve quality of life for such patients.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1B illustrates both A-T and ATM+ cells transfected with HA-ubiquitin, then treated with the protein synthesis inhibitor CHX (marked on top of each lane) for 6 hours, and then lysates analyzed using 15% SDS-PAGE followed by immunoblotting with anti-HA antibody. The symbol  marks the position of polyubiquitylated proteins (compressed due to the gel electrophoresis conditions). Quantitation of the high-molecular-weight (HMW) polyubiquitylated proteins (shown as ) is shown in the bar graph.

FIGS. 2A and 2B illustrate A-T and ATM+ cells transfected with fluorescent reporter proteasome substrates (the ubiquitin fusion degradation substrate, UbG76V-YFP (FIG. 2A), and the N-end rule substrate, ubiquitin-arginine-YFP (Ub-R-YFP) (FIG. 2B) for 12 hours. Proteasome inhibitor MG132 (0.5 μM) was then added to the transfection medium and cells were allowed to grow for an additional 12 hours. After washing (to remove MG132), cells were treated with protein synthesis inhibitor CHX for 3 hours, and then the fluorescent reporter levels were detected with GFP antibodies.

FIG. 2C illustrates A-T and ATM+ cells treated with the protein synthesis inhibitor CHX in the presence (lanes 3 and 6) or absence (lanes 2 and 5) of the proteasome inhibitor MG132 (10 μM) for 6 h, and then cell lysates were analyzed by immunoblotting using an anti-p53 antibody. The intensity of the p53 bands was measured using a Kodak Image station 2000R (BioRad), and the results are shown in the bar graph (right panel). The filter used for immunoblotting was stained with Ponceau S to assure equal protein loading (lower panel). All of the experiments were repeated at least three times and the representative experiments are shown.

FIG. 2D illustrates A-T and ATM+ cells treated with the protein synthesis inhibitor CHX (10 μg/ml) in the presence (lanes 3 and 6) or absence (lanes 2 and 5) of the proteasome inhibitor MG132 (10 μM) for 6 h, and cell lysates were analyzed by immunoblotting using an anti-STAT3 antibody. Intensity of the STAT3 band was measured using Kodak Image station 2000R (BioRad), and the results are shown in the bar graph (right panel). The lower portion of the same membrane filter was immunostained with the anti-tubulin (lower panel) antibody. All of the experiments were repeated at least three times and the representative experiments are shown.

FIGS. 10B and 10D show average values (±SEM) of % degradation of LC3 (FIG. 10B) or p62 (FIG. 10D) from three independent experiments. All control values (−UV and + Bafl) were normalized to 100%, and values for experimental treatments were expressed as percent variations over control.

In FIG. 17B, bar 1: No drug and + Bafl controls; bar 2:+UV; and bar 3: + Bafl+UV.

FIG. 18A illustrates ATM+ cells cultured on fibronectin-coated glass coverslips, and then exposed to UV radiation and allowed to recover for 3 hrs. Cells were then washed (2×1 min) with PBS and stained with Cyt-ID® (Cyt-ID® Autophagy Detection Kit from Enzo Lifesciences) for 30 min at 37° C. in a CO2 incubator. Stained cells were then washed (2×1 min) with PBS and fixed with 4% paraformaldehyde for 20 min at room temperature. After washing with PBS (3×10 min), cells were mounted on slides in anti-fade mounting medium with DAPI (Invitrogen). Images were taken using a 63× oil immersion objective with a Leica DMRA2 upright microscope run through SlideBook software (Intelligent Imaging Innovations).

FIG. 18B illustrates murine organotypic cerebellar brain slices exposed to UV radiation and allowed to recover for 3 hrs. Slices were washed with PBS (2×5 min) and immunostained for LC3 (MBL International Corporation) for 1 h at room temperature. After washing with PBS (2×5 min), cells were incubated with Alexa-Fluor 488 goat anti-mouse IgG secondary antibody (1:100) (Invitrogen) for 1 hr. Brain slices were then washed with PBS and mounted on slides in anti-fade mounting medium with DAPI (Invitrogen). Images were taken using a 63× oil immersion objective with a Leica DMRA2 upright microscope run through SlideBook software (Intelligent Imaging Innovations). The experiments have been repeated twice, and the results were reproducible.

FIG. 18C illustrates murine organotypic brain slices exposed to different doses of UV and allowed to recover for 3 hrs. After three hours, tissue lysates were prepared and then analyzed by Western analysis using LC3 and actin-specific antibodies (FIG. 18C, top panel). Intensity of the total LC3 and corresponding actin bands was quantitated using BioRad Quantity One software, and the results shown in the bar graph (FIG. 18C, lower graph). The amounts of LC3 on the blots were calculated as a ratio between band intensities of LC3 (I and II) and actin (bar chart).

FIG. 19A, bars 1: No drug and + Bafl controls; bars 2:+UV; and bars 3: + Bafl+UV.

In FIG. 19B, bars 1: No drug and + Bafl controls; bars 2:+UV; and bars 3: + Bafl+UV.

FIG. 22 shows ISGylation is elevated in neurodegenerative diseases. Cell lysates were prepared as described in Materials and Methods and analyzed by Western blotting analysis using an anti-human ISG15 antibody. For loading controls, the same membrane was probed using an antibody against β-actin (top panel). Intensities of free ISG15, ISGylation, and β-actin bands were quantitated using Amersham Imager A600 and ImageQuant TL software. The bar graph (bottom panel) shows mean values of the ratio between free ISG15/β-actin and ISGylation/β-actin measured from different lymphocyte lysates. Error bars represent +/−SEM.

FIG. 23 shows number of lymphocyte cell lines screened for ISGylation.

Five fields containing 20-30 cells were selected and the intensity of the green dye was measured using Image J, and is plotted in the bar graph. Scale bar: 10 µm. (C) Flow cytometric analysis of oxidative stress using CellRox Green stain in A-T/LV-control and A-T/LV-ISG15 shRNA cells is shown. Mean values of the median fluorescence intensity from three independent experiments are plotted in the bar graph. In the bar graphs (B and C) fluorescence intensity values from A-T/LV control shRNA cells are normalized to 100%, and values from A-T/LV-ISG15 shRNA cells are expressed as percent variations over control. Error bars represents +/−SEM.

Figure 32:
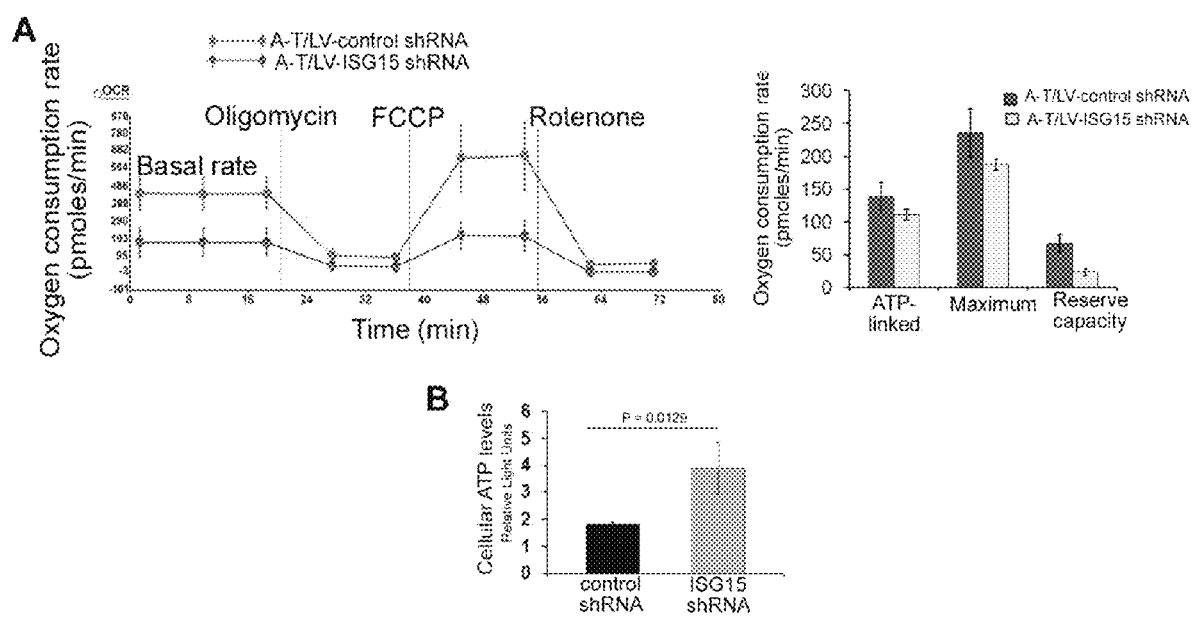

FIG. 32 shows ISG15 shRNA restores mitochondrial functions in A-T cells. (A) Oxygen consumption rates (OCR) were measured using Seahorse Biosciences XF24 flux analyzer in response to indicated mitochondrial inhibitors. A representative run for the mitochondrial functions using Seahorse Extracellular Flux machine is shown in the left panel. Experiment was repeated four times and the mean values from the four different experiments (n=20 samples) are plotted in the bar graph (right panel). (B) Cellular ATP levels were measured in A-T/LV-control and A-T/LV-ISG15 shRNA cells using ATP measuring kit from the Life Technology as described by manufacturer. Data are displayed as mean+/−SEM of triplicates.

Figure 33:
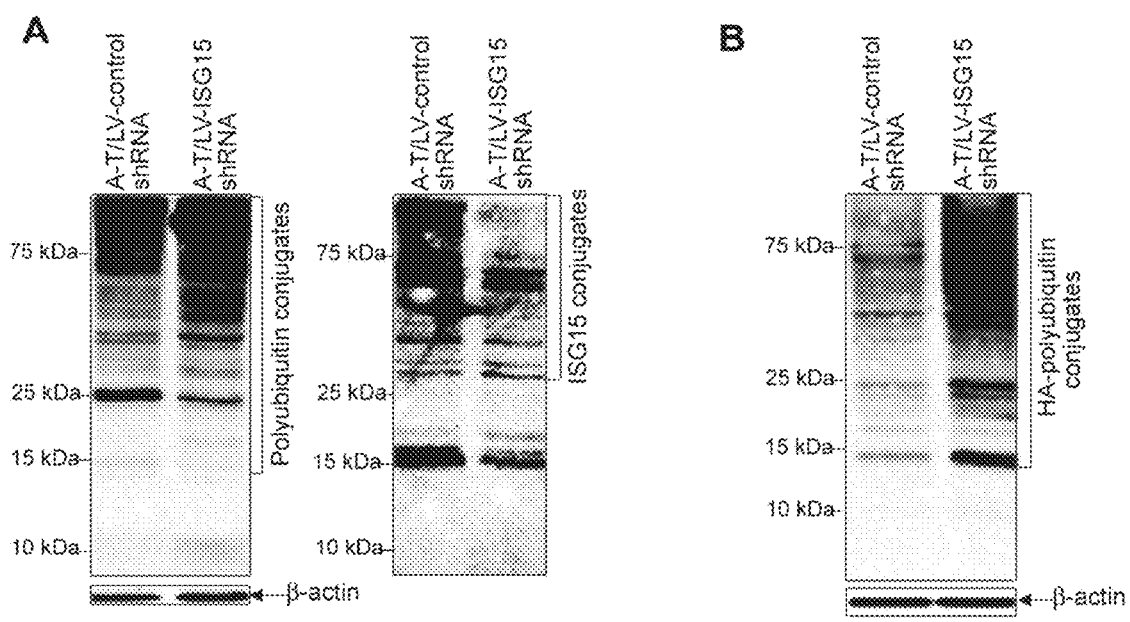
Figure 34:
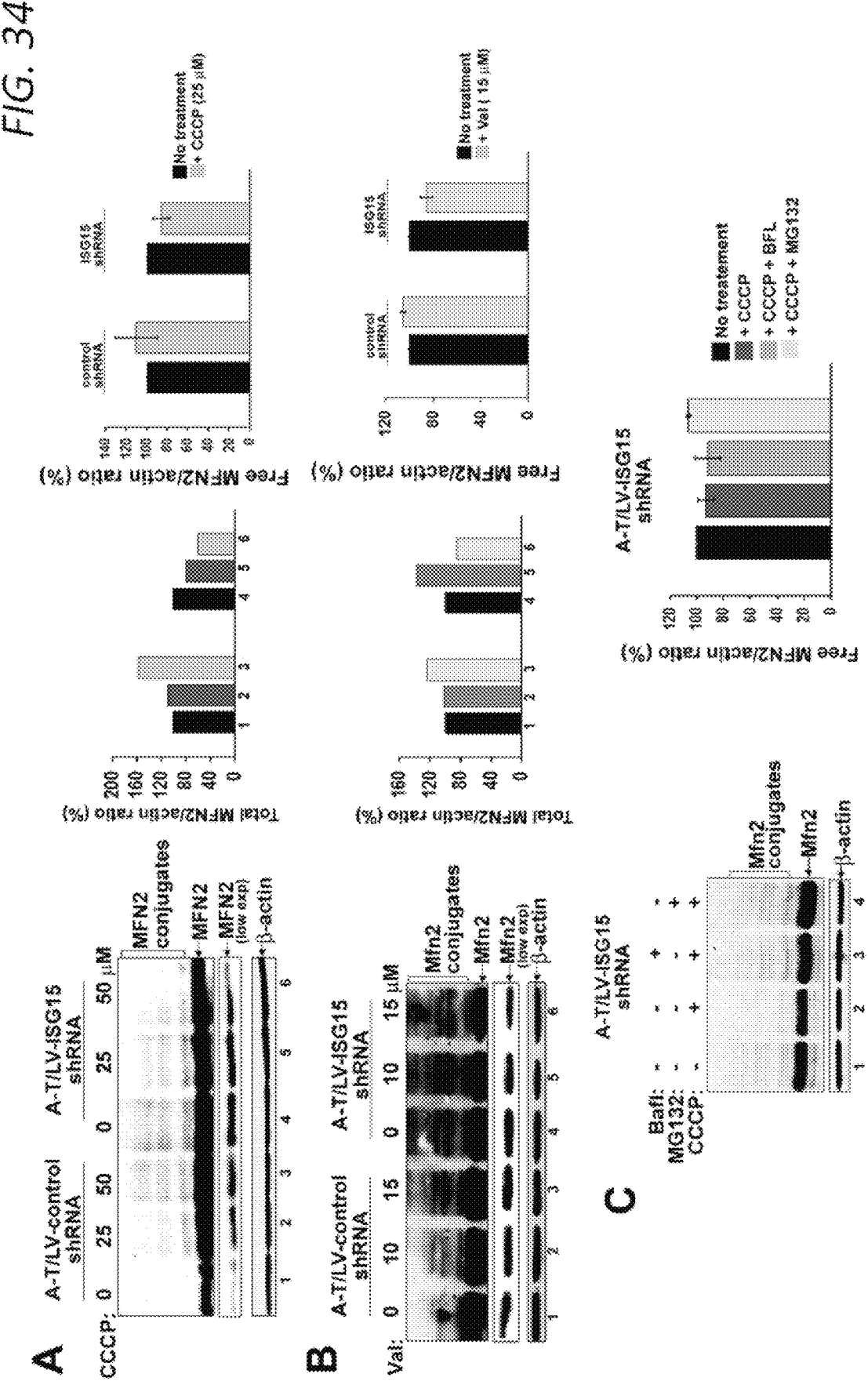

FIG. 33 shows ISG15 inhibits the polyubiquitylation of mitochondrial protein in A-T cells. (A) Mitochondria were isolated from A-T/LV-control and A-T/LV-ISG15 shRNA cells as described in Material and Methods. Mitochondrial protein lysates were analyzed using 15% SDS-PAGE followed by immunoblotting with anti-ubiquitin antibody (left panel). The same membrane shown in the left panel was stripped and sequentially re-probed with anti-ISG15 (right panel) and anti-β-actin (left lower panel) antibodies. Experiment was repeated at least three times and the representative experiment is shown. (B) Mitochondria were isolated from A-T/LV-control and A-T/LV-ISG15 shRNA cells transfected with HA-ubiquitin construct. Analysis of mitochondrial proteins was carried out using anti-HA antibody as described in A FIG. 34 shows ISG15 inhibits degradation of Mfn2 protein in A-T cells. (A) A-T/LV-control and A-T/LV-ISG15 shRNA cells were treated with different concentrations of CCCP for 24 hr. Cells were lysed, and lysates were analyzed using 7.5% SDS-PAGE followed by immunoblotting with anti-Mfn2 antibody (left panel). The same membrane shown in the upper panel was stripped and re-probed with anti-β-actin (lower panel). Intensity of the free Mfn2 and β-actin proteins on the Western blot shown in the first panel was measured using Bio-Rad software. Free Mfn2/β-actin ratio is plotted in the bar graph (second panel). The bar graph in the third panel shows mean values of the ratio between free Mfn2 and β-actin proteins in CCCP-treated A-T/LV-control and A-T/LV-ISG15 shRNA cells measured from eight independent experiments. (B) A-T/LV-control and A-T/LV-ISG15 shRNA cells were treated with different concentrations of valinomycin for 24 hr. Cell lysis, immunoblotting, and measurement of free Mfn2 and β-actin intensities were carried out as described above. Intensity of free Mfn2 and β-actin proteins on the Western blot shown in the first panel was measured using Bio-Rad software. Free Mfn2/β-actin ratio is plotted in the bar graph (second panel). The bar graph in the third panel shows mean values of the ratio between free Mfn2 protein and β-actin in valimomycin-treated A-T/LV-control and A-T/LV-ISG15 shRNA cells measured from three independent experiments. (C) A-T/LV-ISG15 shRNA cells were treated with MG132 (5 µM) or Bafl (100 nm) for one hour where indicated. Cells were then washed with the complete medium, and treated with CCCP (25 uM) together with MG132 (100 nM) or Bafl (100 nm) for additional 24 hr (lanes 4 and 8). Cell lysis, Western blotting using anti-Mfn2 and β-actin antibodies were carried out as described above (first panel). The bar graph shows the % ratio between Mfn2 and β-actin proteins in DMSO-, CCCCP-, CCCP+ Bafl-, and CCCP+MG132-treated A-T/LV-control and A-T/LV-ISG15 shRNA cells measured from three independent experiments. In all bar graphs, control values are normalized to 100%, and values for experimental treatments are expressed as percent variations over control. Error bars represents +/−SEM.

Figure 35:
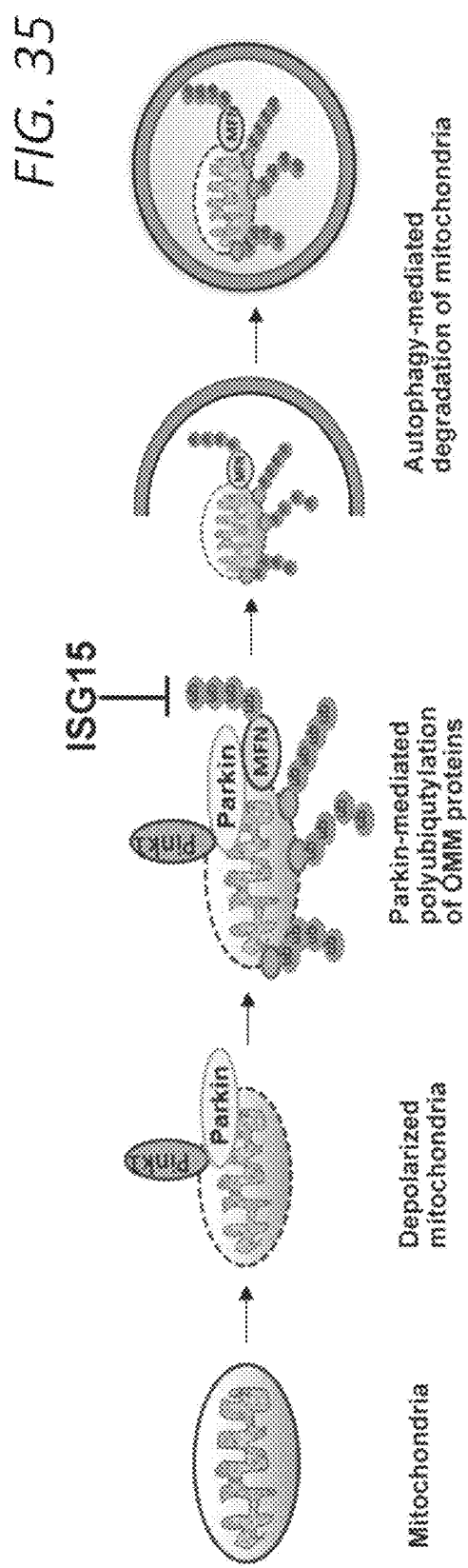

FIG. 35 shows schematic diagram of the proposed mechanism by which ISG15 may inhibit mitophagy in A-T cells. ISG15 may inhibit polyubiquitylation of the outer mitochondrial membrane proteins, a prerequisite signal for the initiation of mitophagy, consequently inhibits mitophagy in A-T cells FIG. 36 comprises photographs of western blots showing that ISG15 inhibits MFN2-SUMO and ubiquitin conjugation and degradation in A-T cells. (FIG. 36A) A-T/LV-control and -ISG15 shRNA cells were treated with different concentrations of CCCP for 24 h. Cell lysates were analyzed using 7.5% SDS-PAGE followed by immunoblotting with anti-MFN2 (upper panel) and anti-β-actin (lower Panel) antibody. (FIG. 36 B-D) The same membrane shown in A was stripped and sequentially re-probed with anti-SUMO-1, anti-SUMO-2/3, and anti-ubiquitin. This experiment was repeated several times. Representative blots are shown. (FIG. 36 E) MFN2 was immunoprecipitated from A-T/LV-control and ISG15 shRNA cells treated with CCCP for 24 h. Immunoprecipitates were analyzed using 4-20% gradient SDS-PAGE followed by immunoblotting with anti-MFN2 antibody (left panel). The same membrane was stripped and re-probed with anti-SUMO-2/3 antibodies (right panel). The bar graph shows mean values of free MFN2 density in CCCP (10 µM)-treated A-T/LV-control and -ISG15 shRNA cells measured from five independent IP experiments (lower panel). In the bar graphs MFN2 density values from A-T/LV control shRNA cells are normalized to 100%, and values from A-T/LV-ISG15 shRNA cells are expressed as percent variations over control. Error bars represents +/−SEM. (FIG. 36F) A-T/LV-control and A-T/LV-ISG15 shRNA cells were treated with different concentrations of Valinomycin for 24 h. Cells were lysed, and lysates were analyzed using 10% SDS-PAGE followed by immunoblotting with anti-MFN2 (upper panel) and anti-β-actin (lower Panel) antibody.

Figure 37:
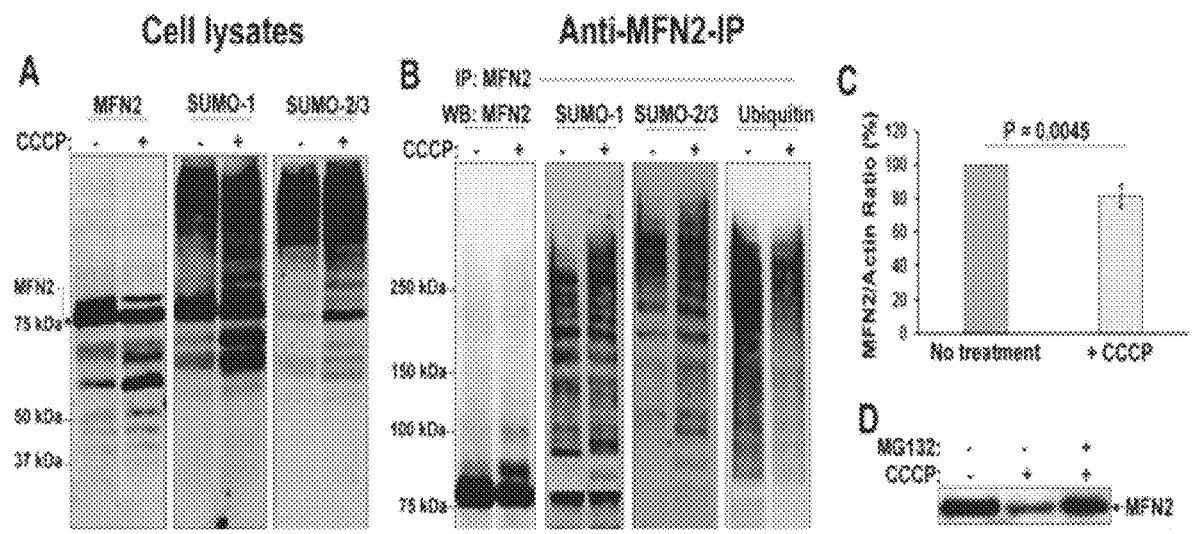

FIG. 37 comprises photographs of western blots showing that MFN2 is conjugated to SUMO and Ubiquitin, and degraded in HEK cells. (FIG. 37A) HEK293 cells were treated with CCCP (10 µM) for 24 h. Cells were lysed, and lysates were analyzed using 7.5% SDS-PAGE followed by immunoblotting with anti-MFN2 antibody (first panel). The same membrane shown in the upper Panel was stripped and re-probed with anti-SUMO 1 (second panel), anti-SUMO 2/3 (third panel) and anti-β-actin (lower Panel). (FIG. 37B) MFN2 was immunoprecipitated from non-treated and CCCP treated HEK cell lysates. Immunoprecipitates were analyzed using 7.5% SDSPAGE followed by immunoblotting with anti-MFN2 antibody (first panel), anti-SUMO 1 (second panel), anti-SUMO 2/3 (third panel), and anti-ubiquitin (fourth panel) (FIG. 37C) The bar graph shows mean values of the ratio between free MFN2 and β-actin proteins in CCCP-treated A-T/LV-control and A-T/LVISG15 shRNA cells measured from three independent experiments. (FIG.

37D) Cells were treated with CCCP or CCCP and MG132 (1 μM) for 24 h. MFN2 was detected as in FIG. 37A.

Figure 38:
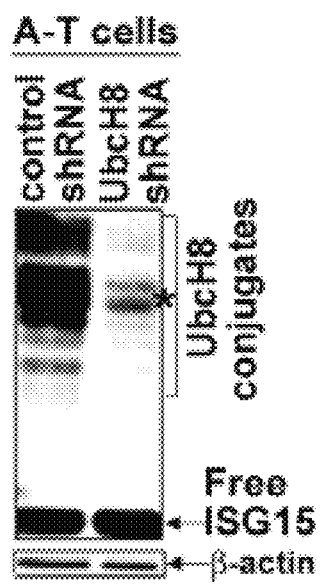

FIG. 38 is a photograph of a western blot showing UbcH8-silenced cells. A-T cells stably transfected with UbcH8 shRNA were generated as described in (82). *non-specific anti-ISG15 antisera crossreactive bands as previously shown (82).

Figure 39:
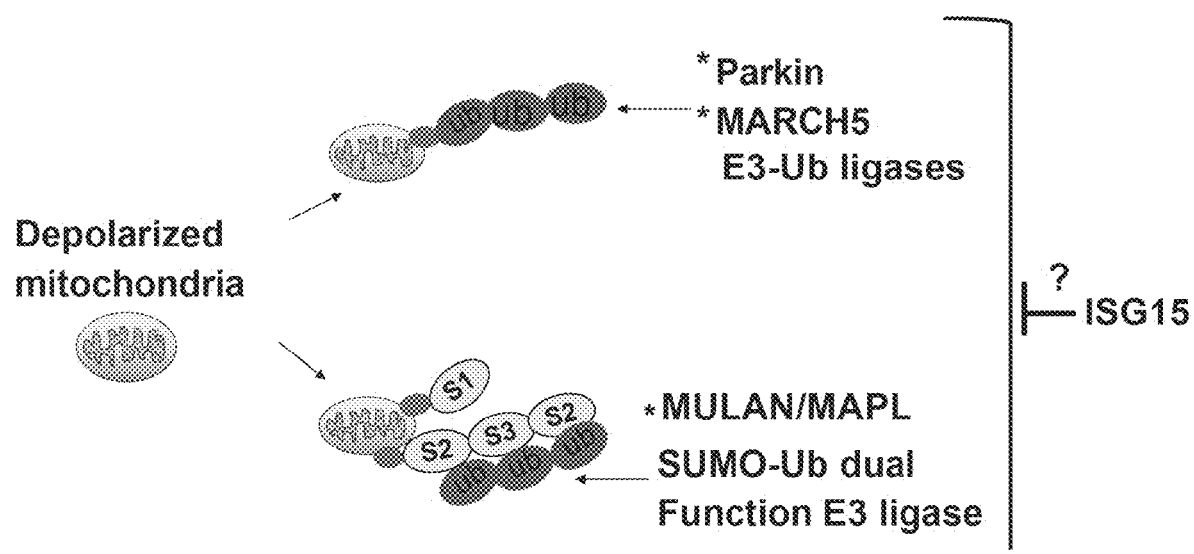

FIG. 39 is a schematic of E3 ligases for MFN2. We have found SUMO-Interacting Motifs (SIMs) on all Parkin, MARCH5, and MULAN using JASSA SIM analyzer indicating that these enzymes are STUbLs.

Figure 40:
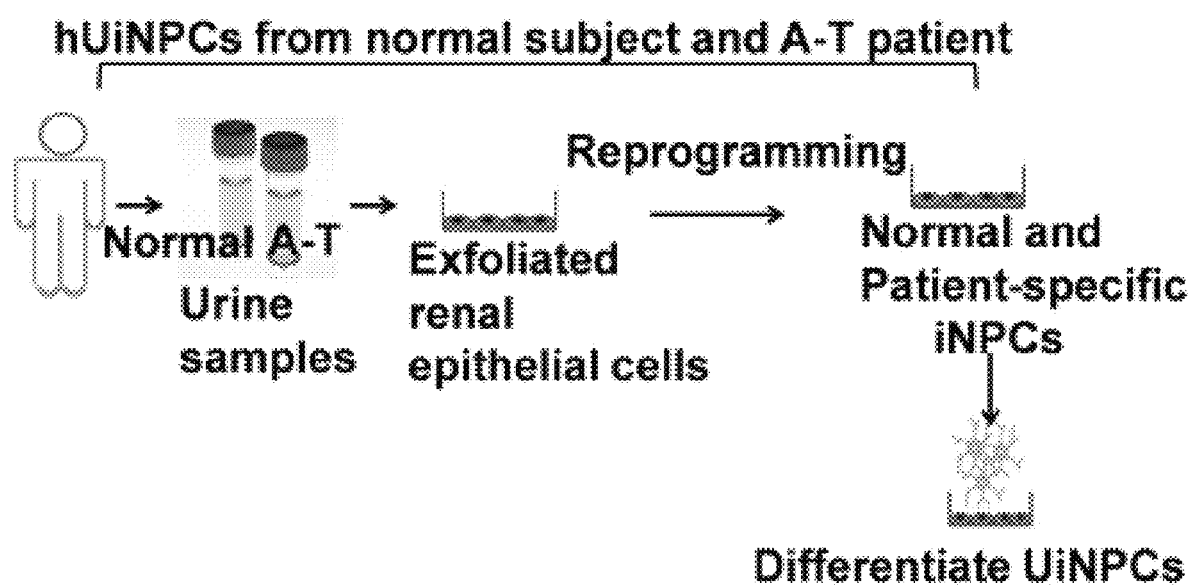
Figure 41:
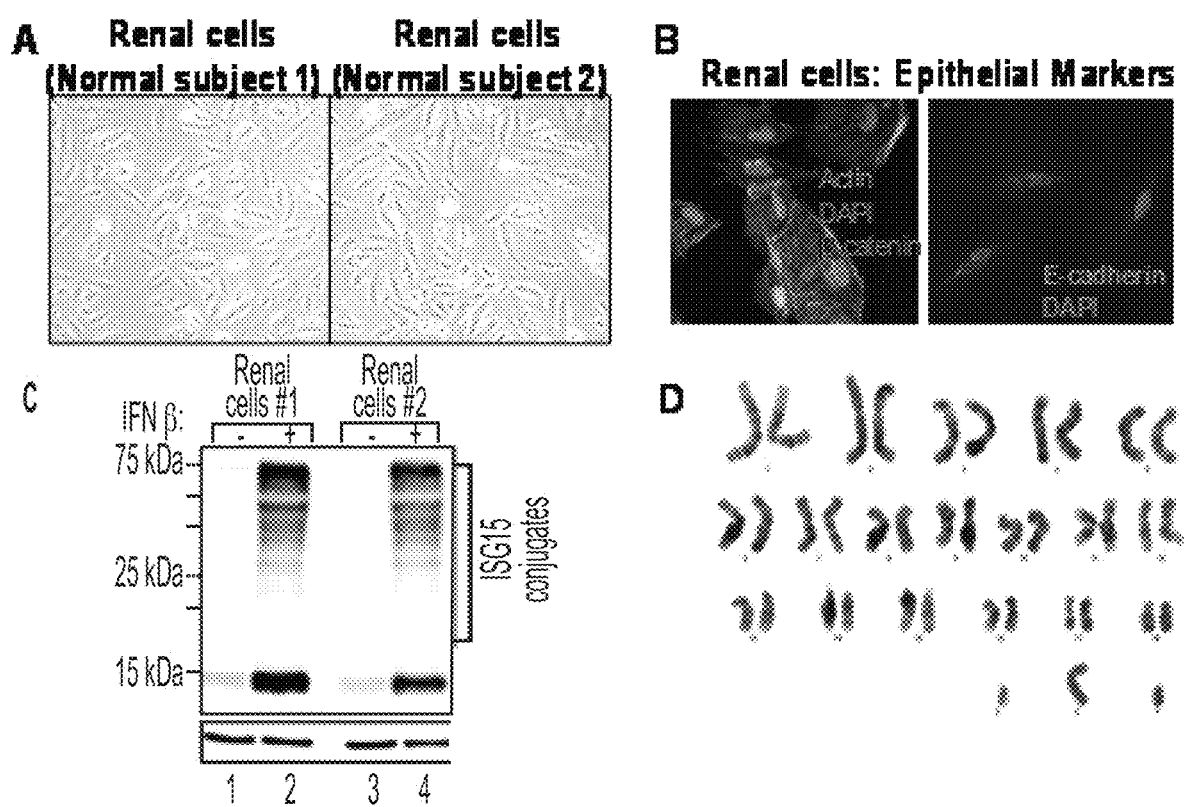

FIG. 40 is a schematic representation of the protocol to make human UiNPC-derived neurons FIG. 41 shows renal cells from normal children. (FIG. 41A) Renal cells from two different children were isolated as described in the Experimental strategy. Images were taken by differential interference microscopy (DIC). Typical images are shown using a 10× objective. (FIG. 41B) Representative fluorescence images of renal cells stained with epithelial markers b-catenin (63×) and E-cadherin (10×) are shown. (FIG. 41C) Renal cells from two distinct patients were treated with IFNβ for 24 h. Cell lysates were analyzed using 7.5% SDSPAGE followed by immunoblotting with anti-ISG15 and bactin antibody. (FIG. 41D) A normal karyotype of the isolated renal cells is shown.

Figure 42:
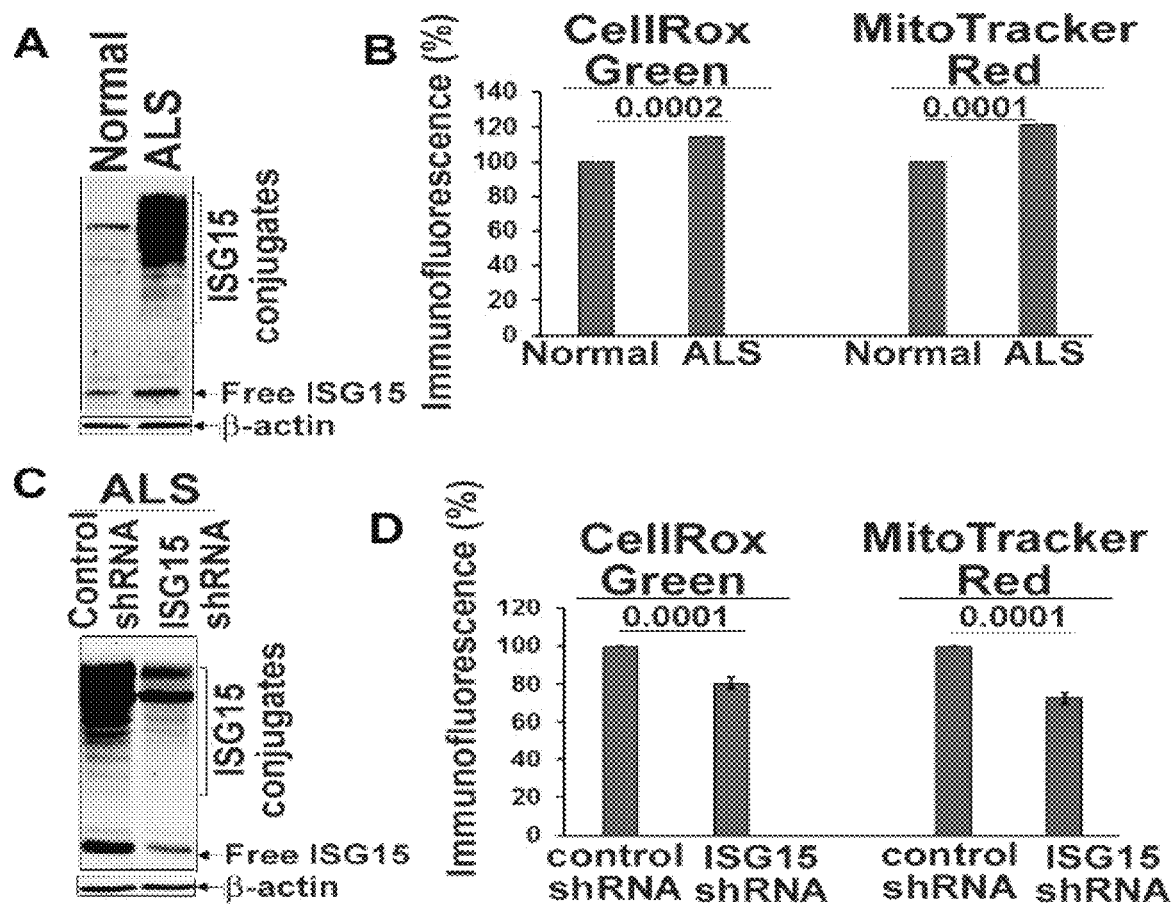

FIG. 42 shows ISG15 inhibits mitophagy in ALS. (FIG. 42A) ISG15 expression. Protein expression of ISG15 in normal and ALS cells is shown in the Western blot. (FIG. 42B) Mitochondrial mass and oxidative stress in increased in ALS cells. Flow cytometric analysis of oxidative stress using CellRox Green and mitochondrial mass using MitoTracker Red in ALS cells is shown. (FIG. 42C) Protein expression of ISG15 in ALS and ISG15-silenced ALS cells is shown in the Western blot. (FIG. 42D) Flow cytometric analysis of oxidative stress using CellRox Green and mitochondrial mass using MitoTracker Red in ALS and ISG15-silenced ALS cells is shown. Mean values of the median fluorescence intensity from three independent experiments are plotted in the bar graphs shown in Panels B (FIG. 42), and D (FIG. 42). In the bar graphs fluorescence intensity values from control cells are normalized to 100%, and values from ALS/ISG15 shRNA cells are underlying ISG15-mediated defective degradation of MFN2 (mitophagy) in ALS cells.

SUMMARY OF THE INVENTION

The invention is directed towards an in vitro method to diagnose a patient with or at risk of developing proteinopathy-induced neurodegeneration and/or a proteinopathy-induced neurodegenerative disease, the method comprising collecting a sample from a subject; detecting the level of unconjugated ISG15 protein, conjugated ISG15 protein, or both in said sample; and comparing the sample unconjugated ISG15 protein level and/or conjugated ISG15 protein level to levels of unconjugated ISG15 protein and/or conjugated ISG15 protein in a control sample; wherein a significantly increased level of unconjugated ISG15 protein and/or conjugated ISG15 protein in the subject sample as compared with the control sample indicates that the subject has or is at risk of developing proteinopathy-induced neurodegeneration and/or a proteinopathy-induced neurodegenerative disease.

The invention is further directed towards a method to diagnose a subject with or at risk of developing proteinopathy-induced neurodegeneration and/or a proteinopathy-induced neurodegenerative disease, the method comprising collecting a sample from a subject; detecting the level of unconjugated ISG15 protein, conjugated ISG15 protein, or both, in said sample; and comparing the sample unconjugated ISG15 protein level, conjugated ISG15 protein level, or both, to levels of conjugated and/or unconjugated ISG15 protein in a control sample; wherein a significantly increased level of conjugated ISG15 protein, unconjugated ISG15 protein, or both in the subject as compared with the control indicates that the patient is prone to neurodegeneration, proteinopathy-induced neurodegeneration, and/or proteinopathy-induced neurodegenerative disease.

In embodiments, the patient is prone to neurodegeneration, proteinopathy-induced neurodegeneration, and/or proteinopathy-induced neurodegenerative disease if the level of unconjugated ISG15 protein, conjugated ISG15 protein, or both, is greater than about 0.05%, 1%, 2%, 3%, 4%, 5%, 6%, 7%, 8%, 9%, 10%, 20%, 30%, 40%, 50%, 60%, 70%, 80%, 90%, 100%, 125%, 150%, 175%, 200%, 225%, 250%, 275% of a control sample.

The invention is further directed towards a method of assessing the effectiveness of a course of treatment for a subject suffering from proteinopathy-induced neurodegeneration and/or proteinopathy-induced neurodegenerative disease, the method comprising measuring a first level of unconjugated ISG15 protein, conjugated ISG15 protein, or both in a sample from the subject at a first time point during the course of treatment with a therapeutic agent; measuring a second level of unconjugated ISG15 protein, conjugated ISG15 protein, or both, in a sample from the subject in a second time point during the course of treatment with a therapeutic agent and comparing the measurements from steps (a) and (b); wherein if the level from step (a) is greater than the level from step (b), then the treatment with the therapeutic agent is effective; and wherein if the level from step (b) is equal to or greater than the level from step (a), then the treatment with the therapeutic agent is not effective; and administering the therapeutic agent to the subject if the treatment is effective.

Embodiments additionally comprise administering a therapeutic agent to the subject.

In embodiments, measuring and/or detecting can comprise an immunoassay, a colorimetric assay, a fluorimetric assay or a combination of both. In embodiments, the immunoassay can comprise a western blot assay, an enzyme-linked immunosorbent assay (ELISA), immunoprecipitation, single molecule immunoassays in femoliter chamber arrays, digital enzyme assays in both single and multiplex forms, or a combination thereof. In embodiments, the detecting comprise contacting the sample with an anti-ISG15 antibody. In embodiments, the anti-ISG15 antibody is a polyclonal or monoclonal antibody. In embodiments, detecting can comprise a kinetic assay, an endpoint assay, Bradford assay, a bicinchoninic acid (BCA) assay, a Lowry assay, a pyrogallol red protein dye-binding assay, a Coomassie blue dye-binding assay, or a combination thereof.

Non-limiting examples of proteinopathy-induced neurodegenerative diseases comprise Ataxia Telangiectasia (A-T), Alzheimer's disease (AD), Parkinson's disease (PD), Huntington's disease (HD), Amyotrophic Lateral Sclerosis (ALS), Friedreich's Ataxia, Multiple Sclerosis (MS), Prion diseases, Spinocerebellar Ataxia (SCA), Spinal Muscular Atrophy (SMA), multiple taupathies, Huntington's disease, Spongiform encephalopathies, Traumatic Brain Injury, and Familial polyneuropathy. In some embodiments, the proteinopathy-induced neurodegeneration and/or proteinopathy-induced neurodegenerative disease is not Ataxia Telangiectasia (A-T).

In embodiments, the sample is selected from the tissue group consisting of human cerebellar tissue sections, cerebrospinal fluid, skin fibroblast cells, renal cells, urine, peripheral blood cells, plasma, and blood serum. Non-limiting examples of samples comprise bone marrow; blood; blood cells; blood mononuclear cells; serum; plasma; ascites; tissue or fine needle biopsy samples; cell-containing body fluids; renal cells; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom.

Embodiments additionally comprise testing the sample for the presence of alphafetoprotein.

Embodiments additionally comprise testing the sample for increased levels of autophagy markers and/or mitophagy markers selected from the group consisting of LC3-I, LC3-II, mitochondrial superoxide, reactive oxygen species, and mitochondrial mass.

The present invention further provides for a kit for diagnosing a subject with proteinopathy-induced neurodegeneration or a proteinopathy-induced neurodegenerative disease. In embodiments, the kit can comprise an ISG15 bio-recognition element, such as an anti-ISG15 antibody, immobilized to a solid support and instructions for use of same. In embodiments, the solid support can comprise plastic, cardboard, or glass. In embodiments, the solid support can comprise a dip stick.

The present invention further provides a diagnostic kit of molecular biomarkers for identifying a subject exhibiting or having a predisposition to develop proteinopathy-induced neurodegeneration or a proteinopathy-induced neurodegenerative disease. In embodiments, the kit can comprise at least one agent for determining levels of unconjugated ISG15 protein, conjugated ISG15 protein, or both; mitophagy markers; autophagy markers; markers selected from the group consisting of LC3-I, LC3-II, mitochondrial superoxide, reactive oxygen species, and mitochondrial mass; wherein together represent a molecular signature that is indicative of the presence of or a predisposition to development of proteinopathy-induced neurodegeneration or a proteinopathy-induced neurodegenerative disease in a subject.

Other objects and advantages of this invention will become readily apparent from the ensuing description.

DETAILED DESCRIPTION OF THE INVENTION

Ataxia-telangiectasia (A-T) is a childhood disease with an incident of 1 in 40,000 children in the U.S. and 1 in 200,000 worldwide each year (1-4). Ataxia refers to uncoordinated movements, such as walking, and telangiectasia is the enlargement of capillaries just below the surface of the skin, a feature characteristically exhibited by A-T patients (3). It is a rare inherited disorder that mainly affects nervous and immune systems (3). A-T patients are also at an increased risk of developing cancer (5). Affected individuals are very sensitive to radiation, including medical x-rays (6, 7). This feature has been attributed to the defective ATM gene (Ataxia Telangiectasia Mutated) in A-T patients (8). ATM is a serine/threonine protein kinase that is activated upon DNA damage (9). Activated ATM kinase phosphorylates several key proteins that initiate activation of the DNA damage checkpoints, cell cycle arrest, and DNA repair to favor cell survival (10). Therefore, a defect in ATM has severe consequences in DNA damaged cells, especially in terminally differentiated cells such as neurons (11). Indeed, a defective DNA repair pathway has been linked to the progressive neurodegeneration in A-T patients (11-14). Whether the defect in DNA repair is solely responsible for neurodegeneration in A-T is unknown.

Altered expression/mutations in genes involved in protein turnover pathways have been linked to neurodegeneration in other neurological diseases. Accumulation of misfolded protein deposits in affected brain regions are reported in neurodegenerative diseases including Alzheimer's, Parkinson's, Creutzfeldt-Jakob, and Huntington's disease (15, 16). In most cases, proteinaceous deposits were composed of ubiquitin conjugates, indicating a failure in their degradation by the ubiquitin/26S proteasome, the major cellular proteolytic machinery responsible for targeted destruction of short-lived and abnormal proteins in mammalian cells (17). The potential accumulation of non-degraded ubiquitylated proteins in neurons of A-T patients has been indicated (12, 13, 18, 19). However, the events leading to the accumulation of non-degradable ubiquitylated proteins and the potential causal relationship to neuronal degeneration in A-T patients is unknown.

ISG15 (Interferon Stimulated Gene 15) protein is a member of the UBL (ubiquitin-like protein) class of proteins (21, 22), and can be induced upon interferon treatment (23). Intracellular ISG15 exists in two forms: (i) free and (ii) conjugated to target proteins. ISG15 is conjugated to its target proteins in an enzymatic cascade involving an E1 (UbEIL), E2 (UbcH8), and E3 (HERCS and others) (21-23). Free ISG15 has been indicated to have cytokine-like activity (23). Conjugated ISG15 exerts its biological effect by inhibiting polyubiquitylation of cellular proteins (24-26).

ISG15 has been shown to inhibit the ubiquitin pathway by modulating the activities of the ubiquitin E2/E3 ligases (27-30). ISG15 inhibits the ubiquitylation of Gag and Tsg101 which prevents their interaction and blocks retroviral replication and release (67). In addition, ISG15 inhibits Nedd4 ubiquitin ligase and, consequently, the ubiquitylation of VP40 viral particles essential for budding of Ebola viruses (27). Furthermore, ISG15 inhibits ubiquitin-mediated degradation of IRF3, a transcription factor involved in the interferon response, and enhances innate antiviral immunity (68). ISG15 also inhibits polyubiquitylation by modulating the activities of selected ubiquitin E2 and E3 ligases (27-29, 69). In normal cells, the ISG15 pathway is not constitutively elevated. However, when aberrantly overexpressed, ISG15 may conjugate to and inhibit the activity of ubiquitin E2/E3 ligases as demonstrated with Nedd4 (27), UbcH6 (69), and UbcH13 (28, 29). ISG15 has also been shown to inhibit bulk polyubiquitylation and the subsequent 26S proteasome-mediated degradation of target proteins in breast cancer cells (24). Elevated expression of ISG15 suppresses camptothecin-induced proteasome-mediated degradation of topoisomerase I in breast cancer cells (37). ISG15 has been shown to be elevated and conjugated to cellular proteins in A-T cells (70).

Under conditions where proteasome function is compromised, the large ubiquitin containing protein aggregates have been shown to be cleared by autophagy (31-34); a second major proteolytic pathway that targets destruction of long-lived cellular proteins, larger macromolecular complexes, and defective organelles through lysosomes (35, 36).

U.S. Patent Application Publication No. 2005/0019847 discloses methods to identify compounds that alter the conjugation of ISG15 with target proteins, and methods to identify patients with a malcondition characterized by an altered level of ISG15-conjugated proteins.

U.S. Patent Application Publication No. 2008/0261226 discloses biomarkers and diagnostic methods of early detection of neural cell injury using a mouse model of amyotrophic lateral sclerosis.

U.S. Patent Application Publication No. 2010/0111874 discloses methods for treating and detecting cancer based on levels of ISG15.

Abbreviations and Definitions

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

The inventor has demonstrated that ATM kinase regulates proteasome-mediated protein turnover through suppression of the expression of the ubiquitin-like protein ISG15 (Interferon Stimulated Gene 15). Using both ATM kinase deficient cells (A-T cells) and ATM kinase proficient cells (ATM+ cells), the following has been shown: (1) The ISG15 pathway is constitutively elevated in A-T cells, and suppressed in ATM+ cells; (2) autophagy is activated to compensate for impaired proteasome function in A-T cells, and is not activated in ATM+ cells; (3) ISG15 inhibits the ubiquitin pathway in A-T cells, while the ubiquitin pathway is functional in ATM+ cells; and (4) genotoxic stress (e.g., UV) induces bafilomycin (an autophagy inhibitor)-resistant degradation of the proteasome and autophagy substrates in A-T cells, and genotoxic stress induces only minimal degradation (which is protected by bafilomycin) of the proteasome and autophagy substrates in ATM+ cells. Silencing of the ISG15 pathway restored both the ubiquitin and autophagy pathways, and the UV-mediated degradation of their substrates in A-T cells. Without being bound by theory, the ATM kinase negatively regulates the ISG15 pathway, and the constitutively elevated ISG15 pathway induces proteinopathy in A-T cells, and in A-T patients. These findings indicate for the first time that protein turnover is impaired in A-T cells due to elevated expression of the ISG15 conjugation pathway, which contributes to progressive neurodegeneration in A-T patients. Thus the ISG15 pathway (for both free ISG15 secreted in blood and intracellular ISG15 conjugates) is a new target for both detection and treatment of A-T. Modulators of the ISG15 pathway that lead to lowered expression of ISG15 can be used to inhibit or attenuate neurodegeneration in A-T patients. In addition, an inhibitor of the early phase of autophagy, 3-MA, and ISG15 shRNA were shown to be effective in restoration of the impaired protein turnover pathways in A-T cells, and thus would be effective in decreasing the neurodegeneration in A-T patients. Defective mitophagy and macroautophagy in A-T patient cells is caused in part by elevated expression of ISG15 in A-T cells. In addition ISG15 inhibitors can attenuate ISG15 expression with the concomitant improvement in the neurodegeneration of A-T patients. This improvement can be monitored by MRI, PET, or other imaging tools.

Ataxia-telangiectasia (A-T) is a childhood disease with diverse clinical manifestations that results from inactivation of the ATM (Ataxia telangiectasia mutated) kinase. Targeted proteasome-mediated degradation is impaired in A-T cells. In addition, reduced protein turnover in A-T cells is associated with elevated expression of ISG15, an ubiquitin-like protein shown to antagonize the ubiquitin pathway. Furthermore, ATM acts as a suppresser of the ISG15 pathway. These results indicate a new functional role for ATM in protein turnover through suppression of constitutively activated ISG15 pathway in normal cells. Due to the inactivation of ATM kinase, ISG15 pathway is elevated which, in turn, inhibits ubiquitin-mediated protein turnover in A-T cells.

As shown herein, ISG15 was elevated in A-T astroglial cells and brain tissue obtained from ATM knockout mice and in A-T patients. In addition, the presence of ubiquitin/ISG15 double-positive inclusions was found in brain sections obtained from A-T patients. Ablation of ATM kinase leads to the elevated expression of ISG15. A clinical treatment for A-T patients can be the use of drugs that inhibit/modulate the ISG15 pathway to decrease ISG15 expression that would prevent proteinopathy associated with A-T and, consequently, neurodegeneration.

The basal autophagy pathway is activated in the ubiquitin pathway-compromised A-T cells. Genotoxic stress (e.g., UV radiation), but not metabolic stress (e.g., serum deprivation), induced irrepressible degradation of polyubiquitylated proteins in the ubiquitin pathway compromised A-T cells, but not in ATM+ cells. The proteasome inhibitor MG132 and autophagy inhibitor Bafilomycin A1 (Bafl A1) blocked the UV-induced degradation of the proteasome and autophagy substrates in ATM+ cells, but neither worked in A-T cells. In addition, camptothecin, another genotoxic agent, triggered Baf1 A1-resistant degradation of polyubiquitylated proteins in A-T cells. Together, these results indicate that genotoxins induce aberrant degradation of autophagic flux in A-T cells. Without wishing to be bound by theory, autophagy provides an alternate compensatory route for degradation of the proteasome and autophagy substrates in the ubiquitin pathway compromised A-T cells.

As seen in the Examples herein, constitutively elevated ISG15 impairs targeted proteasome-mediated degradation in A-T cells, and that basal autophagy is activated in human A-T cells and brains of A-T patients. To test if the impairment of the proteasome and autophagy pathways is due to the increased expression of the ISG15 pathway, ISG15 expression was silenced in A-T cells and then the status of protein turnover pathways was monitored in ISG15-silenced A-T cells. ISG15-specific siRNA restored the proteasome function, also attenuated basally and genotoxin-activated autophagy in A-T cells. Thus, deregulation of the protein turnover pathways is a consequence of the elevated expression of ISG15 in A-T cells, and is a causal contribution of the ISG15-mediated defective protein turnover in A-T neurodegeneration.

Selective inhibitors of ISG15 expression include, but are not limited to, agents such as microRNA, shRNA, siRNA, antisense, or ribozyme molecules specifically targeted to a nucleic acid molecule encoding ISG15 (e.g., GENBANK Accession No. AY168648 (SEQ ID NO:1); human ISG15 mRNA sequence). Such agents can be designed based upon routine guidelines well-known in the art. For siRNA target sites in a gene of interest can be 19-27 nucleotides in length (e.g., the siRNA used herein targeted nucleotides numbered from 232-250 in Accession No. AY168648). (See Example 1 herein, and U.S. Patent Application Publication No. 2009/0131357).

Selective inhibitors of the ISG15 pathway include, but are not limited to, agents such as microRNA, shRNA, antisense, or ribozyme molecules specifically targeted to a nucleic acid molecule encoding UbcH8 (E2-ISG15; e.g., GENBANK Accession No. AF031141 (SEQ ID NO:2) (human UBcH8 mRNA sequence)), UbEIL (E1-ISG15; e.g., GENBANK Accession No. AF294032 (SEQ ID NO:3) (human UbEIL mRNA sequence)), and any one of the several E3 ligases that conjugates ISG15 to the cellular proteins in A-T cells.

ISG15 is elevated in various lymphoblast and fibroblast cells. ISG15 is also highly elevated in the murine $Atm^{-/-}$ and $Atm^{+/-}$ cerebellum, the specific brain region affected by A-T disease. On the other hand, very little expression of ISG15 was seen in the cortex of mice. In agreement with these results, ISG15 was shown to be elevated in brain tissues obtained from different patients diagnosed with A-T disease. In contrast, ISG15 was minimally expressed in normal cells, as well as mice and human brain tissues. Together, these results indicate that ISG15 is constitutively elevated in Ataxia Telangiectasia disease.

The inventor has discovered that "ISG15 proteinopathy" mechanism is an underlying cause of A-T neurodegeneration that is distinct from the current central dogma that defective DNA repair contributes to cerebellar neurodegeneration in A-T patients.

Methods

One embodiment of the invention is directed towards methods to diagnose proteinopathy-induced neurodegeneration, such as that associated with A-T or ALS, using ISG15 in a biological fluid (such as serum) or biological tissue; alphafetoprotein; autophagy markers such as LC3-I and II, lysosomes, and autophagic vacuoles; and mitophagy markers such as complex-I, decreased mitochondrial membrane potential, increased levels of mitochondrial superoxide, and mitochondrial mass in samples from patients as prognostic/diagnostic markers, and to treat proteinopathy-induced neurodegeneration by targeting the elevated ISG15 pathway in afflicted patients.

Embodiments as described herein can involve isolating, collecting, or obtaining a biological sample from a subject. As used herein, the term "collecting a sample" or "isolating a sample", for example, can refer to any process for directly or indirectly acquiring a biological sample from a subject. For example, a biological sample may be obtained (e.g., at a point-of-care facility, e.g., a physician's office, a hospital, laboratory facility) by procuring a tissue sample (such as a skin biopsy) from a subject. Alternatively, a biological sample may be obtained by receiving the biological sample (e.g., at a laboratory facility) from one or more persons who procured the sample directly from the subject. The biological sample may be, for example, a tissue (e.g., biopsy), fluid (e.g., cerebrospinal fluid, plasma, blood, serum) or cell (e.g., skin fibroblast cells, peripheral blood cells) of a subject.

The term "sample" can refer to a biological sample obtained or derived from a source of interest, as described herein. In some embodiments, a source of interest comprises an organism, such as an animal or human. In some embodiments, a biological sample comprises biological tissue or fluid. In some embodiments, a biological sample is or comprises bone marrow; blood; blood cells; blood mononuclear cells; serum; plasma; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, a sample is a "primary sample" obtained directly from a source of interest by any appropriate means. For example, in some embodiments, a primary biological sample is obtained by methods selected from the group consisting of biopsy {e.g., fine needle aspiration or tissue biopsy), surgery, collection of body fluid {e.g., blood, lymph, feces etc.), etc. In some embodiments, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Embodiments are directed towards an in vitro methods to diagnose a patient with or at risk of developing proteinopathy-induced neurodegeneration. The term "in vitro" refers to events that occur in an artificial environment, e.g., in a test tube or reaction vessel, on a strip or dipstick, rather than within an organism.

Aspects of the invention are directed towards diagnosing or identifying a subject as having proteinopathy-induced neurodegeneration. The term "diagnosing" can refer to classifying the type of neurodegeneration as proteinopathy-induced neurodegeneration or non-proteinopathy-induced neurodegeneration determining the severity of proteinopathy-induced neurodegeneration, monitoring the progression of proteinopathy-induced neurodegeneration, forecasting the outcome of proteinopathy-induced neurodegeneration and/or prospects of recovery. The subject can be a healthy subject (e.g., human) undergoing a routine well-being checkup. Alternatively, the subject can be at risk of having proteinopathy-induced neurodegeneration (e.g., a genetically predisposed subject, a subject with medical and/or family history of proteinopathy-induced neurodegeneration, a subject who has been exposed to chemicals, occupational hazard, environmental hazard] and/or a subject who exhibits suspicious clinical signs of neurodegeneration (e.g., stiffness, rigidity, tremors, progressive loss of memory, severe motor restriction, death).

The term "subject" or "patient" can refer to any organism to which aspects of the invention can be performed, e.g., for experimental, diagnostic, prophylactic, and/or therapeutic purposes. Typical subjects to which methods as described herein are performed comprise mammals, such as primates, for example humans. For veterinary applications, a wide variety of subjects are suitable, e.g., livestock such as cattle, sheep, goats, cows, swine, and the like; poultry such as chickens, ducks, geese, turkeys, and the like; and domesticated animals and pets such as dogs and cats. For diagnostic or research applications, a wide variety of mammals are suitable subjects, including rodents (e.g., mice, rats, hamsters), rabbits, primates, and swine such as inbred pigs and the like. The term "living subject" refers to a subject noted herein or another organism that is alive. The term "living subject" refers to the entire subject or organism and not just a part excised (e.g., a liver or other organ) from the living subject.

In embodiments, the subject can be suffering from a proteinopathy-induced neurodegeneration. An individual who is "suffering from" a disease, disorder, and/or condition (e.g., stroke) has been diagnosed with and/or exhibits one or more symptoms of the disease, disorder, and/or condition.

In other embodiments, the subject can be susceptible to a proteinopathy-induced neurodegeneration. An individual who is "susceptible to" a disease, disorder, and/or condition (e.g., any disease, disorder, and/or condition, including, but not limited to, any disease, disorder, and/or condition described herein) is at risk for developing the disease, disorder, and/or condition. In some embodiments, an individual who is susceptible to a disease, disorder, and/or condition does not display any symptoms of the disease, disorder, and/or condition. In some embodiments, an individual who is susceptible to a disease, disorder, and/or condition has not been diagnosed with the disease, disorder, and/or condition. In some embodiments, an individual who is susceptible to a disease, disorder, and/or condition is an individual who has been exposed to conditions associated with development of the disease, disorder, and/or condition (e.g., the individual has been exposed to an agent and/or an environmental hazard thought to cause the disease, disorder, and/or condition; etc.). In some embodiments, a risk of developing a disease, disorder, and/or condition is a population-based risk (e.g., an individual carries a gene and/or allele associated with the disease, disorder, and/or condition).

Embodiments are further directed towards a method of assessing the effectiveness of a course of treatment for a subject suffering from proteinopathy-induced neurodegeneration. For example, the method can comprise measuring a first level of or detecting the presence of conjugated ISG15 in a sample from the subject at a first time point during the course of treatment with a therapeutic agent, measuring a second level of or detecting the presence of conjugated ISG15 in a sample from the subject in a second time point during the course of treatment with a therapeutic agent, and comparing the measurements from steps (a) and (b). If the level from step (a) is greater than the level from step (b), then the treatment with the therapeutic agent is effective; and if the level from step (b) is equal to or greater than the level from step (a), then the treatment with the therapeutic agent is not effective. As desired, the subject can be administered the therapeutically effective amount of a therapeutic agent to the subject if the treatment is effective.

As used herein the term "ISGylation" can refer to the covalent attachment of ISG15 to a protein or a peptide. ISG15 is ubiquitin-like modifier (UbI). Other Ubls include Nedd8, SUMO, Atg8, and others yet to be defined by their sequence homology to ubiquitin or by homology with regard to their mode of conjugation to targets.

As used herein, the phrase "therapeutic agent" can refer to any agent that elicits a desired pharmacological effect when administered to a subject. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is any substance that can be used to alleviate, ameliorate, relieve, inhibit, delay onset of, reduce severity of, and/or reduce incidence of one or more symptoms or features of a disease, disorder, and/or condition.

The term "therapeutically effective amount", as used herein, can refer to an amount of a therapeutic agent whose administration, when viewed in a relevant population, correlates with or is reasonably expected to correlate with achievement of a particular therapeutic effect. The therapeutic effect may be objective (i.e., measurable by some test or marker) or subjective (i.e., subject gives an indication of or feels an effect). In some embodiments, a therapeutically effective amount of a substance is an amount that is sufficient, when administered to a subject suffering from or susceptible to a disease, disorder, and/or condition, to treat, diagnose, prevent, and/or delay and/or alleviate one or more symptoms of the disease, disorder, and/or condition. Disease progression can be monitored by clinical observations, laboratory and neuroimaging investigations apparent to a person skilled in the art. A therapeutically effective amount is administered in a dosing regimen that may comprise multiple unit doses. For any particular therapeutic agent, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts. Furthermore, an effective amount may be administered via a single dose or via multiple doses within a treatment regimen. In some embodiments, individual doses or compositions are considered to contain a "therapeutically effective amount" when they contain an amount effective as a dose in the context of a treatment regimen. Those of ordinary skill in the art will appreciate that a dose or amount may be considered to be effective if it is or has been demonstrated to show statistically significant effectiveness when administered to a population of patients; a particular result need not be achieved in a particular individual patient in order for an amount to be considered to be therapeutically effective as described herein.

In an embodiment, the level or presence of conjugated ISG15 protein in a sample can be compared to that of a control sample, wherein a change in the level or presence in the sample as compared to the control is associated with the subject having or at risk of developing a proteinopathy-induced neurodegeneration. As used herein, "changed as compared to a control" sample or subject can refer to having a level of the analyte or diagnostic or therapeutic indicator (e.g., marker, such as conjugated ISG15) to be detected at a level that is statistically different than a sample from a normal or abnormal state control sample. Determination of statistical significance is within the ability of those skilled in the art, e.g., the number of standard deviations from the mean that constitute a positive or negative result.

In an embodiment, a sample, such as a sample of blood, serum, or cerebrospinal fluid, is isolated or obtained from a subject and the presence or level of a biomarker of proteinopathy-induced neurodegeneration, such as conjugated ISG15, is determined. The presence or level of the biomarker can then be compared to a threshold value which is diagnostic and/or prognostic indicator of proteinopathy-induced neurodegeneration. The "threshold" value can refer to a value derived from a plurality of biological samples, such as donor blood samples or donor cerebrospinal fluid samples.

Detection of ISG15 and autophagy (macroautophagy and mitophagy) markers in subjects and/or human cerebellar tissue sections, skin primary fibroblast cells, renal cells, cerebrospinal fluid (CSF), peripheral blood cells, blood serum, and urine can also be conducted using procedures that are well known in the field, such as immunodetection methods, and similar to those described herein.

The presence of ISG15 in the serum can be used as a diagnostic/prognostic marker for proteinopathy-induced neurodegeneration and proteinopathy-induced neurodegenerative diseases. Consistent with this belief, the most consistent laboratory marker alpha-fetoprotein (AFP) is elevated in A-T patients after the age of two years. Another embodiment of the invention would be to routinely test for ISG15 along with AFP as a serum markers for A-T diagnosis using ELISA and/or immunoblotting analysis.

Another embodiment of the invention is based on the finding that autophagy is elevated in A-T patients. The detection of the autophagy and mitophagy markers (LC3I and II proteins, lysosomes, autophagic vacuoles, various mitochondrial markers) using immunostaining and/or electron microscopy in peripheral blood and skin fibroblast cells obtained from the A-T patients can be used as prognostic/diagnostic markers for A-T. In addition, these markers can be used to evaluate the therapeutic response of various drugs during or after treatment.

Another embodiment of the invention is based on the finding that the ubiquitin pathway is attenuated in A-T cells. Levels of the substrates of the ubiquitin pathway can be tested in peripheral blood cells obtained from the A-T patients and used as prognostic and/or diagnostic markers for A-T. In addition, these markers can be used to evaluate the therapeutic response of various drugs during and/or after treatment.

I will also develop a high-throughput assay to identify potential inhibitors of ISG15 expression in vitro using a cell culture model. For this purpose stable clones of A-T cells expressing ISG15p-fused to luciferase will be generated. Using these cells small molecule inhibitors will be screened that can inhibit the expression of ISG15-luciferase using immunofluorescence and/or Western blotting analysis. Commercially available chemical and natural compound libraries will be used for this experiment.

Alternatively, ISG15 in the medium can be monitored using ELISA or similar monitoring techniques. For high throughput screening of small molecule inhibitors, A-T cells (for example, fibroblast, astrocytes, etc.) will be plated into 96 well plates at 4000 cells/well. The following day, compounds will be added as described herein. The plates will then be incubated at 37° C. in a $CO_2$ incubator for various times (2-4 days). ELISA will be performed on the culture media to detect ISG15 using anti-ISG15. Hits will be identified as those compounds that inhibited the ISG15 readout (luciferase and ELISA) by greater than three standard deviations of the mean of the compounds on each plate as compared to the untreated control. These compounds will be selected and their activity will be confirmed using the same assay.

The invention also provides methods for screening for inhibitors of the ISG15 pathway (ISG15 and its conjugating enzymes UbElL, UbcH8, and one of the several identified and unidentified E3 ligases) that could decrease neurodegeneration in A-T patients using western blotting analysis.

In another embodiment ex vivo brain slices from A-T mice models will be used to test the effect of potential inhibitors that would inhibit ISG15 expression or neurodegeneration by monitoring the decrease in ISG15 concentration or the change in autophagic structures (vacuoles, lysosomes) in the presence/absence of genotoxic stress using electron microscope or immunoblotting assays.

In addition, these inhibitors will also be tested for ability to attenuate the expression of the "ISG15 pathway enzymes" (UbElL, UbcH8 and E3 ligases (identified and as yet unidentified) since ISG15 conjugation contributes to the defective protein turnover in A-T cells.

In another embodiment, the presence of elevated ISG15 in serum can be used to diagnose A-T patients prone to developing neurodegeneration.

In another embodiment, neurodegeneration in A-T patients can be ameliorated or inhibited using compounds that decrease the expression of ISG15, or that restore protein turnover (restores ubiquitin and autophagy pathways) in the absence/presence of genotoxic stress (e.g., UV).

A-T patients are also at an increased risk of developing cancer, such as cancer of immune system cells (lymphoma) and blood cells (leukemia); however, many patients are also predisposed to solid tumors. Since the ISG15 pathway is also elevated in cancer, and ISG15 shRNA reverses cancer phenotypes, without wishing to be bound by theory, inhibitors of the ISG15 pathway could also be used to reduce cancer-risks in A-T patients.

As used herein, an "effective amount" of a compound is an amount, that when administered to a patient (whether as a single dose or as a time course of treatment) inhibits or reduces the expression of ISG15 or that decreases autophagy to a clinically significant degree; or alternatively, to a statistically significant degree as compared to a control. "Statistical significance" means significance at the $P<0.05$ level, or such other measure of statistical significance as would be used by those of skill in the art of biomedical statistics in the context of a particular type of treatment.

By "treating" is meant the medical management of a subject, e.g. an animal or human, with the intent that a prevention, cure, stabilization, or amelioration of the symptoms or condition will result. This term includes active treatment, that is, treatment directed specifically toward improvement of the disorder; palliative treatment, that is, treatment designed for the relief of symptoms rather than the curing of the disorder; preventive treatment, that is, treatment directed to prevention of disorder; and supportive treatment, that is, treatment employed to supplement another specific therapy directed toward the improvement of the disorder. The term "treatment" also includes symptomatic treatment, that is, treatment directed toward constitutional symptoms of the disorder. "Treating" a condition with the compounds of the invention involves administering such a compound, alone or in combination and by any appropriate means, to an A-T patient or an animal with similar symptoms. The effectiveness of a treatment can be monitored in any method known to monitor neurodegeneration, including without limitation, use of MRI or PET imaging techniques.

Assays and Antibodies

Aspects of the invention comprise biomarkers of proteinopathy-induced neurodegeneration and/or proteinopathy-induced neurodegenerative diseases. For example, aspects comprise biomarkers for Ataxia-Telangiectasia, Alzheimer's disease, Parkinson's disease, Huntington's disease and Amyotrophic lateral sclerosis. Non-limiting examples of biomarkers comprise conjugated ISG15, unconjugated ISG15, alphafetoprotein; autophagy markers such as LC3-I and II, lysosomes, and autophagic vacuoles; and mitophagy markers such as complex-I, decreased mitochondrial membrane potential, increased levels of mitochondrial superoxide, mitochondrial mass, or any combination thereof.

Embodiments of the invention comprise measuring or detecting such biomarkers using assays known to the art. Non-limiting examples of assays include an immunoassay, a colorimetric assay, fluorimetric assay or a combination thereof. Non-limiting examples of immunoassays comprise a western blot assay, an enzyme-linked immunosorbent assay (ELISA), immunoprecipitation or a combination thereof. For example, a biological sample collected from a subject can be incubated together with a biomarker specific antibody, such as an anti-ISG15 antibody or fragment thereof, and the binding of the antibody to the biomarker in the sample is detected or measured.

In embodiments, the antibody or fragment thereof can be specific for a biomarker as described herein, such as conjugated ISG15. The antibody can be a polyclonal antibody or a monoclonal antibody. The antibody or fragment thereof can be attached to a molecule that is capable of identification, visualization, or localization using known methods. Suitable detectable labels include radioisotopic labels, enzyme labels, non-radioactive isotopic labels, fluorescent labels, toxin labels, affinity labels, and chemiluminescent labels.

Examples of assays that can be used in methods of the invention, although not intended to be limiting, comprise a Bradford assay, a bicinchoninic acid (BCA) assay, a Lowry assay, a pyrogallol red protein dye-binding assay, a Coomassie blue dye-binding assay, an endpoint assay, a kinetic assay, such as a kinetic assay using a fluorometric substrate such as 4-methyllumbelliferyl phosphate, chemiluminescent substrates such as CSPD and CDP-Star, DynaLight Substrate with RapidGlow enhancer, or colorimetric 4-nitrophenyl phosphate, an assay to detect phosphatase reactions, an assay to detect ATP hydrolysis, or a combination thereof. In embodiments, the assays can be provided in a multi-well format, such as a 6-, 12-, 24-, 48-, or 96-well plate. In embodiments, the assays can be provided in a standard cuvette, such as a 1 ml cuvette.

The enzyme employed in embodiments herein, for example to detect protein levels or enzymatic activity, can be, for example, alkaline phosphatase, horseradish peroxidase, β-galactosidase and/or glucose oxidase; and the substrate can respectively be an alkaline phosphatase, horseradish peroxidase, β-galactosidase or glucose oxidase substrate (see Molecular Probes Handbook—A Guide to Fluorescent Probes and Labeling Technologies, 11th Edition (2010), Invitrogen, which is incorporated by reference herein in its entirety).

In embodiments, the enzyme, such as alkaline phosphatase or horseradish peroxidase, can be attached to a secondary antibody. Without being bound by theory, measurement of alkaline phosphatase can be confounded by signal from secondary antibodies. Isolated alkaline phosphatase can catalytically hydrolyze MUP to form the fluorescent product MU. Secondary antibodies, conjugated to AP, from two different commercial manufacturers, for example, can also hydrolyze MUP to form fluorescent product. When both alkaline phosphatase protein and the secondary antibody are in the same measurement, there is an increased level of catalytic activity observed. This activity can be monitored by both standard spectrophotometric readings of biochemical activity and by Western blot.

Alkaline phosphatase (AP) substrates include, but are not limited to, AP-Blue substrate (blue precipitate, Zymed catalog p. 61); AP-Orange substrate (orange, precipitate, Zymed), AP-Red substrate (red, red precipitate, Zymed), 5-bromo, 4-chloro, 3-indolyphosphate (BCIP substrate, turquoise precipitate), 5-bromo, 4-chloro, 3-indolyl phosphate/nitroblue tetrazolium/iodonitrotetrazolium (BCIP/INT substrate, yellow-brown precipitate, Biomeda), 5-bromo, 4-chloro, 3-indolyphosphate/nitroblue tetrazolium (BCIP/NBT substrate, blue/purple), 5-bromo, 4-chloro, 3-indolyl phosphate/nitroblue tetrazolium/iodonitrotetrazolium (BCIP/NBT/INT, brown precipitate, DAKO, Fast Red (Red), Magenta-phos (magenta), Naphthol AS-BI-phosphate (NABP)/Fast Red TR (Red), Naphthol AS-BI-phosphate (NABP)/New Fuchsin (Red), Naphthol AS-MX-phosphate (NAMP)/New Fuchsin (Red), New Fuchsin AP substrate (red), p-Nitrophenyl phosphate (PNPP, Yellow, water soluble), VECTOR™ Black (black), VECTOR™ Blue (blue), VECTOR™ Red (red), Vega Red (raspberry red color).

Horseradish Peroxidase (HRP, sometimes abbreviated PO) substrates include, but are not limited to, 2,2' Azinodi-3-ethylbenz-thiazoline sulfonate (ABTS, green, water soluble), aminoethyl carbazole, 3-amino, 9-ethylcarbazole AEC (3A9EC, red). Alpha-naphthol pyronin (red), 4-chloro-1-naphthol (4C1N, blue, blue-black), 3,3'-diaminobenzidine tetrahydrochloride (DAB, brown), ortho-dianisidine (green), o-phenylene diamine (OPD, brown, water soluble), TACS Blue (blue), TACS Red (red), 3,3',5,5' Tetramethylbenzidine (TMB, green or green/blue), TRUE BLUE™ (blue), VECTOR™ VIP (purple), VECTOR™ SG (smoky blue-gray), and Zymed Blue HRP substrate (vivid blue).

Glucose Oxidase (GO) substrates, include, but are not limited to, nitroblue tetrazolium (NBT, purple precipitate), tetranitroblue tetrazolium (TNBT, black precipitate), 2-(4-iodophenyl)-5-(4-nitorphenyl)-3-phenyltetrazolium chloride (INT, red or orange precipitate), Tetrazolium blue (blue), Nitrotetrazolium violet (violet), and 3-(4,5-dimethylthiazol-2-yl)-2,5-diphenyltetrazolium bromide (MTT, purple). All tetrazolium substrates require glucose as a co-substrate. The glucose gets oxidized and the tetrazolium salt gets reduced and forms an insoluble formazan which forms the color precipitate.

Beta-Galactosidase substrates, include, but are not limited to, 5-bromo-4-chloro-3-indoyl beta-D-galactopyranoside (X-gal, blue precipitate).

Other examples of alkaline and acid phosphatase substrates comprise 9H-(1,3-dichloro-9,9-dimethylacridin-2-one-7-yl) phosphate, diammonium salt (DDAO phosphate), 6,8-difluoro-4-methylumbelliferyl phosphate (DiFMUP), fluorescein diphosphate, tetraammonium salt (FDP), 4-methylumbelliferyl phosphate, free acid (MUP), and 4-methylumbelliferyl phosphate, dicyclohexylammonium salt, trihydrate (MUP DCA salt).

Alkaline phosphatase activity, such as intestinal alkaline phosphatase activity, can be detected and/or measured with use of chromogenic substrates and/or fluorogenic substrates of alkaline phosphatases. For example, 4-methylumbelliferyl phosphate (MUP) is a fluorogenic substrate for alkaline phosphatases, and alkaline phosphatase mediated hydrolysis of its phosphate substituent yields the blue-fluorescent 4-methylumbelliferyl (excitation/emission 386/448 nm). In embodiments, the alkaline phosphatase substrate can be directly admixed with the biological sample, such as stool, allowing for the direct dectection of the presence of alkaline phosphatase or the measurement of its activity.

Alkaline phosphatase (AP) substrates include, but are not limited to, AP-Blue substrate (blue precipitate, Zymed catalog p. 61); AP-Orange substrate (orange, precipitate, Zymed), AP-Red substrate (red, red precipitate, Zymed), 5-bromo, 4-chloro, 3-indolyphosphate (BCIP substrate, turquoise precipitate), 5-bromo, 4-chloro, 3-indolyl phosphate/nitroblue tetrazolium/iodonitrotetrazolium (BCIP/INT substrate, yellow-brown precipitate, Biomeda), 5-bromo, 4-chloro, 3-indolyphosphate/nitroblue tetrazolium (BCIP/NBT substrate, blue/purple), 5-bromo, 4-chloro, 3-indolyl phosphate/nitroblue tetrazolium/iodonitrotetrazolium (BCIP/NBT/INT, brown precipitate, DAKO, Fast Red (Red), Magenta-phos (magenta), Naphthol AS-BI-phosphate (NABP)/Fast Red TR (Red), Naphthol AS-BI-phosphate (NABP)/New Fuchsin (Red), Naphthol AS-MX-phosphate (NAMP)/New Fuchsin (Red), New Fuchsin AP substrate (red), p-Nitrophenyl phosphate (PNPP, Yellow, water soluble), VECTOR™ Black (black), VECTOR™ Blue (blue), VECTOR™ Red (red), Vega Red (raspberry red color).

Other substrates known in the art, including those described herein, can be used with embodiments of the invention (see Molecular Probes Handbook—A Guide to Fluorescent Probes and Labeling Technologies, 11th Edition (2010), Invitrogen, which is incorporated by reference herein in its entirety). Further, as desired, various fluorophores known in the art can be covalently attached to the substrate, such as MUP.

Enzyme reactions can provide a highly specific, rapid and sensitive assay for detection of specific proteins in a sample, such as iAP in stool. Examples of suitable fluorogenic substrates which can be utilized within the present invention comprise Fluorescein diacetate, 4-Methylumbelliferyl acetate, 4-Methylumbelliferyl casein, 4-Methylumbelliferyl-α-L-arabinopyranoside, 4-Methylumbelliferyl-β-D-fucopyranoside, 4-Methylumbelliferyl-α-L-fucopyranoside, 4-Methylumbelliferyl-β-L-fucopyranoside, 4-Methylumbelliferyl-α-D-galactopyranoside, 4-Methylumbelliferyl-β-D-galactopyranoside, 4-Methylumbelliferyl-α-D-glucopyranoside, 4-Methylumbelliferyl-β-D-glucopyranoside, 4-Methylumbelliferyl-β-D-glucuronide, 4-Methylumbelliferyl nonanoate, 4-Methylumbelliferyl oleate, 4-Methylumbelliferyl phosphate, bis(4-Methylumbelliferyl)phosphate, 4-Methylumbelliferyl pyrophosphate diester, 4-Methylumbelliferyl-β-D-xylopyranoside.

Non-limiting examples of suitable chromogenic substrates for use within the present invention comprise o-Nitrophenyl-β-D-galactopyranoside, p-Nitrophenyl-β-D-galactopyranoside, o-Nitrophenyl-β-D-glucopyranoside, p-Nitrophenyl-α-D-glucopyranoside, p-Nitrophenyl-β-D-glucopyranoside, p-Nitrophenyl-β-D-glucuronide, p-Nitrophenyl phosphate, o-Nitrophenyl-β-D-xylopyranoside, p-Nitrophenyl-α-D-xylopyranoside, p-Nitrophenyl-β-D-xylopyranoside, and Phenolphthalein-β-D-glucuronide.

Aspects of the invention can comprise an article, such as a tube, plate, dipstick, spoon, filter paper or swab, for detecting or measuring biomarkers of proteinopathy-induced neurodegeneration.

In aspects of the invention, the article as described herein can be a component of a kit useful for diagnosing a subject with a proteinopathy-induced neurodegenerative disease. Additional components of kits of the invention can comprise a bio-recognition element, a support structure, and instructions for use thereof. For example, an ISG15 bio-recognition element, such as an antibody as described herein, can be immobilized to a solid support structure.

Non-limiting examples of the composition of the solid support structure comprise plastic, cardboard, glass, plexiglass, tin, paper, or a combination thereof. The solid support can also comprise a dip stick, spoon, scoopula, filter paper or swab.

The article can comprise a biosensor, and can optionally comprise other components known to the art. In embodiments, the biosensor can be an immunosensor, and can further comprise a detection signal. Non-limiting examples of detection signals comprise a radioactive signal, colorimetric signal, a fluorescent signal, chemiluminescent signal, or a combination thereof. For example, the biosensor can produce a new color or change in spectral absorption. In embodiments, the biosensor of the present invention comprises a bio-recognition element, or molecular recognition element, that provides the highly specific binding or detection selectivity for a particular analyte, such as conjugated ISG15. The bio-recognition element, or system, can be a biologically derived material such as an enzyme or sequence of enzymes; an antibody or fragment thereof; a membrane receptor protein; DNA; an organelle, a natural or synthetic cell membrane; an intact or partial viable or nonviable bacterial, plant or animal cell; or a piece of plant or mammalian tissues, and can function to interact specifically with a target biological analyte. The bio-recognition element is responsible for the selective recognition of the analyte and the physico-chemical signal that provides the basis for the output signal. The physico-chemical signal generated by the bio-recognition element or elements can be communicated visually to the wearer or caretaker (i.e., via a color change visible to the human eye). Other embodiments can produce optical signals, which can require other instrumentation to enhance the signal. These include fluorescence, bioluminescence, total internal reflectance resonance, surface plasmon resonance, Raman methods and other laser-based methods.

Alternatively, the signal can be processed via an associated transducer which, for example, can produce an electrical signal (e.g., current, potential, inductance, or impedance) that can be displayed (e.g., on a readout such as an LED or LCD display) or which triggers an audible or tactile (e.g., vibration) signal or which can trigger an actuator, as described herein. The signal can be qualitative (e.g., indicating the presence of the target biological analyte, such as conjugated ISG15) or quantitative (i.e., a measurement of the amount or concentration of the target biological analyte, such as conjugated ISG15). In such embodiments, the transducer can optionally produce an optical, thermal or acoustic signal.

In any case, the signal can also be durable (i.e., stable and readable over a length of time typically at least of the same magnitude as the usage life of the article) or transient (i.e., registering a real-time measurement). Additionally, the signal can be transmitted to a remote indicator site (e.g., via a wire, or transmitter, such as an infrared or rf transmitter) including other locations within or on the article or remote devices. Further, the biosensor, or any of its components, can be adapted to detect and/or signal only concentrations of the target biological analyte above a predefined threshold level (e.g., in cases wherein the target biological analyte is normally present in the bodily waste or when the concentration of the analyte is below a known "danger" level).

Proteinopathy-Induced Neurodegeneration

Aspects of the invention are directed towards methods to diagnose a patient with or at risk of developing proteinopathy-induced neurodegeneration.

Aspects of the invention are also directed towards methods of assessing the effectiveness of a course of treatment for a subject suffering from proteinopathy-induced neurodegeneration.

The term "proteinopathy" or "proteinopathic" can refer to a disease, disorder, and/or condition associated with the pathogenic aggregation and/or accumulation of one or more types of proteins, for example, but not limited to α-synuclein, β-amyloid, and/or tau proteins. In some embodiments, a proteinopathy is characterized by an anomaly in one or more of protein production, folding, aggregation, metabolism, or degradation (e.g. autophagy), transportation or trafficking, secretion, etc. In some embodiments, proteinopathies are neurodegenerative diseases. Specific pathologies such as synucleinopathies, tauopathies, amyloidopathies, TDP-43 proteinopathies and others are examples of proteinopathies. Exemplary proteins implicated in proteinopathies include: α-synuclein in the case of Parkinson's disease, Lewy body disease, and other synucleinopathies; tau and β-amyloid in the case of Alzheimer's disease and certain other neurodegenerative diseases; SOD1 and TDP-43 in the case of amyotrophic lateral sclerosis; huntingtin in the case of Huntington's disease; rhodopsin in the case of retinitis pigmentosa; and proteins involved in lysosomal storage diseases.

The term "neurodegeneration" can refer to the progressive loss of individual or collective structure or function of neurons, up to and including the death of neurons that is associated with many neurodegenerative diseases. For example, "neurodegenerative disease(s)" or "neurodegenerative disorder" can refer to medical conditions that are characterized clinically by their insidious onset and chronic progression. In many instances, particular parts of the brain, spinal cord, or peripheral nerves functionally fail and the neurons of the dysfunctional region die. Neuroanatomically localizable functional impairment and "neurodegeneration" associate with recognizable syndromes or conditions that are ideally distinct, although in clinical and even neuropathologic practice substantial overlap exists. Neurodegenerative diseases are often categorized by whether they initially affect cognition, movement, strength, coordination, sensation, or autonomic control.

Frequently, however, patients will present with symptoms and signs referable to more than one system. Involvement of several systems can occur concomitantly or by the time the patient has functionally declined enough to seek medical attention multiple systems have become involved. In many cases, the diagnosis of a neurodegenerative disease cannot be critically 'confirmed' by a simple test.

Many neurodegenerative diseases are linked to intracellular and/or extracellular accumulation of specific protein aggregates, which can be referred to as proteinopathy-induced neurodegeneration or proteinopathy-induced neurodegenerative disease. In many cases, it is thought that the protein aggregates exert toxic effects on the brain, and contribute to disease pathology.

Proteinopathies caused by molecular lesions in the ubiquitin pathway leading to the neuronal cell death is common in many neurological disorders and also has been recently implicated in A-T neurodegeneration. Like in other neurological disorders, ISG15-mediated proteinopathy in A-T neurons could lead to their death in A-T patients.

Similar to A-T, ISG15 is also elevated in Amyotrophic Lateral Sclerosis (ALS) neurological disorder. Hence, it appears that "ISG15 proteinopathy" is a common cause of neurological disorders thus, making our current study more significant.

Cell culture data is now corroborated by in vivo data that autophagy is activated in various proteinopathy-induced neuronal disorders such as Parkinson's, Huntington's, and Alzheimer's. Autophagy is also activated in brains of human A-T patients and cells.

The perturbation of the ubiquitin-proteasome system, which causes accumulation of protein aggregates, is a common characteristic of several neurodegenerative diseases.

Aberrant activation of autophagy (proteinopathy) leads to neurodegeneration in various neurological disorders.

Concurrently, autophagy is activated and autophagic stress in neurons leads to neuronal cell death in various proteinopathy-induced neuronal disorders Altered expression/mutations in genes involved in protein turnover pathways have been linked to neurodegeneration in other neurological diseases. Accumulation of misfolded protein deposits in affected brain regions are reported in neurodegenerative diseases including Alzheimer's, Parkinson's, Creutzfeldt-Jakob, and Huntington's disease.

Mitochondrial dysfunction due to oxidative stress is associated with various neurological disorders such as Parkinson's, Alzheimer's, and also implicated in A-T neurodegeneration.

Non-limiting examples of diseases and/or conditions characterized by proteinopathy-induced neurodegeneration comprise Amyotrophic lateral sclerosis (ALS), Parkinson's disease, Huntington's disease, Alzheimer's disease, Creutzfeldt-Jakob disease, Ataxia Telangiectasia Friedreich's Ataxia, Multiple Sclerosis (MS), Prion diseases, Spinocerebellar Ataxia (SCA), Spinal Muscular Atrophy (SMA), Traumatic Brain Injury, among several others.

"Parkinson's disease" refers to any medical condition wherein an individual experiences one or more symptoms associated with Parkinson's disease, such as without limitation one or more of the following symptoms: rest tremor, cogwheel rigidity, bradykinesia, postural reflex impairment, good response to L-dopa treatment, the absence of prominent oculomotor palsy, cerebellar or pyramidal signs, amyotrophy, dyspraxia and/or dysphasia.

"Amyotrophic lateral sclerosis" or "ALS" refers to a progressive neurodegenerative disease that affects upper motor neurons (motor neurons in the brain) and/or lower motor neurons (motor neurons in the spinal cord) and results in motor neuron death. The term "ALS" includes all of the classifications of ALS known in the art, including, but not limited to classical ALS (affecting both lower and upper motor neurons), Primary Lateral Sclerosis (PLS, affecting only the upper motor neurons), Progressive Bulbar Palsy (PBP or Bulbar Onset, a version of ALS that begins with difficulties swallowing, chewing and speaking), Progressive Muscular Atrophy (PMA, affecting only the lower motor neurons) and familial ALS (a genetic version of ALS).

"Alzheimer's disease" refers to a degenerative brain disorder characterized clinically by progressive memory deficits, confusion, behavioral problems, inability to care for oneself, gradual physical deterioration and, ultimately, death. Histologically, the disease is characterized by neuritic plaques, found primarily in the association cortex, limbic system and basal ganglia. The major constituent of these plaques is amyloid beta peptide (Aβ), which is the cleavage product of beta amyloid precursor protein (βAPP or APP). APP is a type I transmembrane glycoprotein that contains a large ectopic N-terminal domain, a transmembrane domain and a small cytoplasmic C-terminal tail.

"Huntington's disease" refers to a fatal neurological disorder characterized clinically by symptoms such as involuntary movements, cognition impairment or loss of cognitive function and a wide spectrum of behavioral disorders. Common motor symptoms associated with Huntington's disease include chorea (involuntary writhing and spasming), clumsiness, and progressive loss of the abilities to walk, speak (e.g., exhibiting slurred speech) and swallow. Other symptoms of Huntington's disease can include cognitive symptoms such as loss of intellectual speed, attention and short-term memory and/or behavioral symptoms that can span the range of changes in personality, depression, irritability, emotional outbursts and apathy. Clinical symptoms can appear in the fourth or fifth decade of life. Huntington's disease is a devastating and often protracted illness, with death occurring approximately 10-20 years after the onset of symptoms.

Huntington's disease is inherited through a mutated or abnormal gene encoding an abnormal protein called the mutant huntingtin protein; the mutated huntingtin protein produces neuronal degeneration in many different regions of the brain. The degeneration focuses on neurons located in the basal ganglia, structures deep within the brain that control many important functions including coordinating movement, and on neurons on the outer surface of the brain or cortex, which controls thought, perception and memory.

"Creutzfeldt-Jakob disease" (CJD) refers to a rare, degenerative, invariably fatal brain disorder. In the early stages of disease, people may have failing memory, behavioral changes, lack of coordination and visual disturbances. As the illness progresses, mental deterioration becomes pronounced and involuntary movements, blindness, weakness of extremities, and coma may occur.

The leading scientific theory at this time maintains that CJD is caused by a type of protein called a prion. Prion proteins occur in both a normal form, which is a harmless protein found in the body's cells, and in an infectious form, which causes disease. The harmless and infectious forms of the prion protein have the same sequence of amino acids (the "building blocks" of proteins) but the infectious form of the protein takes a different folded shape than the normal protein. Sporadic CJD may develop because some of a person's normal prions spontaneously change into the infectious form of the protein and then alter the prions in other cells in a chain reaction. Once they appear, abnormal prion proteins aggregate, or clump together. Investigators think these protein aggregates may lead to the neuron loss and other brain damage seen in CJD. However, they do not know exactly how this damage occurs.

"Ataxia-telangiectasia" (A-T) refers to a rare inherited disorder that affects the nervous system, immune system, and other body systems. This disorder is characterized by progressive difficulty with coordinating movements (ataxia) beginning in early childhood, such as before age 5. Affected children can develop difficulty walking, problems with balance and hand coordination, involuntary jerking movements (chorea), muscle twitches (myoclonus), and disturbances in nerve function (neuropathy). The movement problems can cause people to require wheelchair assistance by adolescence. People with this disorder also have slurred speech and trouble moving their eyes to look side-to-side (oculomotor apraxia). Small clusters of enlarged blood vessels called telangiectases, which occur in the eyes and on the surface of the skin, are also characteristic of this condition.

Individuals affected with A-T tend to have high amounts of a protein called alpha-fetoprotein (AFP) in their blood. The level of this protein is normally increased in the bloodstream of pregnant women, but it is unknown why individuals with ataxia-telangiectasia have elevated AFP or what effects it has in these individuals.

"Friedreich's ataxia" (FA) refers to a debilitating, life-shortening, degenerative neuro-muscular disorder that affects about one in 50,000 people in the United States. Most individuals have onset of symptoms of FA between the ages of 5 and 18 years. Adult or late onset FA is less common, <25% of diagnosed individuals, and can occur anytime during adulthood.

FA is an inherited or single gene disorder caused by mutations or DNA changes in the FXN gene. FA in inherited in an autosomal recessive manner, meaning that individuals with FA have two mutated or abnormal copies of the FXN gene. It is estimated that 1 in 100 people are carriers, and carriers do not exhibit symptoms of FA.

The FA gene mutation limits the production of a protein called frataxin. Frataxin is known to be an important protein that functions in the mitochondria (the energy producing factories) of the cell. Frataxin helps to move iron and is involved with the formation of iron-sulfur clusters, which are necessary components in the function of the mitochondria and thus energy production. We also know that specific nerve cells (neurons) degenerate in people with FA, and this is directly manifested in the symptoms of the disease.

"Multiple sclerosis" refers to an inflammatory and demyelinating degenerative disease of the human central nervous system (CNS). It is a worldwide disease that affects approximately 300,000 persons in the United States; it is a disease of young adults, with 70%-80% having onset between 20 and 40 years old (Anderson et al. *Ann Neurology* 31(3): 333-6 (1992); Noonan et al. *Neurology* 58:136-8 (2002)). MS is a heterogeneous disorder based on clinical course, magnetic resonance imaging (MM) scan assessment, and pathology analysis of biopsy and autopsy material (Lucchinetti et al. *Ann Neurol* 47:707-17 (2000)). The disease manifests itself in a large number of possible combinations of deficits, including spinal cord, brainstem, cranial nerve, cerebellar, cerebral, and cognitive syndromes. Progressive disability is the fate of most patients with MS, especially when a 25-year perspective is included. Half of MS patients require a cane to walk within 15 years of disease onset. MS is a major cause of neurologic disability in young and middle-aged adults and, until the past decade, has had no known beneficial treatments. MS is difficult to diagnose because of the non-specific clinical findings, which led to the development of highly structured diagnostic criteria that include several technological advances, consisting of MRI scans, evoked potentials, and cerebrospinal fluid (CSF) studies. All diagnostic criteria rely upon the general principles of scattered lesions in the central white matter occurring at different times and not explained by other etiologies such as infection, vascular disorder, or autoimmune disorder (McDonald et al. *Ann Neurol* 50:121-7 (2001)). MS has four patterns of disease: relapsing-remitting MS (RRMS; 80%-85% of cases at onset), primary progressive MS (PPMS; 10%-15% at onset), progressive relapsing MS (PRMS; 5% at onset); and secondary progressive MS (SPMS) (Kremenchutzky et al. *Brain* 122 (Pt 10):1941-50 (1999); Confavreux et al. *N Engl J Med* 343(20):1430-8 (2000)).

"Prion disease" refers to one of several rapidly progressive, fatal, and untreatable brain degenerative disorders. These can be considered to be transmissible spongiform encephalopathies (TSE), a group that includes, but without limitation: Creutzfeldt-Jakob disease (CJD), new variant CJD, Kuru, Gerstmann-Straussler-Scheinken syndrome (GSS), fatal familial insomnia (FFI) in humans, scrapie in sheep and goats, spongiform encephalopathy in cattle "mad cow disease", as well as recently described prion diseases in cats, and other ruminants. Prion infection has also been observed in chicken, mink, pigs, mice, hamsters, guinea pigs, eland, elk, gemsbok, greater kudu, muledeer, nyala, oryx, and various avian species.

"Spinocerebellar ataxia" (SCA) refers to one of a group of genetic disorders characterized by slowly progressive incoordination of gait and often associated with poor coordination of hands, speech, and eye movements.

"Spinal muscular atrophy" (SMA) refers to a genetic disease affecting the part of the nervous system that controls voluntary muscle movement. Most of the nerve cells that control muscles are located in the spinal cord. SMA is muscular because its primary effect is on muscles, which don't receive signals from these nerve cells. SMA involves the loss of nerve cells called motor neurons in the spinal cord and is classified as a motor neuron disease. The loss of motor neurons leads to weakness and wasting (i.e., atrophy) of muscles used for activities such as crawling, walking, sitting up, and controlling head movement. In severe cases of spinal muscular atrophy, the muscles used for breathing and swallowing are affected. There are many types of spinal muscular atrophy distinguished by the pattern of features, severity of muscle weakness, and age when the muscle problems begin.

As used herein, "traumatic brain injury" (TBI) refers to a form of acquired brain injury that occurs when a sudden trauma causes brain damage. TBI can occur when the head suddenly and violently hits an object, or when an object pierces the skull and enters brain tissue. TBI symptoms can be mild, moderate, or severe, depending on the extent of the damage to the brain.

Although the terms "mild," "moderate," or "severe" can be applied arbitrarily, generally, "mild" traumatic brain injury refers to a traumatic brain injury that results in loss of consciousness for a few seconds to a few minutes; no loss of consciousness, but a dazed, confused or disoriented state; headache; nausea or vomiting; fatigue or drowsiness; difficulty sleeping; sleeping more than usual; and/or dizziness or loss of balance. The mild traumatic brain injury can also create blurred vision; ringing in the ears; a bad taste in the mouth or changes in the ability to smell; and/or sensitivity to light or sound. Cognitive or mental symptoms of mild traumatic brain injury include memory or concentration problems; mood changes or mood swings; and/or feeling depressed or anxious. "Moderate" or "severe" traumatic brain injury refers to a traumatic brain injury that results in loss of consciousness from several minutes to hours; persistent headache or headache that worsens; repeated vomiting or nausea; convulsions or seizures; dilation of one or both pupils of the eyes; clear fluids draining from the nose or ears; inability to awaken from sleep; weakness or numbness in fingers and toes; and/or loss of coordination. Cognitive and mental symptoms include profound confusion; agitation; combativeness or other unusual behavior; slurred speech; coma and/or other disorders of consciousness.

Kits

Embodiments can further comprise a diagnostic and/or prognostic kit of molecular biomarkers, for example for identifying a subject as suffering from or at risk of a proteinopathy-induced neurodegeneration. In one embodiment, the kit comprises (a) a container that contains a tools for obtaining and/or storing a tissue sample from a subject, and optionally (b) informational material. The informational material can be descriptive, instructional, marketing or other material describing the methods described herein and/or the use of the agents for therapeutic benefit or reagents for diagnostic benefit.

The informational material of the kits is not limited in its form. In one embodiment, the informational material can include information about ISG15, proteinopathies and/or proteinopathy-induced neurodegeneration, a list of protein targets and/or biomarkers, molecular weight of the protein targets, information about therapeutic agents (such as concentration, date of expiration, batch or production site information), and so forth. In one embodiment, the informational material described methods of detecting the level of a biomarker, such as conjugated ISG15. The information can be provided in a variety of formats, include printed text, computer readable material, video recording, or audio recording, or an information that provides a link or address to substantive material.

If desired, the composition in the kit can include a therapeutic agent and, optionally, other ingredients, such as a solvent or buffer, a stabilizer, or a preservative. The therapeutic can be provided in any form, e.g., liquid, dried or lyophilized form, substantially pure and/or sterile. When the agents are provided in a liquid solution, the liquid solution can be an aqueous solution. When the agents are provided as a dried form, reconstitution can be by the addition of a suitable solvent. The solvent, e.g., sterile water or buffer, can optionally be provided in the kit.

The kit can include one or more containers for the composition or compositions containing the agents and/or diagnostic reagents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents or amounts of reagents. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight. The kit optionally includes a device suitable for administration of the composition, e.g., a syringe or other suitable delivery device. The device can be provided pre-loaded with one or both of the agents or can be empty, but suitable for loading.

EXAMPLES

Examples are provided herein to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Role for ATM in Regulating Proteasome-Mediated Protein Degradation Through Suppression of ISG15 Conjugation Pathway
Materials and Methods
 Human Tissues and Animal Studies.
 Frozen human mid-brain tissues containing specifically substantia nigra were obtained postmortem from patients with confirmed A-T disease and control individuals (without any known disease). Slides with paraffin-embedded sections of the midbrain tissues were used in immunofluorescence study. Human brain tissues and tissue sections were obtained from the NICHD Brain and Tissue Bank for Developmental Disorders at the University of Maryland under protocols approved by the University of Maryland Institutional Review Board.
 Animal study was carried out in strict accordance with the recommendations in the Guide for the Care and Use of Laboratory Animals of the National Institutes of Health. The protocol was approved by the Louisiana State University Health Sciences Center—NO Institutional Animal Care and Use Committee under its assurance with the Office of Laboratory Animal Welfare of the National Institutes of Health.
 Cells.
 Normal lymphoblast L40 and A-T lymphoblast L3 (ATM−) cells, as well as FT169A (ATM+) and FT169A (ATM−) fibroblast cells, were obtained from Dr. Y Shiloh at Tel Aviv University, Ramat Aviv, Israel. FT169A (ATM−) cells were derived from FT169A cells (ataxia telangiectasia cells) by stable transfection with the expression vector alone as described (71). FT169A (ATM+) cells were derived from FT169A cells by stable transfection with full-length ATM cDNA (71). The lymphoblast and fibroblast cells (normal and A-T) were obtained from the American Type Culture Collection (ATCC), Manassas, Va. FT169A (ATM+) FT169A (ATM−) cells were cultured in DMEM (Dulbecco's Modified Eagle Medium; Cellgro, Manassas, Va.) supplemented with hygromycin B (50 μg/ml) (Cellgro). L40 and L3 cells were cultured in RPMI (Roswell Park Memorial Institute; Cellgro). All other normal and A-T fibroblast cells were cultured in DMEM and lymphoblast cells were cultured in RPMI medium according to ATCC instructions.
 Immunoblotting and Immunofluorescence Analysis.
 Analysis of ISG15 in cultured cells: Cells ($5 \times 10^5$) were cultured in 35 mm tissue culture plates. Cells were then lysed using a SDS-PAGE sample buffer. Cell lysates were analyzed by SDS-PAGE in 15% (unless indicated otherwise) gel and immunoblotted according to the published procedure (48). Cell lysates were analyzed by immunoblotting with anti-ISG15 (raised against human ISG15) as described (23), anti-ubiquitin (Sigma-Aldrich-Aldrich, St. Louis, Mo.), anti-HA (gift from Dr. Walworth at RWJMS/UMDNJ), anti-p53 (Santa Cruz Biotechnology, Santa Cruz, Calif.), anti-STAT3 (Cell Signaling Technology, Danvers, Mass.), and anti-GFP (Abcam, Cambridge, Mass.) antibodies as indicated using the ECL Western procedure (Pierce, Rockford, Ill.) and the Kodak Image Station 2000R.
 Analysis of ISG15 Expression in Brain Tissues of Atm Knockout Mice:
 Atm knockout mice are described (72). Brain tissues were obtained from 3 week-old wild type (WT) or Atm knockout littermates and stored in liquid nitrogen prior to processing. For detecting ISG15 and its conjugates, frozen tissues were weighed, cut into small pieces, and placed in test tubes containing SDS gel sample buffer. Tissue samples were then sonicated with a Tissue-Tearor (Biospec Products, Inc.; Bartlesville, Okla.). Sonicated samples were immediately boiled for 10 minutes at 100° C. and then centrifuged at 13,000×g for 10 minutes. Cleared supernatants containing SDS-solubilized protein extracts were analyzed by SDS-PAGE in 15% gel and immunoblotted using anti-ISG15 raised against mouse ISG15 (a gift from Dr. Knobeloch, Institute of Molecular Pharmacology, Berlin, Germany).
 Analysis of ISG15 Expression in Primary Cortical Astrocytes:
 Primary cortical astrocytes prepared from the brains of postnatal day-4 wild type and Atm knockout littermates were maintained as monolayers in DMEM/F12 (1:1 mix) supplemented with a 15% fetal calf serum, 2 mM L-glutamine, 100 U/ml penicillin, 100 μg/ml streptomycin, and 10 ng/ml of mouse epidermal growth factor (Sigma-Aldrich) and were used at passage 2. Cells were lysed using an SDS gel sample buffer. SDS-PAGE analysis and immunoblotting using mouse anti-ISG15 were carried out as described herein.
 Analysis of ISG15 Expression in Brain Tissues of A-T Patients by Western Blotting:
 Frozen tissues were stored at −80° C. until use. Tissue processing and ISG15 analysis in tissue lysates were carried out as described herein.
 Analysis of ISG15 Expression in Brain Tissue Sections by Immunofluorescence Staining:
 For double immunofluorescence, tissue sections were deparaffinized in xylene and incubated with the ISG15 (polyclonal) (1:100) and polyubiquitin (K63-linkage-specific) (monoclonal HWA4C4 (Enzo Life Sciences; Farmingdale, N.Y.)) primary antibodies (1:100) and for 1 hour. After washing in PBS, sections were stained with Alexa Fluor 488 goat anti-rabbit IgG secondary antibody (Invitrogen; Grand Island, N.Y.) and goat polyclonal secondary antibody to mouse IgG (Cy5®) (Abcam). Sections were mounted in gold antifade mounting medium (Invitrogen) and examined using Nikon E600 epifluorescence microscope (Nikon) (20× magnification). All the operations were performed at room temperature.
 siRNA Knockdown of ISG15.
 A 21-nucleotide duplex siRNA targeting ISG15, and control siRNA were purchased from Dharmacon Research, Inc. (Lafayette, Colo.). The siRNA targeting ISG15 corresponds to region 232-250 (Accession #AY168648). The siRNA transfection protocol was followed with slight modifications as described (73). FT169A (ATM−) cells were cultured to semi-confluency and transfected with ISG15 siRNA using Oligofectamine (Invitrogen). Seventy-two hours after siRNA transfection, cells were further transfected with HA-ubiquitin expression plasmid using PolyFect (Qiagen) for another 24 hours.

siRNA Knockdown of UbcH8.

A 21-nucleotide duplex siRNA targeting UbcH8 siRNA was purchased from Dharmacon Research, Inc. The siRNA targeting UbcH8 corresponds to the region 237-255 (Accession #AF031141). The UbcH8 siRNA transfection, followed by HA-ubiquitin transfection, into FT169A cells was carried out as described herein.

Example 2

Protein Polyubiquitylation and Degradation is Reduced in Cells Deficient in ATM

Figure 1A:
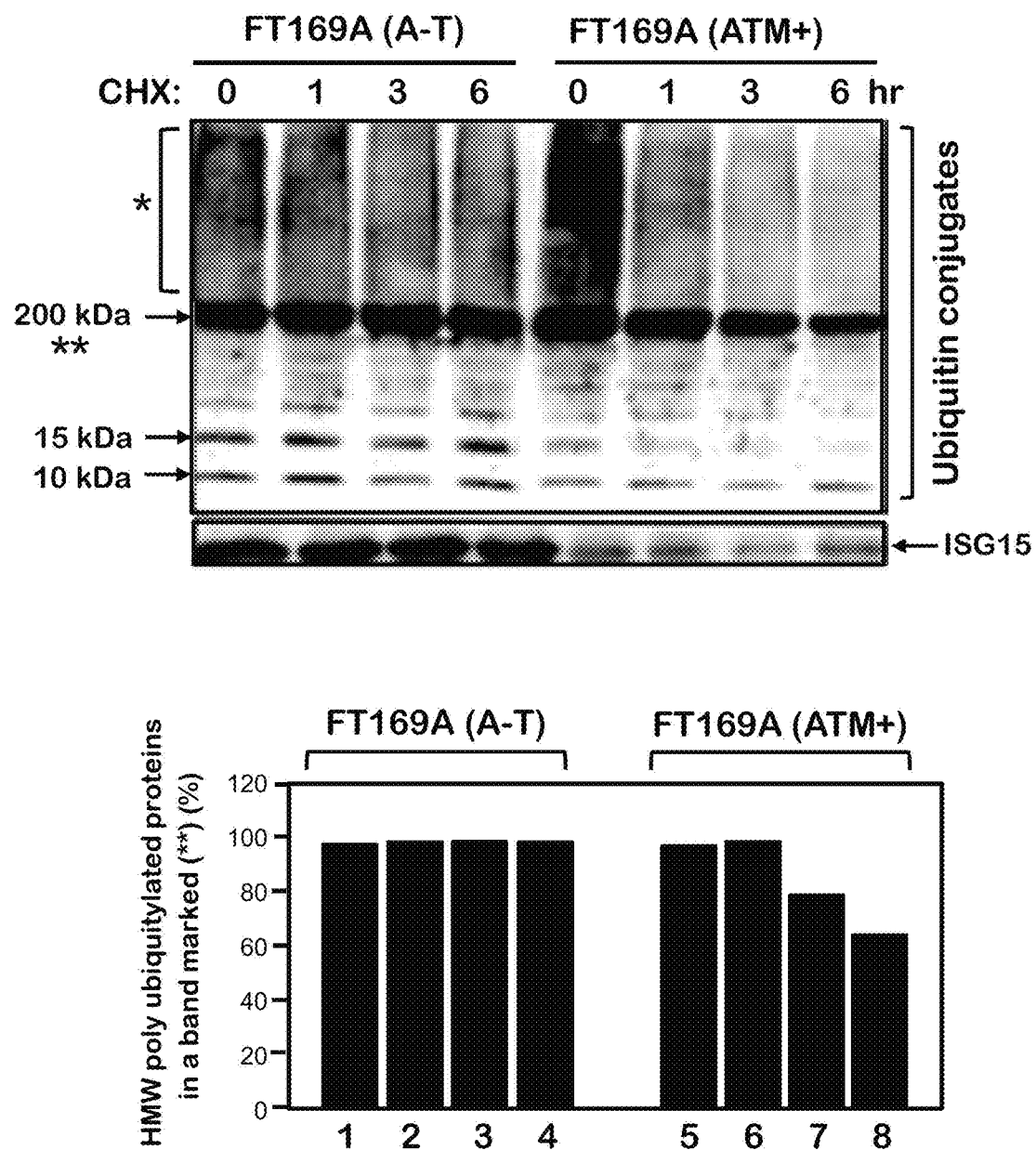
FIG. 1A illustrates cell lysates from A-T cells and ATM+ cells treated with the protein synthesis inhibitor CHX for 0, 1, 3, and 6 hours, and analyzed using discontinuous (15%) SDS-PAGE followed by immunoblotting with anti-ubiquitin antibody. The symbols * and  mark the position of high-molecular-weight (HMW) polyubiquitylated proteins. Quantitation of the high-molecular-weight (HMW) polyubiquitylated proteins (shown as ) is shown in the bar graph.

To test whether the defective ubiquitin-mediated degradation of cellular proteins contributes to neurodegeneration in A-T, the rate of degradation of overall cellular polyubiquitylated proteins was monitored in FT169A (A-T) (ATM null) and FT169A (ATM+) (ATM reconstituted FT169A) isogenic cells as described (71) using the protein synthesis inhibitor cycloheximide (CHX) (Sigma-Aldrich). In FIG. 1A, FT169A (A-T) (lanes 1-4) and FT169A (ATM+) (lanes 5-8) cells were treated with the protein synthesis inhibitor CHX (10 µg/ml) for 0, 1, 3, and 6 hours. Cell lysates were analyzed using discontinuous (15%) SDS-PAGE followed by immunoblotting with anti-ubiquitin antibody. The symbols * and  mark the position of high-molecular-weight (HMW) polyubiquitylated proteins. Quantitation of the high-molecular-weight (HMW) polyubiquitylated proteins (shown as ) is shown in the bar graph.

As shown in FIG. 1A, the level of polyubiquitylated proteins (see protein species marked by * (smear of high molecular weight (HMW) ubiquitin-conjugated (polyubiquitylated) proteins and ** (high molecular weight polyubiquitylated proteins migrating as a compressed band) remained relatively unchanged in FT169A (A-T) cells up to six hours in the presence of CHX (compare lanes 1 and 4 and lower panel for quantification), indicating minimal turnover of polyubiquitylated proteins in A-T cells. By contrast, the level of polyubiquitylated proteins (marked by * and **) was reduced by more than 30% within 6 hours in FT169A (ATM+) cells under the same conditions (FIG. 1A, compare lanes 5 and 8 and lower panel for the quantification). An increased steady state level of the high molecular weight (HMW) ubiquitin-conjugated (polyubiquitylated) proteins (marked by *) was also seen in FT169A (ATM+) as compared to FT169A (A-T) cells (FIG. 1A, compare lanes 1 and 5) in Western analysis using anti-ubiquitin antibodies. The same membrane shown in FIG. 1A was stripped and re-probed with anti-ISG15 antibodies. The band intensities of the ISG15 protein remained the same in FT169A (A-T) (lanes 1-4) and (ATM+) (lanes 5-8) cells (note that ISG15 protein levels are low in ATM+ as compared to A-T cells (see discussion herein)) treated with CHX. These results revealed that targeted degradation of the polyubiquitylated proteins is specifically altered in A-T cells.

The ubiquitin antibody used in the experiments described herein is known to cross-react with free, but not conjugated, ISG15/UCRP (44). In order to rule out the possibility that the polyubiquitylated proteins (see species marked by *) identified in FIG. 1A are not due to a cross-reaction with the ISG15 protein and/or other UBL-protein conjugates, HA-tagged ubiquitin cDNA was transfected into FT169A (A-T) and FT169A (ATM+) cells. The amount of polyubiquitylated proteins, and the rate of turnover of these polyubiquitylated proteins (see the HMW protein species marked by ) were then determined under the same conditions as in FIG. 1A, except that anti-HA, rather than an anti-ubiquitin antibody was used in immunoblotting. As shown in FIG. 1B, FT169A (A-T) (lanes 1 and 2) and FT169A (ATM+) (lanes 3 and 4) cells were transfected with HA-ubiquitin as described herein in Example 1. Forty-eight hours post-transfection, cells were treated with the protein synthesis inhibitor CHX (marked on top of each lane) for 6 hours. Cell lysates were analyzed using 15% SDS-PAGE followed by immunoblotting with anti-HA antibody. The symbol  marks the position of polyubiquitylated proteins (compressed due to the gel electrophoresis conditions). Quantitation of the high-molecular-weight (HMW) polyubiquitylated proteins (shown as **) is shown in the bar graph.

As shown in FIG. 1B, the amount of HMW HA-ubiquitin-conjugated (polyubiquitylated) proteins (marked by **) was elevated in FT169A (ATM+) as compared to FT169A (A-T) cells (FIG. 1B, compare lanes 1 and 4), consistent with results obtained by measuring the endogenous polyubiquitylated proteins in FT169A (A-T) and FT169A (ATM+) cells shown in FIG. 1A. The difference in the migration of polyubiquitylated proteins seen in FIG. 1A (migrating as a smear * and a compressed band ) and FIG. 1B (migrating as a compressed band ) is due to the different gel systems used in these experiments (5 and 15% discontinuous gel vs. 15% gel respectively). The turnover of HA-ubiquitin-conjugated proteins (species marked by **), measured in the presence of CHX (10 µg/ml) for 6 hours, was negligible in FT169A (A-T) cells (FIG. 1B, compare lanes 1 and 2 and lower panels for quantification). By contrast, a significant amount of HA-ubiquitin-conjugated proteins were degraded in FT169A (ATM+) cells within 6 hours under the same conditions (FIG. 1B, compare lanes 3 and 4 and lower panels for quantification).

Figure 1C:
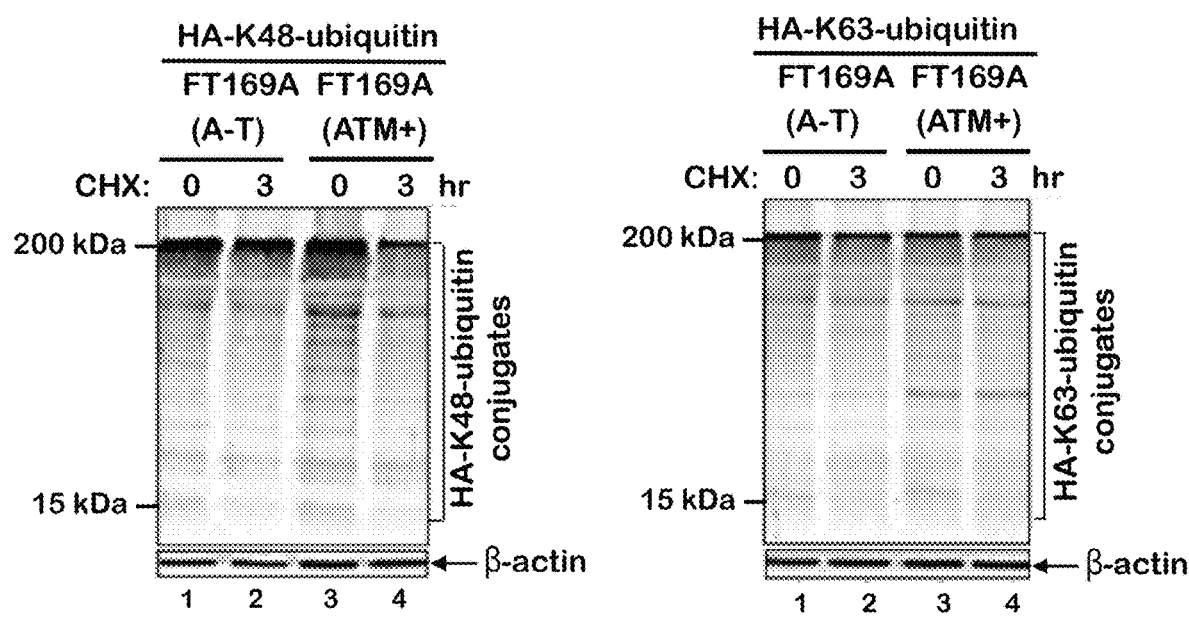
FIG. 1C illustrates A-T and ATM+ cells transfected with HA-Lys48-only (left panel) and Lys63-only (right panel) ubiquitin constructs, then treated with the protein synthesis inhibitor CHX (marked on the top of each lane) for 3 hours, and analyzed by immunoblotting with anti-HA antibodies. The HA-K48-ubiquitin conjugates (left panel) and HA-K63-ubiquitin conjugates (right pane) are shown. All the experiments were repeated at least three times and the representative experiments are shown.
Figure 1D:
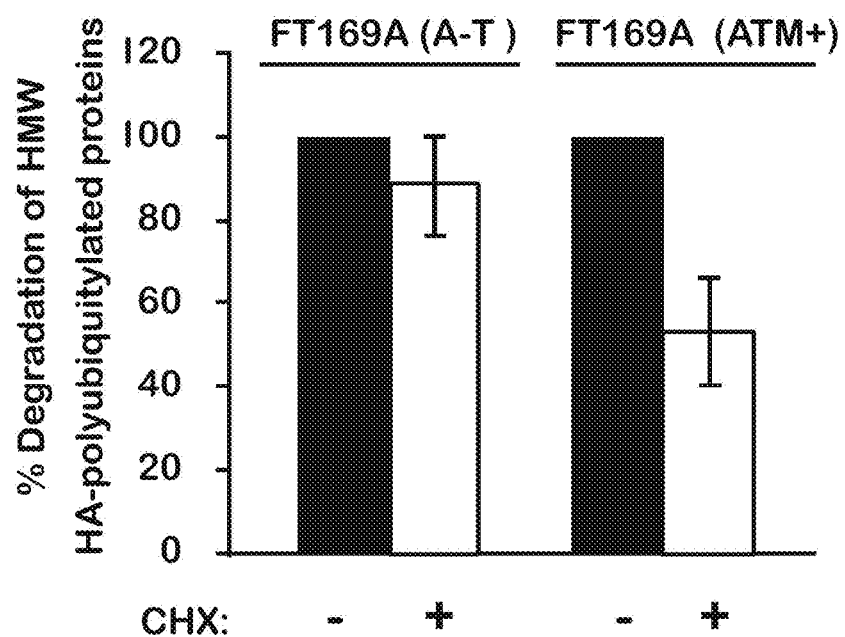
FIG. 1D illustrates A-T and ATM+ cells transfected with HA-ubiquitin, and treated with the protein synthesis inhibitor CHX for 6 hours and then analyzed by immunoblotting with anti-HA antibodies, and the value is the average rate of degradation of high molecular weight (HMW) HA-polyubiquitylated proteins (error bar represents S.E.M.) in A-T and ATM+ cells measured using the Kodak image station 2000R from three independent experiments.

For FIG. 1D, FT169A (A-T) and FT169A cells were transfected with HA-ubiquitin as described herein. Forty-eight hours post-transfection, cells were treated with the protein synthesis inhibitor CHX for 6 hours and then analyzed by immunoblotting with anti-HA antibodies. The high molecular weight HA-polyubiquitylated proteins (in 200 kDa compressed band (see band marked as ** in FIG. 1B)) were detected with HA antibodies. Average rate of degradation of high molecular weight (HMW) HA-polyubiquitylated proteins (error bar represents S.E.M.) in FT169A (A-T) and FT169A (ATM+) cells measured using the Kodak image station 2000R from three independent experiments is shown in the bar graph in FIG. 1D.

The same membrane shown in FIG. 1B was stripped and re-probed with anti-ISG15 antibodies. The band intensities of the ISG15 protein remained unaltered in FT169A (A-T) (lanes 1-2) and (ATM+) (lanes 3-4) cells treated with CHX. These results revealed that targeted degradation of the HA-polyubiquitylated proteins is specifically altered in A-T cells. These results obtained with anti-HA-ubiquitin antibody are consistent with results obtained from the use of an anti-ubiquitin antibody (see Western blots (upper panels) and bar graphs showing quantitation of a 200 kDa band (**) (lower panels) comprised of polyubiquitylated proteins in FIGS. 1A, 1B and 1D), indicating that ATM regulates both the amount and the rate of degradation of polyubiquitylated proteins.

The ubiquitin sequence contains seven lysine residues (at positions 6, 11, 27, 29, 33, 48, and 63) and polyubiquitin chain assembly can occur at any of these lysine residues (74). Lys48-linked polyubiquitylated proteins are targeted for destruction via the 26S proteasome (74). On the other hand, a protein modification with Lys63-linked ubiquitin chains has been implicated in the non-proteolytic regulation of signaling pathways (74). To test if the proteasome-mediated degradation of cellular proteins is impaired in A-T cells, the steady state levels of HA-tagged Lys48- and Lys63-linked polyubiquitylated proteins was examined in FT169A (A-T) and FT169A (ATM+) cells in the presence of CHX. For this purpose, the HA-Lys48-only and HA-Lys63-only constructs were transfected into FT169A (A-T) and FT169A (ATM+) cells. The amount of polyubiquitylated proteins and the rate of turnover of polyubiquitylated proteins (see the BMW protein species marked by *) were determined under the same conditions as in FIG. 1B using the anti-HA antibody in immunoblotting. In FIG. 1C, FT169A (A-T) and FT169A (ATM+) cells were transfected with HA-Lys48-only (left panel) and Lys63-only (right panel) ubiquitin constructs. Thirty hours post-transfection, cells were treated with the protein synthesis inhibitor CHX (marked on the top of each lane) for 3 hours and then analyzed by immunoblotting with anti-HA antibodies as described herein. All the experiments were repeated at least three times and representative experiments are shown.

As shown in FIG. 1C, the level of HA-Lys48-linked polyubiquitylated proteins remained relatively unchanged in A-T cells up to three hours in the presence of CHX (FIG. 1C, left panel, compare lanes 1 and 2), indicating minimal turnover of Lys48-linked polyubiquitylated proteins in A-T cells. On the other hand, the cellular pool of Lys48-linked polyubiquitylated proteins was reduced by more than 70% within 3 hours in FT169A (ATM+) cells under the same conditions (FIG. 1C, left panel, compare lanes 3 and 4). By contrast, the levels of non-proteolytic HA-Lys63-linked polyubiquitylated proteins remained unchanged in both FT169A (A-T) and FT169A (ATM+) cells treated with CHX for 3 hours (FIG. 1C, right panel, compare lanes 1-4). These results indicate that targeted proteasome-mediated degradation of polyubiquitylated proteins is impaired in A-T cells.

To further determine whether proteasome-mediated degradation of cellular proteins are regulated by ATM, the steady state levels of two fluorescent reporter proteasome substrates (the N-end rule substrate, ubiquitin-arginine-YFP (Ub-R-YFP), and the ubiquitin fusion degradation substrate, UbG76V-YFP (gift from Dr. Nico Dantuma, Karolinska Institutet, Stockholm, Sweden and described previously (75), were measured in FT169A (A-T) and FT169A (ATM+) cells in the presence of CHX. Cells expressing these reporter substrates are known to respond to functional impairment of the ubiquitin/proteasome pathway by accumulation of the readily detectable fluorescent reporter substrate (75). Since these fluorescent substrates are short lived and are degraded rapidly by the proteasome in vivo, cells expressing reporter YFP-substrates were pretreated with the reversible proteasome inhibitor MG132 to enhance their accumulation. After 24 hours, cells were washed to remove MG132-mediated block in proteasome inhibition. The fate of these accumulated YFP-substrates was then monitored in the presence of CHX and in the absence of MG132, and Western blotting using anti-GFP antibodies (YFP differs from GFP due to a mutation at T203Y. Antibodies raised against full-length GFP can therefore detect YFP protein). The results are shown in FIGS. 2A and 2B. FT169A (A-T) and FT169A (ATM+) cells were transfected with fluorescent reporter proteasome substrates (the ubiquitin fusion degradation substrate, UbG76V-YFP (FIG. 2A), and the N-end rule substrate, ubiquitin-arginine-YFP (Ub-R-YFP) (FIG. 2B) for 12 hours. Proteasome inhibitor MG132 (0.5 µM) was then added to the transfection medium and cells were allowed to grow for an additional 12 hours. After washing (to remove MG132), cells were treated with protein synthesis inhibitor CHX (10 µg/ml) for 3 hours. The fluorescent reporter levels were detected with GFP antibodies.

As shown in FIGS. 2A and 2B (lanes 2 and 3), little turnover of both UbG76V-YFP and Ub-R-YFP was observed in FT169A (A-T) cells in the presence of CHX for up to three hours. By contrast, both of these YFP-substrates were rapidly degraded within 3 hours of CHX treatment in FT169A (ATM+) cells (FIGS. 2A and 2B, lanes 5 and 6). Turnover of non-specific bands remained unaltered under the same conditions in both of the cases and served as an internal control.

Figure 2F:
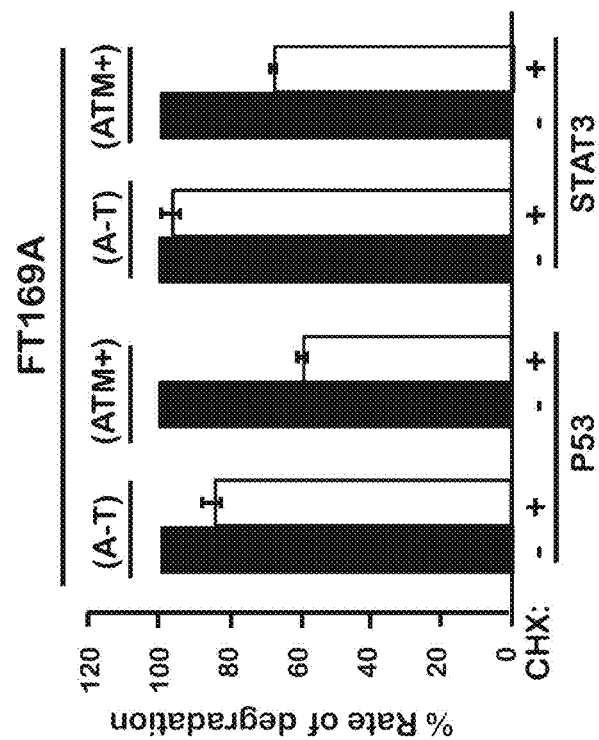
FIG. 2F illustrates A-T and ATM+ cells treated with the protein synthesis inhibitor CHX for 6 h, and the cell lysates were analyzed by immunoblotting using an anti-p53 and/or STAT3 antibody. The average rate of degradation of p53 and STAT3 proteins (error bar represents S.E.M.) in A-T and ATM+ cells were measured using the Kodak image station 2000R, and the results from three independent experiments is shown in the bar graph.
Figure 2E:
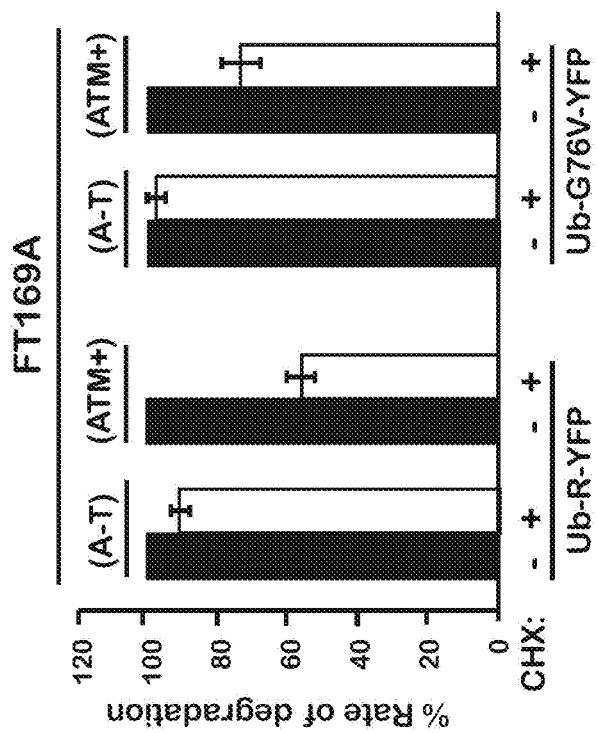
FIG. 2E illustrates A-T and ATM+ transfected with fluorescent reporter proteasome substrates (the ubiquitin fusion degradation substrate, UbG76V-YFP, and the N-end rule substrate, ubiquitin-arginine-YFP (Ub-R-YFP) for 12 h, then treated with the proteasome inhibitor MG132, and cells were allowed to grow for an additional 12 h. After washing (to remove MG132), cells were treated with protein synthesis inhibitor CHX for 3 h, and then the fluorescent reporter levels were detected with GFP antibodies. Average rate of degradation of Ub-G76V-YFP and Ub-R-YFP proteins (error bar represents S.E.M.) in FT169A (A-T) and FT169A (ATM+) cells were measured using the Kodak image station 2000R from three independent experiments, and the results shown in the bar graph.

In FIG. 2E, FT169A (A-T) and FT169A (ATM+) cells were transfected with fluorescent reporter proteasome substrates (the ubiquitin fusion degradation substrate, UbG76V-YFP, and the N-end rule substrate, ubiquitin-arginine-YFP (Ub-R-YFP) for 12 hours. Proteasome inhibitor MG132 (0.5 µM) was then added to the transfection medium and cells were allowed to grow for an additional 12 hours. After washing (to remove MG132), cells were treated with protein synthesis inhibitor CHX (10 µg/ml) for three hours. The fluorescent reporter levels were detected with GFP antibodies. The average rate of degradation of Ub-G76V-YFP and Ub-R-YFP proteins (error bar represents S.E.M.) in FT169A (A-T) and FT169A (ATM+) cells were measured using the Kodak image station 2000R. Results from three independent experiments are shown in FIG. 2E.

Both p53 and STAT3 are known targets of the ubiquitin/26S proteasome pathway. To determine whether steady state level of these proteins is regulated by ATM, turnover of both p53 and STAT3 were measured. In FIG. 2C, FT169A (A-T) and FT169A (ATM+) cells were treated with the protein synthesis inhibitor CHX (10 µg/ml) in the presence (lanes 3 and 6) or absence (lanes 2 and 5) of the proteasome inhibitor MG132 (10 µM) for 6 hours. Cell lysates were analyzed by immunoblotting using an anti-p53 antibody (upper row). The intensity of the p53 bands was measured using a Kodak Image station 2000R (BioRad). Results are shown in the bar graph (right panel). The filter used for immunoblotting was stained with Ponceau S to assure equal protein loading (lower row). As shown in FIG. 2 C (upper row, lanes 1 and 2), little turnover of p53 was observed in FT169A (A-T) cells in the presence of CHX for up to six hours. By contrast, p53 protein was rapidly degraded within 6 hours of CHX treatment in FT169A (ATM+) cells (FIG. 2C, lanes 4 and 5, and bar graph for p53 band quantization). The turnover of p53 in the presence of CHX was blocked by the proteasome inhibitor MG132 (10 µM), indicating that p53 turnover was mediated by the 26S proteasome (FIG. 2C, compare lanes 5 and 6) in ATM+ cells.

In FIG. 2D, FT169A (A-T) (lanes 1-3) and FT169A (ATM+) (lanes 4-6) cells were treated with the protein synthesis inhibitor CHX (10 µg/ml) in the presence (lanes 3 and 6) or absence (lanes 2 and 5) of the proteasome inhibitor MG132 (10 µM) for 6 hours. Cell lysates were analyzed by immunoblotting using an anti-STAT3 antibody as described herein. Intensity of the STAT3 band was measured using Kodak Image station 2000R (BioRad). Results are shown in the bar graph (right panel). The lower portion of the same membrane filter was immunostained with the anti-tubulin (lower row) antibody. All of the experiments were repeated at least three times and the representative experiments are shown.

In FIG. 2F, FT169A (A-T) and FT169A (ATM+) cells were treated with the protein synthesis inhibitor CHX (10 µg/ml) for 6 hours. Cell lysates were analyzed by immunoblotting using an anti-p53 and/or STAT3 antibody. An average rate of degradation of p53 and STAT3 proteins (error bar represents S.E.M.) in FT169A (A-T) and FT169A (ATM+) cells were measured using the Kodak image station 2000R. The results from three independent experiments are shown in FIG. 2F. These results indicate that targeted proteasome-mediated degradation of the proteasome substrates, in this case the artificial proteasome substrates, is impaired in A-T cells. FIG. 2F shows the average (+/−SEM) rate of degradation of p53 and STAT3 proteins in FT169A (A-T) and (ATM+) cells from three independent experiments. These results indicate that ubiquitin/26S proteasome pathway is impaired in A-T cells. This is the first time that the ubiquitin/26S proteasome pathway was shown to be impaired in A-T cells.

Example 3

ATM Negatively Regulates the ISG15 Pathway.

Figure 3A:
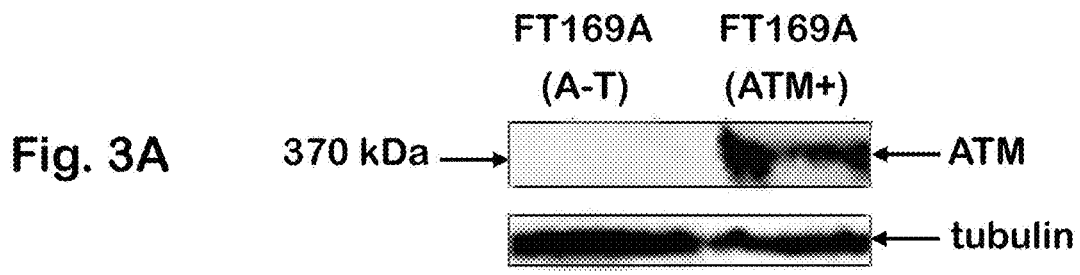
FIGS. 3A-3C illustrate extracts from A-T and ATM+ cells analyzed by 5% (FIG. 3A) or 15% (FIG. 3B) SDS-PAGE, followed by immunoblotting using either anti-ATM (FIG. 3A) or anti-ISG15 antibody (FIG. 3B). The same membranes shown in FIGS. 3A and 3B were stripped and re-probed with anti-tubulin antibody to assure equal protein loading. Average band intensity of the free ISG15 protein (error bar represents SEM) from three independent experiments was quantified using Kodak Image Station 2000R, and the results are shown in the bar graph in FIG. 3C.
Figure 3B:
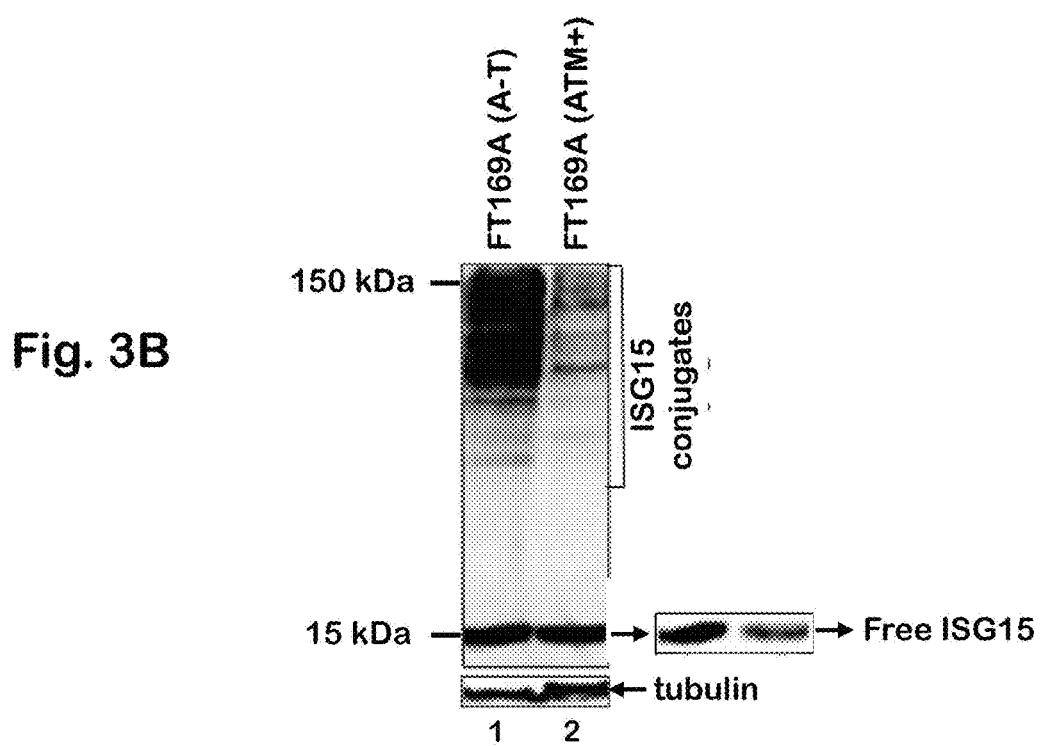
Figure 3C:
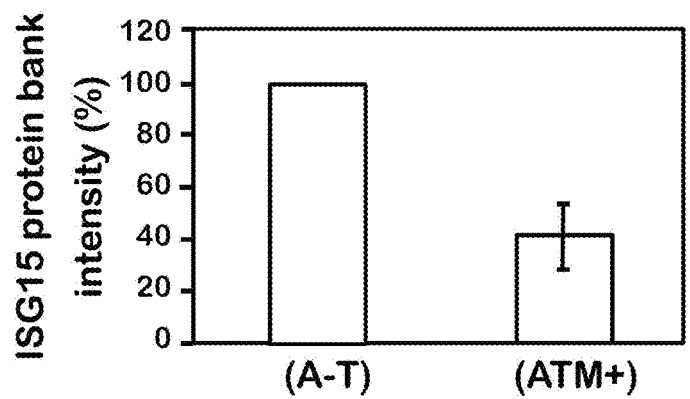

Previous studies have shown that ISG15 is increased in A-T lymphoblasts (70). Overexpression of ISG15 in tumor cells has been linked to reduced protein polyubiquitylation and turnover (24). To determine whether overexpression of the ISG15 pathway is responsible for reduced protein polyubiquitylation in FT169A (A-T) cells as shown herein, the levels of ISG15 and its conjugates were measured in ATM null FT169A (A-T) and ATM-reconstituted FT169A (ATM+) cells using anti-ISG15 antibodies by Western analysis. In FIGS. 3A-3C, extracts of FT169A (A-T) and FT169A (ATM+) cells were analyzed by 5% (FIG. 3A) or 15% (FIG. 3B) SDS-PAGE, followed by immunoblotting using either anti-ATM (FIG. 3A) or anti-ISG15 antibody (FIG. 3B). The same membrane shown in FIG. 3B was stripped and re-probed with anti-tubulin antibody to assure equal protein loading. The average band intensity of the free ISG15 protein (error bar represents SEM) from three independent experiments was quantified using Kodak Image Station 2000R, and the results are shown in FIG. 3C.

As shown in FIG. 3A, no detectable ATM protein is present in FT169A (A-T) fibroblast cells. By contrast, ATM protein is readily detected in their corresponding wild type cells (i.e. FT169A (ATM+) cells). The levels of both free ISG15 and ISG15 conjugates were significantly higher in FT169A (A-T) cells than in their corresponding wild type FT169A (ATM+) cells (FIG. 3B). The bar graph in FIG. 3C shows the average (+/−SEM) band intensities of free ISG15 proteins in FT169A (A-T) and (ATM+) cells from three independent experiments.

These results using A-T fibroblast cells indicate that ISG15 is overexpressed in A-T lymphoblast cells. These results, together with results shown in FIGS. 1A-1D and 2A-2F, indicate that overexpression of the ISG15 pathway results in reduced protein polyubiquitylation and turnover of cellular proteins in A-T cells.

Example 4 siRNA-Mediated Knockdown of ISG15 and UbcH8 Increases Protein Polyubiquitylation and Degradation in A-T Cells.

To further determine whether overexpression of ISG15 and its conjugates in A-T cells are responsible for reduced protein polyubiquitylation and turnover, ISG15 and UbcH8 (the cognate E2 for ISG15 conjugation) siRNAs were employed to knockdown the expression of ISG15 and ISG15 conjugates, respectively, in FT169A (A-T) cells. Seventy-two hours after siRNA transfections, cells were further transfected with HA-ubiquitin cDNA for 24 hours.

Figure 4A:
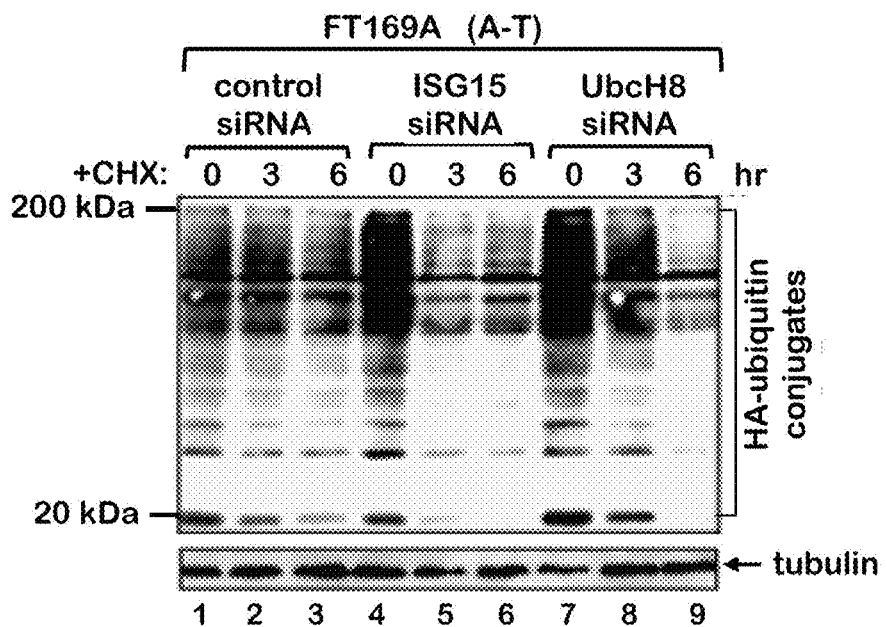
FIGS. 4A-C illustrate A-T cells treated with either control (lanes 1-3), ISG15 (lanes 4-6) or UbcH8 (lanes 7-9) siRNAs for 72 h, followed by transfection with an HA-ubiquitin expression vector for 24 h. Cells were then treated with protein synthesis inhibitor CHX for various times (lanes 2, 3, 5, 6, 8 and 9), and then lysed with 2×SDS gel sample buffer. Cell lysates were analyzed by immunoblotting using anti-HA antibody (FIG. 4A). The same membrane shown in FIG. 4A was stripped and re-probed with anti-tubulin antibody to assure equal protein loading (FIG. 4A, bottom panel). For FIG. 4B, the same samples shown in lanes 1, 4, and 7 were reloaded on a separate gel (15%), followed by immunoblotting using an anti-ISG15 antibody. For FIG. 4C, the same samples shown in lanes 1 and 7 along with purified UbcH8 enzyme were reloaded on a separate gel (15%), followed by immunoblotting using the anti-UbcH8 antibody.

In FIG. 4A, FT169A (A-T) cells were treated with either control (lanes 1-3), ISG15 (lanes 4-6) or UbcH8 (lanes 7-9) siRNAs for 72 hours followed by transfection with an HA-ubiquitin expression vector for 24 hours. Cells were treated with protein synthesis inhibitor CHX (10 µg/ml) for various times (lanes 2, 3, 5, 6, 8 and 9). Cells were then lysed with 2×SDS gel sample buffer. Cell lysates were then analyzed by immunoblotting using anti-HA antibody (FIG. 4A). The same membrane shown in FIG. 4A was stripped and re-probed with anti-tubulin antibody to assure equal protein loading (FIG. 4A, lower panel). The average rate of degradation of HA-polyubiquitylated proteins (error bar represents S.E.M.) in ISG15 or UbcH8 siRNA treated FT169A (A-T) cells measured using the Kodak image station 2000R from three independent experiments is shown in the bar graph presented in FIG. 4G.

Figure 4B:
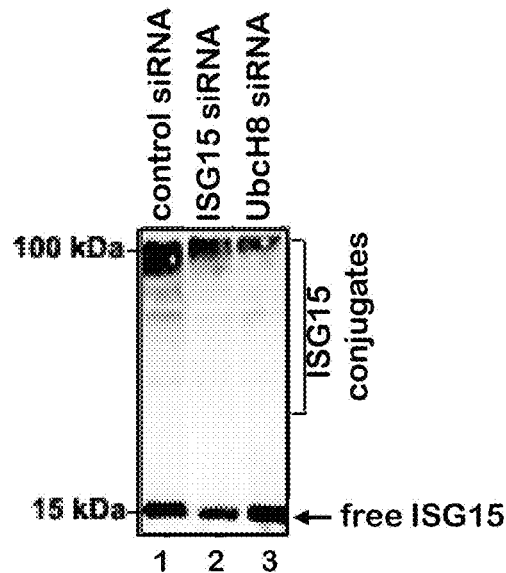
Figure 4C:
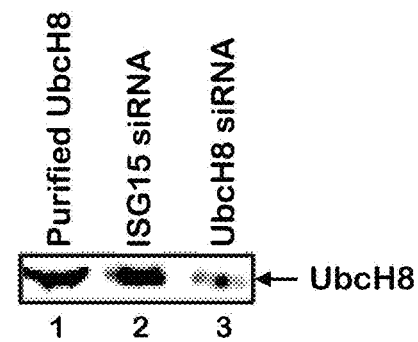

The same samples shown in lanes 1, 4, and 7 of FIG. 4A were reloaded on a separate gel (15%), followed by immunoblotting using an anti-ISG15 antibody, and the results presented in FIG. 4B. The same samples shown in lanes 1 and 7, FIG. 4A, along with purified UbcH8 enzyme were reloaded on a separate gel (15%), followed by immunoblotting using the anti-UbcH8 antibody, and the results shown in FIG. 4C.

Figure 4D:
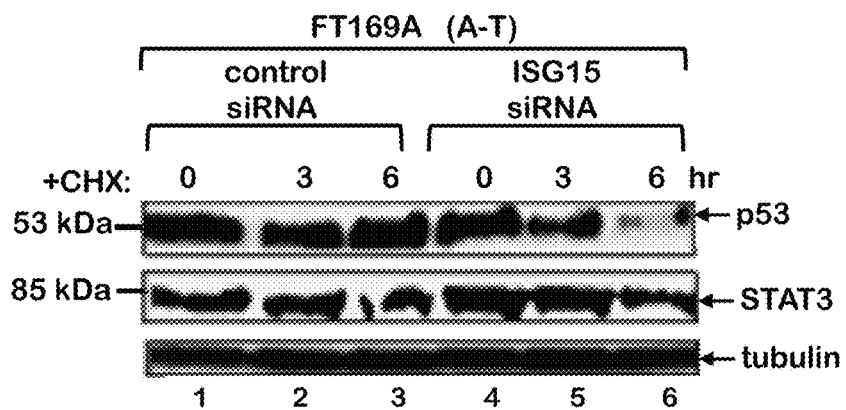
FIGS. 4D-4F illustrate A-T cells transfected with ISG15 siRNA for 72 h, and then treated with the protein synthesis inhibitor CHX for 3 and 6 h. Cell lysates were then analyzed by immunoblotting using anti-p53 (top panel), anti-STAT3 (middle panel) or anti-tubulin (lower panel) antibodies as shown in FIG. 4D. The p53 and STAT3 bands shown in the first and second panels were quantified using the Kodak Image Station 2000R, and the results shown in FIGS. 4E (p53) and 4F (STAT3). All the experiments were repeated at least three times.
Figure 4E:
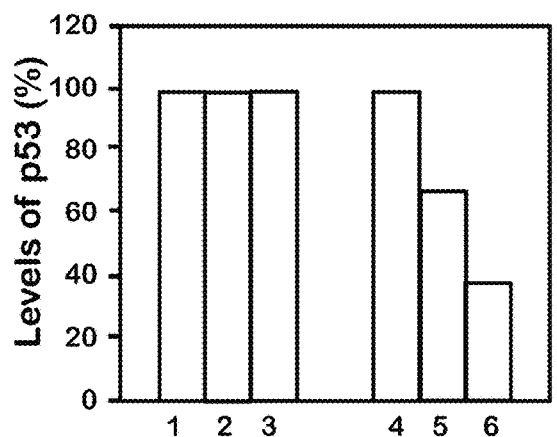
Figure 4F:
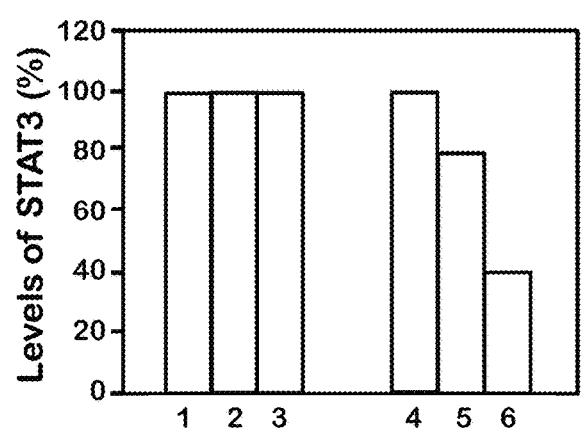
Figure 4G:
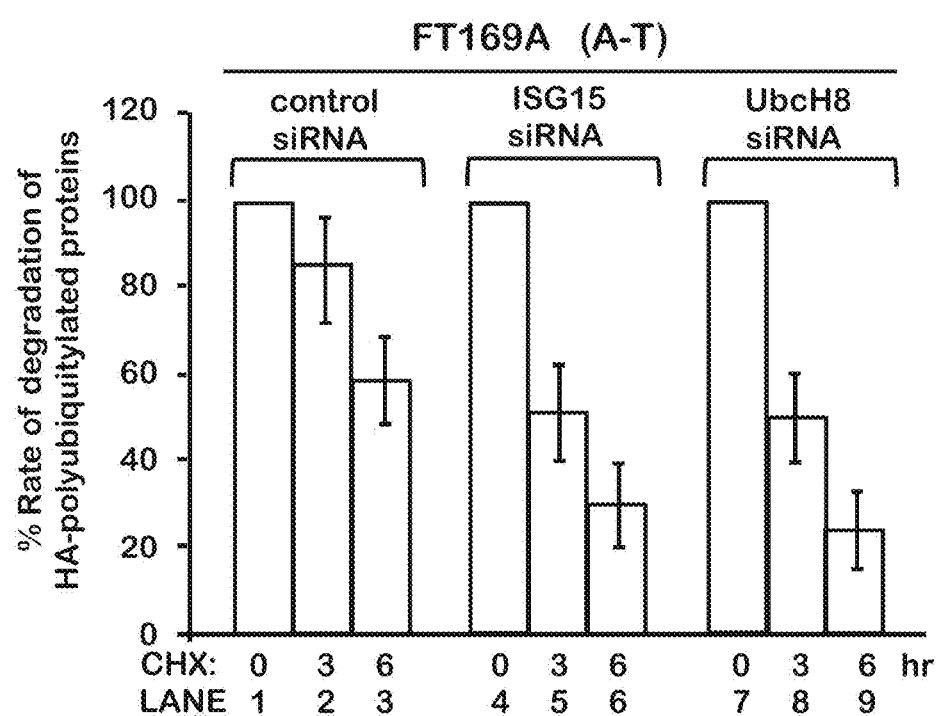
FIG. 4G illustrates A-T cells transfected with ISG15 or UbcH8 siRNA for 72 h, and then treated with the protein synthesis inhibitor CHX for 3 and 6 h. Cell lysates were analyzed by immunoblotting using anti-HA antibodies. The average rate of degradation of HA-polyubiquitylated proteins (error bar represents S.E.M.) in ISG15 or UbcH8 siRNA treated A-T cells measured using the Kodak image station 2000R from three independent experiments is shown in FIG. 4G.

In FIG. 4D, FT169A (A-T) cells were transfected with ISG15 siRNA for 72 hours. Cells were then treated with the protein synthesis inhibitor CHX (10 µg/ml) for 3 and 6 hours. Cell lysates were then analyzed by immunoblotting using anti-p53 (top panel), anti-STAT3 (middle panel) or anti-tubulin (lower panel) antibodies. The p53 and STAT3 bands shown in the first and second panels were quantified using the Kodak Image Station 2000R, and the quantification for p53 and STAT3 is shown in FIGS. 4E and 4F, respectively. All the experiments were repeated at least three times and the representative experiments are shown.

ISG15 siRNA significantly reduced ISG15 expression (70% decrease in the ISG15 band intensity) as revealed by immunoblotting using anti-ISG15 antibody (FIG. 4B, compare lanes 1 and 2). UbcH8 siRNA, on the other hand, significantly reduced the amount of ISG15-protein conjugates without affecting the expression level of free ISG15, as revealed by immunoblotting using anti-ISG15 antibody (FIG. 4B, compare lanes 2 and 3). Western blotting analysis of FT169A (A-T) cells transfected with UbcH8 siRNA showed that the expression level of UbcH8 was reduced by 70% (as judged by the decrease in the UbcH8 band intensity) as compared to FT169A (A-T) cells transfected with control siRNA (FIG. 4C). By contrast, under the same conditions, the amount of HA-ubiquitylated HMW proteins (reflecting polyubiquitylated proteins), revealed by immunoblotting with anti-HA antibodies, was greatly increased in cells treated with either ISG15 or UbcH8 siRNA than in cells treated with control siRNA (FIG. 4A, compare lane 1 with lanes 4 and 7). The turnover of polyubiquitylated proteins was then measured in the presence of CHX (see FIG. 4A). As shown in FIG. 4A, the turnover of HA-ubiquitin-conjugated proteins was negligible in FT169A (A-T) cells (overexpressing ISG15) treated with CHX (10 µg/ml) for 6 hours (compare lanes 1 and 3). By contrast, about two thirds of HA-ubiquitin-conjugated proteins were degraded in FT169A (A-T) cells transfected with either ISG15-specific (FIG. 4A, compare lanes 4 and 6) or UbcH8-specific siRNA (FIG. 4A, compare lanes 7 and 9) within 6 hours under the same conditions. The same membrane filter as shown in FIG. 4A was stripped and re-probed with anti-tubulin to assure equal protein loading (FIG. 4A, lower panel). The turnover of p53 and STAT3, which is reduced in FT169A (A-T) cells transfected with control siRNA, was shown to be restored in FT169A (A-T) cells transfected with ISG15 siRNA (FIG. 4D first and second panel, and FIGS. 4E and 4F for quantitation). These results indicated that protein ISGylation results in reduced protein polyubiquitylation and turnover of cellular proteins in A-T cells. It is also possible that the free ISG15 pool plays an independent role in regulating protein polyubiquitylation and turnover in A-T cells.

Example 5

Expression of ISG15 and its Conjugates is Elevated in Cells Deficient in ATM

Figure 5:
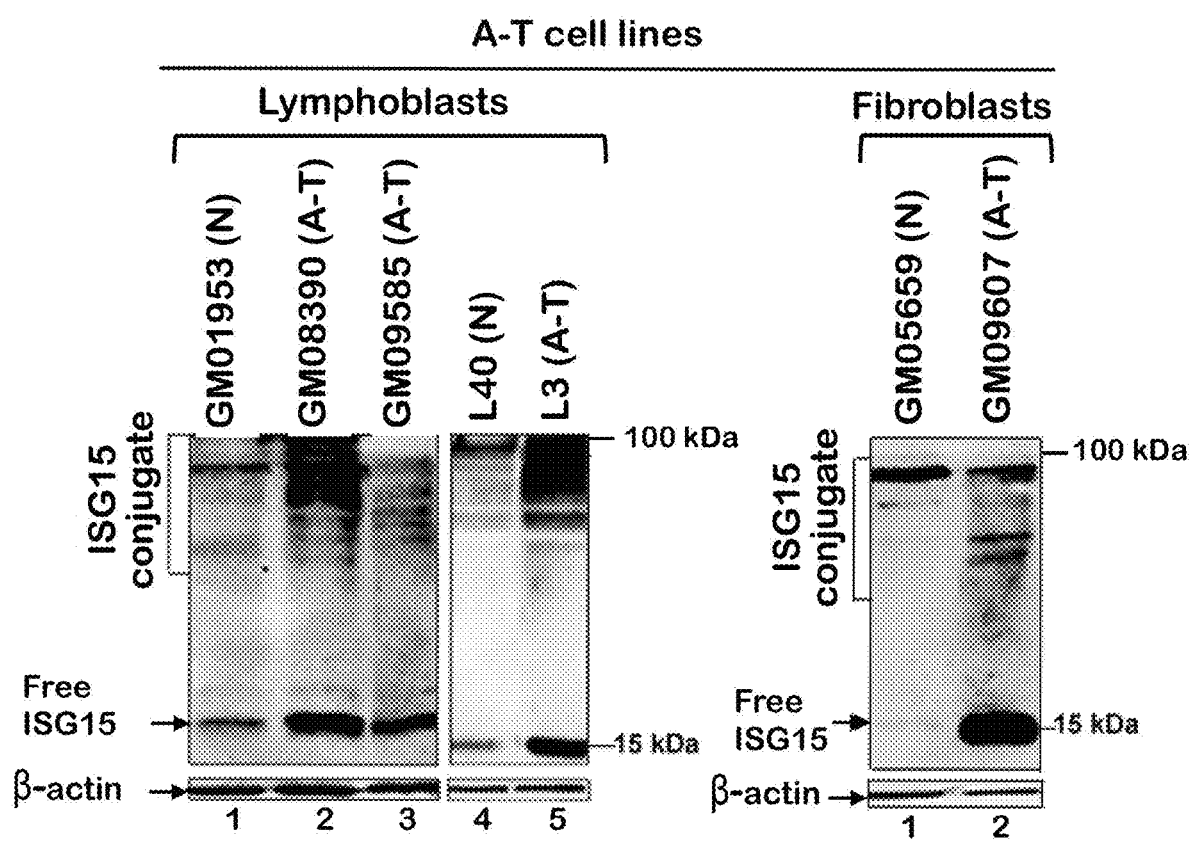
FIG. 5 illustrates normal (N) and Ataxia Telangiectasia (A-T) lymphoblast (left panel) and fibroblast (right panel) cell lysates analyzed by 15% SDS-PAGE, followed by immunoblotting using anti-ISG15 antibody (upper panels). The same membrane shown in the upper panels was stripped and re-probed using anti-β-actin antibody (lower panels). The experiment was repeated at least three times, and a representative experiment is shown.

The levels of ISG15 and its conjugates were measured in several other lymphoblast and fibroblast cell lines derived from A-T patients (A-T) and normal individuals (N). In FIG. 5, Normal (N) and Ataxia Telangiectasia (A-T) lymphoblast (left panel) and fibroblast (right panel) cells were analyzed by 15% SDS-PAGE, followed by immunoblotting using anti-ISG15 antibody (upper panels). The same membrane shown in the upper panels was stripped and re-probed using anti-β-actin antibody (lower panels). The experiment was repeated at least three times and the representative experiment is shown.

As shown in FIG. 5, the levels of ISG15 and its conjugates as measured by immunoblotting using anti-ISG15 antibodies were higher in A-T lymphoblast (left panel, lanes 2, 3 and 5) and fibroblast (right panel, lane 2) cells. On the other hand, very little ISG15 expression (free and conjugated form) was seen in both lymphoblast and fibroblast cells derived from normal cells (left panel, lanes 1 and 4, and right panel, lane 1). These results, together with the results shown in FIGS. 3A-3C, strongly indicate that ATM negatively regulates the expression of ISG15 and its conjugates.

Example 6

Expression of ISG15 and its Conjugates is Elevated in Brains of ATM Knockout Mice and A-T Human Patients.

Figure 6A:
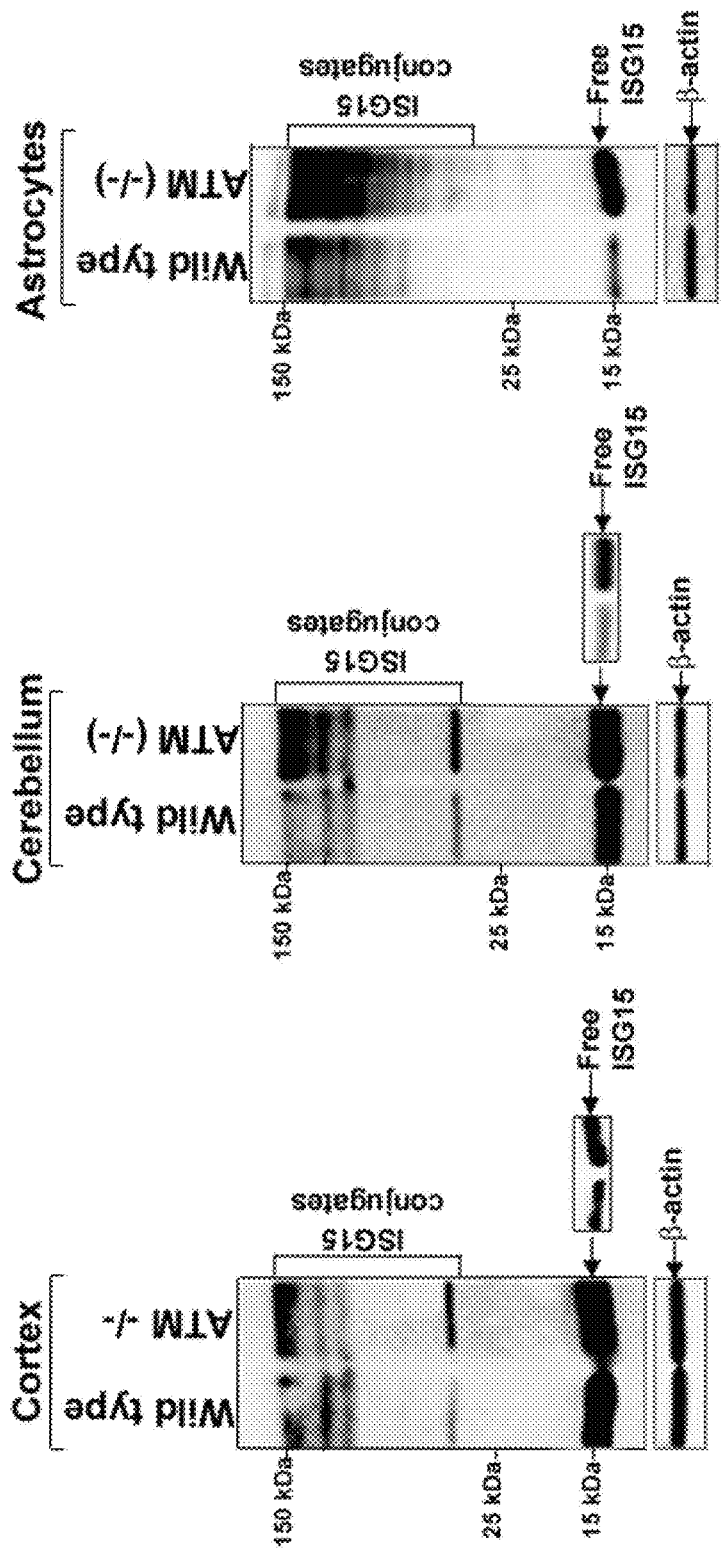
FIG. 6A illustrate lysates from cortex (left panel) and cerebellum (middle panel) tissues, as well as primary cortical astrocytes (right panel), from brains of ATM knockout mice immunoblotted using anti-ISG15 antibodies. All membrane filters were immunostained with anti-tubulin antibody (lower panels). The brain tissue lysates of two animals were pooled and loaded on SDS-PAGE. The experiment was repeated twice with reproducible results.

The results from Examples 2-4 indicate that the ISG15-mediated impairment of protein degradation in A-T neurons could be the basis of the progressive neurodegeneration in A-T patients. To test whether ISG15 expression is elevated in vivo, the expression of ISG15 and its conjugates was assessed in various regions of brain tissues obtained from wild type and ATM knockout mice. In FIG. 6A, lysates from cortex (left panel), cerebellum (middle panel) tissues, and primary cortical astrocytes (right panel), were immunoblotted using anti-ISG15 antibodies as described in Example 1. All membrane filters were immunostained with anti-tubulin antibody (lower panels). The brain tissue lysates of two animals were pooled and loaded on SDS-PAGE. The experiment was repeated two times with reproducible results.

The levels of free ISG15 (see inserts showing lower exposure) and its conjugates were increased in the cortex (FIG. 6A, first panel) and cerebellum (FIG. 6A, second panel) isolated from ATM knockout as compared to wild-type mice. In addition, ATM knockout astrocytes exhibited a striking increase in ISG15 and its conjugates over that from astrocytes derived from wild-type mice (FIG. 6A, third panel).

Figure 6B:
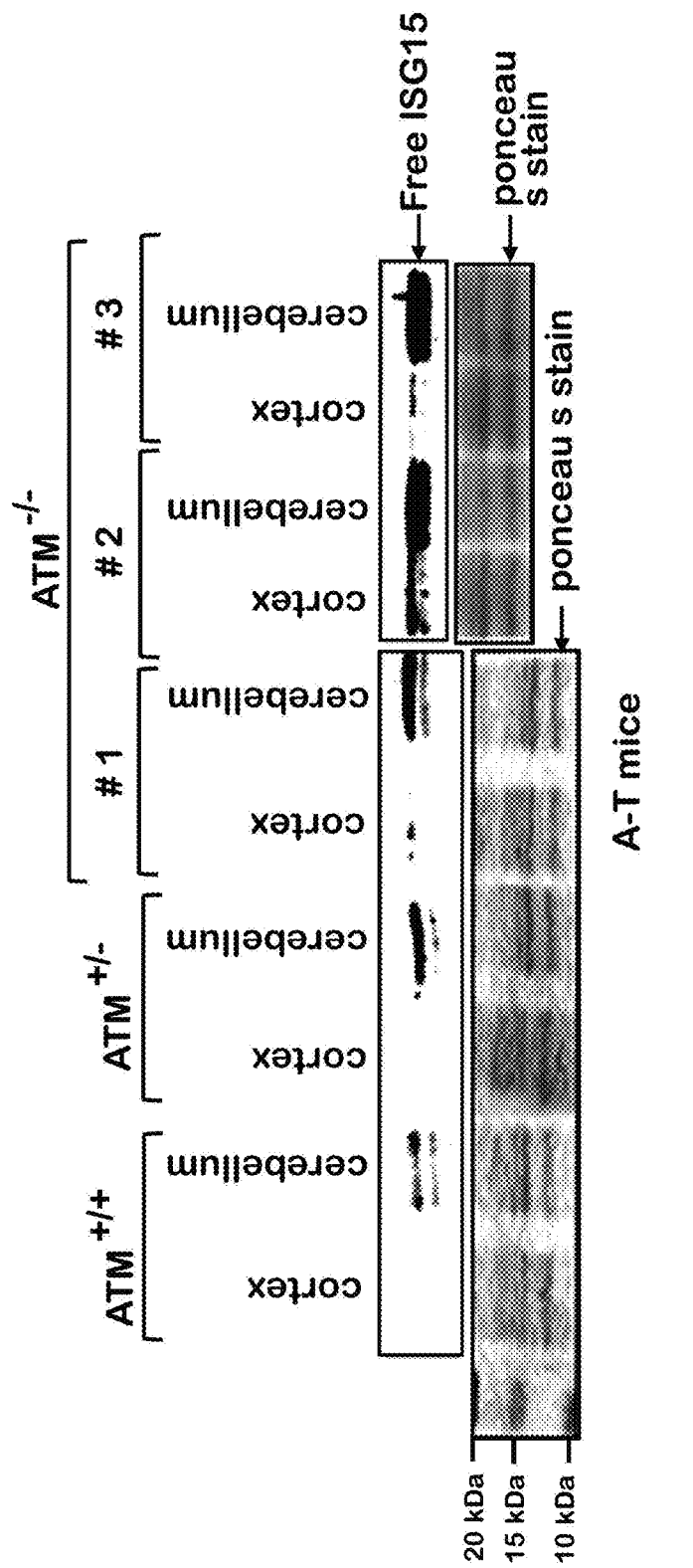
FIG. 6B illustrates lysates from specific brain regions isolated from Atm+ and Atm+/− mice immunoblotted using anti-ISG15 antibodies, and using Ponceau's stain to indicate equal protein loading.

ISG15 was also shown to be elevated in the murine Atm⁺ and Atm cerebellum, the specific brain region affected by A-T disease. Brains from the two strains of mice were assessed as described herein, and the results shown in FIG. 6B. Very little expression of ISG15 was seen in the cortex.

Figure 7A:
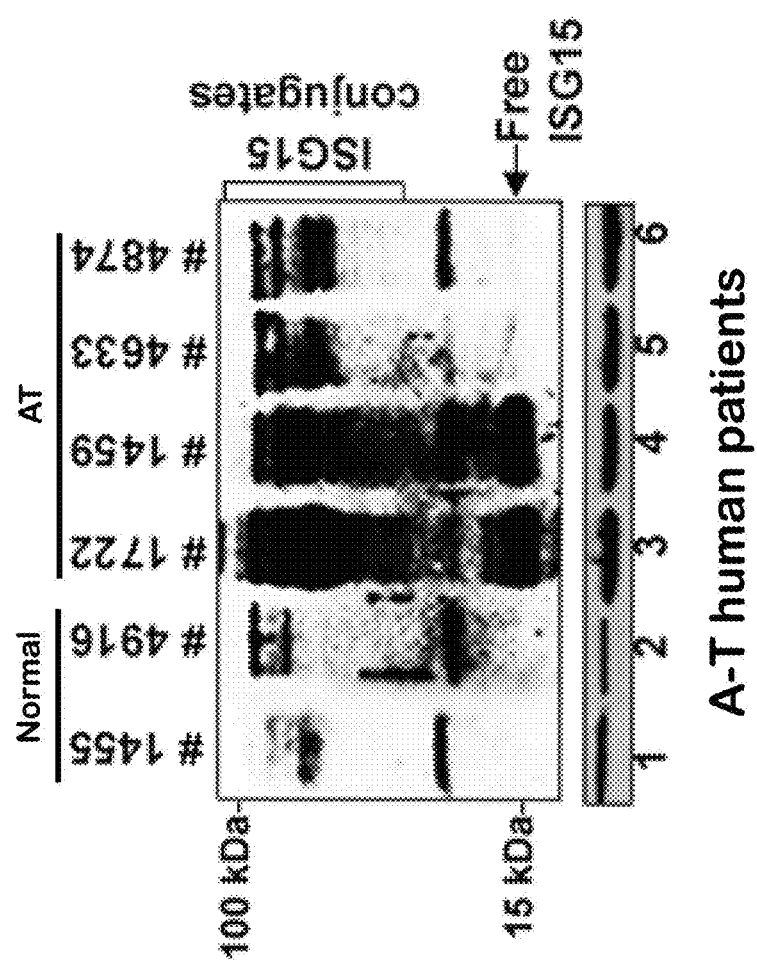
FIG. 7A illustrates frozen mid-brain postmortem tissues from two normal individual (UMB #1455 and 4916) and four A-T patients (UMB #s 1722, 1459, 4663 and 4874), after weighing and sonicating in a SDS sample buffer, and analyzed using anti-ISG15 antibodies. As a loading control, lysates were also immunoblotted against β-actin.

To further examine if ISG15 expression is elevated in vivo, mid-brain regions (specifically containing substantia nigra) obtained postmortem from four different A-T human patients (with confirmed A-T disease (UMB #s 1722, 1459, 4663, and 4874)) and two control individuals (without any disease (UMB #s 1455 and 4916)) were assessed for ISG15 expression by Western blotting using anti-ISG15 antibodies. In FIG. 7A, frozen mid-brain postmortem tissues from two normal individuals (UMB #1455 and 4916) and four A-T patients (UMB #s 1722, 1459, 4663 and 4874) were weighed and sonicated in a SDS sample buffer. Sonicated samples were immediately boiled for 10 min at 100° C. and centrifuged at 13,000×g for 10 min. Cleared supernatants were analyzed using anti-ISG15 antibodies. As a loading control, lysates were also immunoblotted against β-actin.

As shown in FIG. 7 A, ISG15 and its conjugates were highly elevated in two A-T patients (lanes 3 and 4), and moderately elevated in two other A-T patients (lanes 5 and 6). On the other hand, ISG15 expression was modest in brain tissue obtained from normal individuals (lanes 1 and 2).

Figure 7B:
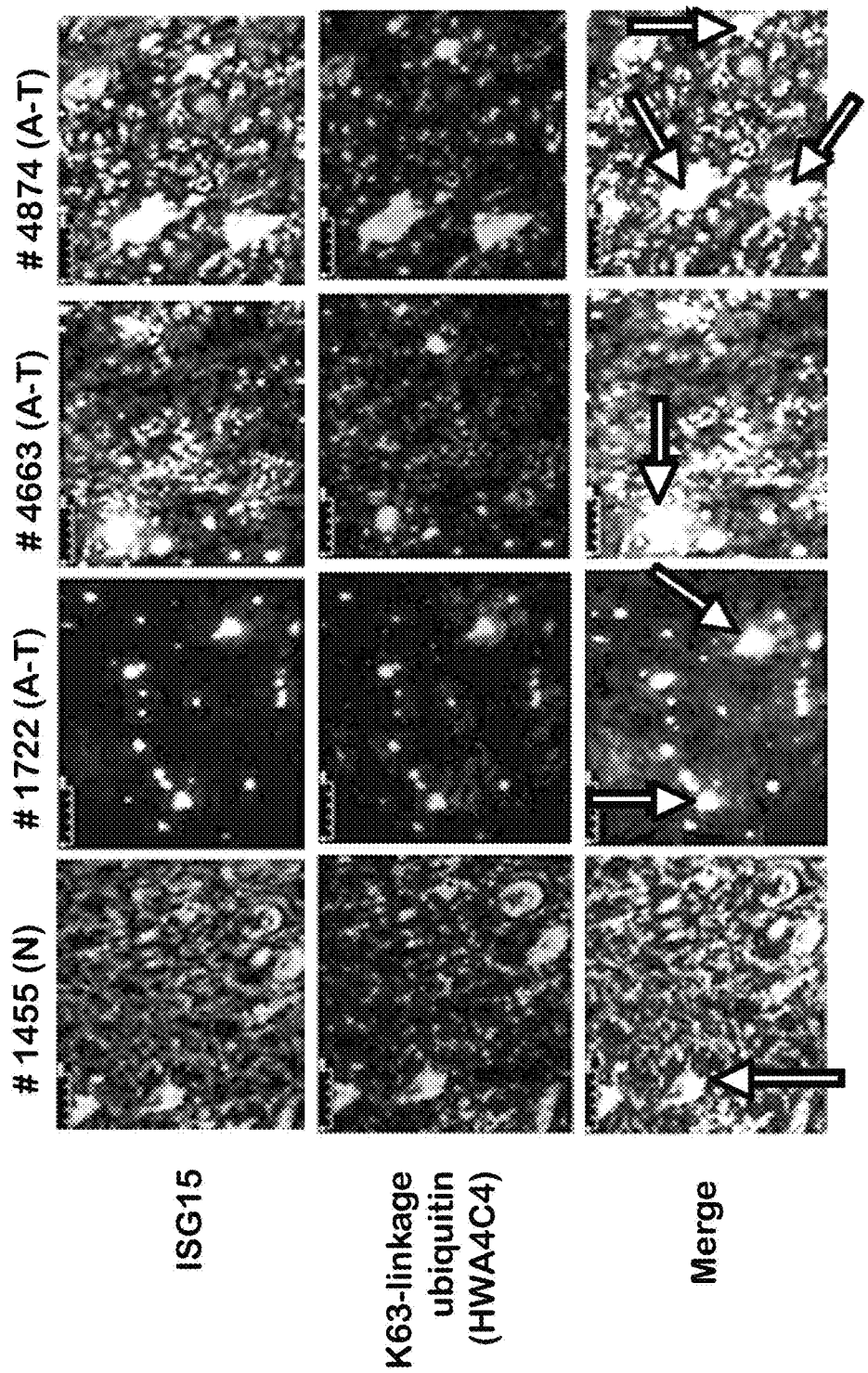
FIG. 7B illustrates the results from deparaffinized human brain tissue sections from the normal subject (UMB #1455) and A-T patients (UMB #1722, 4663) described in FIG. 7A, after being double stained with anti-ISG15 (polyclonal) and anti-K63-linkage specific polyubiquitin (monoclonal) (1:100) antibodies. After washing with PBS, sections were stained with Alexa Fluor 488 goat anti-rabbit IgG secondary antibody to detect ISG15 and goat polyclonal secondary antibody to mouse IgG (Cy5®) to detect Lys63-linked polyubiquitin conjugated proteins. Sections were mounted in gold antifade mounting medium and examined using Nikon E600 epifluorescence microscope (Nikon) (20× magnification, scale bar, 100 um). Arrows in the third panel indicate ubiquitin/ISG15 double-positive inclusions in the merged A-T brain sections.

A double immunofluorescence analysis was performed on the mid-brain tissue sections (containing specifically substantia nigra) obtained from a normal individual (UMB #1455) and A-T patients (UMB #1722, #4663, and #4874) shown in FIG. 7A, using ISG15 (green) and Lys63-linkage-specific polyubiquitin (red) antibodies (FIG. 7B). In FIG. 7B, the deparaffinized human brain tissue sections from the normal subject (UMB #1455) and A-T patients (UMB #1722, 4663) described in FIG. 7A. were double stained with anti-ISG15 (polyclonal) and anti-K63-linkage specific polyubiquitin (monoclonal) (1:100) antibodies. After washing with PBS, sections were stained with Alexa Fluor 488 goat anti-rabbit IgG secondary antibody to detect ISG15 (green) and goat polyclonal secondary antibody to mouse IgG (Cy5®) to detect Lys63-linked polyubiquitin conjugated proteins (red). Sections were mounted in gold antifade mounting medium and examined using Nikon E600 epifluorescence microscope (Nikon) (20× magnification, scale bar, 100 um). One slide each of the deparaffinized human brain tissue sections of A-T patients and normal individuals (obtained from the NICHD Brain and Tissue Bank for Developmental Disorders at the University of Maryland) was used in the experiment. Arrows indicate ubiquitin/ISG15 double-positive inclusions in the merged A-T brain sections.

As shown in FIG. 7 B, the dramatic increase in both ubiquitin/ISG15 double-positive inclusions (see arrows in merged images) was found in the mid-brain sections obtained from all three A-T patients tested. In contrast, no such inclusions were found in brain sections of the normal individual. An immunofluorescence study was also performed on the mid-brain section obtained from another normal subject (UMB #4669); consistent with the results similar to that shown in FIG. 7B for normal subject UMB #1455; i.e., no ISG15 containing inclusion bodies were found in the brain sections obtained from this normal individual using ISG15-specific antibodies ( ). The presence of ISG15/Lys63-linkage specific polyubiquitin containing inclusion bodies in the A-T patient's brain sections further indicates the involvement of a defective ubiquitin-proteasome system in A-T neurodegeneration.

Example 7

ISG15 Deregulates Autophagy in Genotoxin-Treated Ataxia Telangiectasia Cells

Materials and Methods

Cells:

FT169A (A-T) and FT169A (ATM+) fibroblast cells were obtained from Dr. Y. Shiloh at Tel Aviv University, Ramat Aviv, Israel. FT169A (A-T) cells were derived from FT169A cells (ATM null) by stable transfection with the expression vector alone as previously described (39). FT169A (ATM+) cells were derived from FT169A cells by stable transfection with full-length ATM cDNA (39). Both FT169A (A-T) and (ATM+) fibroblast cells were cultured in complete DMEM (Cellgro) supplemented with hygromycin B (100 µg/ml) (Cellgro).

Human Tissues.

Human brain tissues and tissue sections were obtained from the NICHD Brain and Tissue Bank for Developmental Disorders at the University of Maryland (supported by NICHD contract #NO1-HD-4-3368 and NO1-HD-4-3383) under ethics protocols approved by the University of Maryland Institutional Review Board. Frozen human mid-brain tissues containing specifically substantia nigra were obtained postmortem from patients with confirmed A-T disease and control individuals (without any known disease). Slides with paraffin-embedded sections of the mid-brain tissues were used in immunofluorescence study.

Construction of Lentiviral ISG15 shRNA Stable Transfectants of FT169A (A-T) Cell:

Preparation of lentiviral particles was done as described (40). Briefly, five shRNA constructs (TRCN0000007420-5) for the ISG15 in a pLKO1 vector and one control non-targeting shRNA lentiviral vector (SHCOO2V) were purchased from Sigma-Aldrich. Amongst the five shRNA constructs tested, TRCN0000007422 NM 005101.1-295S1C1 shRNA that showed efficient ISG15 knocked-down (>75%) in FT169A cells was used for the production of lentiviral particles. Lentiviral particles were generated by transfecting HEK293T cells with the lentiviral shRNA vector (pLKO.1-Puro harboring ISG15 or SHC002V vector harboring control shRNA), together with the packaging (psPax2) and an envelope (pMD2.G) vector (Addgene; Cambridge, Mass.) using standard calcium phosphate precipitation as described (41). Six to eight hours post-transfections, cells were washed once and replenished with the fresh DMEM medium, and allowed to grow for additional 48 hrs. The viral supernatants were then harvested and filtered through a 0.45-µm pore size filter. For transduction, FT169A (A-T) cells (65,000 cells/ml) were plated in a 6 well tissue culture plate 24 h prior to the lentiviral infection. The next day, culture medium was replaced with the 1 ml of fresh medium containing 6.5 µg/ml of polybrene (Chemicon International; Temecula, Calif.). Cells were infected with lentiviral particles containing ISG15 or control shRNA and incubated in a tissue culture incubator overnight. After 12 h of incubation, all transduced cells were replenished with the fresh culture media without polybrene. Two days post-transduction, cells were split (1:5) and allowed to grow under normal conditions (37° C. and 5% $CO_2$). Selection medium that contained 6.5 µg/ml puromycin dihydrochloride (Sigma-Aldrich) was then added to the cells 48 h after replating. Individual colonies were picked following 5 weeks of puromycin selection and screened for ISG15 expression by Western blotting analysis using anti-ISG15 antisera.

Immunoblotting and Immunofluorescence Analysis:
Immunoblotting Analysis of Proteins in Cultured Cells:

Cells ($5\times10^5$) were cultured in 35 mm tissue culture plates. After various experimental treatments, cells were lysed using a SDS-PAGE sample buffer. Cell lysates were then analyzed by SDS-PAGE (10% for p62 or 15% for LC3 and polyubiquitin conjugates) and immunoblotting analysis using either anti-ISG15 (raised against human ISG15 (23)), anti-ubiquitin (Sigma-Aldrich), anti-HA (gift from Dr. Walworth at Robert Wood Johnson Medical School/University of Medicine and Dentistry of New Jersey; Piscataway, N.J.)), anti-LC3 (MBL International Corporation; Woburn, Mass.), or p62 (Sigma-Aldrich) antibodies, as indicated, using the ECL Western procedure (Pierce) and the BioRad VersaDoc Imaging System.

Immunoblotting Analysis of HA-Ubiquitin Conjugated Proteins in Cells Exposed to UV Radiation.

Cells ($5\times10^5$) were transfected with a hemagglutinin (HA)-ubiquitin plasmid using the PolyFect transfection reagent (Qiagen; Valencia, Calif.) as described (24). Twenty-four h after transfection, cells were treated with either proteasome inhibitor MG132 (1 µM) (Boston Biochemicals; Cambridge, Mass.) or autophagy inhibitor Bafilomycin A1 (Bafl) (1 nM) (Sigma-Aldrich) or 3-Methyladenine (3-MA) (100 nM) for 18 h. Cells were exposed to UV radiation (25 mJoules, using BioRad GS Gene Linker™ UV Chamber) and/or left untreated. Cells were then allowed to recover in the presence of inhibitors for 3 hr. Cell lysis, SDS-PAGE, and immunoblotting analysis to detect HA-ubiquitin conjugated proteins using anti-HA antibodies was carried out as described herein.

Immunofluorescence Analysis in Cells: LC3 Expression.

Cells (100,000/point) were cultured on fibronectin-coated glass coverslips. Next day, cells were fixed in 4% paraformaldehyde. After washing with phosphate-buffered saline (PBS) (2×5 min), cells were incubated with 100 µg/ml Digitonin for 15 min at room temperature. Cells were then washed with PBS (2×5 min) and immunostained for LC3 (MBL International Corporation) for 1 h at room temperature. After washing with phosphate-buffered saline (PBS) (2×5 min), cells were incubated with Alexa-Fluor 488 goat anti-mouse IgG secondary antibody (1:100) (Invitrogen) for 1 h. Cells were then washed with PBS and mounted on slides in anti-fade mounting medium with DAPI (Invitrogen). Images were taken using a 63× oil immersion objective with a Leica DMRA2 upright microscope run through SlideBook software (Intelligent Imaging Innovations; Santa Monica, Calif.).

Autophagasome, Lysosome and Autophagolysosomes Staining.

Cells (100,000/point) were cultured on fibronectin-coated glass coverslips. Cells were treated with autophagy inhibitor Bafl (1 nM) (Sigma-Aldrich) for 18 hr. Cells were then exposed to UV radiation and allowed to recover in the presence of inhibitors for 3 h. Cells were then washed (2×1 min) with PBS and co-stained with Cyt-ID® (Cyt-ID® Autophagy Detection Kit from Enzo Lifesciences; Farmingdale, N.Y.) and Lyso Tracker® Red DND-99 (Invitrogen) for 30 min at 37° C. in a $CO_2$ incubator following manufacturer's protocol. Stained cells were then washed (2×1 min) with PBS and fixed with 4% paraformaldehyde for 20 min at room temperature. After washing with PBS (3×10 min), cells were mounted on slides in anti-fade mounting medium with DAPI (Invitrogen). Images were taken using a 63× oil immersion objective with a Leica DMRA2 upright microscope run through SlideBook software (Intelligent Imaging Innovations).

Immunoblotting Analysis of LC3 Expression in Brain Tissues of A-T Patients by Western Blotting.

Frozen tissues were stored at −80° C. until use. For detecting LC3, frozen tissues were weighed, cut into small pieces, and placed in test tubes containing SDS sample buffer. Tissue samples were then sonicated with a Tissue-Tearor (Biospec Products, Inc.; Bartlesville, Okla.). Sonicated samples were immediately boiled for 10 minutes at 100° C. and subsequently centrifuged at 13,000×g for 10 min. Cleared supernatants containing SDS-solubilized protein extracts were analyzed by 15% SDS-PAGE and immunoblotted using anti-LC3 as described herein.

Immunofluorescence Analysis in A-T Brain Tissue Sections.

For double immunofluorescence, tissue sections were deparaffinized in xylene and incubated with the GFAP (Abcam) and LC3 (MBL International Corporation) primary antibodies (1:100) for 1 hr. After washing in PBS, sections were stained with Alexa Fluor 488 goat anti-rabbit IgG secondary antibody (Invitrogen) and goat polyclonal secondary antibody to mouse IgG (Cy5 ®) (Abcam). Sections were mounted in gold antifade mounting medium (Invitrogen) and examined using Nikon E600 epifluorescence microscope (Nikon). All the operations were performed at room temperature.

Example 8

Figure 8A:
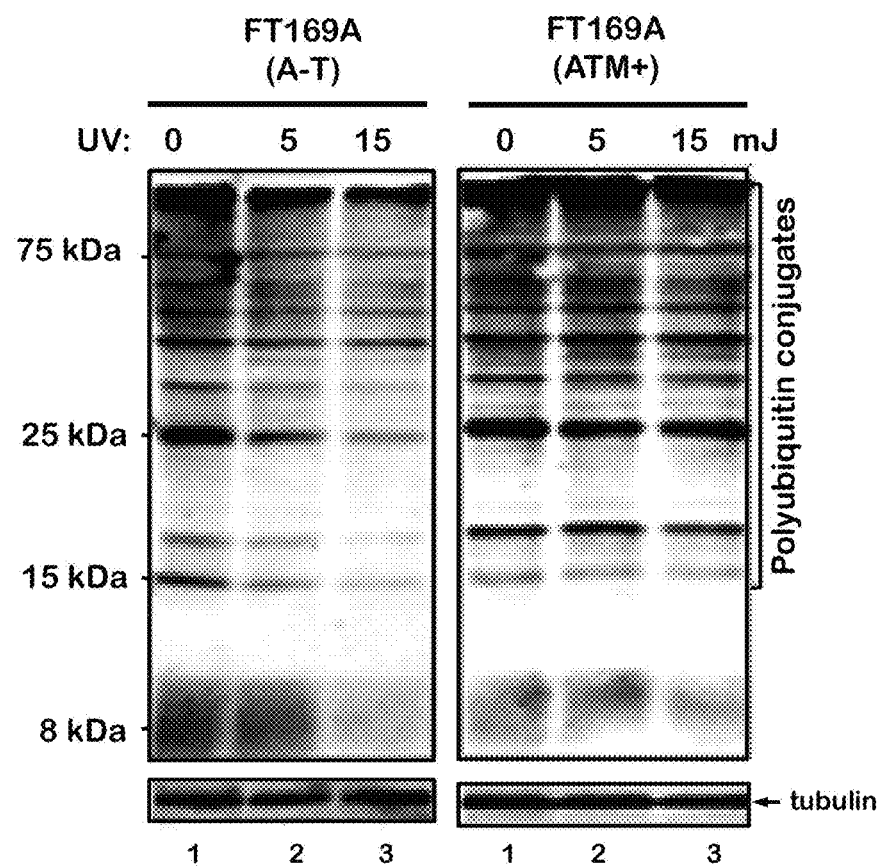
FIG. 8A illustrates A-T and ATM+ cells exposed to different doses of UV and allowed to recover for 3 h. Cells were lysed and lysates were analyzed by Western blotting for polyubiquitylated proteins and tubulin using anti-ubiquitin and anti-tubulin antibodies respectively. The results are shown in FIG. 8A.

UV Induces Degradation of Polyubiquitylated Proteins in A-T but not in ATM+ Cells Previous studies using the FT169A (A-T) (ATM null; henceforth referred to as A-T) and FT169A (ATM+) (ATM reconstituted FT169A; henceforth referred to as ATM+) isogenic pair of fibroblast cells have demonstrated that ISG15, a ubiquitin-like protein known to antagonize the ubiquitin pathway, is elevated and inhibits the ubiquitin pathway in A-T cells (24). The ubiquitin pathway plays a key role in ATM-dependent DNA repair (42). Because A-T cells are defective in both the DNA repair (due to the defective ATM kinase) (43) and ubiquitin (due to the constitutively elevated ISG15 pathway) pathways (20), UV, a genotoxic stressor known to induce DNA damage, was examined for its effect on the global protein polyubiquitylation and their subsequent degradation in A-T cells. In FIG. 8A, A-T and ATM+ cells were exposed to different doses of UV and allowed to recover for three hours. Cells were lysed and lysates were analyzed by Western blotting for polyubiquitylated proteins and tubulin using anti-ubiquitin and anti-tubulin antibodies respectively.

As shown in FIG. 8A, the steady state levels of the endogenous polyubiquitylated proteins and free ubiquitin rapidly decreased in A-T cells exposed to different doses of UV radiation and detected 3 hours post-radiation survival (FIG. 8A, left panel, compare lane 1 with lanes 2 and 3). By contrast, very little decrease in the steady state levels of polyubiquitylated proteins was seen in ATM+ cells under the same conditions (FIG. 8A, right panel, compare lane 1 with lanes 2 and 3). These results reveal that the steady-state levels of polyubiquitylated proteins are decreased in UV-treated A-T but not in ATM+ cells.

Figure 8B:
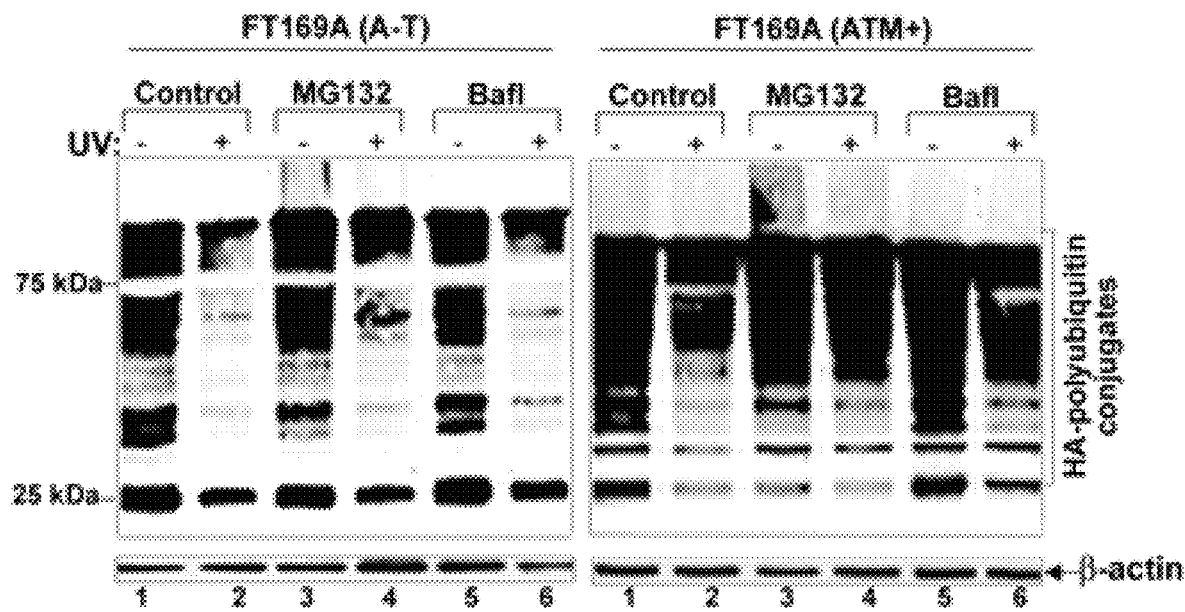
FIGS. 8B-8C illustrate A-T and ATM+ cells transfected with a HA-ubiquitin construct, then treated with MG132 or Bafl for 18 h, and exposed to UV radiation (25 mJ/m2). After recovery in the presence of inhibitors for 3 h, cells were lysed, and the lysates analyzed by Western blotting for HA-polyubiquitylated proteins and actin using anti-HA and anti-actin antibodies respectively. Intensity of the total HA-polyubiquitylated proteins was quantitated using BioRad Quantity One software. The bar graph in FIG. 8C shows average values (±SEM) of % degradation of HA-polyubiquitylated proteins from three independent experiments.
Figure 8C:
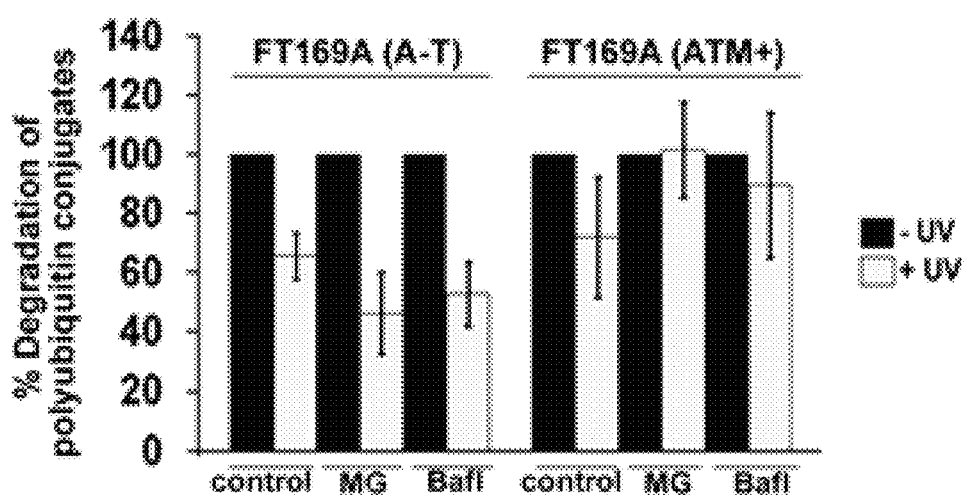

Decrease in the steady state levels of polyubiquitylated proteins could be due to their increased deubiquitylation or increased degradation via the 26S proteasome. Also, the ubiquitin antibody used in the experiment herein is known to cross-react with free ISG15/UCRP (44), and ISG15 protein is elevated in A-T cells (20). An HA-ubiquitin construct was transfected and then the steady state levels of the HA-polyubiquitylated proteins was assessed (to rule out the possibility of protein polyubiquitylation versus protein polyISGlyation), in the absence or presence of the proteasome inhibitor MG132 (to rule out the possibility of protein deubiquitylation versus protein degradation), in UV treated A-T and ATM+ cells. In FIG. 8B, A-T and ATM+ cells were transfected with a HA-ubiquitin construct. Cells were then treated with MG132 (1 µM) or Bafl (1 nM) for 18 hours and exposed to UV radiation (25 mJ/m2). After recovery in the presence of inhibitors for an additional three hours, cells were lysed. Cell extracts were analyzed by Western blotting for HA-polyubiquitylated proteins and actin using anti-HA and anti-actin antibodies respectively. Intensity of the total HA-polyubiquitylated proteins was quantitated using Bio-Rad Quantity One software and results shown in FIG. 8C. FIG. 8C shows average values (±SEM) of % degradation of HA-polyubiquitylated proteins from three independent experiments.

Consistent with the results shown in FIG. 8A, UV also induced degradation of HA-polyubiquitylated proteins in A-T cells (FIG. 8B, left panel, compare lanes 1 and 2). Intriguingly, MG132 failed to protect UV-induced decrease of HA-polyubiquitylated proteins in A-T cells (left panel, lanes 3 and 4). UV also induced moderate degradation of HA-polyubiquitylated proteins in ATM+ cells (FIG. 8B, right panel, compare lanes 1 and 2). However, unlike in A-T cells, MG132 completely blocked the decrease of HA-polyubiquitylated proteins in ATM+ cells exposed to UV (FIG. 8B, right panel, lanes 3 and 4). Inhibition of protein disappearance in MG132-treated ATM+ cells indicated that the UV-induced disappearance of HA-polyubiquitylated proteins in A-T cells is not due to their deubiquitylation, but due to their degradation via the 26S proteasome. The MTT assay for cell survival revealed that the degradation of polyubiquitylated proteins was not due to the decreased viability of UV-treated A-T cells under these experimental conditions.

The autophagy pathway is induced as a compensatory mechanism to degrade cellular proteins in cells defective in the ubiquitin pathway (31-34). In addition the MG132 proteasome inhibitor induces autophagy (45, 46). Whether the UV-induced degradation of polyubiquitylated proteins is via autophagy in the ubiquitin-pathway was tested in ablated A-T cells. To test the involvement of autophagy, the autophagy inhibitor Bafilomycin A1 (Bafl) (47) was used. Similar to MG132, Bafl also failed to block UV-mediated degradation of polyubiquitylated proteins in A-T cells (FIG. 8B, left panel, lanes 5 and 6). In contrast, Bafl significantly blocked the decrease of HA-polyubiquitylated proteins in ATM+ cells exposed to UV (FIG. 8B, right panel, lanes 5 and 6). Protein degradation in the presence of 50 nM Bafl was assessed, and even this high concentration of Bafl failed to protect UV-induced degradation of cellular proteins in A-T cells. The results using ATM+ cells and inhibitors indicates that the failure of Bafl and MG132 to block UV-induced degradation of the polyubiquitylated proteins in A-T cells is not due to the limiting concentration of MG132 and Bafl used, as these inhibitors efficiently blocked the degradation of polyubiquitylated proteins in ATM+ cells. The bar graph of FIG. 8C shows average values (±SE) of % degradation of polyubiquitylated proteins measured from three independent experiments confirming reproducibility of the qualitative results shown in FIG. 8B. Together, these results revealed that UV induces MG132- and Bafilomycin-resistant degradation of polyubiquitylated proteins in A-T cells, but not in ATM+ cells.

Figure 8D:
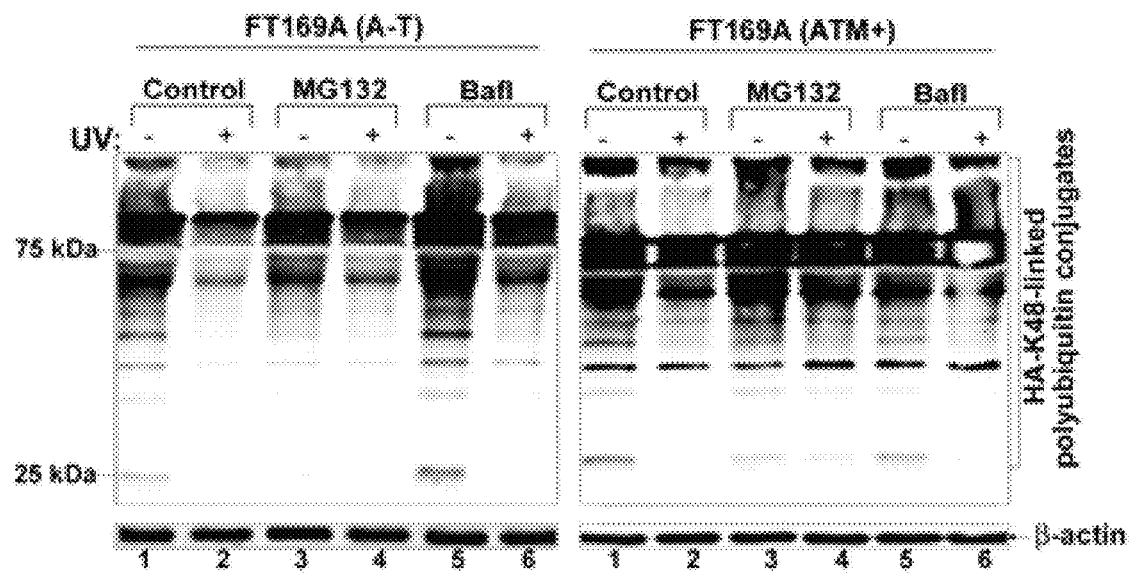
FIG. 8D illustrates A-T and ATM+ cells transfected with HA-Lys48 only ubiquitin construct, and similar treatment as in FIG. 8B. The experiment was repeated two times with reproducible results.

To complement the results shown in FIG. 8B, another construct was used that expresses HA-ubiquitin and that can preferentially make polyubiquitin chains linked through Lys48 on the substrates (20). In FIG. 8D, A-T and ATM+ cells were transfected with HA-Lys48 only ubiquitin construct. The inhibitor and UV treatments, cell lysis, SDS-PAGE, and immunoblotting analysis to detect HA-ubiquitin conjugated proteins using anti-HA antibodies was carried out as described herein. The experiment was repeated two times with the reproducible results. Similar results were obtained using this distinct HA-ubiquitin construct (FIG. 8D) as obtained herein (FIG. 8B); UV induced MG132- and Bafilomycin-resistant degradation of HA-Lys48-linked polyubiquitylated proteins in A-T cells, but not in ATM+ cells.

Figure 8E:
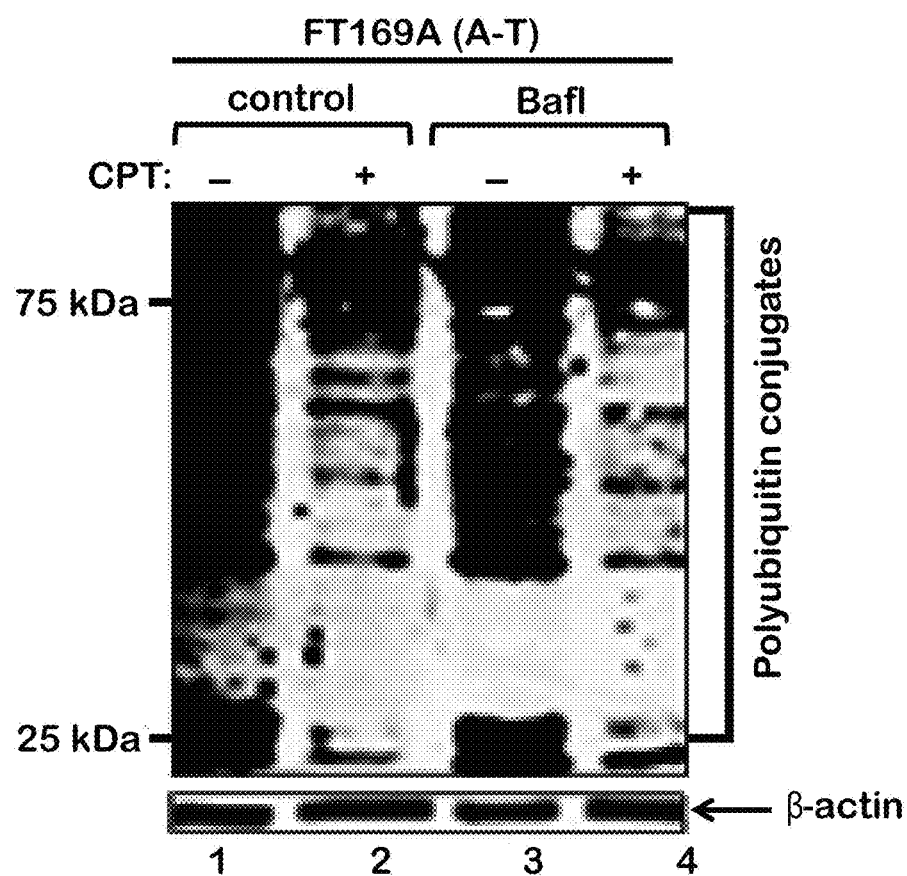
FIG. 8E illustrates A-T cells treated with camptothecin in the presence or absence of Bafl for 24 h, and then ubiquitin conjugated proteins using anti-ubiquitin antibodies detected as described in FIG. 8A.

To test the generality of this observation, the anticancer drug camptothecin (CPT), a genotoxic agent (37, 48-50), which is known to sensitize A-T cells (37), like UV, was used to induce degradation of polyubiquitylated proteins in A-T cells. In FIG. 8E, A-T cells were treated with camptothecin (CPT; 10 μm) in the presence or absence of Bafl (1 nm) for 24 hr. Ubiquitin conjugated proteins using anti-ubiquitin antibodies were detected as described herein for FIG. 8A. The experiment was repeated three times. Similar to UV, CPT also induced degradation of endogenous polyubiquitylated proteins (FIG. 8D, lanes 1 and 2) ($p<0.0001$), and Bafl failed to protect CPT-mediated degradation of polyubiquitylated proteins (FIG. 8D, lanes 3 and 4) in A-T cells ($p<0.0001$). These results indicate that genotoxins such as UV and CPT induce aberrant degradation of polyubiquitylated cellular proteins in the proteasome function-ablated A-T cells.

Example 9

Basal Autophagy is Activated in A-T Cells Impaired in the Ubiquitin Pathway—

Figure 9A:
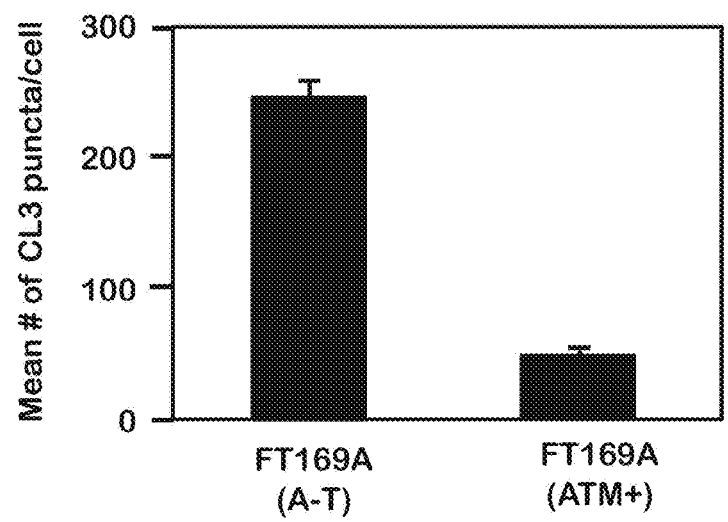
FIG. 9A illustrates the results from immunofluorescence imaging of LC3 puncta in A-T and ATM+ cells, and the average number (±SEM) of puncta counted in 50 cells in different fields shown in the bar graph.

Basal autophagy is activated in Atm knockout mice brains (51); and it is possible that basal autophagy is also activated and genotoxins deregulate activated autophagy leading to aberrant degradation of polyubiquitylated proteins in human A-T cells. To test this, the status of endogenous LC3 puncta, a biological marker used to trace induction of autophagy in mammalian cells (52-54), was measured. Immunofluorescence images of LC3 puncta in A-T and ATM+ cells were made and the average number (±SEM) of puncta counted in 50 cells in different fields was counted. The results are shown in FIG. 9A. As shown in FIG. 9A, A-T cells showed a significant increase in LC3 puncta as compared to ATM+ cells. These results reveal that, like in Atm knockout mice, basal autophagy was activated in human A-T cells that are impaired in the ubiquitin pathway.

Figure 9B:
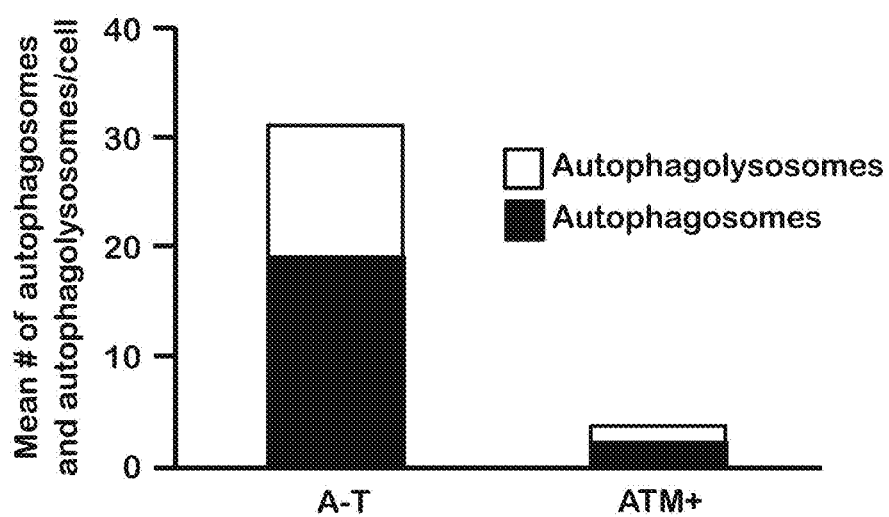
FIG. 9B illustrates the results from imaging A-T and ATM+ cells co-stained with Cyt-ID® and LysoTracker Red® dyes and green (autophagosomes; from Cyt-ID®-stained images; clear (or white) bars) and yellow (autophagolysosomes; from merged images; black bars) dots in cells counted manually using the ImageJ plug-in cell counter. The average number (±SEM) of dots/cell is shown in FIG. 9B. Experiments were repeated two times with similar results.

Autophagy was also examined using Cyto-ID® and LysoTracker Red stains. Cyto-ID® selectively labels autophagic vacuoles (pre-autophagosomes, autophagosomes, and autophagolysosomes) and a fluorescent acidotropic probe LysoTracker Red labels acidic organelles such as lysosomes and autophagolysosomes (54). Appearance of green dots indicated the formation of autophagosomes; red dots indicated lysosomes; and yellow dots in merged images (green dots that overlay red dots in merged images) indicated autophagolysosomes (autophagosomes fused with lysosomes) (Color images not shown). Images of A-T (panels 1-3) and ATM+(panels 4-6) cells co-stained with Cyt-ID® and LysoTracker Red® dyes were made as described; and images were merged. Green (autophagosomes; from Cyt-ID®-stained panels) and yellow (autophagolysosomes; from merged panels) dots in cells were counted manually using the ImageJ plug-in cell counter. The average number (±SEM) of dots/cell is shown in FIG. 9B, with autophagolysosome number represented by the white bar; and autophagosome number represented by the black bar. Experiments were repeated two times with similar results.

As shown in FIG. 9B, increased autophagosome numbers were seen in A-T compared to ATM+ cells (compare the black bars in FIG. 9B), indicating increased autophagic activity in A-T cells. In addition, there was a significant increase in autophagolysosome numbers in A-T compared to ATM+ cells (compare the white bars in FIG. 19B). Together, immunofluorescence data using anti-LC3 antibodies and Cyto-ID/LysoTrack Red dyes revealed that basal autophagy is activated in A-T cells.

Example 10

Degradation of Autophagy Substrates is Deregulated in UV-Exposed A-T Cells—

Figure 10A:
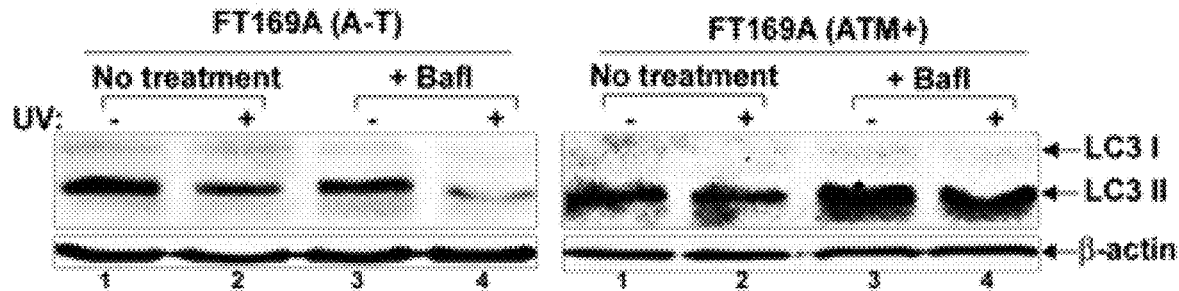
FIGS. 10A-10D illustrate Western blot analysis of A-T and ATM+ cells treated with Bafl, and then exposed to UV as indicated (25 mJ/m2). After recovery for 3 h in the presence of inhibitors, cells were lysed, and the lysates analyzed by Western blotting for LC3 (FIG. 10A), p62 (FIG. 10C), and actin (lower panels, FIGS. 10A and 10D) using their specific antibodies. Intensity of the total LC3 (LC3-I+II) and p62 proteins was quantitated using BioRad Quantity One software, and the results shown in FIGS. 10B and 10D, respectively.
Figure 10B:
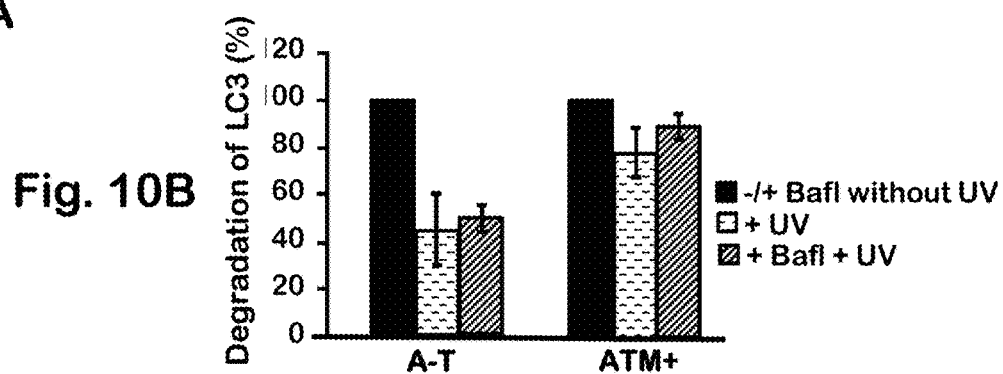
Figure 10C:
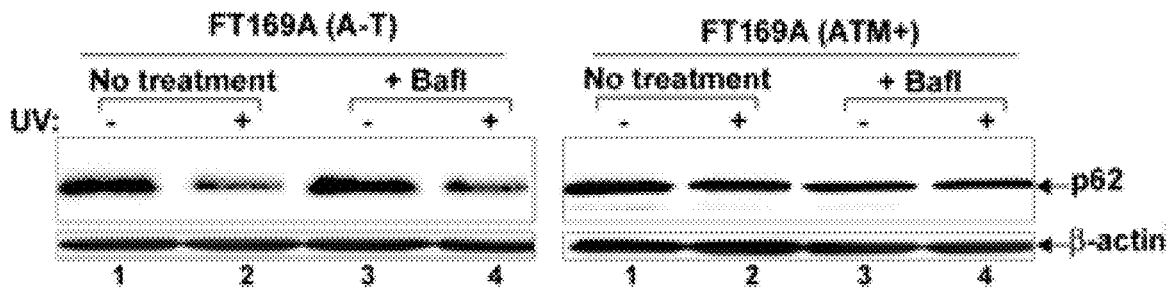
Figure 10D:
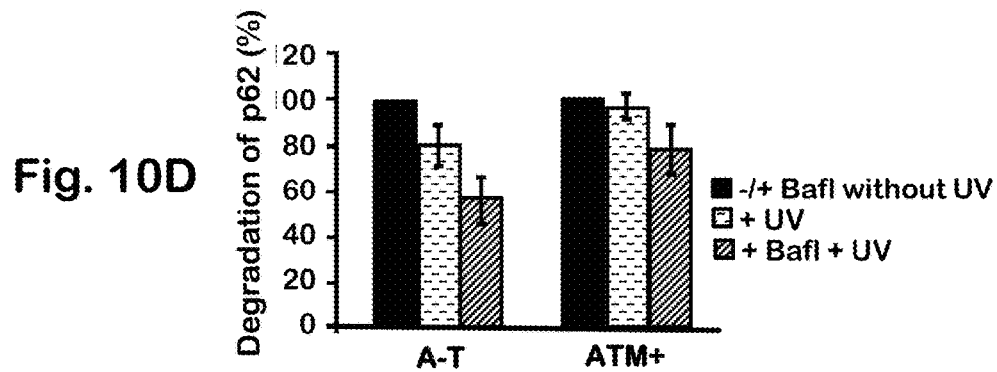

Because degradation of proteasome substrates is deregulated in A-T cells, the degradation of the autophagy substrates (autophagic flux) LC3 and p62 was assessed in UV-exposed A-T and ATM+ cells (55). For FIGS. 10A-10D, A-T and ATM+ cells were treated with Bafl (1 nM for 18 h) and then exposed to UV as indicated (25 mJ/m2). Three hours after recovery in the presence of inhibitors, cells were lysed. Cell lysates were analyzed by Western blotting for LC3 (FIG. 10A), p62 (FIG. 10B), and actin (lower panels in FIGS. 10A and 10C) using their specific antibodies. Intensity of the total LC3 (LC3-I+II) and p62 proteins was quantitated using BioRad Quantity One software, and the results shown in FIGS. 10B and 10D, respectively. FIGS. 10B and 10C show average values (±SEM) of % degradation of LC3 and p62 from three independent experiments. All control values (−UV and + Bafl) are normalized to 100%, and values for experimental treatments were expressed as percent variations over control As shown in FIGS. 10A-10D, UV induced degradation of LC3 and p62 (FIGS. 10A and 10C, left panels, lanes 1 and 2) in A-T cells. The autophagy inhibitor Bafl failed to protect UV-mediated degradation of LC3 and p62 in A-T cells (FIGS. 10A and 10C, left panels, lanes 3 and 4). On the other hand, no apparent changes in LC3 and p62 levels were detected in ATM+ cells treated with UV in the absence or presence of Bafl (FIGS. 10A and 10C, right panels). FIGS. 10B and 10D show average (+/−SEM) degradation of LC3 (LC3-I and II) and p62 proteins in UV-exposed A-T and ATM+ cells treated with Bafl from three independent experiments. These results revealed that, like the proteasome substrates (Example 8), UV also induces aberrant degradation of autophagy substrates in A-T cells.

Figure 11A:
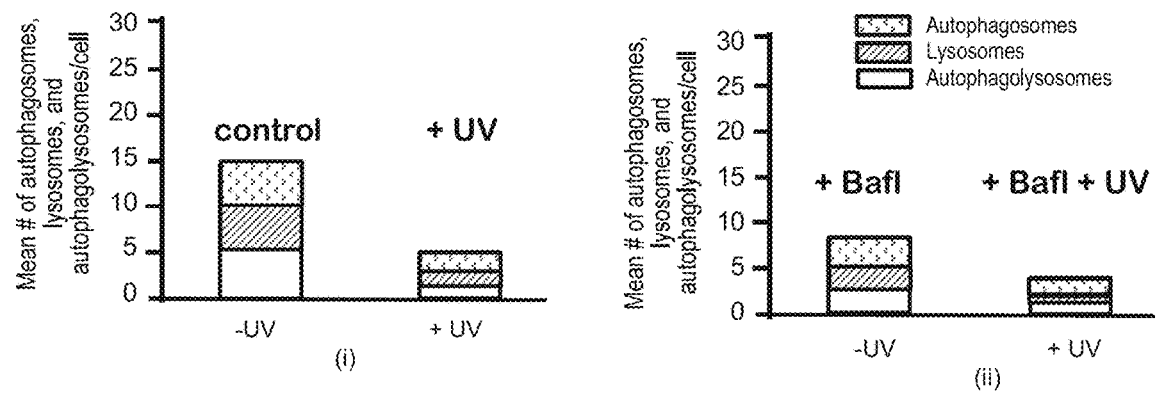
FIGS. 11A and 11B illustrate the results from A-T (FIG. 11A) and ATM+(FIG. 11B) cells treated with Bafl and exposed to UV. Three hours after recovery in the presence of inhibitors, cells were co-stained with Cyt-ID® and LysoTracker Red® dyes. Green (autophagosomes; from Cyt-ID®-stained panels; stippled bars), red (lysosomes; from LysoTracker Red-stained panels; lined bars), and yellow (autophagolysosomes; from merged panels; clear (or white) bars) dots in A-T (FIG. 11A) and ATM+(FIG. 11B) cells were counted manually using the ImageJ plug-in Cell Counter. Mean number of dots/cell are shown in FIGS. 11A and 11B. Experiments were repeated two times with similar results.
Figure 11B:
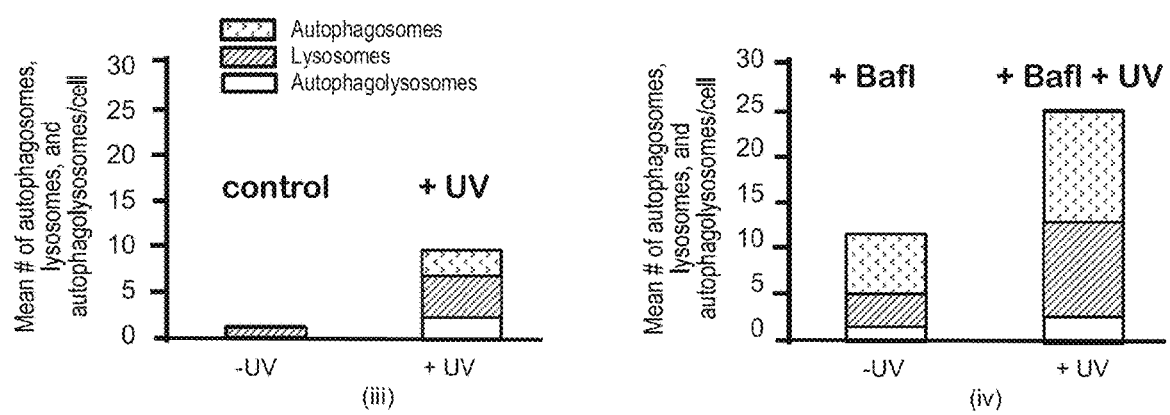

Autophagic flux was also monitored using Cyto-ID® and LysoTrack Red dyes. The quantitation of the immunofluorescence data is shown in FIGS. 11A and 11B. A-T and ATM+ cells were treated with Bafl (1 nM for 18 h) and then exposed to UV (25 mJ/m2) as indicated. Three hours after recovery in the presence of inhibitors, cells were co-stained with Cyt-ID® and LysoTracker Red® dyes. Fluorescence images of Cyt-ID® and LysoTracker Red® stained cells were made (Color images not shown). Green (autophagosomes; from Cyt-ID®-stained panels), red (lysosomes; from LysoTracker Red-stained panels), and yellow (autophagolysosomes; from merged panels) dots in A-T and ATM+ cells were counted manually using the ImageJ plug-in Cell Counter. Mean number of dots/cell is shown in FIGS. 11A and 11B, respectively. In FIGS. 11A and 11B, the number of autophagosomes (green dots) is represented by stippled bars; the number of lysosomes (red dots) is presented by lined bar; and the number of autophagolysosomes (yellow dots) is represented by clear (white) bars. Experiments were repeated two times with similar results.

As shown by the numbers in FIGS. 11A and 11B, autophagolysosomes were formed in UV/Bafl-treated/untreated cells. In the colored images, when the green dots did not overlay red dots and appeared as green in merged images, indicated a failure of fusion between autophagosomes and autolysosomes in UV/Bafl-treated/untreated cells. Decrease in the number of green, red and yellow dots was taken as an indication of increased autophagic flux in UV/Bafl-treated/untreated cells as the autophagolysosomes break down and disappear at the end of autophagy. As shown in FIGS. 11A and 11B, control A-T cells displayed increased autophagic activity over control ATM+ cells. However, upon UV-treatment, most colored dots disappeared in A-T cells. In contrast, the number of colored dots was markedly increased in UV-treated ATM+ cells (compare FIG. 11A(i) with FIG. 11B(iii)). Disappearance of the autophagic organelles in A-T and appearance of the autophagic organelles in ATM+ cells revealed that UV induces autophagic flux in A-T, but not in ATM+ cells.

Bafilomycin inhibits autophagic flux by blocking fusion between autophagosomes and autolysosomes. A decreased appearance of autophagolysosomes (yellow dots) in cells treated with Bafl was expected. Surprisingly, increased number of autophagolysosomes were consistently seen in Bafl-treated A-T cells as compared to the Bafl-treated ATM+ cells. (See FIGS. 11A(ii) and 11B(iv)). In contrast, more autophagosomes were seen in Bafilomycin treated ATM+ cells as compared to A-T cells. These results indicated that Bafl blocked fusion between autophagosomes and lysosomes in ATM+ cells, but failed to do so in A-T cells.

Additionally, as shown in FIGS. 11A and 11B, UV/Bafl co-treatment decreased autophagy activity in A-T cells as compared to A-T cells treated with Bafl alone. The disappearance of yellow dots representing autophagolysosomes in A-T cells indicated that UV induced autophagic flux and Bafl failed to protect autophagic flux in UV/Bafl-treated A-T cells (See FIG. 11A(ii)). Since lysosomal number and size decreases upon autophagy maturation, decrease in lysosomal dots in UV-treated A-T cells further supports that UV-mediated induction of autophagy leads to increased autophagic flux in A-T cells. Although UV/Bafl co-treatment increased autophagosomes, the number of autophagolysosomes remained unaltered in UV/Bafl-treated ATM+ cells as compared to ATM+ cells treated with Bafl alone (FIG. 11B(iv)). This result indicated that UV induced formation of autophagosomes, but Bafl blocked their fusion with lysosomes, i.e. formation of autophagolysosomes, in ATM+ cells. In addition, the unaltered number of autophagolysosomes in Bafl-treated versus UV/Bafl-treated ATM+ cells provided evidence that UV did not induce autophagic flux in Bafl-treated ATM+ cells.

Together, results using A-T and ATM+ cells revealed that: (a) UV induces aberrant degradation of the proteasome substrates in A-T cells; (b) basal autophagy is activated in A-T cells; (c) UV induces aberrant autophagic flux in A-T cells; (d) Bafilomycin blocked formation of autophagolysosomes and, consequently, autophagic flux in UV-treated ATM+ cells; and (e) Bafilomycin failed to block fusion between autophagosomes and lysosomes resulting in sustained formation of autophagolysosomes and, thus, increased autophagic flux in UV-treated A-T cells. Similar findings were observed in cells treated with another autophagy inhibitor $NH_4Cl$ in A-T cells.

Example 11

Figure 12A:
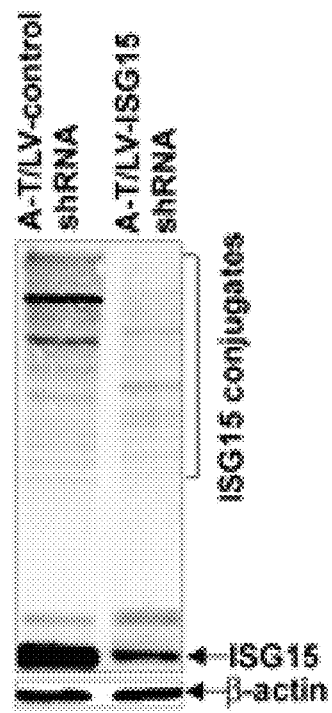
FIGS. 12A and 12B illustrate extracts of A-T/LV-control and ISG15 shRNA cells as analyzed by Western blotting for ISG15 and actin (FIG. 12A), and representative immunofluorescence images of LC3 puncta in A-T/control (left panel) and ISG15 (right panel) shRNA cells (Scale bar: 10 µM) (FIG. 12B).

Induction of Basal Autophagy is a Consequence of Constitutively Elevated ISG15 in A-T Cells As discussed herein, ISG15 siRNA was shown to restore impaired proteasome function indicating the involvement of the constitutively elevated ISG15 pathway in inhibiting the ubiquitin pathway in A-T cells. If induction of basal autophagy compensates ISG15-impaired proteasome function, ISG15 siRNA should restore the proteasome function and suppress activated autophagy in A-T cells. To test whether this is indeed the case, stable clones of FT169A (A-T) cells expressing lentiviral ISG15 shRNA (A-T/LV-ISG15 shRNA) or control shRNA (A-T/LV-control shRNA) were generated. In FIG. 12A, extracts of A-T/LV-control and ISG15 shRNA cells were analyzed by Western blotting for ISG15 and actin. The Western blot in FIG. 12A confirmed the efficient knock-down of ISG15 expression in A-T/LV-ISG15 shRNA cells.

Figure 12B:
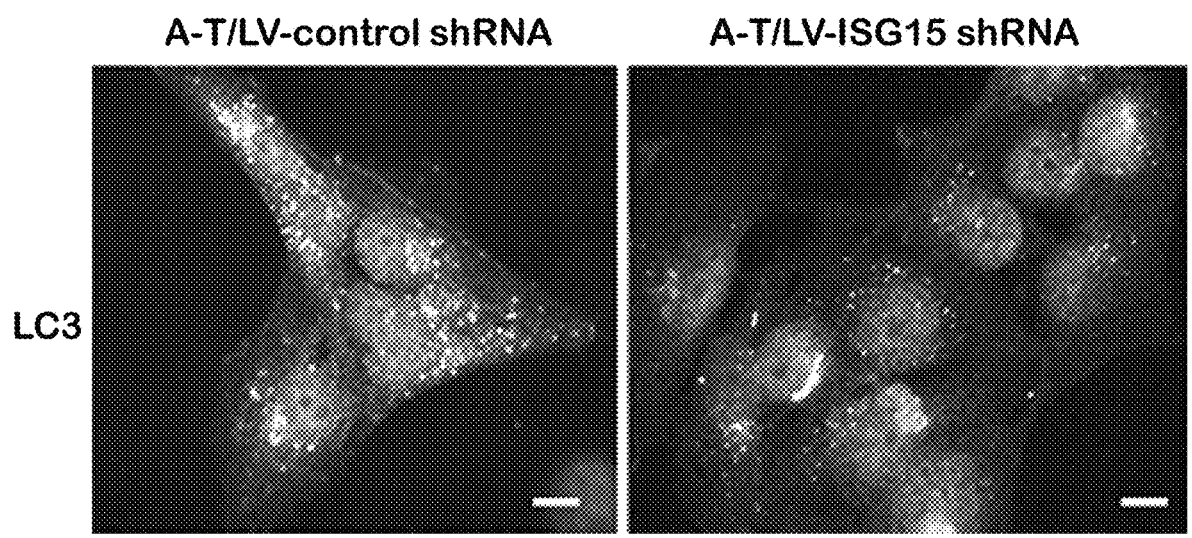

In FIG. 12B, representative immunofluorescence images of LC3 puncta in A-T/control (left panel) and ISG15 (right panel) shRNA cells are shown (Scale bar: 10 To test if the autophagy pathway is restored, LC3 puncta was measured in ISG15-silenced A-T cells. As shown in FIG. 12B, A-T/LV-control shRNA cells exhibited increased number of LC3-positive puncta (average # of 67 puncta/cell) as compared to A-T/LV-ISG15 shRNA cells (average number of 5 puncta/cell). These results revealed that basal autophagy is activated, and activated autophagy is due to the elevated expression of ISG15 in A-T cells.

To further test whether silencing of ISG15 expression attenuated autophagy, these cells were stained with Cyto-ID® and LysoTracker Red dye as described in FIGS. 9A and 9B. The same criteria were used to judge autophagic activity in immunofluorescence analysis as described in FIGS. 9A and 9B. Images of A-T/control and ISG15 shRNA cells co-stained with Cyt-ID® and LysoTracker Red® (Red; for lysosomes) dyes were made, with a yellow color in the merged images indicating autophagolysosomes. A decreased number of green and yellow dots was seen in A-T/LV-ISG15 shRNA as compared to A-T/LV-control shRNA cells, indicating attenuation of autophagic activity in A-T/ISG15-shRNA cells.

Together, immunofluorescence data using anti-LC3, Cyto-ID, and LysoTrack Red dyes revealed that, as shown herein in FT169A (A-T) cells (FIGS. 10A-10C), basal autophagic activity is increased in A-T/LV-control shRNA cells, and activated autophagy is due to the elevated expression of ISG15 in A-T/LV control cells.

Example 12

Degradation of Autophagy Substrates is Restored in the ISG15-Silenced A-T Cells

Whether ISG15 gene knock down restores autophagy and rescues UV-induced autophagic flux was assessed using A-T/LV-control/ISG15-shRNA stable clones. In FIGS. 13A-13D, A-T/LV-control and ISG15 shRNA cells were treated with Bafl (1 nM for 18 h) or left untreated. Cells were then exposed to UV (25 mJ/m2). Three hours after recovery in the presence of inhibitors, cells were lysed and lysates were analyzed by Western blotting for LC3 (FIG. 13A) and p62 (FIG. 13C), and actin (lower panels, FIGS. 13A and 13C) using their specific antibodies. Intensity of the total LC3 (LC3-I+II) and p62 proteins was quantitated using BioRad Quantity One software, and the results shown in FIGS. 13B and 13D. FIGS. 13B and 13D show average values (±SEM)

of % degradation of LC3 and p62 from three independent experiments. All control values (−UV and + Bafl) are normalized to 100%, and values for experimental treatments were expressed as percent variations over control.

Figure 13A:
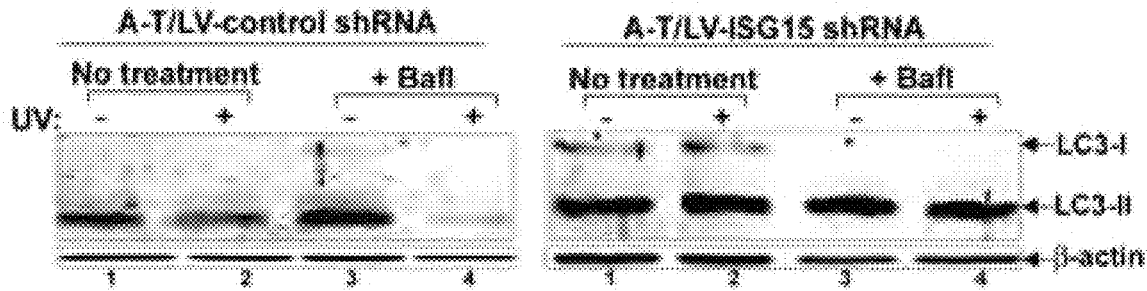
FIGS. 13A-13D illustrate Western blot analysis of A-T/LV-control and ISG15 shRNA cells treated with Bafl or left untreated, and then exposed to UV. Three hours after recovery in the presence of inhibitors, cells were lysed and lysates were analyzed by Western blotting for LC3 (FIG. 13A) and p62 (FIG. 13C), and actin (lower panels for FIGS. 13A and 13C) using their specific antibodies. Intensity of the total LC3 (LC3-I+II) and p62 proteins was quantitated using BioRad Quantity One software. The bar graphs in (FIGS. 13B and 13D) show average values (±SEM) of % degradation of LC3 and p62 from three independent experiments. All control values (−UV and + Bafl) are normalized to 100%, and values for experimental treatments were expressed as percent variations over control.
Figure 13B:
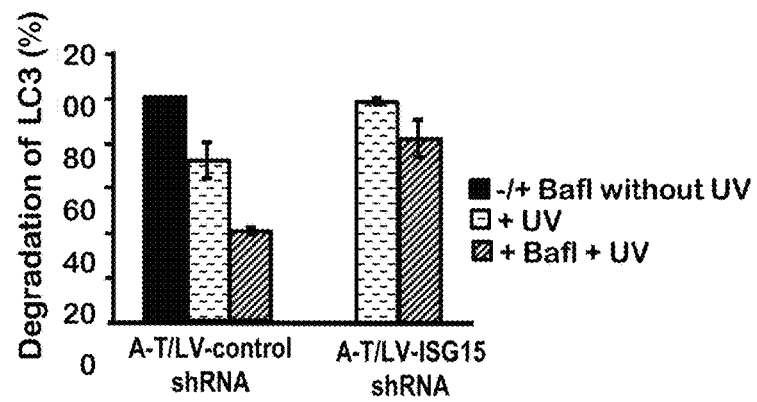
Figure 13C:
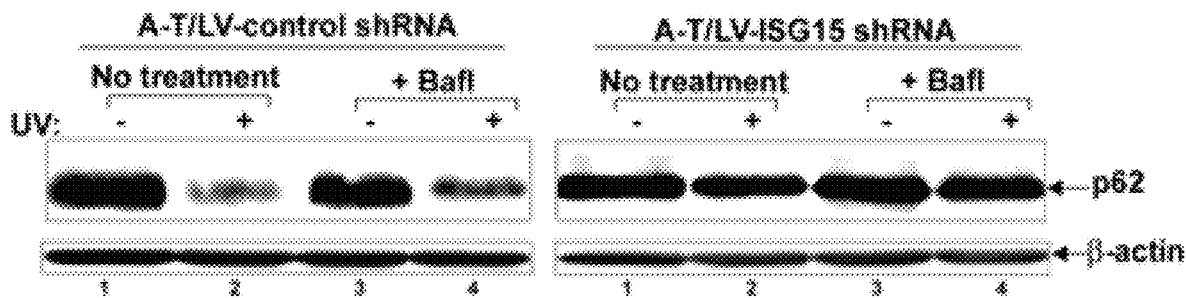
Figure 13D:
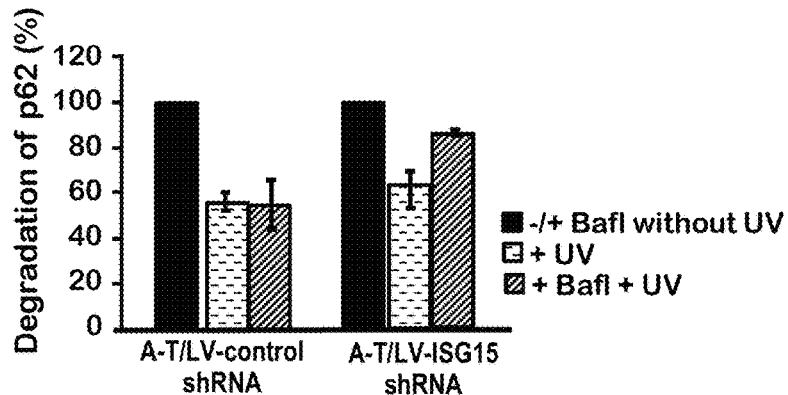

As shown in FIGS. 13A-13D, UV also was found to induce MG132 and Bafl-resistant degradation of LC3 and p62 in A-T/control-shRNA cells but not in A-T/ISG15-shRNA cells (FIGS. 13A and 13C). The bar graph in FIGS. 13B and 13D show average (±SEM) degradation of LC3 (LC3-I and II) and p62 proteins in UV-exposed A-T/LV-control/ISG15 shRNA cells treated with Bafl from three independent experiments. These results further revealed that the constitutively elevated ISG15 pathway contributes to the UV-induced aberrant autophagic flux in A-T cells.

Autophagic flux was also assessed using Cyto-ID® and LysoTrack Red dyes as described herein in FIGS. 9A, 9B, and 11. The same criteria were used to judge autophagic activity in immunofluorescence analysis as described for FIGS. 11A and 11B. UV induced disappearance of autophagosomes (green dots) and autophagolysosomes (yellow dots) in bafilomycin untreated (mean # of green dots/cell=4.6 vs. 1.8 and mean # of yellow dots/cell=3.8 vs. 1) and treated [mean # of green dots/cell=6 vs. 0.8 and mean # of yellow dots/cell=5.8 vs. 1.5] A-T/control shRNA cells. (Color images not shown) Since disappearance of autophagolysosomes indicates increased autophagic flux, these results indicated that Bafilomycin failed to protect UV-mediated autophagic flux in A-T/LV-control shRNA cells.

Figure 14A:
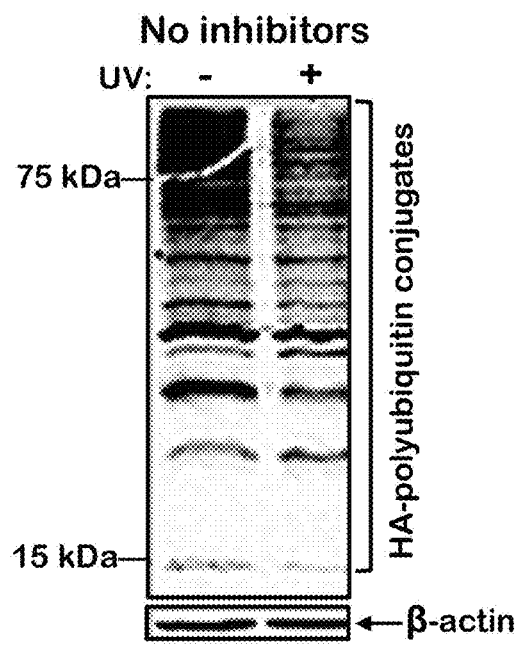
FIG. 14A illustrates HA-ubiquitin-transfected A-T/LV-control shRNA cells exposed to UV. After three hours of recovery, assessment of HA-polyubiquitylated proteins was carried out as described for FIG. 8B.
Figure 14B:
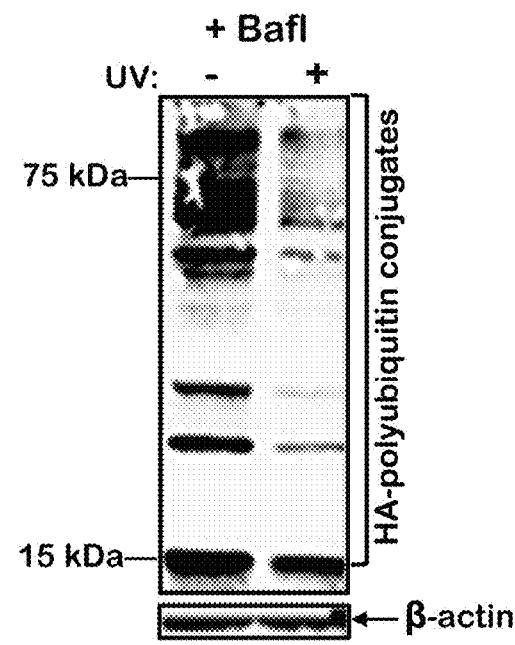
FIG. 14B illustrates HA-ubiquitin-transfected A-T/LV-control shRNA cells treated with Bafl, and then exposed to UV. After three hours of recovery in the presence of the inhibitor, assessment of HA-polyubiquitylated proteins was conducted as in FIG. 8B.

For FIG. 14A, HA-ubiquitin-transfected A-T/LV-control shRNA cells were exposed to UV (25 mJ/m2). After three hours of recovery, assessment of HA-polyubiquitylated proteins was carried out as described herein for FIG. 8B. In FIG. 14B, HA-ubiquitin-transfected A-T/LV-control shRNA cells were treated with Bafl (1 nm for 18 h). Cells were then exposed to UV (25 mJ/m2). After three hours of recovery in the presence of the inhibitor, assessment of HA-polyubiquitylated proteins was carried out as described for FIG. 14A. For FIG. 14C, HA-ubiquitin-transfected A-T/LV-control shRNA cells were treated with MG132 (1 nm for 18 h). Cells were then exposed to UV (25 mJ/m2). After three hours of recovery in the presence of the inhibitor, assessment of HA-polyubiquitylated proteins was carried out as described for FIG. 14A. For FIG. 14D, HA-ubiquitin-transfected A-T/LV-control shRNA cells were treated with 3-MA (10 nm for 18 h). Cells were then exposed to UV (25 mJ/m2). After three hours of recovery in the presence of the inhibitor, assessment of HA-polyubiquitylated proteins was carried out as described for FIG. 14A. All experiments shown in FIGS. 14A-14D were performed at least three times and yielded similar results.

Figure 14C:
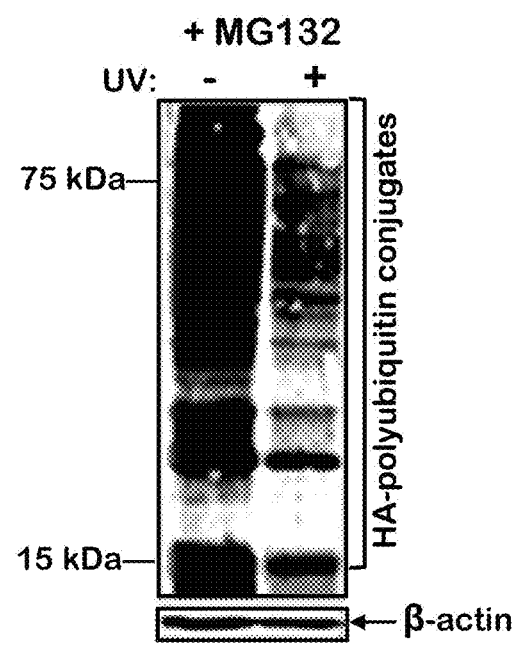
FIG. 14C illustrates HA-ubiquitin-transfected A-T/LV-control shRNA cells treated with MG132, and then exposed to UV. After three hours of recovery in the presence of the inhibitor, assessment of HA-polyubiquitylated proteins was carried out as described in FIG. 8B.

Using Western blot analysis, UV treatment was shown to induce degradation of HA-polyubiquitylated proteins in Bafilomycin-untreated (FIG. 14A)/treated (FIG. 14B) A-T/LV-control cells. This degradation was not due to the proteasome as MG132, a proteasome inhibitor failed to block UV-mediated degradation of proteins in A-T/LV-control shRNA cells (FIG. 14C).

Figure 14D:
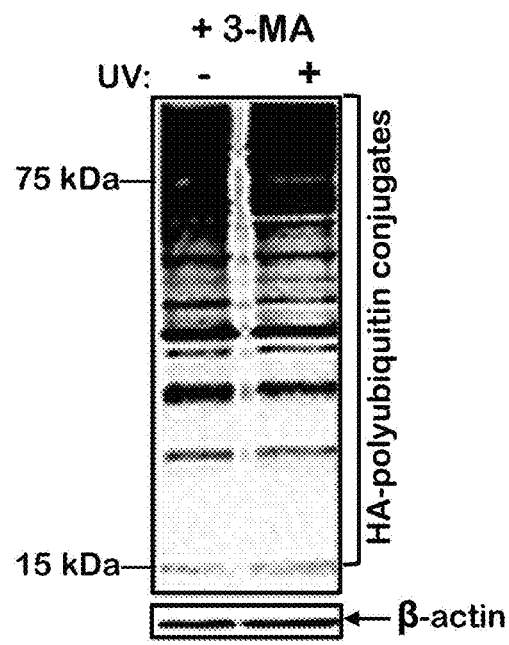
FIG. 14D illustrates HA-ubiquitin-transfected A-T/LV-control shRNA cells treated with 3-MA, and then exposed to UV. After three hours of recovery in the presence of the inhibitor, assessment of HA-polyubiquitylated proteins was carried out as described in FIG. 8B. All experiments shown in FIGS. 14A-14D were performed at least three times and yielded similar results.

Bafilomycin inhibits autophagy at a late stage (47). Whether 3-methyl adenine (3-MA), an autophagy inhibitor known to inhibit autophagy at early stage by inhibiting formation of autophagosomes (56), could block UV-induced autophagic flux was tested in A-T/LV-control shRNA cells. Using Cyto-ID® and LysoTrack Red dyes as described herein in FIGS. 9A, 9B, 11A and 11B, the same criteria were used to judge autophagic activity in immunofluorescence analysis as described for FIGS. 11A and 11B. A marked decrease in both green (mean dots/cell=4.6 vs. 0.16) and yellow (mean dots/cell=3.8 vs. 0.5) dots was seen, indicating decreased formation of autophagosomes and autophagolysosomes in 3-MA-treated A-T/LV-control shRNA cells. Moreover, both green dots and yellow dots remained unaltered in A-T/LV-control shRNA cells co-treated with 3-MA and UV These results indicated that 3-MA blocked autophagic activity and UV-mediated autophagic flux in A-T/LV-control shRNA cells. Consistent with these results, using Western blot analysis, UV-induced degradation of HA-polyubiquitylated proteins was markedly blocked in 3-MA/UV-treated A-T/LV/control shRNA cells (FIG. 14D). These results using 3-MA and Bafilomycin reveal that UV over-activates autophagy in A-T cells. Bafilomycin is unable to block the over-activated autophagy leading to aberrant autophagic flux in A-T cells. In contrast, 3-MA that inhibits autophagosome formation markedly blocked autophagic flux in A-T cells.

The effect of 3-MA on UV-induced autophagic flux was tested in A-T/LV-ISG15 shRNA cells. A-T/LV-ISG15 shRNA cells were either left untreated or treated with 3-MA (10 nM for 18 h), and cells were then exposed to UV (25 mJ/m2). Three hours after recovery in the presence of the inhibitor, cells were co-stained with Cyt-ID® and LysoTracker Red® dyes. Fluorescence images of Cyt-ID® and LysoTracker Red® stained cells were made. No apparent change was noted in autophagic activity in ISG15-silenced A-T and 3-MA-treated ISG15-silenced A-T cells exposed to UV.

Figure 15A:
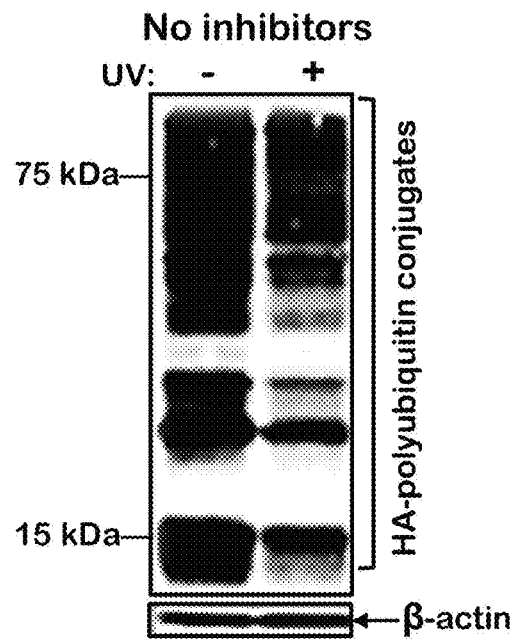
FIG. 15A illustrates HA-ubiquitin-transfected A-T/LV-ISG15 shRNA cells exposed to UV. After three hours of recovery, assessment of HA-polyubiquitylated proteins was carried out as described in FIG. 8B.

In FIG. 15A, HA-ubiquitin-transfected A-T/LV-ISG15 shRNA cells were exposed to UV (25 mJ/m2). After three hours of recovery, assessment of HA-polyubiquitylated proteins was carried out as described as herein for FIGS. 8A-8E. For FIG. 15B, HA-ubiquitin-transfected A-T/LV-ISG15 shRNA cells were treated with 3-MA (10 nm for 18 h). Cells were then exposed to UV (25 mJ/m2). After three hours of recovery in the presence of the inhibitor, assessment of HA-polyubiquitylated proteins was carried out as described herein. For FIG. 15C, HA-ubiquitin-transfected A-T/LV-control shRNA cells were treated with MG132 (1 nm for 18 h). Cells were then exposed to UV (25 mJ/m2). After three hours of recovery in the presence of inhibitor, assessment of HA-polyubiquitylated proteins was carried out as described. All experiments shown in FIGS. 15A-15C were performed at least three times and yielded similar results.

Figure 15B:
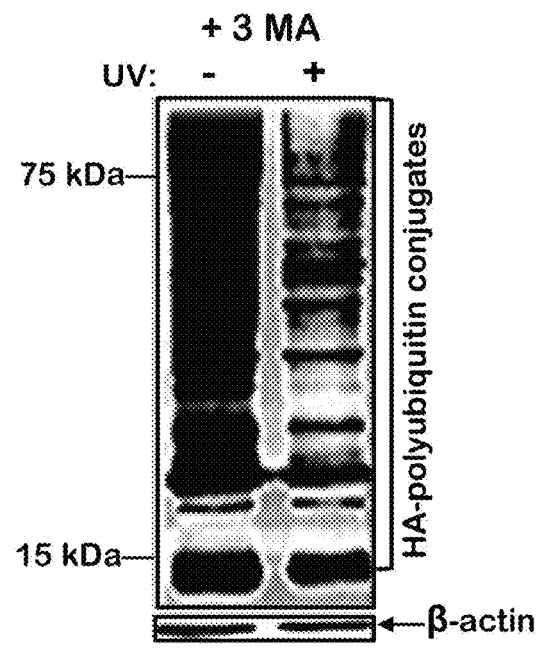
FIG. 15B illustrates HA-ubiquitin-transfected A-T/LV-ISG15 shRNA cells treated with 3-MA, and then exposed to UV. After three hours of recovery in the presence of the inhibitor, assessment of HA-polyubiquitylated proteins was carried out as described in FIG. 8B.
Figure 15C:
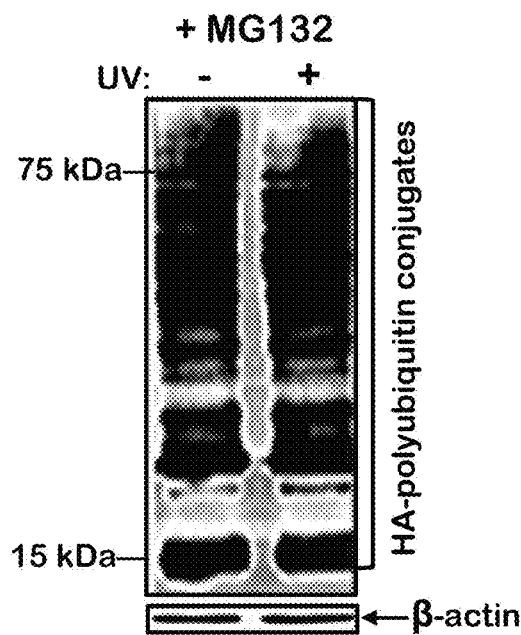
FIG. 15C illustrates HA-ubiquitin-transfected A-T/LV-control shRNA cells treated with MG132, and then exposed to UV. After three hours of recovery in the presence of inhibitor, assessment of HA-polyubiquitylated proteins was carried out as described in FIG. 8B. All experiments in FIGS. 15A-15C were performed at least three times and yielded similar results.

Although autophagy was attenuated, UV induced degradation of HA-polyubiquitylated proteins in both 3MA untreated and treated ISG15-silenced cells (FIGS. 15A and 15B). Without wishing to be bound by this theory, it is believed that the degradation of HA-polyubiquitylated proteins is due to the restoration of proteasome function in ISG15-silenced A-T cells. Indeed, the MG132 proteasome inhibitor was found to completely block degradation of HA-polyubiquitylated proteins, indicating that UV-mediated degradation of HA-polyubiquitylated proteins in 3-MA-treated A-T cells was due to their degradation via the proteasome in ISG15-silenced A-T cells.

These results indicate that autophagy is activated in A-T cells presumably to compensate for the impaired proteasome function in A-T cells. Genotoxic stress over-activates this compensatory mechanism, triggering aberrant autophagic flux in A-T cells. 3-MA attenuated over-activated autophagy and resulted in attenuation of autophagic flux in genotoxin-treated autophagy.

Example 13

The Autophagy Pathway is Activated in Brains of Human A-T Patients—

Astroglial cell dysfunction has been implicated in the pathogenesis of various neurological disorders, (57) and ISG15 is elevated in A-T astrocytes as shown herein. Evidence of autophagy induction was assayed in the A-T human brains. The deparaffinized human brain tissue sections from the normal subject and A-T patient were double stained with anti-LC3- and anti-GFAP-specific antibodies (scale bar: 100 µm), as described herein. A dramatic increase in both LC3 (autophagy marker)/GFAP (astrocytes marker) double-positive stained inclusions was seen in the mid-brain sections obtained from the A-T patient. Although LC3/GFAP inclusions were also present in brain sections of the normal individual, the intensity of the LC3/GFAP double-positive staining was much higher in the brain section A-T patient as compared to the normal individual. Similar increases in the LC3/GFAP double-positive staining were noted in the brain sections of the two other A-T patients.

Figure 16:
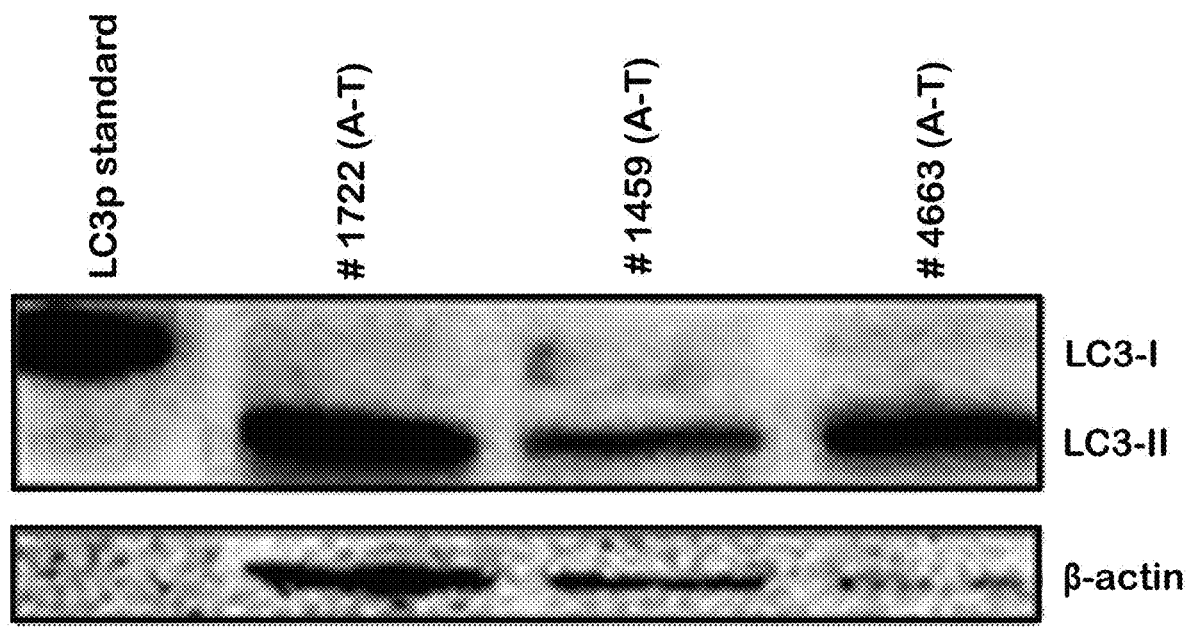
FIG. 16 illustrates Western blot analysis using anti-LC3 antibodies of frozen mid-brain postmortem tissue lysates from human brains of A-T patients. Positive control for anti-LC3 protein (HA-tagged) (MBL International) was loaded in lane 1.

Tissue lysates of mid-brain regions (specifically containing substantia nigra) obtained postmortem from A-T human patients with confirmed A-T disease were examined for autophagy induction by Western blotting using anti-LC3 antibodies. Frozen mid-brain postmortem tissue lysates were analyzed by Western blotting using anti-LC3 antibodies. Positive control for anti-LC3 protein (HA-tagged) (MBL International) was loaded in lane 1. The results are shown in FIG. 16. The presence of LC3-II form in brain tissue lysates is indicative of a strong induction of autophagy in these patients, as LC3-II form is an indicator of an active autophagy. Together, these results indicate that autophagy is aberrantly activated in A-T patients.

The herein results are relevant for improving the health status of A-T patients who are constantly exposed to environmental genotoxic agents such as sunlight, viral infections, high temperature, and human made mutagenic chemicals during their life time. In addition, A-T patients are vulnerable to oxidative stress (69) which can lead to protein damage. Without wishing to be bound by this theory, I believe that genotoxic agents and oxidative stress can induce autophagic stress in A-T neurons which, in turn, leads to their autophagic death. Previously, the hypersensitivity to the genotoxic stress has been principally linked to defective DNA repair in A-T. The results indicate that, in addition to the deregulated DNA repair, deregulation of the protein turnover in part contributes to the genotoxic stress-mediated hypersensitivity in A-T patients. Knowing that constitutively elevated ISG15 is causally related to the deregulation of both the major protein turnover pathways in A-T fibroblast cells allows targeting the ISG15 pathway to reduce neurodegeneration and ataxia associated with it in A-T patients. In addition, attenuating autophagy with pharmacological inhibitors of autophagy (e.g. 3-MA) can prevent neurodegeneration in A-T.

Example 14

Use of A-T Models

Past studies demonstrate that astrocytes are important players in various neurological disorders. As shown herein, the autophagy marker LC3 was elevated in human A-T astrocytes. In addition, ISG15 is elevated in A-T astrocytes obtained from A-T knockout mice. These results indicate that ISG15-mediated defective turnover of proteins in A-T astrocytes could lead to astrocyte death which in turn could lead to non-cell-autonomous cerebellar neuronal cell death in A-T. Using A-T mouse model (ex vivo and in vivo), the genotoxins-induced ISG15-mediated defects in the protein turnover pathways (ISG15 proteinopathy) will be shown to contribute to A-T neurodegeneration. I will develop $Atm^{-/-}$/$ISG15^{-/-}$ and $Atm^{-/-}$/GFP-LC3 double knockout mouse models to be used to test the role of ISG15 and autophagy in A-T neurodegeneration. Both mice models will be useful to understand the molecular mechanism(s) underlying neurodegeneration in A-T.

$Atm^{-/-}$ mice do not show obvious neuropathology, and this apparent lack of neuropathology acts as an obstacle in studying neurodegeneration in $Atm^{-/-}$ mice. The concept that the genotoxic stress is needed to trigger ISG15 proteinopathy-induced neurodegeneration in $Atm^{-/-}$ mice will be tested. These results will allow for the use of $Atm^{-/-}$ mice for studying neurodegeneration. Also, experiments will be run to confirm that ISG15, which is elevated in A-T astrocytes, consequently impairs astrocyte function; impaired astrocyte function in turn leads to non-autonomous A-T cerebellar neuronal cell death.

Currently there is no cure or preventive therapy for A-T disease. Knowing that the constitutively elevated ISG15 pathway is causally related to the deregulation of both the major protein turnover pathways in A-T cells, a cause of neurodegeneration in A-T, provides targets for development of inhibitors to target the ISG15 pathway to reduce neurodegeneration and prevent or reduce ataxia associated with neurodegeneration. Small molecular inhibitors targeting the ISG15 pathway could be developed and tested using the model system for protein turnover in A-T cells.

Analysis of the Autophagy Substrates Using Fluorescence Microscopy:

To monitor autophagy in cerebellar astrocytes (in tissue sections), brain sections will be co-immunostained for p62 and/or LC3, both autophagy substrates and markers, together with the astrocytes cell-specific marker GFAP or calbindin. To monitor autophagy in cerebellar neurons (in tissue sections), brain sections will be co-immunostained for p62 and/or LC3, together with the neuronal-specific marker Neu-N.

Analysis of Autophagy Substrates and ISG15 Using Immunoblotting.

A-T mice and human brain sections, cells, and serum will be processed for the detection of ISG15 and autophagy markers using Western blotting analysis.

Autophagy Organelles Using Transmission Electron Microscopy:

The autophagic organelles [autophagosomes (double-membrane structures containing undigested cytoplasmic contents, which have not fused with a lysosome), and autophagolysosomes (a single limiting membrane structures that contains cytoplasmic materials at various stages of degradation)] will be analyzed using electron microscopy.

Tissue Fractionation:

Endogenous p62 becomes Triton X-100-insoluble in the presence of protein aggregates, a characteristic of neurodegenerative diseases. Triton X-100-insoluble proteins isolated from A-T human and mice brain sections will be analyzed using anti-p62 antibodies in Western analysis.

Quantitation of Autophagy:

The number of LC3- and/or LysoTracker-positive puncta/total intensity of the stain in brain slices will be quantitated using image J software. Western blotting results will be quantitated using BioRad and/or Kodak data analysis software.

The Ex Vivo Organotypic Brain Slice Culture Model:

Several studies show that neuronal morphology, cellular, and anatomical relations and network connections are maintained in organotypic brain slice cultures. The organotypic brain slices obtained from A-T knockout mice have been used by others to examine the ATM-mediated DNA damage response in murine cerebellar neurons. This study demonstrated that ATM is autophosphorylated in the nuclei after DNA damage (X-ray irradiation) in ATM+, but not in A-T mouse brain slices. This result reveals that the DNA damage repair response pathway is intact in the organotypic brain slice cultures, and demonstrates the feasibility of using this ex vivo model for analysis of the ISG15 and autophagy pathways (presence/absence of putative ISG15 pathway inhibitors). There are three major advantages of using this ex-vivo model: a) it will reduce the number of experimental animals; b) it will generate quick information on whether genotoxic stress indeed induces neurodegeneration in A-T mice; and c) it will establish organotypic A-T brain slices as an ex vivo model to test the efficacy of potential drugs (e.g. small molecule inhibitors targeting the ISG15 pathway) in preventing A-T neurodegeneration.

Culturing of the Organotypic Brain Slices:

Organotypic brain slices will be prepared and maintained in culture. In brief, A-T and wild type mice (one-four weeks old) will be anesthetized and decapitated. The brain tissue will be removed and dissected in Hanks' balanced salt solution-based medium. Brain slices (400 μm thick) will be obtained using a McIlwain tissue chopper (The Mickle Lab Eng. Co. Ltd). Slices will be placed on Millicell culture plate inserts (Millipore, Mass.) and incubated for 3 days in OptiMem-based medium at 37° C. in a humidified atmosphere of 5% $CO_2$ and 95% air. Inserts will then be transferred and maintained in neurobasal medium. Slices will be used for experiments after 4 to 7 days in culture. This procedure has previously been standardized in the lab.

Postmortem examination of A-T patients showed significant loss of Purkinje cells in the cerebellum. The alpha synuclein inclusions were also found in the substantia nigra of Atm mice. In addition, the ISG15/ubiquitin/LC3 inclusions were found in the midbrain regions (containing substantia nigra tissues) obtained from A-T human patients. Ex vivo brain slices of cerebellum and midbrain regions of the A-T and wild type mice will be used to monitor "protein inclusions" and neurodegeneration in $Atm^{-/-}$ mice.

Assessing Neurodegeneration.

Brain Slices will be prepared for immunofluorescence analysis using MTT, anti-tyrosine hydroxylase (substantia nigra neurons), anti-calbindin (cerebellum neurons) (for survived neurons) and Fluoro Jade B (for degenerating neurons). In addition, propidium iodide uptake and lactate dehydrogenase efflux will be measured to assess neuronal cell death.

Assessing Serum Levels of ISG15:

Serum levels of ISG15 in mice and human A-T patients will be assessed using ELISA assays.

Example 15

UV-Induces Bafilomycin-Resistant Degradation of Polyubiquitylated Proteins in Organotypic Cerebellar Brain Slices Grown in Culture Experiments were conducted to determine if UV would induce degradation of the ubiquitin-conjugated cellular proteins in A-T organotypic brain slices grown in culture, similar to the findings described herein for A-T cells (See FIGS. 8A-8B). Two-month-old mice were used irrespective of the gender. Cerebellar organotypic brain slices (400 μm thick) from three mice were obtained using a McIlwain tissue chopper (The Mickle Lab Eng. Co. Ltd). Slices from two A-T mice and three ATM+/– mice were pooled and randomly placed on Millicell culture plate inserts (Millipore, Mass.). Brain slices were then incubated for 1 day in OptiMem-based medium at 37° C. in a humidified atmosphere of 5% CO2 and 95% air. One day later, slices were treated with Bafilomycin A1 for 18 hrs. Slices were then exposed to UV (150 mJ)) or left untreated. After three hours, tissue lysates were prepared as described herein. Lysates were then analyzed by Western analysis using anti-ubiquitin antibody as described herein, and the results shown in FIG. 17A. Intensity of the total polyubiquitylated proteins and free ubiquitin was quantitated using BioRad Quantity One software. All control values (–UV and + Bafl) were normalized to 100%, and values for experimental treatments were expressed as percent variations over control to give the results shown in FIG. 17B. In the bar graphs in FIG. 17B, the labels for both A-T and ATM+/– are the following: bar 1: No drug and + Bafl controls; bar 2:+UV; and bar 3: + Bafl+UV.

Figure 17A:
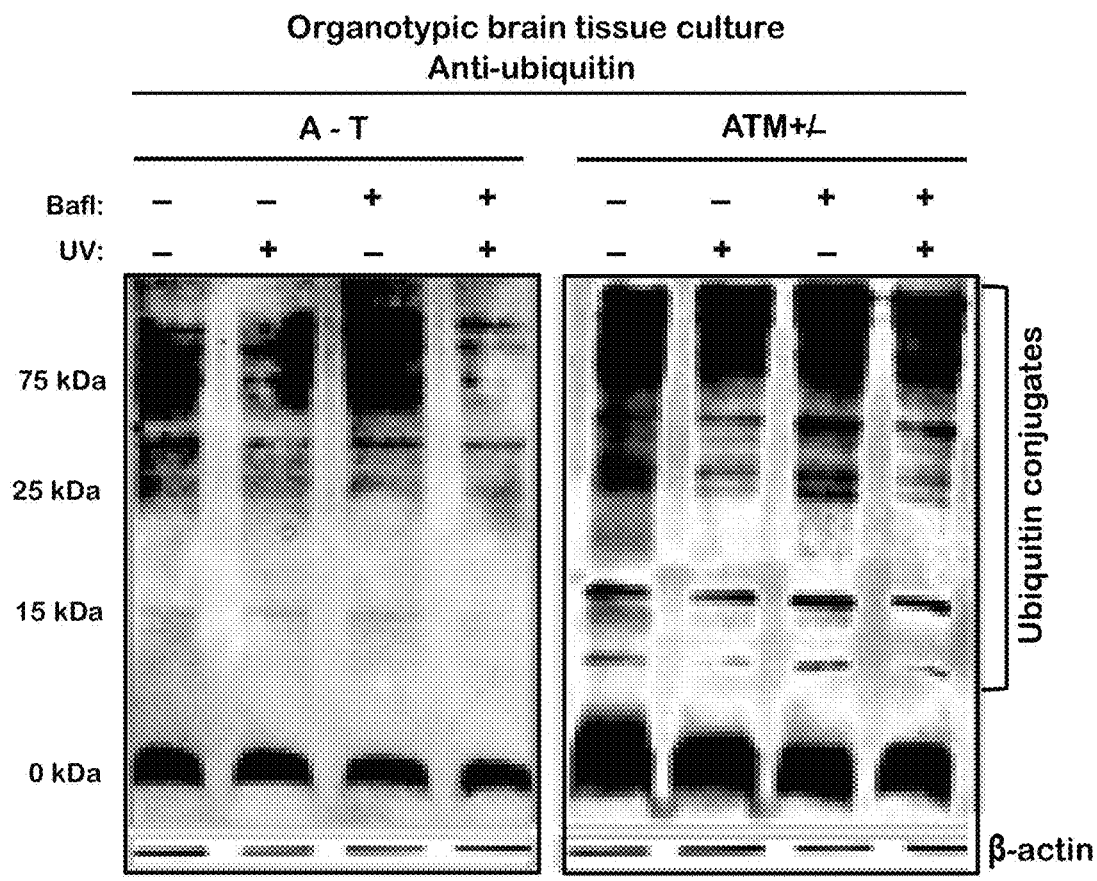
FIG. 17A-17B illustrate cerebellar organotypic brain slices from Atm knockout (A-T) and hetero (ATM+/−) mice incubated for 1 day in OptiMem-based medium at 37° C. in a humidified atmosphere of 5% CO2 and 95% air, then treated with Bafilomycin A1 for 18 hrs. Slices were then exposed to UV or left untreated. After three hours, tissue lysates were prepared and analyzed by Western analysis using anti-ubiquitin antibody (FIG. 17A). Intensity of the total polyubiquitylated proteins and free ubiquitin was quantitated using BioRad Quantity One software, and the results shown in FIG. 17B. All control values (−UV and + Bafl) are normalized to 100%, and values for experimental treatments were expressed as percent variations over control.
Figure 17B:
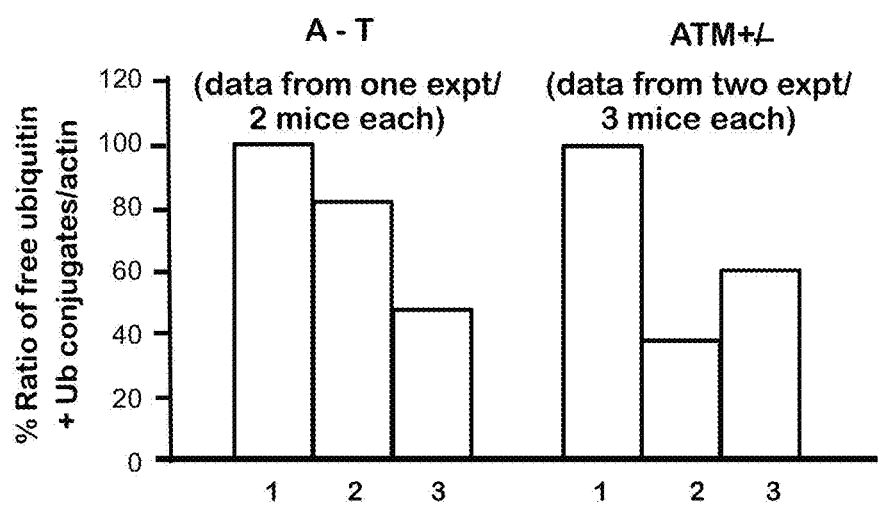

As shown in FIG. 17A (left panel), Bafilomycin failed to protect UV-mediated degradation of polyubiquitylated proteins in A-T brain slices. In contrast, similar to ATM+ cells, Bafilomycin markedly protected UV-induced degradation of polyubiquitylated proteins in ATM+/– brain slices (right panel). These results indicate that genotoxic stress induces bafilomycin-resistant aberrant autophagic flux (degradation) of polyubiquitylated proteins in the ubiquitin pathway ablated A-T cells, and in the cerebellar brain tissue. FIGS. 8A and 8B show that ISG15 inhibits polyubiquitylation of cellular proteins in A-T cells. A similar decrease in the endogenous polyubiquitylated proteins is seen in A-T compared to ATM+/– mice brains (FIG. 17A, compare lane 1 of A-T and ATM+ panels). Hence, similar to A-T cells, polyubiquitylation is also defective in A-T mice brains. Polyubiquitylation is a prerequisite for degradation of cellular proteins via the proteasome. Because polyubiquitylation is defective, degradation of cellular proteins is impaired in A-T cells. ISG15-mediated proteinopathy leads to accumulation of neuronal proteins which in turn leads to neuronal cell death in A-T.

Example 16

UV Induces Massive Autophagy in A-T Cells and the Organotypic Mice Brain Slices.

To determine whether UV induces autophagy in ATM+ cells and ATM+/– organotypic cerebellar brain slices grown in culture, the following experiment was conducted. ATM+ cells were cultured on fibronectin-coated glass coverslips. Cells were then exposed to UV radiation and allowed to recover for 3 hrs. Cells were then washed (2×1 min) with PBS and stained with Cyt-ID® (Cyt-ID® Autophagy Detection Kit from Enzo Lifesciences) for 30 min at 37° C. in a $CO_2$ incubator following manufacturer's protocol. Stained cells were then washed (2×1 min) with PBS and fixed with 4% paraformaldehyde for 20 min at room temperature. After washing with PBS (3×10 min), cells were mounted on slides in anti-fade mounting medium with DAPI (Invitrogen). Images were taken using a 63× oil immersion objective with a Leica DMRA2 upright microscope run through SlideBook software (Intelligent Imaging Innovations). The results are shown in FIG. 18A.

In addition, UV induced autophagy in ATM+/– brain slices grown in culture. Using Immunofluorescence analysis, organotypic cerebellar brain slices were prepared as described herein in Example 15. Slices were then exposed to UV radiation and allowed to recover for 3 hrs. Slices were washed with PBS (2×5 min) and immunostained for LC3 (MBL International Corporation) for 1 h at room temperature. After washing with PBS (2×5 min), cells were incubated with Alexa-Fluor 488 goat anti-mouse IgG secondary antibody (1:100) (Invitrogen) for 1 h. Brain slices were then washed with PBS and mounted on slides in anti-fade mounting medium with DAPI (Invitrogen). Images were taken using a 63× oil immersion objective with a Leica DMRA2 upright microscope run through SlideBook software (Intelligent Imaging Innovations). The experiments have been repeated twice, and the results were reproducible. Representative images are shown in FIG. 18B.

UV induces autophagy in ATM+/− brain slices grown in culture as shown in FIG. 18C. Using Western analysis, organotypic brain slices were prepared as described herein. Slices were then exposed to different doses of UV and allowed to recover for 3 h. After 3 h, tissue lysates were prepared as described herein. Lysates were then analyzed by Western analysis using LC3 and actin-specific antibodies as described herein. Intensity of the total LC3 and corresponding actin bands was quantitated using BioRad Quantity One software. The amounts of LC3 on the blots were calculated as a ratio between band intensities of LC3 (I and II) and actin and the results shown in the bar chart. UV induced autophagy in ATM+ cells (FIG. 18A), and ATM+/− cerebellar brain slices (FIG. 18B-18C). Consistent with the immunofluorescence analysis (FIG. 18B), LC3 protein expression was also increased in ATM+/− brain tissue lysates in Western analysis (FIG. 18C). The effect of UV on autophagy in A-T brain slices grown in culture will also be assayed.

Example 17

UV-Induces Bafilomycin-Resistant Degradation of Autophagy Substrate LC3 in A-T Mice Brain Slices Grown in Culture.

Figure 19A:
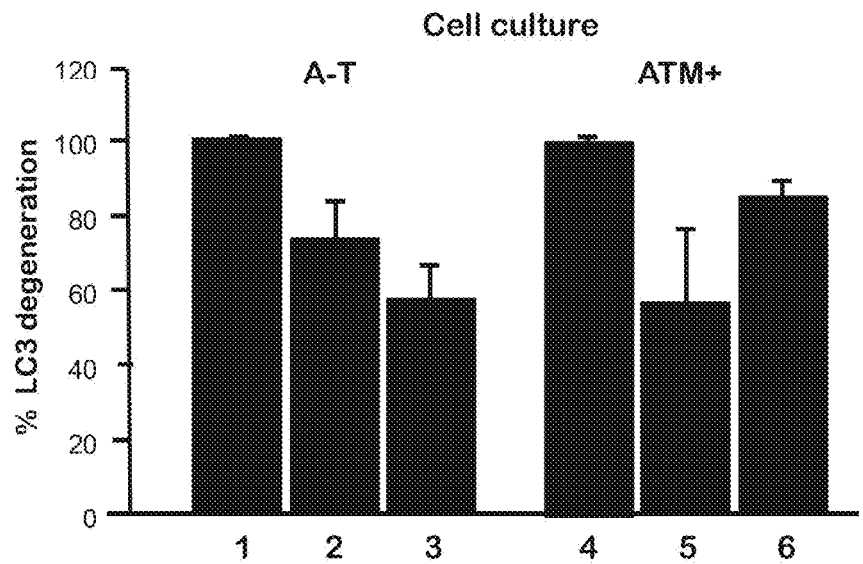
FIG. 19A illustrates A-T and ATM+ cells either left untreated or treated with the autophagy inhibitor Bafilomycin A1 for 18 h, and then exposed to UV radiation or left untreated. Cells were then allowed to recover in the presence of inhibitors for additional three hours. Cell lysis, SDS-PAGE, and immunoblotting analysis to detect LC3 was carried out. Intensities of the total LC3 bands were quantitated using BioRad Quantity One software, and the results shown in FIG. 19A. The bar graph shows average values (±SE) of % degradation of LC3 measured from three independent experiments.

UV induces aberrant degradation of autophagy substrate LC3 in A-T cells and brain slices. In FIG. 19A, LC3 degradation in UV-treated A-T cells is shown. A-T and ATM+ cells were either left untreated or treated with the autophagy inhibitor Bafilomycin A1 (1 nM) for 18 h. Cells were then exposed to UV radiation (25 mJ) or left untreated. Cells were then allowed to recover in the presence of inhibitors for additional 3 h. Cell lysis, SDS-PAGE, and immunoblotting analysis to detect LC3 were carried out as described herein. Intensities of the total LC3 bands were quantitated using BioRad Quantity One software. The bar graph in FIG. 19A shows average values (±SE) of % degradation of LC3 measured from three independent experiments.

Figure 19B:
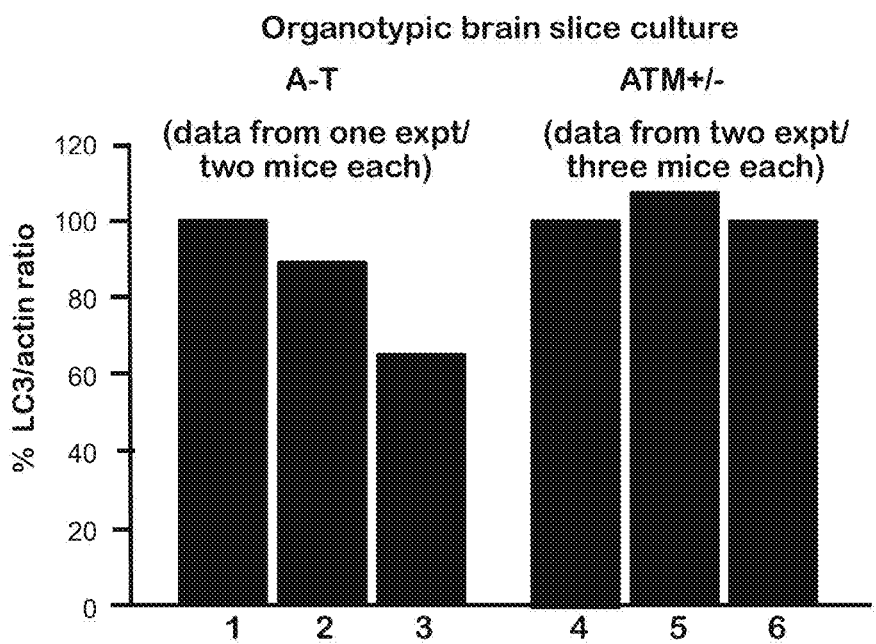
FIG. 19B illustrates tissue lysates prepared from A-T and ATM+/− brains described for FIG. 17A that were analyzed for LC3 and actin proteins. Intensity of the total LC3 and corresponding actin bands was quantitated using BioRad Quantity One software, and the results shown in FIG. 19B. The percent changes in LC3 amounts were calculated as a ratio between band intensities of LC3 (I and II) and actin (bar chart).

In FIG. 19B, LC3 degradation in UV-treated A-T brain slices is shown. The same tissue lysates prepared from A-T and ATM+/− brains used in FIG. 17A were analyzed for LC3 and actin proteins. Intensity of the total LC3 and corresponding actin bands was quantitated using BioRad Quantity One software. The percent changes in LC3 amounts were calculated as a ratio between band intensities of LC3 (I and II) and actin (bar chart). In FIGS. 19A and 19B, the bar graphs have the following legends: bars 1: No drug and + Bafl controls; bars 2:+UV; and bars 3: + Bafl+UV.

Result shown in FIGS. 19A and 19B indicate that similar to A-T cells (FIG. 19A, compare lanes 1 and 2) genotoxic stress induces bafilomycin-resistant aberrant autophagic flux (degradation) of autophagy substrates in A-T cerebellar brain slices (FIG. 19B, compare lanes 1 and 3) grown in culture. In contrast, Bafilomycin protected UV-induced autophagic flux in both ATM+ cells (FIG. 19A, compare lanes 4 and 6) and ATM+/− cerebellar slices (FIG. 19B, compare lanes 4 and 6).

Example 18

Elevated ISG15 Expression Causes Defective Mitophagy

Mitochondrial dysfunction due to oxidative stress is associated with various neurological disorders such as Parkinson's, Alzheimer's (76-78), and also implicated in A-T neurodegeneration (51, 79). Defective mitophagy, a selective form of autophagy that degrades abnormal mitochondria, was shown responsible for mitochondrial dysfunction in A-T (51, 79). Other mitochondrial abnormalities seen in A-T cells were elevated reactive oxygen species, increased aberrant mitochondria, high cellular respiratory capacity, and decreased mitophagy (51). As shown herein, it has been demonstrated that autophagy is activated, and autophagy is deregulated in response to genotoxic stress in A-T cells. In addition, as shown herein, autophagy was restored in ISG15-silenced A-T cells.

Figure 20:
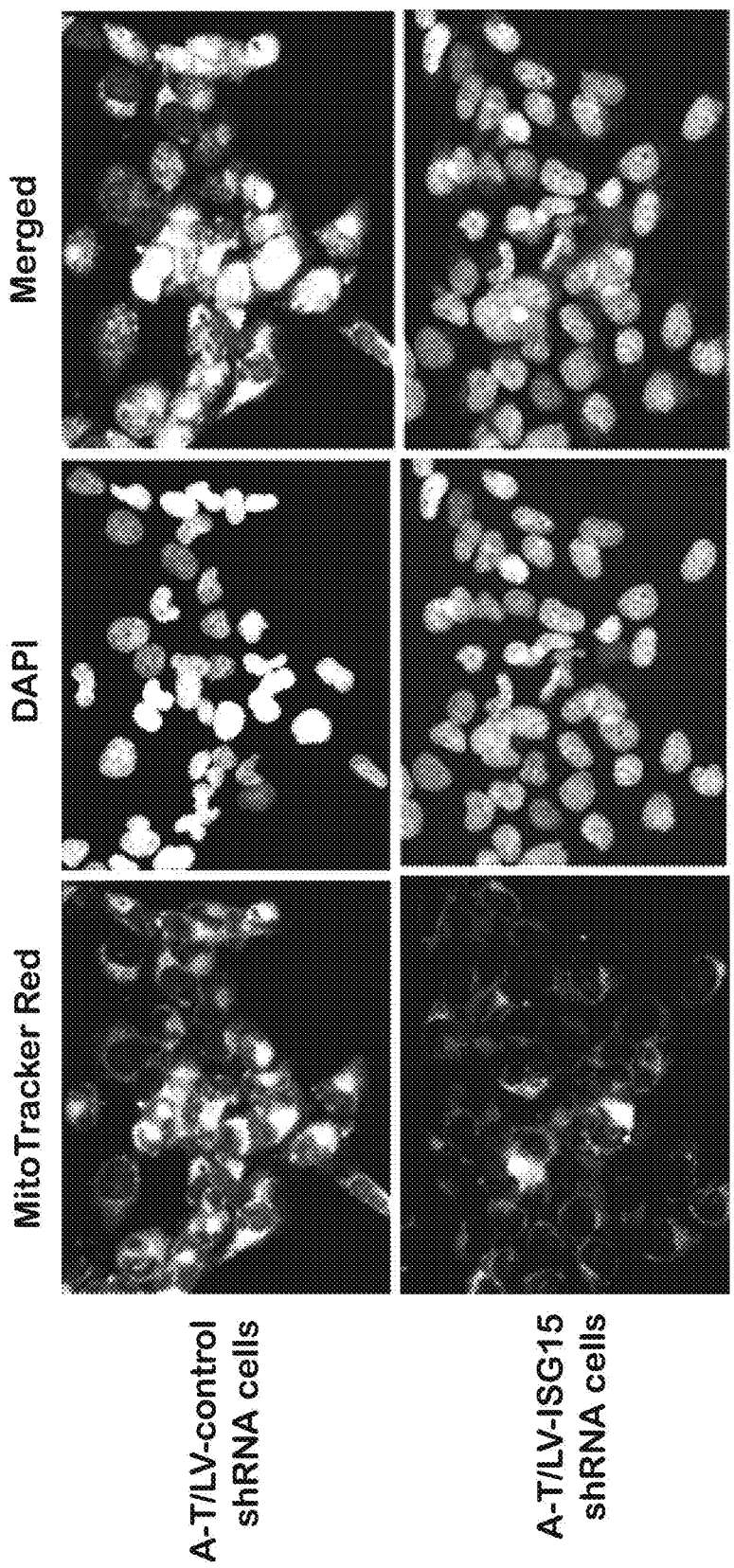
FIG. 20 illustrates representative fluorescence images of A-T/LV-control shRNA cells (upper panels) and A-T/LV-ISG15 shRNA cells (lower panels) co-stained with MitoTracker Red® dye and DAPI.

Representative fluorescence images of A-T/LV-control shRNA (upper panels) and A-T/LV-ISG15 shRNA (lower panels) cells co-stained with MitoTracker Red® dye and DAPI are shown (Scale bar: 10 μM) in FIG. 20. These cells were prepared as discussed herein in Example 7. Using MitoTracker Red® dye, mitochondrial mass was shown to increase in A-T cells (see FIG. 20, top panels). However, mitochondrial mass was markedly decreased in ISG15-silenced A-T cells (FIG. 20, lower panels). Together our studies have revealed that defective mitophagy and macroautophagy in A-T cells is in part is caused by the elevated expression of ISG15.

In addition to ISG15 levels and macroautophagy markers, mitochondrial markers such as complex-I, decreased mitochondrial membrane potential, increased levels of mitochondrial superoxide, and mitochondrial mass, can be used to detect ISG15-mediated proteinopathies in blood mononuclear cells (or other cells) obtained from A-T patients. The examples herein show the increased levels of mitochondrial mass in A-T cells. Future experiments will demonstrate that complex-I, mitochondrial membrane potential, and mitochondrial superoxide that change in A-T cells are also caused in part by increased ISG15 expression. These markers can also be used to diagnose a patient with ataxia telangiectasia prone to neurodegeneration.

REFERENCES INCLUDED IN EXAMPLES 1-18

1. Frappart, P. O., and McKinnon, P. J. (2006) Ataxia-telangiectasia and related diseases. Neuromolecular Med. 8, 495-511
2. Lavin, M. F., and Khanna, K. K. (1999) ATM: the protein encoded by the gene mutated in the radiosensitive syndrome ataxia-telangiectasia. Int. J. Radiat. Biol. 75, 1201-1214
3. Boder, E. (1985) Ataxia-telangiectasia: an overview. Kroc Found. Ser. 19, 1-63
4. Chun, H. H., and Gatti, R. A. (2004) Ataxia-telangiectasia, an evolving phenotype. DNA Repair (Amst) 3, 1187-1196
5. Easton, D. F. (1994) Cancer risks in A-T heterozygotes. Int. J. Radiat. Biol. 66, S177-182
6. Sun, X., Becker-Catania, S. G., Chun, H. H., Hwang, M. J., Huo, Y., Wang, Z., Mitui, M., Sanal, O., Chessa, L., Crandall, B., and Gatti, R. A. (2002) Early diagnosis of ataxia-telangiectasia using radiosensitivity testing. J. Pediatr. 140, 724-731

7. Taylor, A. M., Hamden, D. G., Arlett, C. F., Harcourt, S. A., Lehmann, A. R., Stevens, S., and Bridges, B. A. (1975) Ataxia telangiectasia: a human mutation with abnormal radiation sensitivity. Nature, 258, 427-429

8. Lavin, M. F., Scott, S., Gueven, N., Kozlov, S., Peng, C., and Chen, P. (2004) Functional consequences of sequence alterations in the ATM gene. DNA Repair (Amst), 3, 1197-1205

9. Savitsky, K., Bar-Shira, A., Gilad, S., Rotman, G., Ziv, Y., Vanagaite, L., Tagle, D. A., Smith, S., Uziel, T., Sfez, S., Ashkenazi, M., Pecker, I., Frydman, M., Harnik, R., Patanjali, S. R., Simmons, A., Clines, G. A., Sartiel, A., Gatti, R. A., Chessa, L., Sanal, O., Lavin, M.

F., Jaspers, N. G., Taylor, A. M., Arlett, C. F., Miki, T., Weissman, S. M., Lovett, M., Collins, F. S., and Shiloh, Y. (1995) A single ataxia telangiectasia gene with a product similar to PI-3 kinase. Science 268, 1749-1753

10. Matsuoka, S., Ballif, B. A., Smogorzewska, A., McDonald, E. R., 3rd, Hurov, K. E., Luo, J., Bakalarski, C. E., Zhao, Z., Solimini, N., Lerenthal, Y., Shiloh, Y., Gygi, S. P., and Elledge, S. J. (2007) ATM and ATR substrate analysis reveals extensive protein networks responsive to DNA damage. Science 316, 1160-1166

11. Shiloh, Y. and Rotman, G. (1996) Ataxia-telangiectasia and the ATM gene: linking neurodegeneration, immunodeficiency, and cancer to cell cycle checkpoints. J. Clin. Immunol. 16, 254-260

12. Katyal, S. and McKinnon, P. J. (2008) DNA strand breaks, neurodegeneration and aging in the brain. Mech. Ageing Dev. 129, 483-491

13. Biton, S., Barzilai, A., and Shiloh, Y. (2008) The neurological phenotype of ataxia-telangiectasia: solving a persistent puzzle. DNA Repair (Amst), 7, 1028-1038

14. Rolig, R. L., and McKinnon, P. J. (2000) Linking DNA damage and neurodegeneration. Trends Neurosci. 23, 417-424

15. Ross, C. A., and Pickart, C. M. (2004) The ubiquitin-proteasome pathway in Parkinson's disease and other neurodegenerative diseases. Trends Cell Biol. 14, 703-711

16. Schmitt, H. P. (2006) Protein ubiquitination, degradation and the proteasome in neurodegenerative disorders: no clear evidence for a significant pathogenetic role of proteasome failure in Alzheimer disease and related disorders. Med. Hypotheses 67, 311-317

17. Ciechanover, A. (2005) Early work on the ubiquitin proteasome system, an interview with Aaron Ciechanover. Interview by CDD. Cell Death Differ, 12, 1167-1177.

18. Eilam, R., Peter, Y., Groner, Y., and Segal, M. (2003) Late degeneration of nigro-striatal neurons in ATM−/− mice. Neuroscience 121, 83-98

19. Agamanolis, D. P., and Greenstein, J. I. (1979) Ataxia-telangiectasia. Report of a case with Lewy bodies and vascular abnormalities within cerebral tissue. J. Neuropathol. Exp. Neurol. 38, 475-489

20. Wood, L. M., Sankar, S., Reed, R. E., Haas, A. L., Liu, L. F., McKinnon, P., and Desai, S. D. (2011) A Novel Role for ATM in Regulating Proteasome-Mediated Protein Degradation through Suppression of the ISG15 Conjugation Pathway. PLoS One 6, e16422

21. Narasimhan, J., Potter, J. L., and Haas, A. L. (1996) Conjugation of the 15-kDa interferon-induced ubiquitin homolog is distinct from that of ubiquitin. J. Biol. Chem. 271, 324-330

22. Zhang, D., and Zhang, D. E. (2011) Interferon-stimulated gene 15 and the protein ISGylation system. J Interferon Cytokine Res. 31, 119-130.

23. Haas, A. L., Ahrens, P., Bright, P. M., and Ankel, H. (1987) Interferon induces a 15-kilodalton protein exhibiting marked homology to ubiquitin. J. Biol. Chem. 262, 11315-11323

24. Desai, S. D., Haas, A. L., Wood, L. M., Tsai, Y. C., Pestka, S., Rubin, E. H., Saleem, A., Nur, E. K. A., and Liu, L. F. (2006) Elevated expression of ISG15 in tumor cells interferes with the ubiquitin/26S proteasome pathway. Cancer Res. 66, 921-928

25. Lu, G., Reinert, J. T., Pitha-Rowe, I., Okumura, A., Kellum, M., Knobeloch, K. P., Hassel, B., and Pitha, P. M. (2006) ISG15 enhances the innate antiviral response by inhibition of IRF-3 degradation. Cell Mol. Biol. (Noisy-le-grand), 52, 29-41

26. Okumura, A., Pitha, P. M., and Harty, R. N. (2008) ISG15 inhibits Ebola VP40 VLP budding in an L-domain-dependent manner by blocking Nedd4 ligase activity. Proc. Natl. Acad. Sci. USA 105, 3974-3979

27. Malakhova, O. A., and Zhang, D. E. (2008) ISG15 inhibits Nedd4 ubiquitin E3 activity and enhances the innate antiviral response. J. Biol. Chem. 283, 8783-8787

28. Takeuchi, T., and Yokosawa, H. (2005) ISG15 modification of Ubc13 suppresses its ubiquitin-conjugating activity. Biochem. Biophys. Res. Commun. 336, 9-13

29. Zou, W., Papov, V., Malakhova, O., Kim, K. I., Dao, C., Li, J., and Zhang, D. E. (2005) ISG15 modification of ubiquitin E2 Ubc13 disrupts its ability to form thioester bond with ubiquitin. Biochem. Biophys. Res. Commun. 336, 61-68

30. Zou, W., Wang, J., and Zhang, D. E. (2007) Negative regulation of ISG15 E3 ligase EFP through its autoISGylation. Biochem. Biophys. Res. Commun. 354, 321-327

31. Pandey, U. B., Batlevi, Y., Baehrecke, E. H., and Taylor, J. P. (2007) HDAC6 at the intersection of autophagy, the ubiquitin-proteasome system and neurodegeneration. Autophagy 3, 643-645

32. Pandey, U. B., Nie, Z., Batlevi, Y., McCray, B. A., Ritson, G. P., Nedelsky, N. B., Schwartz, S. L., DiProspero, N. A., Knight, M. A., Schuldiner, O., Padmanabhan, R., Hild, M., Berry, D. L., Garza, D., Hubbert, C. C., Yao, T. P., Baehrecke, E. H., and Taylor, J. P. (2007) HDAC6 rescues neurodegeneration and provides an essential link between autophagy and the UPS. Nature 447, 859-863

33. Nedelsky, N. B., Todd, P. K., and Taylor, J. P. (2008) Autophagy and the ubiquitin-proteasome system: collaborators in neuroprotection. Biochim. Biophys. Acta. 1782, 691-699

34. Rubinsztein, D. C. (2007) Autophagy induction rescues toxicity mediated by proteasome inhibition. Neuron 54, 854-856

35. Mizushima, N. (2007) Autophagy: process and function. Genes Dev. 21, 2861-2873

36. Klionsky, D. J., and Emr, S. D. (2000) Autophagy as a regulated pathway of cellular degradation. Science 290, 1717-1721

37. Desai, S. D., Wood, L. M., Tsai, Y. C., Hsieh, T. S., Marks, J. R., Scott, G. L., Giovanella, B. C., and Liu, L. F. (2008) ISG15 as a novel tumor biomarker for drug sensitivity. Mol. Cancer Ther. 7, 1430-1439

38. Liu, L. F. (1989) DNA topoisomerase poisons as antitumor drugs. Annu. Rev. Biochem. 58, 351-375
39. Wu, X., Rathbun, G., Lane, W. S., Weaver, D. T., and Livingston, D. M. (2000) Interactions of the Nijmegen breakage syndrome protein with ATM and BRCA1. Cold Spring Harb. Symp. Quant. Biol. 65, 535-545
40. Desai, S. D., Reed, R. E., Burks, J., Wood, L. M., Pullikuth, A. K., Haas, A. L., Liu, L. F., Breslin, J. W., Meiners, S., and Sankar, S. (2012) ISG15 disrupts cytoskeletal architecture and promotes motility in human breast cancer cells. Exp. Biol. Med. (Maywood), 237, 38-49.
41. Pear, W. S., Nolan, G. P., Scott, M. L., and Baltimore, D. (1993) Production of high-titer helper-free retroviruses by transient transfection. Proc. Natl. Acad. Sci. USA, 90, 8392-8396
42. Thomson, T. M., and Guerra-Rebollo, M. (2010) Ubiquitin and SUMO signaling in DNA repair. Biochem. Soc. Trans. 38, 116-131
43. Lavin, M. F., Birrell, G., Chen, P., Kozlov, S., Scott, S., and Gueven, N. (2005) ATM signaling and genomic stability in response to DNA damage. Mutat. Res. 569, 123-132
44. Loeb, K. R., and Haas, A. L. (1992) The interferon-inducible 15-kDa ubiquitin homolog conjugates to intracellular proteins. J. Biol. Chem. 267, 7806-7813
45. Wu, W. K., Wu, Y. C., Yu, L., Li, Z. J., Sung, J. J., and Cho, C. H. (2008) Induction of autophagy by proteasome inhibitor is associated with proliferative arrest in colon cancer cells. Biochem. Biophys. Res. Commun. 374, 258-263
46. Ge, P. F., Zhang, J. Z., Wang, X. F., Meng, F. K., Li, W. C., Luan, Y. X., Ling, F., and Luo, Y. N. (2009) Inhibition of autophagy induced by proteasome inhibition increases cell death in human SHG-44 glioma cells. Acta Pharmacol. Sin. 30, 1046-1052
47. Yamamoto, A., Tagawa, Y., Yoshimori, T., Moriyama, Y., Masaki, R., and Tashiro, Y. (1998) Bafilomycin A1 prevents maturation of autophagic vacuoles by inhibiting fusion between autophagosomes and lysosomes in rat hepatoma cell line, H-4-II-E cells. Cell Struct. Funct. 23, 33-42
48. Desai, S. D., Li, T. K., Rodriguez-Bauman, A., Rubin, E. H., and Liu, L. F. (2001) Ubiquitin/26S proteasome-mediated degradation of topoisomerase I as a resistance mechanism to camptothecin in tumor cells. Cancer Res. 61, 5926-5932
49. Desai, S. D., Liu, L. F., Vazquez-Abad, D., and D'Arpa, P. (1997) Ubiquitin-dependent destruction of topoisomerase I is stimulated by the antitumor drug camptothecin. J. Biol. Chem. 272, 24159-24164
50. Desai, S. D., Zhang, H., Rodriguez-Bauman, A., Yang, J. M., Wu, X., Gounder, M. K., Rubin, E. H., and Liu, L. F. (2003) Transcription-dependent degradation of topoisomerase I-DNA covalent complexes. Mol. Cell Biol. 23, 2341-2350
51. Valentin-Vega, Y. A., Maclean, K. H., Tait-Mulder, J., Milasta, S., Steeves, M., Dorsey, F. C., Cleveland, J. L., Green, D. R., and Kastan, M. B. (2012) Mitochondrial dysfunction in ataxia-telangiectasia. Blood, 119: 1490-1500.
52. Tanida, I., Ueno, T., and Kominami, E. (2004) LC3 conjugation system in mammalian autophagy. Int. J. Biochem. Cell Biol. 36, 2503-2518
53. Kabeya, Y., Mizushima, N., Ueno, T., Yamamoto, A., Kirisako, T., Noda, T., Kominami, E., Ohsumi, Y., and Yoshimori, T. (2000) LC3, a mammalian homologue of yeast Apg8p, is localized in autophagosome membranes after processing. EMBO J. 19, 5720-5728
54. Klionsky, D. J., et al. (2008) Guidelines for the use and interpretation of assays for monitoring autophagy in higher eukaryotes. Autophagy 4, 151-175
55. Komatsu, M., and Ichimura, Y. (2010) Physiological significance of selective degradation of p62 by autophagy. FEBS Lett. 584, 1374-1378
56. Seglen, P. O., and Gordon, P. B. (1982) 3-Methyladenine: specific inhibitor of autophagic/lysosomal protein degradation in isolated rat hepatocytes. Proc. Natl. Acad. Sci. USA, 79, 1889-1892
57. Maragakis, N. J., and Rothstein, J. D. (2006) Mechanisms of Disease: astrocytes in neurodegenerative disease. Nat. Clin. Pract. Neurol. 2, 679-689
58. Wang, R., Yang, B., and Zhang, D. (2011) Activation of interferon signaling pathways in spinal cord astrocytes from an ALS mouse model. Glia 59, 946-958
59. Figueiredo-Pereira, M. E., and Cohen, G. (199) The ubiquitin/proteasome pathway: friend or foe in zinc-, cadmium-, and H2O2-induced neuronal oxidative stress. Mol. Biol. Rep. 26, 65-69
60. Barlow, C., Ribaut-Barassin, C., Zwingman, T. A., Pope, A. J., Brown, K. D., Owens, J. W., Larson, D., Harrington, E. A., Haeberle, A. M., Mariani, J., Eckhaus, M., Herrup, K., Bailly, Y., and Wynshaw-Boris, A. (2000) ATM is a cytoplasmic protein in mouse brain required to prevent lysosomal accumulation. Proc. Natl. Acad. Sci. USA, 97, 871-876
61. Bregman, D. B., Halaban, R., van Gool, A. J., Henning, K. A., Friedberg, E. C., and Warren, S. L. (1996) UV-induced ubiquitination of RNA polymerase II: a novel modification deficient in Cockayne syndrome cells. Proc. Natl. Acad. Sci. USA 93, 11586-11590
62. Sharma, A., Kaur, M., Kar, A., Ranade, S. M., and Saxena, S. (2010) Ultraviolet radiation stress triggers the down-regulation of essential replication factor Mcm10. J. Biol. Chem. 285, 8352-8362
63. Metcalf, D. J., Garcia-Arencibia, M., Hochfeld, W. E., and Rubinsztein, D. C. (2012) Autophagy and misfolded proteins in neurodegeneration. Exp Neurol. 238, 22-28
64. Lehman, N. L. (2009) The ubiquitin proteasome system in neuropathology. Acta Neuropathol. 118, 329-347
65. Cherra, S. J. and Chu, C. T. (2008) Autophagy in neuroprotection and neurodegeneration: A question of balance. Future Neurol. 3, 309-323
66. Chu, C. T. (2006) Autophagic stress in neuronal injury and disease. J. Neuropathol. Exp. Neurol. 65, 423-432.
67. Okumura A, Lu G, Pitha-Rowe I, Pitha P M (2006) Innate antiviral response targets HIV-1 release by the induction of ubiquitin-like protein ISG15. Proc Natl Acad Sci USA 103: 1440-1445.
68. Lu G, Reinert J T, Pitha-Rowe I, Okumura A, Kellum M, et al. (2006) ISG15 enhances the innate antiviral response by inhibition of IRF-3 degradation. Cell Mol Biol (Noisy-le-grand) 52: 29-41.
69. Takeuchi T, Iwahara S, Saeki Y, Sasajima H, Yokosawa H (2005) Link between the Ubiquitin Conjugation System and the ISG15 Conjugation System: ISG15 Conjugation to the UbcH6 Ubiquitin E2 Enzyme. J Biochem (Tokyo) 138: 711-719.
70. Siddoo-Atwal C, Haas A L, Rosin M P (1996) Elevation of interferon beta-inducible proteins in ataxia telangiectasia cells. Cancer Res. 56: 443-447.
71. Wu X, Ranganathan V, Weisman D S, Heine W F, Ciccone D N, et al. (2000) ATM phosphorylation of Nijmegen breakage syndrome protein is required in a DNA damage response. Nature 405: 477-482.
72. Herzog K H, Chong M J, Kapsetaki M, Morgan J I, McKinnon P J (1998) Requirement for Atm in ionizing radiation-induced cell death in the developing central nervous system. Science 280: 1089-1091.
73. Sakaguchi A, Kikuchi A (2004) Functional compatibility between isoform alpha and beta of type II DNA topoisomerase. J Cell Sci 117: 1047-1054.
74. Ikeda F, Dikic I (2008) Atypical ubiquitin chains: new molecular signals. 'Protein Modifications: Beyond the Usual Suspects' review series. EMBO Rep 9: 536-542.
75. Menendez-Benito V, Verhoef L G, Masucci M G, Dantuma N P (2005) Endoplasmic reticulum stress compromises the ubiquitin-proteasome system. Hum Mol Genet 14: 2787-2799.
76. Browne, S. E. and Beal, M. F. Oxidative damage and mitochondrial dysfunction in neurodegenerative diseases. Biochem Soc Trans, 22: 1002-1006, 1994.
77. Lin, M. T. and Beal, M. F. Mitochondrial dysfunction and oxidative stress in neurodegenerative diseases. Nature, 443: 787-795, 2006.
78. Johri, A. and Beal, M. F. Mitochondrial dysfunction in neurodegenerative diseases. J Pharmacol Exp Ther, 342: 619-630.
79. Ambrose, M., Goldstine, J. V., and Gatti, R. A. Intrinsic mitochondrial dysfunction in ATM-deficient lymphoblastoid cells. Hum Mol Genet, 16: 2154-2164, 2007.

Example 19

Description of the Embodiments of the Technology

Without wishing to be bound by theory, elevated levels of ISG15 (Interferon-Stimulated Gene 15) conjugates (ISGylation) could be used as a prognostic/diagnostic biomarker for assessing proteinopathy, a predicted underlying cause of neurodegeneration, in rare and common neurodegenerative diseases.

Neurodegenerative diseases, rare and common, place an enormous burden on patients and caregivers globally. Over 6 million people in the United States alone suffer from neurodegenerative diseases, all of which are chronic, incurable, and with causes unknown. Identifying a common molecular mechanism underpinning neurodegenerative disease pathology is urgently needed to aid in the design of effective therapies to ease suffering for patients, reduce economic cost, and improve quality of life for such patients. Proteinopathy, i.e., defects in the protein turnover pathways (ubiquitin/26S proteasome and autophagy) have been recognized as common cause of many neurodegenerative diseases. However, the molecular mechanism underlying these defects remains elusive. Without wishing to be bound by theory, we identified constitutively elevated ISG15 conjugates (ISGylation) as mediators of these defects in Ataxia Telangiectasia (A-T), a rare neurological disorder.

ISG15 is an ubiquitin-like protein that is minimally expressed in human normal cells and tissues. However, its gene and protein expressions are highly elevated in response to type I interferons (IFNs) in all cell lineages. ISG15 protein is synthesized from the ISG15 gene and either remains in an intracellular free form, appended to proteins in cells (conjugated form), or secreted from cells (extracellular form) by an unknown mechanism. ISG15-specific enzymes E1 (UbEIL), E2 (UbcH8), and E3 (HERCS, EFP, and several others) are also IFN-stimulated proteins that conjugate intracellular free ISG15 to cellular proteins, a mechanism referred to as ISGylation. Empirical evidence from our lab has revealed that ISGylation predominantly antagonizes the canonical ubiquitin pathway in cancer cells. Since polyubiquitylation of cellular proteins is a prerequisite for protein turnover via the 26S proteasome, and ubiquitin-mediated protein turnover is crucial in maintaining cellular homeostasis, ISG15 proteinopathy (ISG15-mediated defective protein turnover) can be an underlying cause of malignancy in human and mouse experimental disease models.

ISG15 is also constitutively elevated in Ataxia Telangiectasia (A-T), a rare neurodegenerative disease (1 in 40,000-100,000 births) due to aberrant activation of the IFN pathway. Like cancer cells, we have demonstrated that ISGylation antagonizes the ubiquitin pathway in A-T cells. Additionally, ISG15 is also elevated in human A-T brains and mouse cerebellums, the part of the brain principally affected in A-T. Moreover, our results have revealed signs of ISG15 proteinopathy in both A-T human (obtained postmortem) and mouse (grown in ex vivo culture) brain tissues. Notably, like A-T, the interferon pathway is also aberrantly expressed in the spinal cords of affected mice in an Amyotrophic Lateral Sclerosis (ALS) murine model (Wang et al. Glia 59, 946-958 (2011)). Free ISG15 is also elevated in the spinal cords of human ALS patients. However, whether ISGylation is elevated in human ALS patients has not been investigated. Previous literature has demonstrated that ISG15 is elevated in injured neurons and that ISG15 (Wang et al. Sheng Li Xue Bao 64, 577-583 (2012)). Since neuronal injury is common to all neurodegenerative diseases, and proteinopathy is an underlying cause of neurodegeneration in several neurodegenerative diseases, ISGylation-mediated proteinopathy may be an underlying cause of neurodegeneration.

A Study was Initiated to Test Whether Increased ISGylation is a Common Trait in Neurodegenerative Diseases in which Proteinopathy has been Implicated as an Underlying Cause of Neurodegeneration.

We assessed ISGylation in easily accessible patient-derived lymphocytes (Coriell Cell Repository). Using Western analysis, we show that ISGylation (ISG15 conjugates) is significantly increased in all patient-derived A-T, ALS, Parkinson, and Alzheimer lymphocytes compared to lymphocytes obtained from normal individuals. Based on the observations that ISG15 conjugates induce proteinopathy in human and mouse A-T experimental models, that ISG15 is a neuronal injury biomarker, and current observations that ISG15 conjugates are elevated in neurological disorders, ISG15 conjugates using Western analysis could be used as a prognostic biomarker for predicting proteinopathy in neurodegenerative disorders.

Description of the Uses and Commercial Applications of Embodiments of the Technology Proteinopathy, defective protein turnover that leads to aggregation of toxic protein in neurons, has been identified as a common cause of neurodegeneration in several neurological disorders. However, currently no clinical test/biomarker is available to predict proteinopathy in patient's neurons, as these studies are impractical to conduct in living human patients. Without wishing to be bound by theory, ISGylation could be used as a biomarker for predicting proteinopathy, and in turn risk for neurodegeneration in patients afflicted with Alzheimer's disease, Parkinson disease, ALS, and related neurological disorders as described herein. Moreover, this diagnostic test can be performed easily using lymphocytes (blood-based) from living patients. Western-based diagnostic tests are currently licensed for use in veterinary and human clinical practices, rendering Western blotting to measure ISGylation in patient-derived lymphocytes one approach. At present, no clinical tests are available that can assess the risk of proteinopathy-induced neurodegeneration, making this study a new one.

Examples of Advantages of Embodiments of the Invention

Without wishing to be bound by theory, ISGylation could be used for assessing a risk for proteinopathy-induced neurodegeneration in patients with neurodegenerative diseases.

Although proteinopathy has been identified as an underlying cause of neurodegeneration in several neurodegenerative diseases (using cell culture and brain tissues obtained post-mortem), there remains no clinical test available to predict a risk for proteinopathy-induced neurodegeneration in living patients.

This diagnostic test for ISGylation can be performed easily using lymphocytes from living patients. Thus, ISGylation in patient-derived lymphocytes could be used as a marker for proteinopathy in brains of living patients.

Without wishing to be bound by theory, a simple western-blotting can be used test to assess ISGylation in easily available lymphocytes derived from living patients.

This technology, together with our other ongoing mechanistic studies, can aid drug discovery efforts (development of small molecule inhibitors of the ISG15 pathway, and provide ways to stop/prevent neurodegeneration in A-T patients. See US patent application publication US2016/0216279, issued as U.S. Pat. No. 9,599,626, each of which are incorporated herein by reference in their entireties.

As described herein, studies have revealed that ISG15 inhibits mitophagy by inducing proteinopathy (inhibiting degradation of mitochondrial proteins) in A-T cells. Thus, this test could be used for "mitophagy defects" in neurological disorders, as mitochondrial defects leading to neurodegeneration is implicated in various neurological disorders.

Example 20

Introduction

To establish ISGylation (ISG15 (Interferon-Stimulated Gene 15) conjugates) as a biomarker for neurodegenerative diseases, and a time-effective (3 h), automated, and quantitative Western-blot assay to increase its commercialization potential.

The cause(s) of neurodegenerative diseases is mainly unknown, and there are no effective diagnostic markers for predicting them, rendering the development of effective treatments for neurodegenerative diseases difficult. This lack of fundamental knowledge is one reason the failure rate of research and development projects in this field is so high. With no effective diagnostic biomarkers available, therapies may not be implemented in the early stages of these diseases when they are expected to have their greatest impact (1). Hence, identification of diagnostic biomarkers that can predict a risk for neurodegeneration in patients is urgently needed. Notably, through research on a neurodegenerative disease Ataxia Telangiectasia (A-T), "ISGylation", conjugation of ISG15 to cellular proteins, has been identified as a diagnostic/prognostic biomarker for A-T, and more recently, for other neurodegenerative diseases. As described herein, we shall validate the authenticity of using ISGylation as a diagnostic/prognostic biomarker for neurodegenerative diseases in the clinic. Moreover, we shall also develop a time-effective (such as 3 hours), automated, and quantitative Western-blot assay to assess ISGylation in patient-derived lymphocytes (blood cells). Western-based diagnostic tests are currently licensed for use in veterinary and human clinical practices (2-4), rendering Western blotting to measure ISGylation in patient-derived lymphocytes one approach in the clinical setting. Presently, no blood-based biomarkers to assess a risk for neurodegeneration in living patients are available thus, making this technology a unique one.

Embodiments will require not only the demonstration of the new marker but also a retrospective study that demonstrates a high degree of correlation between the marker and verified cases of the disease, followed by a prospective study that correlates with the eventual diagnosis of the disease. Notably, in addition to the identification of ISGylation as a diagnostic biomarker, research in my group has also identified ISGylation as an inducer of proteinopathy, a determined underlying cause of neurodegeneration in various neurodegenerative diseases (U.S. Pat. No. 9,599,626) (13, 14). By doing so, we have identified ISGylation as a therapeutic target for treating neurodegenerative disorders. Thus, with our published and ongoing mechanistic studies, together with results generated from the current study, a new biomarker can be identified that can diagnose and predict a risk for proteinopathy-induced neurodegeneration in patients with neurological disorders such as Ataxia Telangiectasia (A-T), Amyotrophic Lateral Sclerosis (ALS), Parkinson disease (PD), Alzheimer disease (AD), among several others.

Aspects of the invention comprise biomarkers and assays to measure the levels of these biomarkers in patient/normal subjects-derived blood cells (lymphocytes). Market Size: The global market for the diagnosis and treatment of neurodegenerative diseases includes Ataxia Telangiectasia (A-T), Alzheimer's disease (AD), Parkinson's disease (PD), Huntington's disease (HD), Amyotrophic Lateral Sclerosis (ALS), Friedreich's Ataxia, Multiple Sclerosis (MS), Prion diseases, Spinocerebellar Ataxia (SCA), Spinal Muscular Atrophy (SMA), multiple taupathies, Huntington's disease, Spongiform encephalopathies, and Familial polyneuropathy.

Factors that forecast to drive the growth of the market for the diagnosis and treatment of neurodegenerative diseases include the following: First, the increased aging population, which is leading to an increase in the incidence of neurodegenerative diseases. Second, high unmet medical need. Third, new product launches, which may limit the impact of upcoming expirations of patents for major therapies in the market. Fourth, reformulation of currently marketed drugs. Fifth, research and development for both the diagnosis and the treatment of neurodegenerative diseases. Finally, a growing awareness among physicians of the benefits of these therapies (5-11).

Factors that forecast to restrain market growth include the following: First, major companies in the market will face competition due to market erosion from the introduction of generic competition. Second, there will be a lack of comprehensive curative treatments because of the complex nature of these diseases. Finally, the cause of neurodegenerative diseases is mostly unknown, resulting in poor results for R&D projects (5,6,8,9).

Societal Need: The lack of effective diagnostics and therapies for these diseases creates an enormous burden. In the U.S., approximately 7 million people are living with Alzheimer, Parkinson, or ALS. An estimated 5.3 million individuals suffer from Alzheimer disease in the U.S. alone, making it by far the most prevalent neurodegenerative disease, carrying an estimated health care burden of $172 billion. The number of people affected with Alzheimer disease in the U.S. is expected to triple by 2050 to ~16 million, costing $1.2 trillion in health care, long-term care, and hospice care. Parkinson disease affects an estimated 1.5 million people in the U.S., with approximately 50,000 new cases diagnosed each year, and the costs of Parkinson disease were estimated at $11 billion per 500,000 affected Americans in 2009 (12). In advanced stages of the disease, caring for these patients can cost up to $200,000 a year, thus imposing an enormous financial and emotional toll on affected families. Hence, there is urgent need to find new therapies and diagnostic/prognostic markers to treat and predict the pathology of these neurodegenerative diseases, respectively. Current study will establish such a biomarker.

Competition and Competitive Advantages

There is a large, active pipeline of candidate drugs to treat neurodegenerative diseases, with an estimated 1,494 products in development. Many of these compounds are new active pharmaceutical ingredients, and only a small proportion of products are generics or repositioned drugs from other indications. Most of these candidate drugs are still at Phase I. This indicates some degree of progress regarding different molecules developed as therapeutic agents within the neurodegenerative pipeline. On the other hand, there is significantly less activity in the development of diagnostic markers (1,7). Notably, our lab research has identified a unique "ISGylation" biomarker for diagnosing/predicting neurodegenerative diseases. In this Example, through experimentation, we will confirm its utility as a diagnostic/prognostic biomarker for neurodegenerative diseases. We shall also develop a time-effective (such as 3 hours), automated, and quantitative Western-blot assay for ISGylation assessment. Without wishing to be bound by theory, this non-invasive blood-based (using lymphocytes) diagnostic test provides an attractive alternative to the currently used radiation-based diagnostic tests (e.g. brain PET scan), especially for patients who are abnormally sensitive to radiation (e.g. Ataxia Telangiectasia). Presently, no such biomarkers and tests are available for predicting neurodegeneration in living patients thus, ruling out the possibility of competition in the market.

Figure 21:
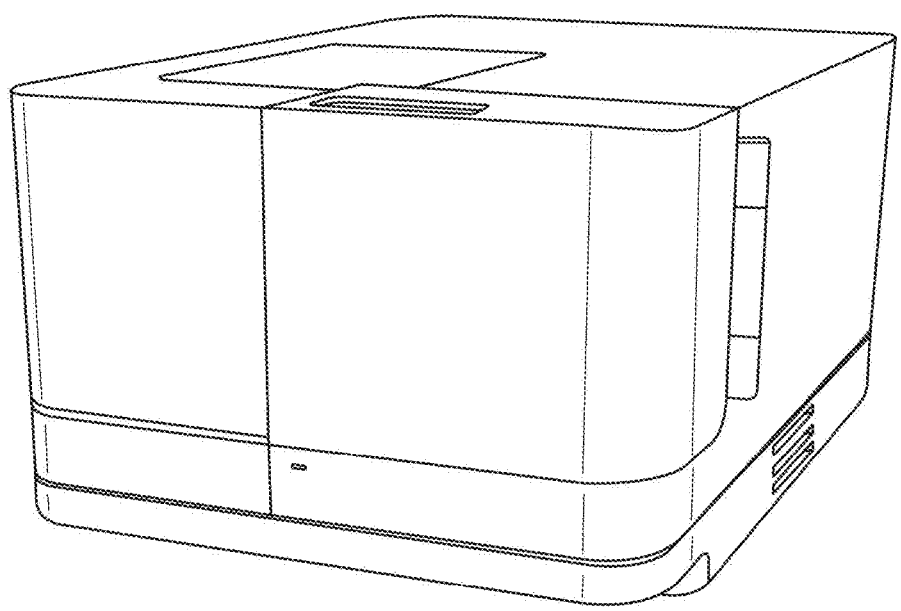
FIG. 21 shows Wes machine for Western blot analysis.
Figure 24:
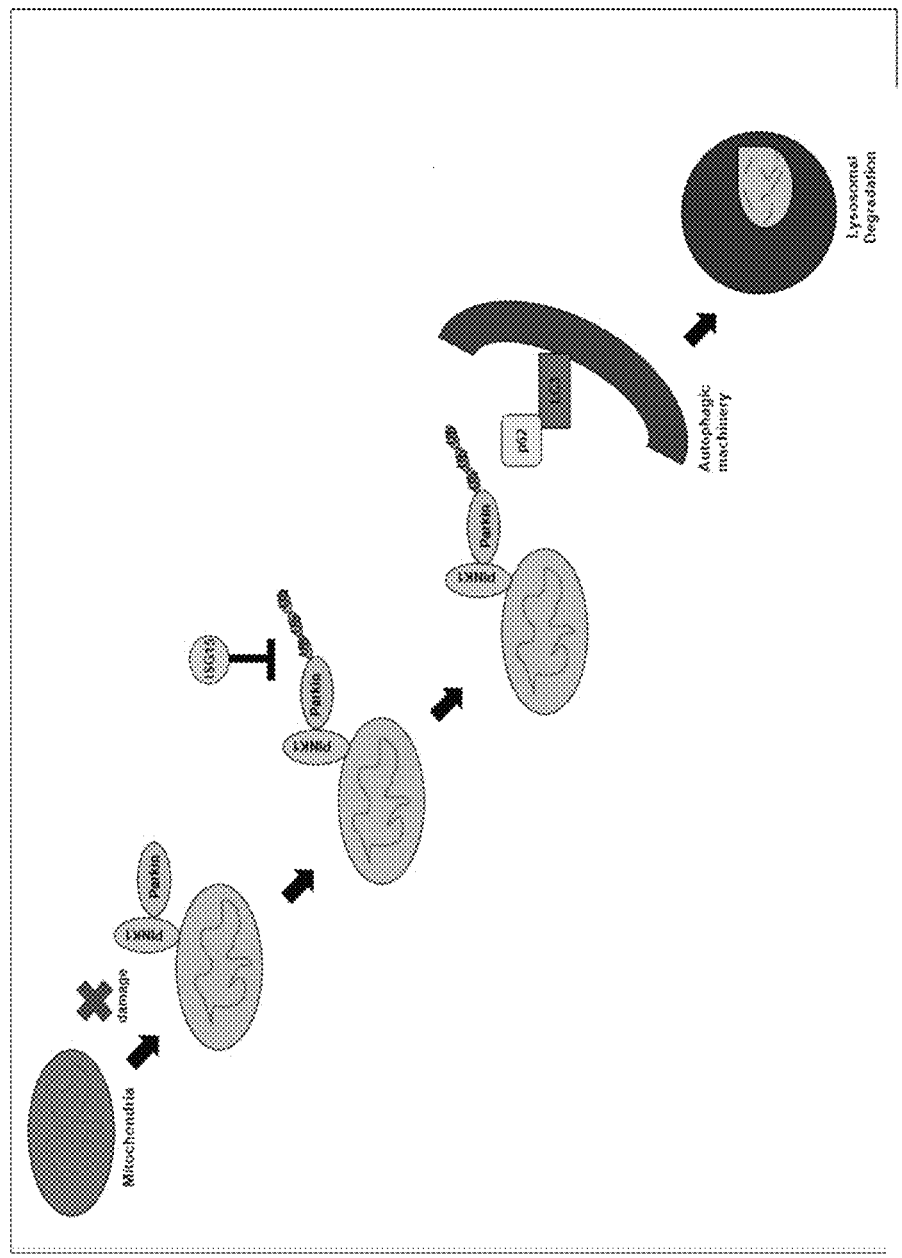
FIG. 24 shows a mechanism by which ISG15 inhibits mitophagy. Aberrantly expressed free ISG15 is conjugated to protein targets through a multi-enzyme pathway parallel to that of ubiquitin. These ISG15 conjugates inhibit ubiquitin-dependent protein degradation and mitophagy, the latter of which is regulated by ubiquitin-dependent signaling through Parkin, an E3 ubiquitin ligase.
Figure 25:
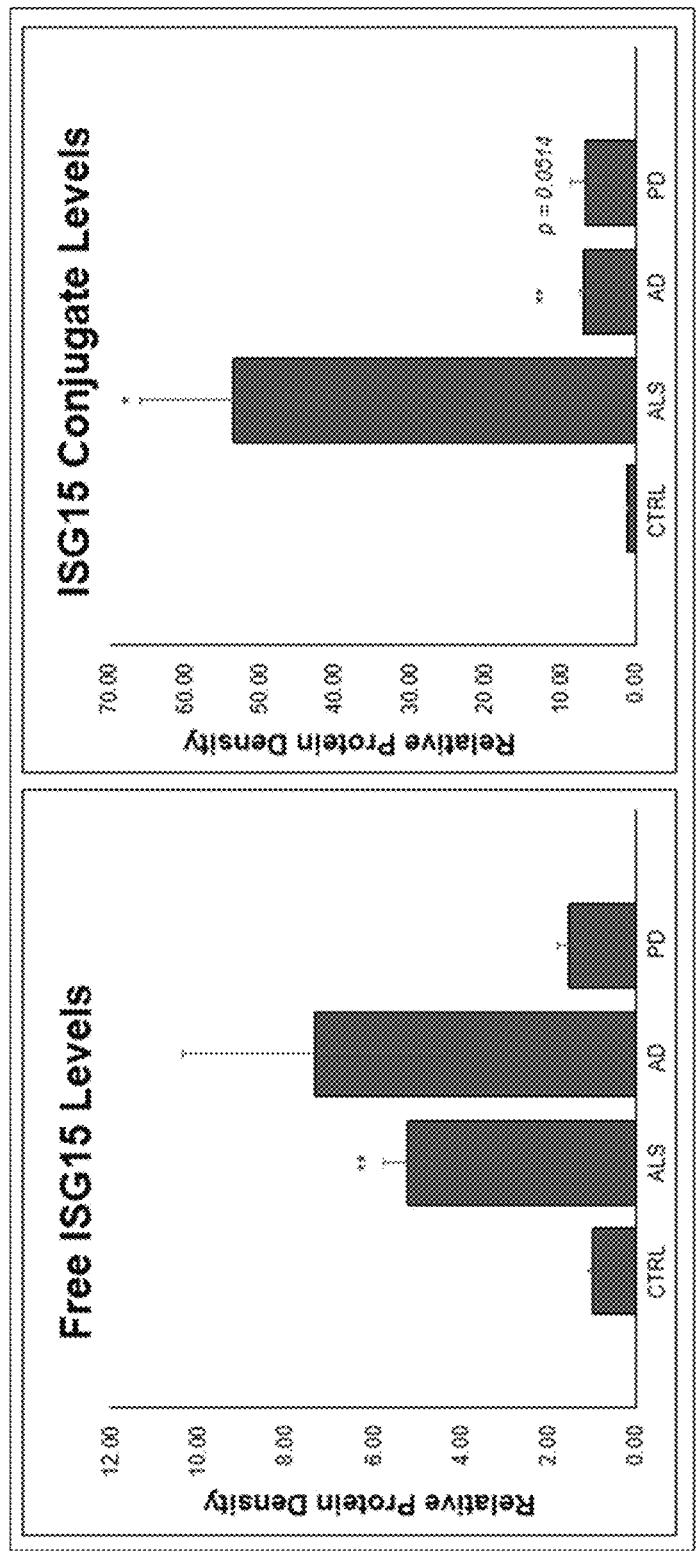
FIG. 25 shows ISG15 is elevated in neurological disease. Protein expression was assessed via Western blotting, and analysis was performed using ImageQuant TL software. In the bar graphs, protein density values from control lymphocytes are normalized to 100%, and values from ALS, AD (Alzheimer's disease), and PD (Parkinson's disease) cells are expressed as percent variations over control. Error bars represent +/−SEM. *p<0.05 **p<0.001

An initial study using a small number of normal, Ataxia Telangiectasia, Amyotrophic Lateral Sclerosis, Alzheimer disease, and Parkinson disease lymphocytes has revealed the potential of using ISGylation as a diagnostic/prognostic biomarker for neurodegenerative diseases in the clinic (see R&D plan herein). These lymphocytes were de-identified. The current study will expand upon these observations using an automated, quantitative Western-blot assay. For that, funds are requested to buy a Wes machine (see FIG. 21) from ProteinSimple and reagents for this analysis.

Normal/Patient-derived lymphocytes (free of cost): More than 5,000 normal and diseased lymphocytes from the National Institute of Neurological Disorders and Stroke (NINDS) Cell Repository are available free of cost to academic researchers through Coriell Cell Repository, Camden, N.J. Using these lymphocytes, we have demonstrated that ISGylation is increased in patient-derived compared to normal lymphocytes. To generate this data, we used traditional Western blot assay that can takes three days to analyze ten samples. In contrast, with the Wes machine, we will be able to assess 25 samples in 3 hours. Thus, this machine will allow us to assess large number of samples required for establishing ISGylation as a biomarker.

Anti-ISG15 antibodies: We have generated anti-ISG15 antibodies in the lab, which are useful to detect ISGylation.

Research

The goal described herein is two-fold: to develop a quick, automated, and quantitative blood-based assay for measuring ISGylation, and to test if elevated ISGylation is a common trend in distinct neurodegenerative diseases using the Wes machine.

The rationale for using Western blotting for measuring ISGylation: We chose to use Western blotting for measuring ISGylation (ISG15 conjugates), as this technique will allow us to detect and quantitate both free ISG15 and ISGylation in the same cell lysates. This is not possible using simpler techniques like dot-blotting or gene expression analyses. See FIG. 22 for a typical Western blot performed using the traditional three-day Western blot procedure for measuring ISGylation.

The rationale for using the Wes machine (FIG. 21): Western blotting is a biochemical technique used to detect a protein of interest from cell/tissue lysates. On the other hand, using the Wes machine, all steps of Western blotting, including protein loading and separation, immunoblotting, washing, detection and quantitative analysis of data, are automated. Thus, manual factors that can negatively impact reproducibility, quantitation, time to result, and overall reliability of the generated data are eliminated. This machine is not available on the LSU New Orleans campus.

How does the Wes machine function? Samples are prepared following conventional procedures. Samples are then mixed with Simple Western Sample Buffer and standards (provided by ProteinSimple) to a final concentration of 1 µg/µL, reduced, and denatured. The prepared samples, primary and secondary antibodies, and chemiluminescent substrate are dispensed in microliter volumes into designated wells in a low-volume 384-well assay plate. Simple Western assay buffers, nanovolume capillaries, and the prepared assay plate are placed in Simon, which carries out all assay steps automatically. Proteins are separated in capillaries as they migrate through a stacking and separation matrix. The separated proteins are immobilized to the capillary wall via a photoactivated capture chemistry. Target proteins are then identified with a primary antibody (in our case, an ISG15-specific antibody) and subsequent immunodetection using a horseradish peroxidase (HRP)-conjugated secondary antibody and chemiluminescent substrate (commercial reagents). Molecular weight and signal for immunodetected proteins are automatically reported. Simultaneous analysis of up to 25 samples can be performed in a single experiment, and results are available in 3 h. The software reports molecular weight, area, percent area, and signal-to-noise ratios for each protein detected.

Data

ISGylation is Elevated in Neurodegenerative Diseases.

We assessed ISGylation in lysates of normal, A-T, ALS, Alzheimer, and Parkinson lymphocytes using an ISG15-specific antibody in traditional Western blot analysis. A typical Western blot of free ISG15, its conjugates (ISGylation), and β-actin in normal lymphocytes (two samples from distinct individuals) is shown in FIG. 22, top panel. Intensities of free ISG15, ISGylation, and β-actin were quantitated using an Amersham Imager A600 and ImageQuant TL software. The bar graph in FIG. 22 (bottom panel) shows the ratios between free ISG15/b-actin and ISGylation/b-actin from Western blots in this study. When normalized to β-actin, ISGylation levels were significantly increased in lymphocytes obtained from A-T ($p=0.0006$), ALS ($p=0.0001$), Alzheimer ($p=0.0011$), and Parkinson ($p=0.0024$) patients compared to normal individuals. Although levels of free ISG15 were also elevated in A-T ($p=0.0090$), ALS ($p=0.0051$), Alzheimer ($p=0.0523$), and Parkinson (p=0.0805) lymphocytes, there was a striking significant increase in ISGylation in all diseases compared to normal lymphocytes.

ISGylation is elevated in neurodegenerative diseases. Cell lysates were prepared as described in (13,14) and analyzed by Western blotting analysis using an anti-human ISG15 antibody. For loading controls, the same membrane was probed using an antibody against β-actin (left panel). Intensities of free ISG15, ISGylation, and β-actin bands were quantitated using Amersham Imager A600 and ImageQuant TL software. The bar graph (FIG. 22, bottom panel) shows mean values of the ratio between free ISG15/b-actin and ISGylation/b-actin measured from different lymphocyte lysates. Error bars represent +/−SEM.

Conclusion

Increased ISGylation in lymphocytes of neurodegenerative diseases compared to normal indicate that ISGylation could be used as a clinical diagnostic/prognostic biomarker for neurodegenerative diseases. However, screening of large number of samples is needed to validate these findings before considering using ISGylation test for neurological disorders in clinic.

The Research Plan:

Normal and patient-derived lymphocytes: Number of lymphocyte cell lines from Corriell Cell Repository that will be screened for ISGylation are shown in FIG. 23. All cells will be cultured in Roswell Park Memorial Institute Medium 1640 with 2 mM L-glutamine and 15% Fetal Bovine Serum (not inactivated) and grown in a 37° C. incubator with 5% $CO_2$.

Immunodetection of ISGylation by Western blot analysis: Cells (200,000 viable cells/ml) will be lysed in 4% SDS lysis buffer (50 mM Tris-HCl, pH 7.5, 4% SDS), sonicated, and boiled for 10 minutes at 100° C. Lysates will be clarified via centrifugation at 13,000 rpm for five minutes. Protein concentrations will be determined by measuring absorbance at 280 nm using a Beckman Coulter Spectrophotometer, and proteins will be adjusted to equal protein amounts. Normalized samples will be mixed with equal amounts of SDS sample buffer. Samples will be boiled for 10 min at 100° C., and then analyzed using the Wes machine's automated program.

Statistical Analysis:

Statistical analysis (unpaired t-test) on the data obtained from the Wes machine will be performed with GraphPad software. A p-value <0.05 will be considered statistically significant. Large number of samples will also allow us to calculate Positive and Negative Predictive Values (PPV and NPV) [PPVs and NPVs are the proportions of positive and negative results in statistics and diagnostic tests that are true positive and true negative results, respectively].

Without wishing to be bound by theory, we expect to see increased ISGylation in patient-derived compared to normal subjects-derived lymphocytes.

Summary of the Scope of Work:
Overall Goals and Objectives:
(i) to develop a quick, automated, and quantitative blood-based assay for measuring ISGylation
(ii) to test if elevated ISGylation is a common trend in distinct neurodegenerative diseases using the Wes machine.

Steps:
Phase I: Purchasing and installation of the Wes machine
Phase II: Standardization of the assay on the Wes machine
Phase III: Screening samples and data analysis Outcome:

Without wishing to be bound by theory, this study will establish ISGylation as a diagnostic/prognostic biomarker in patients and establish a blood-based assay to assess ISGylation in living patients. These results will also reveal ISGylation as an biomarker to assess the risk for proteinopathy-induced neurodegeneration in patients with neurodegenerative disorders, as we have demonstrated that ISGylation induces proteinopathy in A-T, a neurodegenerative disease.

Relevance and Significance:

Presently, no biomarkers, and blood-based tests to assess a risk for proteinopathy-induced neurodegeneration in living patients are available thus, this study is a unique one.

Similar to neurological disorders, ISGylation is also elevated and induces proteinopathy in most cancer and pathogen-infected cells (16-19). Moreover, empirical evidence from my lab has revealed that ISGylation could serve as tumor biomarker for assessing efficacy of clinically used anticancer drug camptothecin in cancer patients. Recently, these observations are confirmed in several independent clinical trials thus, warranting a clinical test that can predict levels of ISGylation consequently, drug efficacy, in cancer patients. Thus, an ISGylation assay as described herein could also be used as a biomarker for predicting efficacy of the anticancer drug in cancer patients. This is certainly one approach, as Alpha Fetoprotein (AFP) biomarker test, also a blood-based test, is currently being used in clinics to diagnose both Ataxia Telangiectasia as well as cancer, as similar to ISGylation, AFP is elevated both in A-T (20,21) and cancer (22) patients.

REFERENCES CITED IN THIS EXAMPLE

1. Neurodegenerative drugs market to reach $45 billion by 2022 worldwide, PharmaAsia, Feb. 22, 2017.
2. Rapid HIV testing: a review of the literature and implications for the clinician. Curr HIV/AIDS Rep 3, 169-175, 2016.
3. Evaluation of a new in-clinic test system to detect feline immunodeficiency virus and feline leukemia virus infection. Vet Clin Pathol 39, 210-214, 2010.
4. Monoclonal antibody blocking tests for the detection of HSV-1- and HSV-2-specific humoral responses: comparison with western blot assay. J Virol Methods 55, 27-35 1995.
5. Neurodegenerative Disease Market: Global Industry Analysis and Opportunity Assessment 2015-2025, Future Market Insights, April 2017.
6. Neurodegenerative Disease Market: Global Industry Analysis and Opportunity Assessment 2015-2025, Future Market Insights, April 2017.
7. Global Neurodegenerative Disease Market—Growth, Trends, and Forecasts (2016-2021), Mordor Intelligence, August 2016.
8. Neurodegenerative Disease Market: By Drug Class (NMDA, SSRIs, Dopamine Inhibitors) & by Indications (Parkinson's & Huntington disease, Amyotrophic Lateral Sclerosis, Alzheimer's disease) & Geography-Forecast (2016-2021), Industry ARC, Jan. 15, 2016.
9. Global Neurodegenerative Disease Market—Growth, Trends, and Forecasts (2016-2021), Mordor Intelligence, August 2016.
10. Neurodegenerative Diseases Market to Survive Patent Cliff, Thanks to New Therapeutics, GBI Research, May 13, 2013.
11. Neurodegenerative Diseases Market to Grow at 4.7% CAGR to 2019, PR Newswire, May 14, 2915.

12. Stem Cell Approaches for Treatment of Neurodegenerative Diseases, OMICS International, Nov. 17, 2014.
13. ISG15 Deregulates Autophagy in Genotoxin-treated Ataxia Telangiectasia Cells. J Biol Chem 288, 2388-2402, 2013.
14. A novel role for ATM in regulating proteasome-mediated protein degradation through suppression of the ISG15 conjugation pathway. PLoS One 6, e16422, 2011.
15. Total protein analysis as a reliable loading control for quantitative fluorescent Western blotting. PLoS One 8, e72457, 2013.
16. Mycobacterial disease and impaired IFN-gamma immunity in humans with inherited ISG15 deficiency. Science 337, 1684-1688, 2012.
17. ISG15: A double edged sword in cancer. Oncoimmunology 4, e1052935, 2015.
18. Elevated expression of ISG15 in tumor cells interferes with the ubiquitin/26S proteasome pathway. Cancer Res 66, 921-928, 2006.
19. Antiviral Properties of ISG15. Viruses 2, 2154-2168, 2010.
20. Alpha-fetoprotein as a biomarker for recessive ataxias. Arq Neuropsiquiatr 68, 953-955, 2010.
21. Alpha-fetoprotein, a fascinating protein and biomarker in neurology. Eur J Paediatr Neurol 18, 243-248, 2014.
22. Use of Biomarkers in Screening for Cancer. Adv Exp Med Biol 867, 27-39, 2015.

Example 21

Abstract

ISG15 (Interferon-Stimulated Gene 15), an ubiquitin-like protein, is aberrantly elevated in cells and brain tissues obtained from Ataxia Telangiectasia (A-T) patients. ISG15 protein is synthesized from the ISG15 gene and either remains in a free form or conjugated to intracellular proteins in a process called ISGylation. Our previous studies have revealed that elevated ISGylation induces proteinopathy (aberrant protein degradation) in A-T cells. Based on these observations that ISG15 is elevated in injured neurons and Amyotrophic Lateral Sclerosis (ALS), a proteinopathy-mediated neurodegenerative disease like A-T, ISGylation could be used as a clinical diagnostic/prognostic biomarker for predicting a risk for proteinopathy in neurodegenerative diseases. To confirm this, we examined the expression of free ISG15 and ISGylation in easily accessible lymphocytes from normal individuals, as well as A-T, ALS, Alzheimer, and Parkinson patients, using an ISG15-specific antibody by Western blotting analysis. We show that, although levels of both free ISG15 and ISGylation were significantly elevated, increases in ISGylation were prominent in all diseases compared to normal lymphocytes. Increased ISGylation could be used as a general diagnostic/prognostic biomarker for assessing a risk for proteinopathy-induced neurodegeneration in patients.

Over six million people in the United States alone suffer from neurodegenerative diseases, all of which are chronic and incurable. The cause(s) of these diseases is mainly unknown, and there are no effective diagnostic markers for predicting them, rendering the development of effective treatments for neurodegenerative diseases difficult. Notably, proteinopathy (defects in protein degradation) has been identified as an underlying cause of neurodegeneration in several neurodegenerative diseases. However, there is no clinical test available to assess proteinopathy in these diseases. Our previous studies have identified ISGylation as a mediator of proteinopathy in Ataxia Telangiectasia. Here, we show that ISGylation is significantly elevated in ALS, Alzheimer, and Parkinson diseases wherein neurodegenerative proteinopathies are common. This study thus provides an ISG15 paradigm to understand the etiology of proteinopathy and, without wishing to be bound by theory, identifies ISGylation to be a diagnostic/prognostic biomarker for assessing the risk for proteinopathy-induced neurodegeneration in patients with neurodegenerative diseases.

Introduction

Interferon-Stimulated Gene 15 (ISG15) is an ubiquitin-like protein that is minimally expressed in human normal cells and tissues[1-5]. However, its gene and protein expressions are highly elevated in response to type I interferons (IFNs) in all cell lineages[6-9]. ISG15 protein is synthesized from the ISG15 gene and either remains in an intracellular free form, appended to proteins in cells (conjugated form), or secreted from cells (extracellular form) by an unknown mechanism[3,10,11]. ISG15-specific enzymes E1 (UbEIL), E2 (UbcH8), and E3 (HERCS, EFP, and several others) are also IFN-stimulated proteins that conjugate intracellular free ISG15 to cellular proteins, a mechanism referred to as ISGylation[8,12-14]. Empirical evidence from our lab has revealed that ISGylation predominantly antagonizes the canonical ubiquitin pathway in cancer cells[12]. Since polyubiquitylation of cellular proteins is a prerequisite for protein turnover via the 26S proteasome, and ubiquitin-mediated protein turnover is crucial in maintaining cellular homeostasis, ISG15 proteinopathy (ISG15-mediated defective protein turnover) can be an underlying cause of malignancy in human[3,4,12] and mouse 15 experimental disease models.

ISG15 is also constitutively elevated in Ataxia Telangiectasia (A-T), a rare neurodegenerative disease (1 in 40,000-100,000 births) due to aberrant activation of the IFN pathway[16,17]. Like cancer cells, we have demonstrated that ISGylation antagonizes the ubiquitin pathway in A-T cells[17]. Additionally, ISG15 is also elevated in human A-T brains and mouse cerebellums, the part of the brain principally affected in A-T[17]. Moreover, our results have revealed signs of ISG15 proteinopathy in both A-T human (obtained post-mortem)[17] and mouse (grown in ex vivo culture) brain tissues. Notably, like A-T, the interferon pathway is also aberrantly expressed in the spinal cords of affected mice in an Amyotrophic Lateral Sclerosis (ALS) murine model18. Free ISG15 is also elevated in the spinal cords of human ALS patients[18]. However, whether ISGylation is elevated in human ALS patients has not been investigated. Previous literature has demonstrated that ISG15 is elevated in injured neurons. Since neuronal injury is common to all neurodegenerative diseases, and proteinopathy is an underlying cause of neurodegeneration in several neurodegenerative diseases, ISGylation-mediated proteinopathy may be an underlying cause of neurodegeneration.

The current study was initiated to demonstrate increased ISGylation is prevalent in neurodegenerative diseases in which proteinopathy has been implicated as an underlying cause of neurodegeneration. We chose to assess ISGylation in easily accessible patient-derived lymphocytes (Coriell Cell Repository). Using Western blot analysis, we show that ISGylation is significantly elevated in all patient-derived A-T, ALS, Alzheimer, and Parkinson lymphocytes compared to lymphocytes obtained from normal individuals. Based on observations that ISGylation induces proteinopathy in human and mouse A-T experimental disease models, that ISG15 is a biomarker for neuronal injury, and that ISGylation is elevated in neurodegenerative diseases, ISGylation could be used as a diagnostic/prognostic biomarker for predicting a risk for proteinopathy-induced neurodegeneration in neurological diseases.

Materials and Methods

Normal and Patient-Derived Lymphocytes

De-identified normal (ND03975, ND03375, ND03664, ND03549, ND03712, ND05154, ND03465, ND03976, ND03835, ND03972, ND04887, ND04946, ND05125) and patient-derived A-T (GM0332A, GM0332B, GM0334A, GM0334B, GM013819A, GM013819B, GM03189A, GM03189B, GM03187A, GM03187B), ALS (ND11267, ND07156, ND14964, ND09508, ND14911, ND02380, ND08980), Alzheimer (AG17529, AG17512, AG08142, AG08143, AG06839, AG08111, AG17511), and Parkinson (ND07931, ND07254, ND08996, ND00931, ND00196, ND08917, ND00264) lymphocytes were obtained from the Coriell Cell Repository for Medical Research (Camden, N.J., USA). No patient contact was made. All cells were cultured in Roswell Park Memorial Institute Medium 1640 with 2 mM L-glutamine and 15% Fetal Bovine Serum (not inactivated) and grown in a 37° C. incubator with 5% CO2.

ISG15 Immunodetection by Western Blot Analysis

Cells (200,000 viable cells/ml) were lysed in 4% SDS lysis buffer (50 mM Tris-HCl, pH 7.5, 4% SDS), sonicated, and boiled for 10 minutes at 1000 C. Lysates were clarified via centrifugation at 13,000 rpm for five minutes. Protein concentrations were determined by measuring absorbance at 280 nm using a Beckman Coulter Spectrophotometer, and proteins were adjusted to equal protein amounts. Normalized samples were mixed with equal amounts of 6×SDS Laemmli sample buffer (final concentration of 3×). Samples were boiled for 10 min at 100° C. before loading them on 15% SDS polyacrylamide gels. After transfer onto a nitrocellulose membrane and blocking membranes in 5% milk in TBST (Tris-Buffered Saline containing Tween-20) for 1 h, blots were incubated with a primary anti-ISG15 antibody (1:1000 in 2% Bovine Serum Albumin) for 18 h7. Blots were then washed in TBST (3×10 min) and incubated with horseradish peroxidase-conjugated rabbit secondary (Cat. No. NA934V, GE Healthcare, New Orleans, La., USA) antibodies (1:10000) for 1 h. After washing three times with TBST for 10 min, blots were developed using Prime Western Blotting Detection Reagent and Amersham Imager A600 as indicated. Equal protein loading was confirmed by re-probing the same membrane with anti-βactin (Cat. No. ab6276, Abcam, Cambridge, UK) primary (1:5000) and horseradish peroxidase-conjugated mouse secondary (Cat. No. NA931V, GE Healthcare, New Orleans, La., USA) antibodies (1:10000) as described herein. Protein quantitation was performed using ImageQuant TL software.

Statistical Analysis

Statistical analysis (unpaired t-test) was performed with GraphPad software. P value <0.05 was considered statistically significant.

Results

ISGylation is Elevated in Neurodegenerative Diseases.

We assessed ISGylation in lysates of normal, A-T, ALS, Alzheimer, and Parkinson lymphocytes using an ISG15-specific antibody in Western blot analysis. A typical Western blot of free ISG15, its conjugates (ISGylation), and β-actin in normal lymphocytes (two samples from distinct individuals) is shown in FIG. 22, top panel. Intensities of free ISG15, ISGylation, and β-actin were quantitated using an Amersham Imager A600 and ImageQuant TL software.

The bar graph in FIG. 22, bottom panel, shows the ratios between free ISG15/β-actin and ISGylation/β-actin from Western blots in this study. When normalized to β-actin, ISGylation levels were significantly increased in lymphocytes obtained from A-T (p=0.0006), ALS (p=0.0001), Alzheimer (p=0.0011), and Parkinson (p=0.0024) patients compared to normal individuals. Although levels of free ISG15 were also elevated A-T (p=0.0090), ALS (p=0.0051), Alzheimer (p=0.0523), and Parkinson (p=0.0805) there was a striking significant increase in ISGylation in all diseases compared to normal lymphocytes. Since empirical evidence from our lab reveals that increased ISGylation contributes to proteinopathy, and proteinopathy contributes to neurodegeneration, increased levels of ISGylation may also be used as a prognostic/diagnostic biomarker for predicting a risk for proteinopathy-induced neurodegeneration in neurological disorders.

Discussion

This study stems from our ongoing research using an A-T neurodegenerative disease model. Although a rare disease, A-T shares a key pathologic neurodegeneration event with other rare (e.g. ALS, Creutzfeldt-Jakob, among others) and more common (e.g. Alzheimer, Parkinson, among others) neurodegenerative diseases. In most neurodegenerative diseases, proteinopathy has been identified as an underlying cause of neurodegeneration. Accumulation of misfolded protein deposits in affected brain regions has been reported in many neurodegenerative diseases[20-27]. In most cases, proteinaceous deposits are composed of ubiquitin conjugates, indicating a failure in their degradation via the ubiquitin/26S proteasome system[20-27]. Recently, we have demonstrated that aberrantly elevated ISGylation induces proteinopathy in A-T cells[17,28]. These results, together with previous literature reporting that ISG15 is elevated in ALS[18] and that ISG15 is a biomarker of neuronal injury[19], implies that induction of increased ISGylation may be a common cause of proteinopathy in most neurodegenerative diseases wherein neuronal injury is common.

The current study was initiated to determine whether ISGylation is elevated in neurodegenerative diseases. We chose to use Western blotting for this analysis, as this technique allowed us to detect and quantitate both free ISG15 and ISGylation in the same cell lysates. This was not possible using simpler techniques like dot-blotting or gene expression analyses. Our results have revealed that ISGylation is elevated in all neurodegenerative diseases tested. Notably, we are the first to report that the ISG15 pathway is constitutively elevated in Alzheimer and Parkinson diseases. Taken together, these results indicating that ISGylation could be used as a clinical diagnostic/prognostic biomarker for predicting a risk of proteinopathy-induced neurodegeneration in patients. Western-based diagnostic tests are currently licensed for use in veterinary and human clinical practices[29-31], rendering Western blotting to measure ISGylation in patient-derived lymphocytes one approach. Moreover, the Western-based diagnostic test that is described here can be performed easily using blood-based lymphocytes from living patients. It is important to note that ISGylation is also elevated and induces proteinopathy in most cancer and pathogen-infected cells[3,10]. Without wishing to be bound by theory, the ISGylation test can be used in conjunction with physical phenotypes and patient medical history for accurate clinical diagnosis of proteinopathy in neurodegenerative diseases. Another blood-based biomarker test, the Alpha Fetoprotein (AFP) test, utilizes this comprehensive approach since, like ISGylation, AFP is elevated in both cancer and recessive ataxias (e.g. Ataxia Telangiectasia)[32]. Nevertheless, at present, no clinical tests are available that can assess the risk of proteinopathy-induced neurodegeneration, thereby making this biomarker study a new one.

REFERENCES CITED IN THIS EXAMPLES

1. Bektas N, Noetzel E, Veeck J, Press M F, Kristiansen Naami A, Hartmann A, Dimmler A, Beckmann M W, Knuchel R, Fasching P A, Dahl E. The ubiquitin-like molecule interferon-stimulated gene 15 (ISG15) is a potential prognostic marker in human breast cancer. Breast Cancer Res 2008; 10: R58
2. Chen R H, Du Y, Han P, Wang H B, Liang F Y, Feng G K, Zhou A J, Cai M Y, Zhong Q, Zeng M S, Huang X M. ISG15 predicts poor prognosis and promotes cancer stem cell phenotype in nasopharyngeal carcinoma. Oncotarget 2016; 7:16910-16922
3. Desai S D. ISG15: A double edged sword in cancer. Oncoimmunology 2015; 4:e1052935
4. Desai S D, Haas A L, Wood L M, Tsai Y C, Pestka S, Rubin E H, Saleem A, Nur E K A, Liu L F. Elevated expression of ISG15 in tumor cells interferes with the ubiquitin/26S proteasome pathway. Cancer Res 2006; 66: 921-928
5. Zuo C, Sheng X, Ma M, Xia M, Ouyang L. ISG15 in the tumorigenesis and treatment of cancer: An emerging role in malignancies of the digestive system. Oncotarget 2016; 7: 74393-74409
6. Haas A L, Ahrens P, Bright P M, Ankel, H. Interferon induces a 15-kilodalton protein exhibiting marked homology to ubiquitin. J Biol Chem 1987; 262:11315-11323
7. Loeb K R, Haas A L. The interferon-inducible 15-kDa ubiquitin homolog conjugates to intracellular proteins. J Biol Chem 1992; 267:7806-7813
8. Narasimhan J, Potter J L, Haas A L. Conjugation of the 15-kDa interferon-induced ubiquitin homolog is distinct from that of ubiquitin. J Biol Chem 1996; 271:324-330
9. Tecalco Cruz A C, Mejia-Barreto K. Cell type-dependent regulation of free ISG15 levels and ISGylation. J Cell Commun Signal 2017; [Epub ahead of print]
10. Bogunovic D, Boisson-Dupuis S, Casanova J L. ISG15: leading a double life as a secreted molecule. Exp Mol Med 2013; 45, e18
11. D'Cunha J, Ramanujam S, Wagner R J, Witt P L., Knight E, Jr, Borden E C. In vitro and in vivo secretion of human ISG15, an IFN-induced immunomodulatory cytokine. J Immunol 1996:157, 4100-4108
12. Burks J, Reed R E, and Desai S D. ISGylation governs the oncogenic function of Ki-Ras in breast cancer. Oncogene 2014; 33:794-803.
13. Dastur A, Beaudenon S, Kelley M, Krug R M, Huibregtse J M. Herc5, an interferon-induced HECT E3 enzyme, is required for conjugation of ISG15 in human cells. J Biol Chem 2006 281: 4334-4338
14. Haas A L. ISG15-dependent Regulation. In Protein Degradation Mayer R J, Ciechnover A, Rechsteiner M (ed). Wiley-VCH Verlag GmbH & Co., Weinheim, Germany, 2006; 103-131
15. Burks J, Reed R E, Desai S D. Free ISG15 triggers an antitumor immune response against breast cancer: a new perspective. Oncotarget 2015; 6:7221-7231
16. Siddoo-Atwal C, Haas A L, Rosin M P. Elevation of interferon beta-inducible proteins in ataxia telangiectasia cells. Cancer Res 1996; 56:443-447
17. Wood L M, Sankar S, Reed R E, Haas A L, Liu L F, McKinnon P, Desai S D. A novel role for ATM in regulating proteasome-mediated protein degradation through suppression of the ISG15 conjugation pathway. PLoS One 2011; 6:e16422
18. Wang R, Yang B, Zhang D. Activation of interferon signaling pathways in spinal cord astrocytes from an ALS mouse model. Glia 2011; 59:946-958
19. Wang R G, Kaul M, Zhang D X. Interferon-stimulated gene 15 as a general marker for acute and chronic neuronal injuries. Sheng Li Xue Bao 2012; 64:577-583
20. Nedelsky N B, Todd P K, Taylor J P. Autophagy and the ubiquitin-proteasome system: collaborators in neuroprotection. Biochim Biophys Acta 2008; 1782:691-699
21. Ross C A, Pickart C M. The ubiquitin-proteasome pathway in Parkinson's disease and other neurodegenerative diseases. Trends Cell Biol 2004; 14:703-711
22. Li X J, Li S. Proteasomal dysfunction in aging and Huntington disease. Neurobiol Dis 2011; 43:4-8
23. Mittal S, Ganesh S. Protein quality control mechanisms and neurodegenerative disorders: Checks, balances and deadlocks. Neurosci Res 2010; 68:159-166
24. Lehman N L. The ubiquitin proteasome system in neuropathology. Acta Neuropathol 2009; 118: 329-347
25. Schmitt H P. Protein ubiquitination, degradation and the proteasome in neurodegenerative disorders: no clear evidence for a significant pathogenetic role of proteasome failure in Alzheimer disease and related disorders. Med Hypotheses 2006; 67:311-317
26. Hegde A N, Upadhya S C. Role of ubiquitin-proteasome-mediated proteolysis in nervous system disease. Biochim Biophys Acta 2011; 1809:128-140
27. Finkbeiner S, Mitra S. The ubiquitin-proteasome pathway in Huntington's disease. ScientificWorldJournal 2008; 8:421-433
28. Desai S D, Reed R E, Babu S, Lorio E A. ISG15 Deregulates Autophagy in Genotoxin-treated Ataxia Telangiectasia Cells. J Biol Chem 2013; 288:2388-2402
29. Franco-Paredes C, Tellez I, del Rio C. Rapid HIV testing: a review of the literature and implications for the clinician. Curr HIV/AIDS Rep 2006; 3:169-175
30. Sand C, Englert T, Egberink H, Lutz H, Hartmann K. Evaluation of a new in-clinic test system to detect feline immunodeficiency virus and feline leukemia virus infection. Vet Clin Pathol 2010; 39:210-214
31. Slomka M J, Ashley R L, Cowan F M, Cross A, Brown D W. Monoclonal antibody blocking tests for the detection of HSV-1- and HSV-2-specific humoral responses: comparison with western blot assay. J Virol Methods 1995; 55:27-35
32. Braga-Neto P, Dutra L A, Pedroso J L, Barsottini O G Alpha-fetoprotein as abiomarker for recessive ataxias. Arq Neuropsiquiatr 2010; 68; 953-955

Example 22

Abstract

Over 6 million people in the United States suffer from neurodegenerative diseases, all of which are chronic, incurable, and with causes unknown. Identifying a common molecular mechanism underpinning neurodegenerative disease pathology is urgently needed to aid in the design of effective therapies to ease suffering, reduce economic cost, and improve quality of life. Recent studies from our laboratory have demonstrated that aberrant expression of the ubiquitin-like protein Interferon-Stimulated Gene 15 (ISG15) conjugation pathway inhibits ubiquitin-dependent protein degradation in both cancer and neurodegenerative cell models. Additionally, defective mitophagy, or clearance of damaged mitochondria, has been implicated in the pathogenesis of many neurodegenerative diseases. Here we show that mitophagy is indeed defective in both Ataxia Telangiectasia (A-T) and Amyotrophic Lateral Sclerosis (ALS) neurodegenerative cell models, and that this defective mitophagy is due to elevated levels of ISG15 conjugates. ISG15 conjugates are also significantly elevated in Alzheimer's and Parkinson's diseases, indicating that aberrant expression of the ISG15 conjugation pathway is a global problem. Knowing ISG15 inhibits E3 ubiquitin ligases, and that Parkin is an E3 ubiquitin ligase with an integral role in the regulation of mitophagy, I am currently testing whether the constitutively elevated ISG15 ligation pathway inhibits ubiquitin-dependent regulation of mitophagy by inhibiting Parkin in ALS lymphocytes. I will accomplish this by examining structural (via Transmission Electron Microscopy), physiological (via MitoTracker Red, CellRox Green, and JC1 staining agents), and functional (via Biosciences Seahorse XF24 flux analyzer to measure oxygen consumption rates) properties of mitochondria in ALS vs. ISG15-silenced ALS cells. Completion of this project will lead to an understanding of whether constitutively elevated ISG15 is an underlying cause of mitochondrial pathology in ALS and will elucidate the molecular mechanism underlying defective mitophagy in other neurological diseases where ISG15 is also elevated.

Materials and Methods

Cell Lines: A-T fibroblast cell lines and ALS, Alzheimer's, and Parkinson's lymphocyte cell lines were purchased from the Coriell Biorepository in Camden, N.J. A-T fibroblasts were grown in complete Dulbecco's Modified Eagle Medium supplemented with hygromycin B (100 µg/ml) and puromycin (6.5 µg/ml). ALS, Alzheimer's, and Parkinson's lymphocytes were grown in Roswell Park Memorial Institute medium supplemented with 15% Fetal Bovine Serum (not inactivated) and 2 mM L-glutamine. All cells were incubated at 37° C. Both ISG15-silenced A-T fibroblasts and ALS lymphocytes were created in the Desai Lab.

Western Blotting: SDS-PAGE was performed on 15% polyacrylamide gels at 187 V for one hour. Gels were transferred onto nitrocellulose membranes overnight at 30 V. Membranes were then blocked in 5% milk and subsequently blotted with primary Haas ISG (1:1,000) in 2% BSA and secondary anti-rabbit (1:10,000).

Flow Cytometry: Both control and ALS lymphocytes were seeded to a density of one million cells per BD Falcon 352054 tube. Half of the samples were stained with 50 nM of MitoTracker Red 580 (Invitrogen M22425) dye for 45 minutes. Remaining samples were stained with 500 nM CellRox Green for 30 minutes. All samples were fixed in 3.7% formaldehyde then run through a BD FACSCanto II flow cytometer.

Conclusions

ISG15 is elevated in other neurological diseases, indicating that elevation of the ISG15 conjugation pathway is a global problem.

Constitutively elevated ISG15 inhibits mitophagy in A-T and ALS. When ISG15 is silenced, levels of reactive oxygen species and mitochondrial mass are, in part, restored in both A-T fibroblasts and ALS lymphocytes.

Understanding how elevated ISG15 levels lead to defective mitophagy in neurological diseases will identify this biological process as a potential target for the development of much needed therapies.

Test whether ISG15 inhibits Parkin-mediated mitofusin-2 (MFN2) degradation in ALS lymphocytes.

Determine if altered ISG15 levels inhibit mitophagy in ALS iPSC-differentiated motor neurons, a more physiologically relevant cell type.

Example 23

The laboratory research focuses on understanding the functional impact of the aberrantly-expressed ubiquitin-like ISG15 (Interferon-Stimulated Gene-15 kDa) pathway in cancer. It was demonstrated that the induction of the ISG15 conjugation pathway inhibits the canonical ubiquitin-dependent protein degradation pathway in cancer cells, confirmed by others in distinct cancer models. We have also shown that the ISG15 conjugation pathway is also constitutively elevated in Ataxia Telangiectasia (A-T), a severe neurological disorder. We have also shown that the constitutively elevated ISG15 conjugation pathway in A-T cells inhibits ubiquitin-dependent protein degradation and mitophagy, the latter of which is regulated by ubiquitin-dependent signaling through a subset of ligases including Parkin, MARCH5, and MULAN/MAPL. Because defects in mitophagy have also been identified in Amyotrophic Lateral Sclerosis (ALS) and that the ISG15 pathway is elevated in ALS, constitutively elevated ISG15 inhibits mitophagy and contributes to neurodegeneration as a general etiological feature of these neurological disorders. As described in this Example, molecular mechanism(s) by which ISG15 inhibits mitophagy in A-T and ALS will be identified and the impact of ISG15 induction on mitophagy in A-T and ALS will be examined.

What is the Molecular Mechanism Underlying Defective Mitophagy in Human A-T Cells?

We have shown that the mitophagy protein MFN2 is conjugated to the ubiquitin-like proteins SUMO-1, SUMO-2/3, and ubiquitin prior to its proteasomal degradation to trigger mitophagy and that ISG15 conjugation inhibits this process. Here, we will determine whether ISGylation inhibits mitochondrial ubiquitin (MARCH5 and Parkin) and/or SUMO/ubiquitin (MULAN/MAPL) dual function E3 ligases, which in turn inhibits mitophagy in A-T patient-derived fibroblasts using various biochemical assays and reagents that we have established in our laboratory.

Is Mitophagy Defective in Human A-T Neurons?

Mitophagy is defective in human A-T fibroblasts and mouse A-T thymocytes. Our studies have revealed that defective mitophagy is due to the elevated ISG15 pathway in human A-T fibroblasts. We have also found that the ISG15 pathway is elevated in both A-T mouse and human cerebellums. Since both A-T human patients and mice have elevated ISG15 expression, and cerebellar neurodegeneration is a hallmark of A-T, a more complete understanding of the functional impact of ISG15-mediated defects in mitophagy in neurons in A-T patients is warranted. However, such studies are impractical to conduct in human patients. Also, Atm homozygous mice are scarcely available for experimentation. Therefore, we shall establish a unique "A-T humanized neuronal model" to examine the impact of ISG15 induction on mitophagy in A-T patient-derived neurons, a cell type majorly affected in A-T disease. For that, we shall make normal- and A-T patient-specific induced Neural Progenitor cells from renal cells in urine (UiNPCs), and differentiate them into neurons. So far, we have isolated renal cell colonies from the urine samples of normal subjects. We have demonstrated that these normal renal cells show epithelial morphology, express epithelial markers, and retain normal karyotype in culture. As typical normal cells, these cells barely express ISG15. However, the ISG15 conjugation pathway is induced in response to interferon treatment. Here, we shall isolate A-T renal cells using the same protocol. Normal and A-T renal cells will then be used to generate UiNPCs and neurons to address what is the molecular mechanism underlying defective mitophagy in human A-T cells.

Does the ISG15 Conjugation Pathway Inhibit Mitophagy in ALS?

Without wishing to be bound by theory, ISG15 is causative for mitophagy defects in ALS cells. We shall confirm these observations using various mitophagy assays described in our Studies. We shall also investigate whether ISG15 inhibits mitophagy by inhibiting SUMO/Ubiquitin E3 ligases in ALS patient-derived lymphocytes as described herein this Example.

Overall, this study will allow for the development of a new ISG15 mechanism using a unique protocol that will revolutionize current understanding of the defective mitophagy in A-T, and pave the way for development of similar protocol(s) for studying other neurological disorders such as ALS in which ISG15 is also elevated.

Example 24

ISG15: A Therapeutic Target for ALS

ALS and Military Service:

Amyotrophic Lateral Sclerosis (ALS), also known as a Lou Gehrig's disease, is a rare, incurable, and fatal neurodegenerative disease. ALS affects upper motor neurons in the brain, and lower motor neurons in the brain stem and spinal cord. Collectively, both upper and lower motor neurons control voluntary muscle movements of the body such as chewing, walking, breathing, and talking. The loss of these motor neurons, therefore, causes the muscles under their control to weaken, leading to the loss of all voluntary body functions, and ultimately paralysis. ALS can affect individuals of any age, but it mostly affects late/middle-aged individuals (45-55 years). ALS can be familial (hereditary) or sporadic (spontaneous due to environmental conditions). About 5-10% of ALS cases are familial, and 90% are sporadic, indicating the contribution of environmental conditions as a cause of ALS. Remarkably, research supported by the Department of Veterans Affairs and the Department of Defense have revealed that veterans who have served in the military are at a nearly 60% greater risk of being diagnosed with ALS than those with no history of military service (1). An independent study conducted by investigators at the Harvard University and Institute of Medicine supports these conclusions (1). However, what causes the disease in normal individuals and why the incidence of ALS is higher in veterans is not known. Recent research from my group indicates a link between the high incidence of ALS and military service.

ISG15 and Neurodegenerative Diseases (Desai Lab Results):

In recent years, using human and mouse models, my group has identified the constitutively elevated ISG15 pathway as prospective mediators of neurodegeneration in Ataxia Telangiectasia (A-T), a rare neurodegenerative disease like ALS (2-4). ISG15 is a ubiquitin-like protein. Protein degradation by ubiquitin is crucial for many cellular functions including mitophagy, a process in which abnormal mitochondria are eliminated from cells. We have demonstrated that aberrantly elevated ISG15 inhibits the ubiquitin-mediated degradation of cellular proteins and mitophagy in A-T cells. Defective protein turnover and mitophagy in neurons have been identified as key players in the pathogenesis of many neurodegenerative diseases, including ALS. Notably, much like A-T, the ISG15 ligation pathway is also constitutively elevated in the spinal cords of ALS mice and patients (5). We have demonstrated that ISG15 is also elevated in Alzheimer and Parkinson diseases (manuscript under review). However, it is not known whether as in A-T cells, ISG15 is causally responsible for inhibiting protein and mitochondrial turnover in ALS, Alzheimer, and Parkinson diseases. Without wishing to be bound by theory, constitutively elevated ISG15 pathway inhibits protein turnover and mitophagy, thus contributing to neurodegeneration in these neurodegenerative diseases.

Linking ALS, ISG15, and Brain Injury:

ISG15 levels are dramatically increased in the brains of mice subjected to traumatic brain injury (TBI). TBI caused by explosions, motor vehicle accidents, and gunshot wounds during war are seen in veterans. TBI injures neurons, and ISG15 has been identified as a biomarker for neuronal injury. However, whether ISG15 expression after TBI is transient or sustained, and whether elevated ISG15 inhibits protein and mitochondrial degradation in motor neurons, has not been studied. Without wishing to be bound by theory, ISG15 elevation in response to TBI inhibits protein turnover and mitophagy in neurons. Accumulation of toxic proteins and abnormal mitochondria, in turn, leads to motor neurodegeneration and permanent loss of motor neurons in ALS veterans. Consequently, the incidence of ALS diagnosis is higher in veterans who are exposed to events that cause TBI.

Development of the Project:

1: To test if the elevated expression of ISG15 impairs protein turnover and mitophagy in ALS human motor neurons. Using biochemical and genetic experiments established in our lab for our A-T studies, we shall test if ISG15 is constitutively elevated, and if elevated ISG15 inhibits protein turnover and mitophagy, in iPSC-derived ALS motor neurons (iXCells Biotechnologies). Normal motor neurons will be used as controls.

2: To test if the elevated expression of ISG15 induces ALS motor neurodegeneration. Current literature indicates that neurodegeneration is not limited to proteinopathies and mitochondriopathies within target neurons, but is also strongly influenced by astrocytes that have intimate contact with their target neurons. Interestingly, ISG15 is highly elevated in astrocytes of an ALS murine model, prompting us to question whether ISG15-mediated proteinopathy/mitochondriopathy in astrocytes contributes to the non-cell-autonomous motor neuron cell death in murine and human ALS models. Using ALS/normal motor neuron and astrocyte (iXCells Biotechnologies) co-culture assays, along with a lentiviral shRNA-mediated ISG15 gene silencing approach, we shall test whether motor neuron cell death is autonomous or non-cell-autonomous and whether this cell death is ISG15-dependent.

3: Experiments to test a potential link between TBI and Veterans. ISG15 is elevated in lymphoblastoid cell lines derived from ALS patients. Here, we shall test if the ISG15 pathway is elevated in lymphocytes obtained from normal individuals, non-TBI and TBI veterans with/without ALS.

Results: These results will lead to a clear understanding of whether constitutively elevated ISG15 is an underlying cause of protein and mitochondrial turnover in ALS. These results will also establish a potential link between TBI and ALS in veterans, and by doing so, it will establish ISG15 as a diagnostic biomarker in blood lymphocytes for TBI, and as a surrogate prognostic biomarker for predicting a risk for ALS (proteinopathy-induced neurodegeneration) in living veterans exposed to TBI. This new knowledge will also establish ISG15 as a therapeutic target to restore, in part, protein and mitochondrial homeostasis, and thus neuronal health, in ALS and TBI-ALS veterans.

REFERENCES CITED IN THIS EXAMPLE

1. ALS in the Military: Unexpected consequences of Military services. Report by the ALS Association, 2013. http://www.alsa.org/assets/pdfs/advocacy/2013_als_in_military.pdf
2. Desai, S. D., Reed, R. E., Babu, S., ISG15 Deregulates Autophagy in Genotoxin-treated Ataxia Telangiectasia Cells. (2013) J Biol Chem, 288, 2388-2402,
3. Kim, C. D., Reed, R. E., Juncker, et al. Evidence for the Deregulation of Protein Turnover Pathways in Atm-Deficient Mouse Cerebellum: An Organotypic Study. (2017) J Neuropathol Exp Neurol, In press.
4. Wood, L. M., Sankar, S., Reed, R. E., et al. A novel role for ATM in regulating proteasome-mediated protein degradation through suppression of the ISG15 conjugation pathway. (2011) PLoS One 6, e16422
5. Wang, R., Yang, B., and Zhang, D. Activation of interferon signaling pathways in spinal cord astrocytes from an ALS mouse model. (2011) Glia 59, 946-958
6. Rossi, J. L., Todd, T., Daniels, Z., et al. Interferon-Stimulated Gene 15 Upregulation Precedes the Development of Blood-Brain Barrier Disruption and Cerebral Edema after Traumatic Brain Injury in Young Mice. (2015) J Neurotrauma 32, 1101-1108
7. Wang, R. G, Kaul, M., and Zhang, D. X. Interferon-stimulated gene 15 as a general marker for acute and chronic neuronal injuries. (2012) Sheng Li Xue Bao 64, 577-583

The complete disclosures of all references cited in this specification are hereby incorporated by reference. Also incorporated by reference are the complete disclosures of the following: (1) L. M. Wood et al., "A novel role for ATM in regulating proteasome-mediated protein degradation through suppression of the ISG15 conjugation pathway," PLoS ONE, vol. 6(1): e16422, published Jan. 26, 2011; (2) S. D. Desai and R. E. Reed, "Rethinking neurodegeneration in Ataxia Telangiectasia: Role of proteinopathy," an abstract submitted for the 14$^{th}$ International Workshop on Ataxia-Telangiectasia and ATM, to be held in Delhi, India, Feb. 7-11, 2012; (3) S. D. Desai et al., "ISG15 disrupts cytoskeletal architecture and promotes motility to human breast cancer cells," Exp. Biol. Med. (Maywood), 237: 38-49 (2012); (4) S. D. Desai, "Therapeutic and Diagnostic Method for Ataxia-Telangiectasia," Provisional Application Ser. No. 61/565,715, filed 1 Dec. 2011; and (5) S. D. Desai, "An Improvement to Targeting the ISG15 Pathway in Ataxia-Telangiectasia: A Novel Therapeutic Approach for Treating A-T," U.S. Provisional Application Ser. No. 61/706,863, filed 28 Sep. 2012; and U.S. patent application Ser. No. 13/688,384, now U.S. Pat. No. 9,599,626. In the event of an otherwise irreconcilable conflict, however, the present specification shall control.

Example 25

Abstract

Ataxia Telangiectasia (A-T) is a hereditary childhood disease. Immunodeficiency and cancer are the most common direct causes of A-T death. However, the symptoms of progressive cerebellar neurodegeneration take an enduring and devastating toll on A-T children. There is currently no means to slow the progression of neurodegeneration because molecular mechanisms underlying neurodegeneration in A-T are largely unknown. It is, however, becoming clear that deregulation of the mitophagy pathway, the selective degradation of damaged/old mitochondria via autophagy, is a common underlying cause of neurodegeneration in several neurodegenerative diseases. Mitophagy is also defective in A-T. However, the molecular mechanism underlying defective mitophagy in A-T is currently unknown. Here, we provide evidence that the elevated expression of Interferon-Stimulated Gene 15 (ISG15), an antagonist of the ubiquitin pathway, inhibits mitophagy consequently alters mitochondrial dynamics (mitochondrial mass, physiology, and functions) in A-T cells. Moreover, ISG15 inhibits polyubiquitylation of mitochondrial proteins in A-T cells. Both mitophagy and polyubiquitylation of mitochondrial proteins in part are restored in ISG15-silenced A-T cells. Together, our results indicate that ISG15-mediated defective polyubiquitylation of mitochondrial proteins, an obligatory initiation signal for mitophagy, may be in part an underlying cause of the defective mitophagy in A-T cells. These findings open up new perspectives for understanding and treatment of A-T neurodegeneration and other neurological syndromes caused due to the defective mitophagy such as Amyotrophic Lateral Sclerosis (ALS), as the ISG15 pathway is also elevated in ALS.

Introduction

Ataxia Telangiectasia (Boder-Sedgwick/Louis-Bar syndrome) is an hereditary childhood disease (1-5). Some early symptoms often seen in children with A-T include delayed development of motor skills, poor balance, and slurred speech. Approximately 70% of children suffering from A-T have a weakened immune system (6), and about 20% subsequently develop cancer, most frequently acute lymphocytic leukemia or lymphoma (7). Most patients die in their teens or early 20s. A-T results from loss-of-function in the Atm gene, which is located on the long arm of the chromosome 11 at 11q22-23, and which codes for ATM kinase (8). The ATM kinase activity normally functions in the regulation of various cellular processes such as cell cycle control, mitotic recombination, telomere length monitoring, apoptosis, and DNA repair (1-5). The phenotypic manifestations of A-T is mainly due to the defective phosphorylation of various key regulatory proteins involved in these cellular processes.

Although the incidence is rare, A-T is an important disease to study as it shares key pathologic events with more common neurodegenerative disorders such as Alzheimer, Parkinson, Amyotrophic Lateral Sclerosis (ALS), and Huntington disease. The most prominent pathologic event that A-T shares with the other neurodegenerative diseases is a progressive cerebellar neurodegeneration (9). Many studies have revealed that the defective DNA repair in neurons is a key factor in the progression of A-T neurodegeneration (1,10). On the other hand, it is becoming increasingly clear that the proteinopathy resulting from the alterations in the ubiquitin, autophagy, and mitophagy pathways play major roles in the neurodegeneration in other neurological disorders (11-16), and may also play role in neurodegeneration associated with A-T disease. Recent studies from our group reveal that elevated expression of the ubiquitin-like protein called ISG15 (Interferon-Stimulated Gene 15), an antagonist of the ubiquitin pathway (17), is responsible for inducing the ISG15 proteinopathy presumably responsible for altered proteasomal degradation and subsequent changes in cellular autophagy in A-T cells (18,19).

ISG15 is composed of two ubiquitin-like domains connected by a small linker region with each domain sharing 33% homology with ubiquitin (20,21). The mature functional ISG15 protein is synthesized from a 17 kDa precursor protein by co-translational proteolytic processing of eight amino acids from the C terminus (22). The mature 15 kDa free form of ISG15, like ubiquitin and other UBLs, retains the canonical LRLRGG sequence required for its conjugation to intracellular targets (23). Free ISG15 conjugates to the cellular proteins (ISGylation) using an ISG15-specific ligation pathway, and exerts its biological effects through such post-translational modifications (for review see (24)). Previous studies demonstrated that ISG15 expression is elevated in cultured human A-T cells, and in clinical and synthetic brain tissues from human and mice respectively, but not in their normal counterparts (19,25) indicating that ISG15 expression is negatively regulated by the ATM kinase. While free ISG15 is consistently elevated, the extent of ISGylation inexplicably varies in different human A-T cells and brain tissues (19). Previous studies from our group reveal that ISGylation, but not free ISG15, inhibits cellular protein polyubiquitylation and the subsequent targeted degradation of the adducts via the ubiquitin/proteasome pathway in A-T cells (19). We have also demonstrated that the autophagy pathway is elevated to compensate for the impaired degradation of the cellular proteins through the ubiquitin pathway (18). The functions of both the ubiquitin and autophagy pathways are restored in ISG15-silenced A-T cells revealing linked causality between the ubiquitin and autophagy pathways through elevated expression of ISG15 in response to loss of ATM function (18,19).

Studies from other groups demonstrate that mitophagy, a process that leads to the degradation of the aged/defective mitochondria via autophagy, is defective in A-T cells (26, 27). Our current studies concur with these observations and show that mitochondrial morphology and function are defective in A-T cells. Because the ISG15 pathway inhibits ubiquitin-dependent signaling (17,19) and ubiquitylation of mitochondrial proteins is an obligatory commitment step for mitophagy (28,29), we examined whether elevated ISG15 inhibits polyubiquitylation of the mitochondrial targets as a mechanism to explicate the observed block in mitophagy in A-T cells. Here, we demonstrate that polyubiquitylation of the mitochondrial proteins is significantly ablated in A-T cells and that ISG15-dependent mitophagy, mitochondrial functions, and polyubiquitylation of the mitochondrial proteins are in part restored in ISG15-silenced A-T cells. Together, these results indicate that defective mitophagy is due to the elevated ISG15 pathway in ATM kinase-ablated A-T cells.

Because defective mitophagy is implicated in the onset of neurodegeneration in various neurological disorders (11,16), our results indicate that the ISG15 pathway is a potential therapeutic target for the treatment of A-T neurodegeneration as well as other neurological disorders such as ALS (30), in which ISG15 is elevated.

Experimental Procedures

Cells—

The FT169A (A-T) fibroblast cells expressing control shRNA (A-T/LV-control shRNA) and ISG15 shRNA (A-T/LV-ISG15 shRNA) cell lines and their culture conditions were those described previously (18).

MitoTracker Red 580 Staining—

For imaging analysis, cells were grown on fibronectin-coated glass coverslips in 12-well cell culture plates. For staining, culture medium was replaced with prewarmed medium containing 50 nm MitoTracker Red 580 (Invitrogen, M22425). Cells were then incubated for 20 min at 37° C. in CO2 incubator. Cells were washed with the prewarmed culture medium then fixed in culture medium containing 4% (v/v) formaldehyde for 20 min. Cells were then washed with PBS for 3×10 min and mounted on slides in anti-fade mounting medium with DAPI. Images were acquired at room temperature using a Leica DMRA2 upright microscope fitted with a 40× oil immersion objective. Images were analyzed with SlideBook software (Intelligent Imaging Innovations). For FACS analysis, $1\times10^6$ cells were first placed into 5 ml Falcon tube and washed with phosphate-buffered saline then stained with 50 nm MitoTracker Red 580 for 45 minutes at 37° C. Cells were then washed with PBS, and fixed with 3.7% (v/v) paraformaldehyde. Flow cytometry was performed using BD FACSCanto II flow cytometer (BD Bioscience) and analyzed with BD FACSDiva ver 6.1.3 (BD Bioscience).

JC1 Staining—

JC1 staining was carried out using a MitoPT™ kit (Immunochemistry Technologies, 924). For imaging analysis, cells were grown on fibronectin-coated glass coverslips in 12-well cell culture plates. Next day, culture media was removed and 1× MitoPT™ JC1 solution (2 µg/ml) was added to cover the cells on the slides. Cells were then incubated for 20 min at 37° C. in CO2 incubator. Stain was then removed and cells were washed with 2 ml of 1× assay buffer. Cells were then covered with the coverslips and emission fluorescence was detected using TRITC (590 nm for red color J aggregates in the intact mitochondria) and FITC (530 nm for green color monomers in cytoplasm) channels simultaneously. Images were taken using a Leica DMRA2 upright microscope as described above. For FACS analysis, JC1 staining of cells was carried out using MitoPT™ kit and the manufacturer's protocol (Immunochemistry Technologies, 924). Flow cytometry was performed using BD FACSCanto II flow cytometer (BD Bioscience) as described above.

CellRox Green Staining—

For imaging analysis cells were seeded on the fibronectin-coated coverslips as described above and stained with the CellRox reagent (Molecular Probes, C10448) at the final concentration of 5 µM for 30 min at 37° C. in CO2 incubator. Cells were then washed with PBS, fixed, mounted on slides with DAPI, and viewed using Leica DMRA2 upright microscope as described above. For FACS analysis, cells ($1\times10^6$) were stained with 5 □M CellRox reagent for 30 minutes at 37° C. Cells were then washed with PBS, and fixed with 3.7% (v/v) paraformaldehyde. Flow cytometry was performed as described above.

ATP Measurement—

Cellular ATP levels were measured using the ATP Determination Kit (Invitrogen, A22066) following the protocol provided by manufacturer.

Measurement of the Oxygen Consumption Rate (OCR) Using XF24 Flux Analyzer—

Mitochondrial functions were analyzed using a Seahorse Biosciences XF24 flux analyzer (Seahorse Bioscience) as described previously (34). Briefly, 100,000 cells per well were seeded in XF microplates (Seahorse Biosciences). After 24 hr, the culture medium was replaced with XF Assay medium (Seahorse Biosciences) supplemented with 11 mM glucose and 0.1 mM sodium pyruvate. Cells were sequentially treated with 1 µg/ml oligomycin (Sigma, 04876), 0.5 µM FCCP (Sigma, C2920), and 100 nM rotenone (Sigma, R8875)+antimycin A (Sigma, A8674). The ATP-linked OCR, maximum OCR, and reserve capacity of mitochondria were calculated using the integrated XF software.

Immunoblotting Analysis of Mitochondrial Proteins—

Mitochondria were isolated from A-T/LV control and ISG15 shRNA cells using the Miochondrial Isolation Kit (Thermo Scientific Company, 89874). The Dounce homogenization protocol described by the manufacturer was used to isolate mitochondria from cells. Mitochondrial pellets were resuspended in lysis buffer containing 50 mM Tris pH 7.5 and 4% (v/v) SDS. Samples were homogenized and boiled for 10 min. Lysates containing equal protein were then mixed with 6× Laemmli SDS sample buffer (3× final concentration). Samples were boiled again and mitochondrial proteins were analyzed by SDS-PAGE. Immunoblotting analyses using either anti-ISG15 (raised against human ISG15) (20), anti-ubiquitin (gift from Dr. Arthur Haas, at LSUHSC—New Orleans), or anti-mitofusin 2 (Abcam, ab88569) antibodies were carried out using the ECL Western procedure (Pierce, 34076) and the BioRad VersaDoc Imaging System (BioRad). Immunoblotting Analysis of HA Polyubiquitylated Proteins in Cells: Cells were transfected with HA-ubiquitin using the PolyFect transfection reagent (Qiagen, 301105). Twenty four hours after transfection, mitochondria were isolated as described above. Mitochondrial lysis, SDS-PAGE, and immunoblotting analysis to detect HA-ubiquitin conjugated proteins using anti-HA antibodies were carried out as described above. Immunoblotting Analysis of Mfn2 in Cells: Cells were lysed in lysis buffer containing 50 mM Tris-HCl, pH 7.5, 2% SDS, and protease inhibitor cocktail. Lysates were sonicated, boiled, and cleared by centrifugation. Lysates containing equal protein were then mixed with 6× Laemmli SDS sample buffer (3× final concentration). Samples were boiled again and proteins were separated by 15% SDS-PAGE. Immunoblotting analysis was carried out using anti-Mfn2 antibodies (Abcam) as described above. Intensity of the Mfn2 bands was quantitated using BioRad Quantity One software. Statistical analysis—Statistical analysis was carried out using GraphPad software.

Results

ISG15 shRNA Decreases Mitochondrial Mass in A-T Cells

Figure 29:
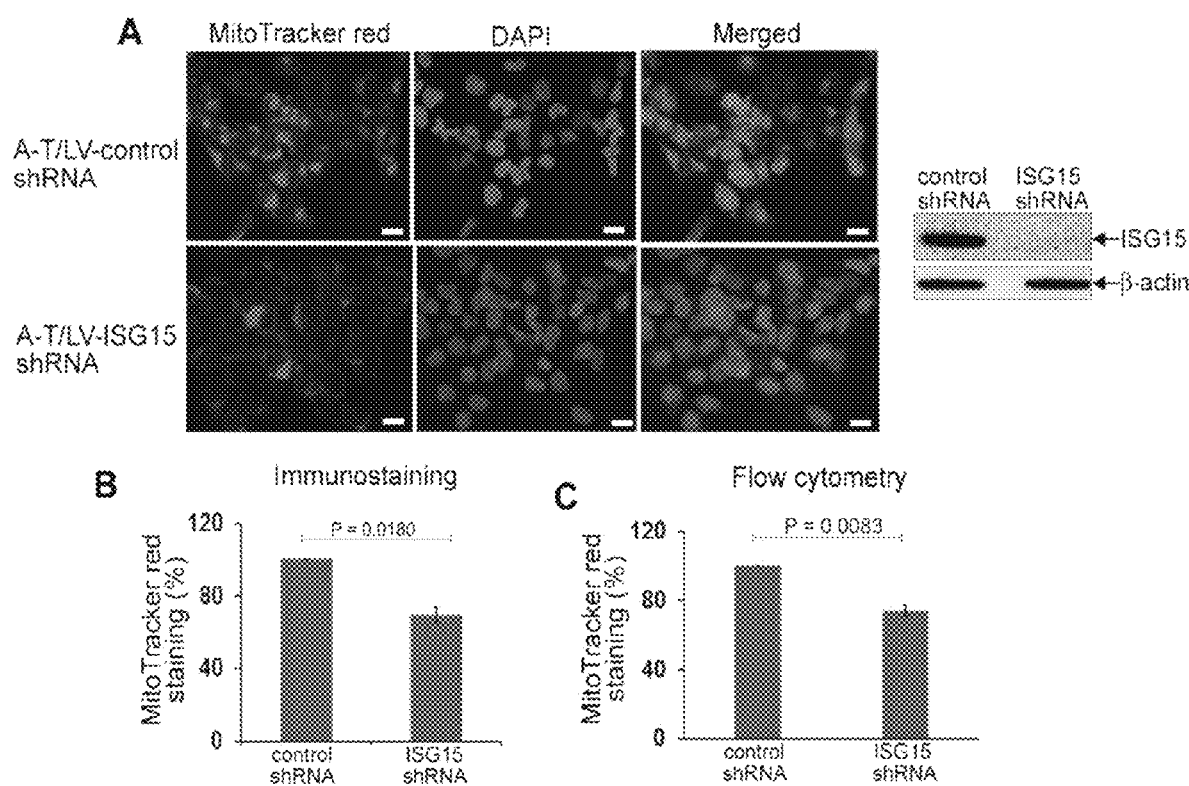
FIG. 29 shows ISG15 shRNA decreases mitochondrial mass in A-T cells. (A) A-T/LV-control (upper panels) and A-T/LV-ISG15 shRNA (lower panels) cells were stained with the MitoTracker Red stain and DAPI as described in Material and Methods. Images were taken using a 40× oil immersion objective with a Leica DMRA2 upright microscope run through SlideBook software. ISG15 expression in A-T/LV-control and ISG15 shRNA cells is shown in the Western blot. Scale bar: 10 µm. (B) Five random fields containing 20-30 cells were selected, and the intensity of the MitoTracker Red stain was measured using Image J, and is plotted in the bar graph. (C) Flow cytometric analysis of mitochondrial mass using MitoTracker Red stain in A-T/LV-control and A-T/LV-ISG15 shRNA cells is shown. Mean values of the median fluorescence intensity from three independent experiments are plotted in the bar graph. In the bar graphs (B and C), fluorescence intensity values from A-T/LV control shRNA cells are normalized to 100%, and values from A-T/LV-ISG15 shRNA cells are expressed as percent variations over control. Error bars represents +/−SEM.

The elevated ISG15 pathway inhibits the ubiquitin pathway in ATM kinase null cells (19). We therefore initiated a study to test whether mitophagy, a process that requires the presence of the functional ubiquitin pathway (31), is defective due to ISG15-mediated impairment of the ubiquitin pathway in A-T cells. To test whether mitophagy is defective, and defective mitophagy is due to the elevated ISG15, we first assessed the mitochondrial mass in A-T control and ISG15 shRNA cells as mitochondrial mass is increased due to the defective mitophagy in A-T cells (27). To assess mitochondrial mass we used the mitochondria-specific MitoTracker Red FM stain in A-T/LV-control and A-T/LV-ISG15 shRNA cells. Western blot shows the effective knockdown of ISG15 in A-T/LV-ISG15 shRNA cells (FIG. 29). As also seen in FIG. 29, A-T/LV-ISG15 shRNA cells exhibited a 33% decrease in mitochondrial mass, as evidenced by the decreased intensity of the MitoTracker Red dye staining, as compared to A-T/LV-control shRNA cells (compare upper and lower panels stained with MitoTracker Red stain and the corresponding bar graph). Increased mitochondrial mass indicates that mitophagy is defective in A-T/LV-control shRNA cells as observed previously by (26,27). On the other hand, decreased mitochondrial mass indicates that mitophagy is restored in A-T/LV-ISG15 shRNA cells. We also assessed mitochondrial mass by flow cytometry using the MitoTracker Red stain. The flow cytometric assay yielded quantitatively similar results as that of imaging analysis shown in FIG. 29 B (FIG. 29C). Together, our results that the mitochondrial mass is restored in the ISG15-silenced ATM-kinase ablated A-T cells indicates that increased mitochondrial mass may, in part, be due to the increased expression of ISG15 in A-T cells.

ISG15 shRNA Increases the Level of Healthy Mitochondria in A-T Cells

Figure 30:
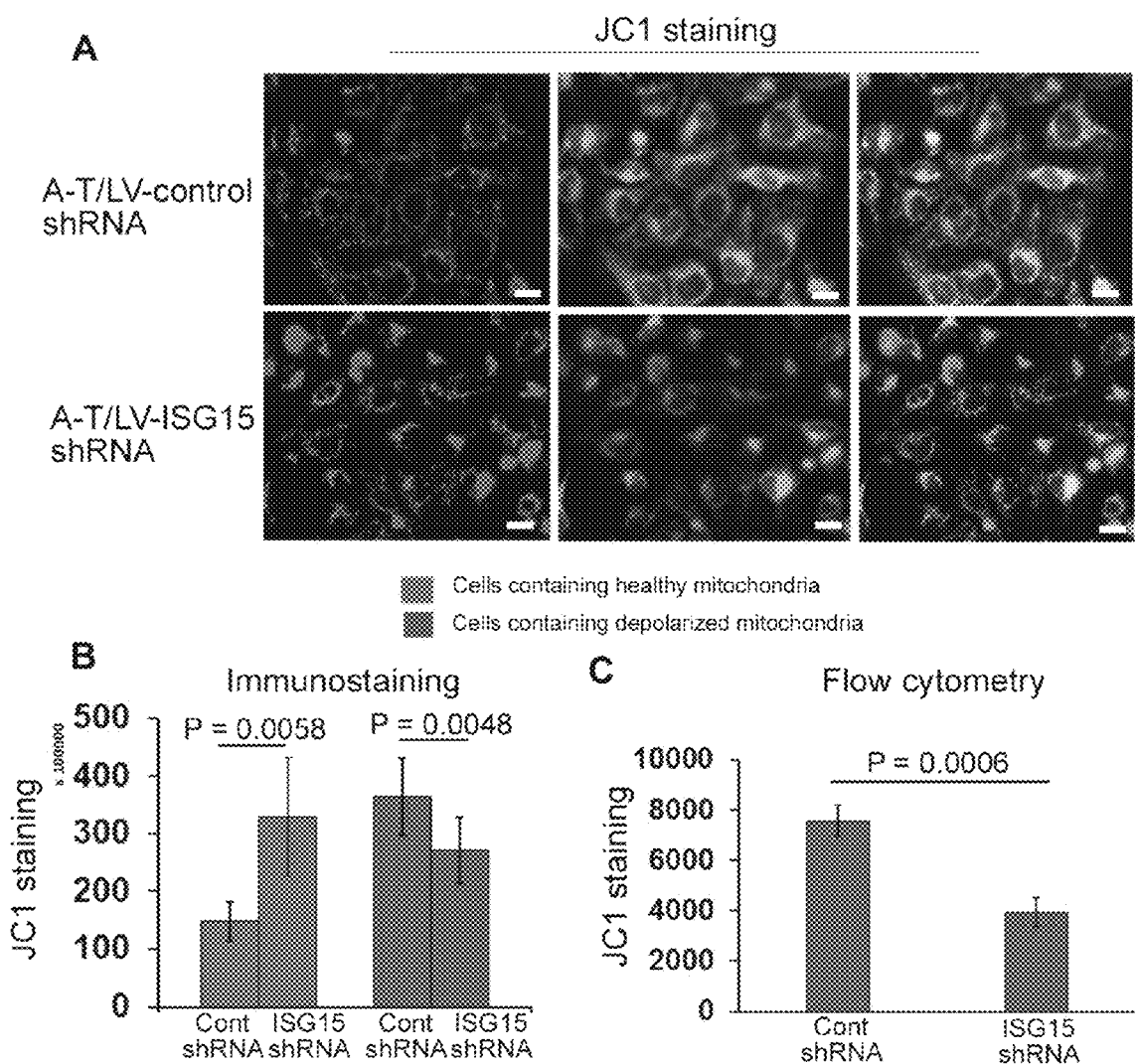
FIG. 30 shows ISG15 shRNA decreases the level of depolarized mitochondria in A-T cells. Mitochondrial membrane potential was monitored in A-T/LV-control and A-T/LV-ISG15 shRNA cells using JC-1 dye as described in Material and Methods. Emission fluorescence was detected using TRITC (590 nm) and FITC (530 nm) channels simultaneously. Images were taken as described in FIG. 1. (B) Five fields containing 20-30 cells were selected and the intensity of the red and green stain was measured using Image J, and is plotted in the bar graph. Scale bar: 10 µm. (C) Flow cytometric analysis of depolarized mitochondria using JC1 stain in A-T/LV-control and A-T/LV-ISG15 shRNA cells is shown. Mean values of the median fluorescence intensity from three independent experiments are plotted in the bar graph. In the bar graphs (B and C), fluorescence intensity values from A-T/LV control shRNA cells are normalized to 100%, and values from A-T/LV-ISG15 shRNA cells are expressed as percent variations over control. Error bars represents +/−SEM.

Previous studies have shown that ATM kinase-ablated cells contained larger numbers of mitochondria with decreased membrane potential than ATM kinase-positive control cells (26,27). To test whether mitochondrial membrane potential (MMP) is decreased, and decreased MMP is due to the elevated ISG15, we examined the mitochondrial membrane potential in A-T/LV-control shRNA and A-T/LV-ISG15 shRNA cells using JC-1 dye. JC-1 dye exhibits membrane potential-dependent accumulation in mitochondria. In healthy mitochondria, JC-1 dye forms J-aggregates and fluoresces orange-red (32). When the mitochondrial membrane potential collapses, JC-1 dye can no longer concentrate within the mitochondria (32). Instead, it is dispersed throughout the cell in a monomeric form and emits a green fluorescence (32,33). Increased green staining seen in FIG. 30 (upper panels) indicates loss of mitochondrial membrane potential in A-T/LV-control shRNA cells (see bar graph for quantitation). On the other hand, increased red staining indicates intact mitochondrial membrane potential in ISG15-silenced A-T cells (FIG. 30, lower panels and bar graph). These results were also confirmed using flow cytometric analysis to show that number of cells containing depolarized mitochondria (evidenced by green staining) is decreased in A-T/LV-ISG15 shRNA cells (FIG. 29C). Together, these results support reports that the number of mitochondria with decreased mitochondrial membrane potential is increased in A-T cells (26,27). Furthermore, the present results reveal that elevated ISG15 may be causally responsible for the decreased mitochondrial membrane potential in A-T cells.

ISG15 shRNA Decreases the Levels of Reactive Oxygen Species in A-T Cells—

Figure 31:
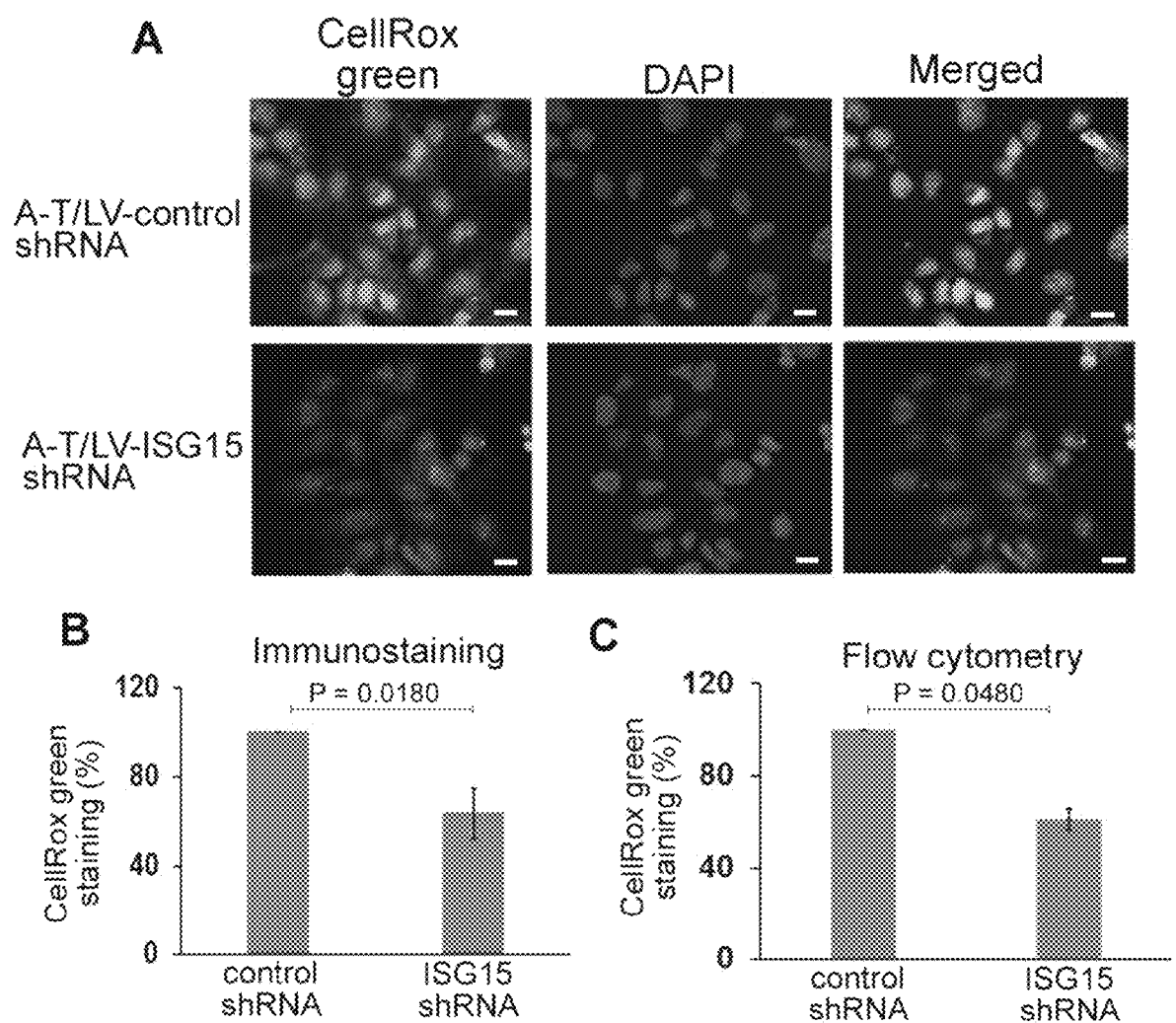
FIG. 31 shows ISG15 shRNA decreases oxidative stress in A-T cells. (A) Cellular ROS level was monitored using CellRox Green reagent (2 µg/ml) as described in Material and Methods. Emission fluorescence was detected using FITC channel. Images were taken as described in FIG. 1. (B)

Defective mitochondria lead to increased ROS in A-T cells (26,27). Decreased number of defective mitochondria (shown in FIG. 30) is therefore expected to decrease the level of ROS in ISG15-silenced A-T cells. To test the level of ROS, we stained A-T/LV-control and A-T/LV-ISG15 shRNA cells with the CellRox® Green reagent. CellRox® Green Reagent is a DNA dye that upon oxidation binds to DNA. Thus, its signal is localized primarily in the nucleus and mitochondria in cells. Increased nuclear staining with the CellRox green reagent indicates that ROS increases in A-T/LV-control shRNA cells (FIG. 31, upper panels and bar graph). In contrast, decreased ROS staining in ISG15-silenced A-T cells indicates that increased ROS is due to the elevated levels of ISG15 in A-T cells (FIG. 31 lower panels and bar graph). Once again, we also assessed ROS using flow cytometric analysis and results were found to be comparable with the imaging analysis (FIG. 29C).

ISG15 ShRNA Restores Mitochondrial Functions in A-T Cells—

Next we assessed mitochondrial functions in A-T/LV-control and A-T/LV-ISG15 shRNA cells by the Seahorse Extracellular Flux (XF) technology that uses pharmacological inhibitors to probe the functions of individual components of the respiratory chain (34). Mitochondrial functions were analyzed using oligomycin (ATP synthase inhibitor; 1 µg/ml final concentration), FCCP (proton ionophore uncoupler; 0.5 µM final concentration), and rotenone (electron flux inhibitor; 100 nm) and antimycin A (complex III inhibitor;

1 µm final concentration) by injecting them sequentially through ports in the XF assay cartridges. Representative data for mitochondrial functions measured by Seahorse Extracellular Flux machine is shown in the FIG. 32A (left panel) and the mean values from the four different experiments (n=20 samples) are plotted in the bar graph (right panel). Basal rate represents mitochondrial activity in the cells prior to addition of inhibitors. The signal following Oligomycin treatment provides the amount of oxygen consumed that is linked to ATP synthesis (ATP-linked OCR (Oxygen Consumption Rate)) (34). Reserve respiratory capacity representing the energy available to cells for increased work to cope with the environmental stress was calculated as the maximal OCR rate minus the basal OCR rate (34). In agreement with literature studies (27), increased rates of OCRs indicate increased bioenergetic demand due to the presence of defective mitochondria in ATM kinase ablated A-T/LV-control shRNA cells. On the other hand, decreased OCRs indicate decreased bioenergetic demand due to the presence of healthy mitochondria in ISG15-silenced-ATM kinase ablated A-T cells. In all four experiments, mean values of OCRs were consistently lower in ISG15-silenced as compared to ISG15 overexpressing cells. However, due to the fluctuations in oxygen consumption rates from experiment to experiment, we were unable to find statistically significant difference between mean OCRs of A-T control and ISG15-silenced cells. To complement these results, we analyzed cellular ATP levels as an indicator of mitochondrial function status in A-T/LV-control and A-T/LV-ISG15 shRNA cells. Consistent with the results that defective mitochondria are increased (FIGS. 30-31), cellular ATP level is significantly reduced (46% decrease) in A-T cells compared to ISG15-silenced A-T cells (FIG. 32B). The restoration of ATP levels thus indicates that ISG15 shRNA has restored the mitochondrial ATP production function in A-T cells. Together, our results indicate that the elevated ISG15 is causally responsible in part for the defective mitochondrial functions in A-T cells.

ISG15 Inhibits the Polyubiquitylation of Mitochondrial Protein in A-T Cells

ISG15 inhibits the ubiquitin pathway (17,19), and ubiquitylation of the mitochondrial proteins is a prerequisite for the initiation of mitophagy (28,29). Without being bound by theory, ISG15 can inhibit polyubiquitylation of the mitochondrial proteins that initiate mitophagy in A-T cells. Thus, we tested whether ISG15 inhibits polyubiquitylation of mitochondrial proteins in A-T/LV-control shRNA cells. As shown in FIG. 33 A (left panel), the steady state levels of polyubiquitylated mitochondrial proteins is decreased in A-T/LV-control shRNA as compared to A-T/LV-ISG15 shRNA cells. In contrast, when the same membrane shown in the left panel was re-probed with anti-ISG15 antibodies, ISG15 conjugates were increased in A-T/LV-control shRNA cells (FIG. 33A, right panel). These results together with the actin staining (FIG. 33A, left lower panel) indicate that decreased polyubiquitylation seen in A-T/LV-control shRNA cells is not due to the differences in the protein loading but is due to the defective ISG15-mediated polyubiquitylation of mitochondrial proteins in A-T cells.

Anti-ubiquitin antibodies cross-react with ISG15 (17,19). Hence, to confirm that anti-ubiquitin antibodies used to stain polyubiquitylated proteins in FIG. 33 A indeed stained polyubiquitylated and not ISGylated proteins, we transfected HA-ubiquitin, isolated mitochondria, and then tested the levels of HA-ubiquitin-conjugated mitochondrial proteins in A-T/LV-control and A-T/LV-ISG15 shRNA cells. As shown in FIG. 33B, the steady-state levels of HA-ubiquitin-conjugated proteins were decreased in A-T/LV-control shRNA cells. On the other hand, there was a dramatic increase in the steady-state levels of HA-ubiquitin-conjugated proteins in ISG15-silenced A-T cells. These results together with the results shown in FIG. 33 A indicate that ISG15 inhibits polyubiquitylation of mitochondrial proteins in A-T cells.

Many outer mitochondrial membrane (OMM) proteins are ubiquitylated and degraded via the 26S proteasome prior to mitophagy in cells treated with the mitochondrial depolarizing agents (28,29). To test whether ISG15 inhibits polyubiquitylation of OMNI proteins, we assessed the fate of Mfn2, an OMNI protein and proteasome substrate, in A-T/LV-control and A-T/LV-ISG15-silenced cells treated with two different mitochondrial depolarizing agents, valinomycin and carbonylcyanide m-chlorophenylhydrazone (CCCP). Consistent with the literature reports (29,35,36), we observed a ladder of high molecular weight anti-Mfn2 cross-reactive bands above the 86 kDa Mfn2 protein band that is reminiscent of polyubiquitylation, in both ISG15-silenced and ISG15 overexpressing A-T cells (FIGS. 34 A and B, left panels). The endogenous level of these high molecular weight Mfn2 cross-reactive bands was remarkably higher in ISG15-silenced as compared to the ISG15-overexpressing A-T cells in the absence of any drugs (FIGS. 34A and B, first panels, compare lanes 1 and 4). These results indicated that endogenous Mfn2 protein is constitutively modified and that this modification is ablated in ISG15 overexpressing cells. Notably, the level of these anti-Mfn2 cross-reactive high molecular weight bands increased with increasing doses of both valinomycin and CCCP in ISG15 overexpressing A-T cells. In contrast, the level of these Mfn2 cross-reactive high molecular weight bands decreased under the same drug treatment conditions in ISG15-silenced A-T cells (FIGS. 34A and B, first panels, lanes 4-6, and the accompanying bar graph in the second panel for quantitation). Additionally, a modest decrease (15-20%) in the free Mfn2 level was noted in ISG15-silenced A-T cells treated with both valinomycin and CCCP for 24 hr. On the other hand, free Mfn2 protein level was slightly increased in both valinomycin and CCCP-treated ISG15 overexpressing A-T cells. The bar graphs in FIGS. 34 A and B, third panels, show mean values of the ratio between free Mfn2 (86 kDa band) and actin proteins (±SEM) in CCCP-treated A-T/LV-control and ISG15 shRNA cells measured from eight independent experiments, and valinomycin-treated A-T/LV-control and ISG15 shRNA cells measured from three independent experiments respectively.

Since Mfn2 is ubiquitylated and degraded via the proteasome (29,35,36), disappearance of HMW bands and free Mfn2 in ISG15-silenced cells indicated that Mfn2 is polyubiquitylated and degraded via the proteasome in valinomycin and CCCP-treated ISG15-silenced A-T cells. We therefore tested this possibility, finding that the proteasome inhibitor MG132, but not the autophagy inhibitor Bafilomycin (BAFL), restored free Mfn2 degradation in CCCP-treated ISG15-silenced A-T cells (FIG. 34 C, compare lanes 2 and 4, and bar graph for the mean values of free Mfn2/actin ratio from three different experiments using MG132). The difference between the control and drug(s)-treated groups were found consistent among three different experiments. Appearance of high molecular weight bands and modest decreases in Mfn2 protein levels in valinomycin and CCCP– treated ISG15-silenced cells was also observed in unrelated RAW247 macrophage cells under the same condition, indicating that appearance of the HMW bands and disappearance of Mfn2 is not a cell type-specific effect.

Together, our results demonstrated that Mfn2 is ubiquitylated in ISG15-silenced A-T cells and that this modification is largely defective, consequently affecting targeted Mfn2 degradation via the proteasome in ISG15 overexpressing A-T cells.

Discussion

Mitophagy is the process wherein defective/damaged mitochondria are specifically removed by the autophagy pathway (37,38). We and others have demonstrated that basal autophagy is activated in A-T cells (18,27). Intriguingly, although basal autophagy is activated, mitophagy is defective in A-T cells [current study and (27)]. These results indicate that a process upstream of the autophagy-mediated degradation of mitochondria may be defective in A-T cells. The events occurring in autophagy-mediated clearance of damaged mitochondria includes: 1) PINK1 (PTEN-induced putative kinase 1) protein recruitment of Parkin onto the damaged mitochondria (31); 2) Parkin-mediated conjugation of ubiquitin to several outer mitochondrial proteins (e.g. mitofusin-1 and 2, VDAC, Miro, and other identified proteins) (31); 3) LC3-associated p62 protein binds to these ubiquitylated proteins on mitochondria (31); and 4) p62 shuttles ubiquitylated mitochondria to the autophagosomes for their degradation (31). However, p62 null cells have no defects in Parkin-mediated mitophagy (28,29). To explain these results ubiquitin-mediated degradation of outer mitochondrial proteins may help disperse mitochondria into small individual units which are then targeted to destruction via autophagy in human cells (29). Nevertheless, it is clear that the presence of a functional ubiquitin pathway is essential for autophagy-mediated clearance of defective mitochondria in cells. Because ISG15 inhibits the ubiquitin pathway and polyubiquitylation is necessary for mitophagy, ISG15 may inhibit polyubiquitylation of the mitochondrial outer membrane proteins to block initiation of mitophagy in A-T cells. Failure to initiate mitophagy in turn leads to increased number of defective mitochondria in A-T cells. The current study was undertaken, finding that ISG15 indeed inhibits polyubiquitylation of the mitochondrial proteins and that the level of defective mitochondria is elevated in A-T cells.

Outer mitochondrial membrane protein Mfn2 is ubiquitylated by Parkin E3 ubiquitin ligase and degraded prior to mitophagy (29,35,36). In the current study, we have also noted a ladder of high molecular weight anti-Mfn2 cross-reactive bands in cells treated with mitochondrial depolarizing agents. We do not know whether these high molecular weight Mfn2 bands are comprised of polyubiquitin chains. However, the 8 kDa spacing between these bands in the ladder, and inhibition of CCCP-mediated Mfn2 degradation by a proteasome inhibitor MG132 indicate the possibility that Mfn2 may be conjugated to Lys48-linked polyubiquitin chains by Parkin in order to target its degradation via the proteasome in ISG15-silenced A-T cells.

Contrasting the report that showed a robust proteasome-mediated degradation of Mfn2 in CCCP-treated clonal HeLa cells overexpressing Parkin (29), we noticed only a modest degradation of Mfn2 in CCCP-treated ISG15-silenced A-T cells. It is likely that the robust degradation of Mfn2 observed by the earlier study may be due to the forced overexpression of Parkin in HeLa S3 cells (29). A-T cells probably express low levels of Parkin, resulting in a rate of degradation that is proportionately slower in these cells compared to the Parkin overexpressing HeLa cells. Alternatively, it is also possible that the majority of the modification of Mfn2 we have observed is not for the purpose of its targeted degradation via proteasome. Instead, Mfn2 may be conjugated to Lys63-linked polyubiquitin chains, a signal that does not target proteins for degradation (39). In line with this notion, Parkin also conjugates Lys63-linked polyubiquitin chains onto the outer mitochondrial membrane proteins (29). Regardless of the polyubiquitin chain linkages for Mfn2, our observations that the intensity of the endogenous levels of high molecular weight bands is increased in ISG15-silenced vs ISG15 overexpressing A-T cells indicate that ISG15 has an inhibitory effect on polyubiquitylation of mitochondrial proteins in A-T cells.

It is unclear how ISG15 may inhibit the conjugation of Mfn2 protein; however, ISG15 inhibits polyubiquitylation by modulating the activities of the ubiquitin E2 and E3 ligases (40-42). The ISG15 pathway is not constitutively elevated in normal cells; however, when aberrantly overexpressed, as in the case of cancer (19) and A-T cells (11), UbcH8, the ISG15-specific E2 ligase, may partner with certain ubiquitin E3 ligases to append ISG15 instead of ubiquitin to target proteins (24). Alternatively, UbcH8 may directly append ISG15 to the ubiquitin E2/E3 ligases to block their activity as shown for Nedd4 (43, 44), UbcH6 (42), and UbcH13 (40,41). Thus, one can speculate that the Parkin-specific use of UbcH7 may allow the related UbcH8-ISG15 to conjugate ISG15 instead of ubiquitin to its targets (FIG. 34) or direct ISGylation of Parkin to inhibit polyubiquitylation of Mfn2 in A-T cells. Whether Parkin-mediated ISGylation blocks proteasome targeting or ISG15 inhibits Parkin remains unsolved. In either case, it is expected to decrease protein polyubiquitylation of the outer mitochondrial membrane proteins, as demonstrated in the current study (FIG. 34). Identification of more Parkin substrates, the type of the post-translational modification on these substrates (Lys48 vs Lys63 ub conjugation, ISG15 conjugation), and the fate of these proteins (degradation vs stabilization) will provide further insights into the role of ISG15 in inhibiting the Parkin-mediated induction of mitophagy in A-T cells. We conclude that the ISG15-mediated inhibition of the polyubiquitylation is causally related to the defective mitophagy in A-T cells. These results also explain why mitophagy is attenuated in spite of the fact that rates of basal autophagy are activated in A-T cells.

Interestingly, in a study using A-T lymphocytes obtained from an A-T patient, Amrose et al. showed an abnormal distribution of mitochondria, i.e., mitochondria are accumulated at one pole of the A-T lymphoblast cells. On the other hand, mitochondrial distribution was homogenous in the lymphoblast cells harboring functional ATM kinase (26). Consistent with these observations, in our study we also noted that mitochondria accumulate at one pole of the most A-T/LV-control shRNA cells, while, mitochondria were evenly distributed in A-T/LV-ISG15 shRNA cells (FIG. 29, lower panels). We note that both A-T/LV-control and ISG15 shRNA cells are devoid of the ATM kinase activity, and the only difference between these cells is a differential expression of ISG15. These qualitative imaging results indicate that the altered distribution of mitochondria are in part be due to the elevated ISG15 levels in A-T cells. Similar alterations in the mitochondrial distribution and mass in two different cell lineages, fibroblasts (current study) and lymphoblasts (Ambrose et al study (26)), obtained from two distinct A-T patients, indicate these findings are relevant to A-T disease.

Understanding of the precise mechanism by which mitophagy is induced is particularly important because defective mitophagy in neurons has been implicated in neurodegeneration associated with several neurological disorders such as Parkinson, Alzheimer, Huntington, and ALS (11). In Parkinson disease, it is clear that defective mitophagy is due to the mutations in Parkin and PINK1 proteins (43). However, in other neurological disorders in which Parkin is functional, the reason(s) for the defective mitophagy is largely unknown. We do not know whether defective mitophagy is also due to the elevated expression of ISG15 in Alzheimer and Huntington diseases. However, ISG15 is elevated, and mitochondrial anomalies are observed in ALS (30,44) thus, indicating that like in A-T, defective mitophagy may be due to the elevated ISG15 in ALS. Interestingly, ISG15 can be a biomarker for detecting neuronal injuries in the CNS (45). It is thus possible that as in A-T and ALS, elevation of ISG15 following traumatic brain injury due to the neuronal injury also occurs in Alzheimer and Huntington diseases. Our current results thus indicate that targeting of the ISG15 pathway could be a potential strategy to restore mitophagy and consequently abrogate neurodegeneration in A-T and other neurological diseases.

REFERENCES CITED IN THIS EXAMPLE

1. Shiloh, Y., and Ziv, Y. (2013) The ATM protein kinase: regulating the cellular response to genotoxic stress, and more. *Nat. Rev. Mol. Cell Biol.* 14, 197-210
2. Boder, E. (1985) Ataxia-telangiectasia: an overview. *Kroc Found Ser* 19, 1-63
3. Frappart, P. O., and McKinnon, P. J. (2006) Ataxia-telangiectasia and related diseases. *Neuromolecular Med.* 8, 495-511
4. Crawford, T. O. (1998) Ataxia telangiectasia. *Semin. Pediatr. Neurol.* 5, 287-294
5. Lavin, M. F. (2008) Ataxia-telangiectasia: from a rare disorder to a paradigm for cell signalling and cancer. *Nat. Rev. Mol. Cell Biol.* 9, 759-769
6. McKinnon, P. J. (2001) Ataxia telangiectasia: new neurons and ATM. *Trends Mol Med* 7, 233-234
7. McKinnon, P. J. (2004) ATM and ataxia telangiectasia. *EMBO Rep.* 5, 772-776
8. Savitsky, K., Sfez, S., Tagle, D. A., Ziv, Y., Sartiel, A., Collins, F. S., Shiloh, Y., and Rotman, G. (1995) The complete sequence of the coding region of the ATM gene reveals similarity to cell cycle regulators in different species. *Hum. Mol. Genet.* 4, 2025-2032
9. Eilam, R., Peter, Y., Groner, Y., and Segal, M. (2003) Late degeneration of nigro-striatal neurons in ATM-/- mice. *Neuroscience* 121, 83-98
10. Frappart, P. O., and McKinnon, P. J. (2008) Mouse models of DNA double-strand break repair and neurological disease. *DNA Repair* (Amst) 7, 1051-1060
11. Palikaras, K., and Tavernarakis, N. (2012) Mitophagy in neurodegeneration and aging. *Front. Genet.* 3, 297
12. Nedelsky, N. B., Todd, P. K., and Taylor, J. P. (2008) Autophagy and the ubiquitin-proteasome system: collaborators in neuroprotection. *Biochim. Biophys. Acta* 1782, 691-699
13. Mittal, S., and Ganesh, S. Protein quality control mechanisms and neurodegenerative disorders: Checks, balances and deadlocks. *Neurosci. Res.* 68, 159-166
14. Lehman, N. L. (2009) The ubiquitin proteasome system in neuropathology. *Acta. Neuropathol.* 118, 329-347
15. Hegde, A. N., and Upadhya, S. C. Role of ubiquitin-proteasome-mediated proteolysis in nervous system disease. *Biochim. Biophys. Acta* 1809, 128-140
16. Itoh, K., Nakamura, K., Iijima, M., and Sesaki, H. (2013) Mitochondrial dynamics in neurodegeneration. *Trends Cell Biol.* 23, 64-71
17. Desai, S. D., Haas, A. L., Wood, L. M., Tsai, Y. C., Pestka, S., Rubin, E. H., Saleem, A., Nur, E. K. A., and Liu, L. F. (2006) Elevated expression of ISG15 in tumor cells interferes with the ubiquitin/26S proteasome pathway. *Cancer Res.* 66, 921-928
18. Desai, S. D., Reed, R. E., Babu, S., and Lorio, E. A. (2013) ISG15 Deregulates Autophagy in Genotoxin-treated Ataxia Telangiectasia Cells. *J. Biol. Chem.* 288, 2388-2402
19. Wood, L. M., Sankar, S., Reed, R. E., Haas, A. L., Liu, L. F., McKinnon, P., and Desai, S. D. (2011) A novel role for ATM in regulating proteasome-mediated protein degradation through suppression of the ISG15 conjugation pathway. *PLoS One* 6, e16422
20. Haas, A. L., Ahrens, P., Bright, P. M., and Ankel, H. (1987) Interferon induces a 15-kilodalton protein exhibiting marked homology to ubiquitin. *J. Biol. Chem.* 262, 11315-11323
21. Narasimhan, J., Wang, M., Fu, Z., Klein, J. M., Haas, A. L., and Kim, J. J. (2005) Crystal structure of the interferon-induced ubiquitin-like protein ISG15. *J. Biol. Chem.* 280, 27356-27365
22. Potter, J. L., Narasimhan, J., Mende-Mueller, L., and Haas, A. L. (1999) Precursor processing of pro-ISG15/UCRP, an interferon-beta-induced ubiquitin-like protein. *J. Biol. Chem.* 274, 25061-25068
23. Narasimhan, J., Potter, J. L., and Haas, A. L. (1996) Conjugation of the 15-kDa interferon-induced ubiquitin homolog is distinct from that of ubiquitin. *J. Biol. Chem.* 271, 324-330
24. Haas, A. L. (2006) *ISG15-dependent Regulation*. In Protein Degradation, R. J. Mayer, A. Ciechnover, and M. Rechsteiner (ed). Wiley-VCH Verlag GmbH & Co., Weinheim, Germany, pp 103-131.
25. Siddoo-Atwal, C., Haas, A. L., and Rosin, M. P. (1996) Elevation of interferon beta-inducible proteins in ataxia telangiectasia cells. *Cancer Res.* 56, 443-447
26. Ambrose, M., Goldstine, J. V., and Gatti, R. A. (2007) Intrinsic mitochondrial dysfunction in ATM-deficient lymphoblastoid cells. *Hum. Mol. Genet.* 16, 2154-2164
27. Valentin-Vega, Y. A., Maclean, K. H., Tait-Mulder, J., Milasta, S., Steeves, M., Dorsey, F. C., Cleveland, J. L., Green, D. R., and Kastan, M. B. (2012) Mitochondrial dysfunction in ataxia-telangiectasia. *Blood* 119, 1490-1500
28. Chan, N. C., and Chan, D. C. (2011) Parkin uses the UPS to ship off dysfunctional mitochondria. *Autophagy* 7, 771-772
29. Chan, N. C., Salazar, A. M., Pham, A. H., Sweredoski, M. J Kolawa, N. J., Graham, R. L., Hess, S., and Chan, D. C. (2011) Broad activation of the ubiquitin-proteasome system by Parkin is critical for mitophagy. *Hum. Mol. Genet.* 20, 1726-1737
30. Wang, R., Yang, B., and Zhang, D. (2011) Activation of interferon signaling pathways in spinal cord astrocytes from an ALS mouse model. *Glia* 59, 946-958
31. Tanaka, A. (2010) Parkin-mediated selective mitochondrial autophagy, mitophagy: Parkin purges damaged organelles from the vital mitochondrial network. *FEBS Lett.* 584, 1386-1392

32. Cossarizza, A., Baccarani-Contri, M., Kalashnikova, G., and Franceschi, C. (1993) A new method for the cytofluorimetric analysis of mitochondrial membrane potential using the J-aggregate forming lipophilic cation 5,5', 6,6'-tetrachloro-1,1',3,3'-tetraethylbenzimidazolcarbocyanine iodide (JC-1). *Biochem. Biophys. Res. Commun.* 197, 40-45

33. Reers, M., Smith, T. W., and Chen, L. B. (1991) J-aggregate formation of a carbocyanine as a quantitative fluorescent indicator of membrane potential. *Biochemistry* 30, 4480-4486

34. Nicholls, D. G., Darley-Usmar, V. M., Wu, M., Jensen, P. B., Rogers, G. W., and Ferrick, D. A. (2010) Bioenergetic profile experiment using C2C12 myoblast cells. *J. Vis. Exp.* 46, pii: 2511

35. Glauser, L., Sonnay, S., Stafa, K., and Moore, D. J. (2011) Parkin promotes the ubiquitination and degradation of the mitochondrial fusion factor mitofusin 1. *J. Neurochem.* 118, 636-645

36. Rakovic, A., Grunewald, A., Kottwitz, J., Bruggemann, N., Pramstaller, P. P., Lohmann, K., and Klein, C. (2011) Mutations in PINK1 and Parkin impair ubiquitination of Mitofusins in human fibroblasts. *PLoS One* 6, e16746

37. Zhu, J., Wang, K. Z., and Chu, C. T. (2013) After the banquet: Mitochondrial biogenesis, mitophagy and cell survival. *Autophagy* 9

38. Kubli, D. A., and Gustafsson, A. B. (2012) Mitochondria and mitophagy: the yin and yang of cell death control. *Circ. Res.* 111, 1208-1221

39. Tenno, T., Fujiwara, K., Tochio, H., Iwai, K., Morita, E. H., Hayashi, H., Murata, S., Hiroaki, H., Sato, M., Tanaka, K., and Shirakawa, M. (2004) Structural basis for distinct roles of Lys63- and Lys48-linked polyubiquitin chains. *Genes Cells* 9, 865-875

40. Zou, W., Papov, V., Malakhova, O., Kim, K. I., Dao, C., Li, J., and Zhang, D. E. (2005) ISG15 modification of ubiquitin E2 Ubc13 disrupts its ability to form thioester bond with ubiquitin. *Biochem. Biophys. Res. Commun.* 336, 61-68

41. Takeuchi, T., and Yokosawa, H. (2005) ISG15 modification of Ubc13 suppresses its ubiquitin-conjugating activity. *Biochem. Biophys. Res. Commun.* 336, 9-13

42. Takeuchi, T., Iwahara, S., Saeki, Y., Sasajima, H., and Yokosawa, H. (2005) Link between the Ubiquitin Conjugation System and the ISG15 Conjugation System: ISG15 Conjugation to the UbcH6 Ubiquitin E2 Enzyme. *J. Biochem.* (Tokyo) 138, 711-719

43. Jin, S. M., and Youle, R. J. PINK1- and Parkin-mediated mitophagy at a glance. *J. Cell. Sci.* 125, 795-799

44. Wang, W., Li, L., Lin, W. L., Dickson, D. W., Petrucelli, L., Zhang, T., and Wang, X. (2013) The ALS disease-associated mutant TDP-43 impairs mitochondrial dynamics and function in motor neurons. *Hum. Mol. Genet.* 22, 4706-4719

45. Wang, R. G., Kaul, M., and Zhang, D. X. (2012) Interferon-stimulated gene 15 as a general marker for acute and chronic neuronal injuries. *Sheng. Li. Xue. Bao.* 64, 577-583

Abbreviations

A-T, Ataxia Telangiectasia; ISG15, Interferon-Stimulated Gene 15; ATM, Ataxia Telangiectasia Mutated; ALS, Amyotrophic Lateral Sclerosis; MMP, Mitochondrial Membrane Potential; OMNI, Outer Mitochondrial Membrane; Mfn2, Mitofusin2

Example 26

Research focuses on a ubiquitin-like protein ISG15 (Interferon-Stimulated Gene 15) in cancer. This research is based on the two seminal findings from my group: that ISG15 expression is elevated in most human malignancies and that ISG15 conjugates (ISGylation) inhibit the canonical ubiquitin pathway (1), a master regulator of cell survival and death (2-4). An early publication stating that ISG15 is also constitutively elevated due to the aberrant activation of the IFN pathway in Ataxia Telangiectasia (A-T), a rare neurodegenerative disease (1 in 40,000-100,000 births), stimulated my research interest in A-T (5). Based on our findings that ISGylation inhibits the ubiquitin pathway in cancer cells (6-9) and literature indicating that lesions in the ubiquitin pathway (proteinopathy) lead to neurodegeneration in several neurological disorders (10-13), we speculated that elevated ISG15 conjugates may inhibit degradation of ubiquitinated proteins, and accumulation of non-degraded proteins may contribute to the progressive neurodegeneration in A-T patients. We tested this and found that, as in cancer cells, constitutively elevated ISG15 conjugates indeed inhibit the canonical ubiquitin pathway in A-T cells (14). Additionally, inclusion bodies containing ISG15/ubiquitinated proteins are formed in the brain tissues obtained post-mortem from A-T patients (14). It has also demonstrated that a compensatory basal autophagy pathway is activated in response to ISG15 conjugation-mediated inhibition of the ubiquitin pathway in A-T cells (15). Genotoxic stress overactivates this compensatory mechanism, triggering aberrant autophagic flux and A-T cell death (15). These observations of proteinopathy in our A-T disease model parallel previous literature utilizing different neurological disease models, such as Parkinson and Alzheimer, among others (16,17). Importantly, we have identified constitutively elevated ISG15 conjugates as prospective mediators of these defects in A-T cells (14).

Figure 26:
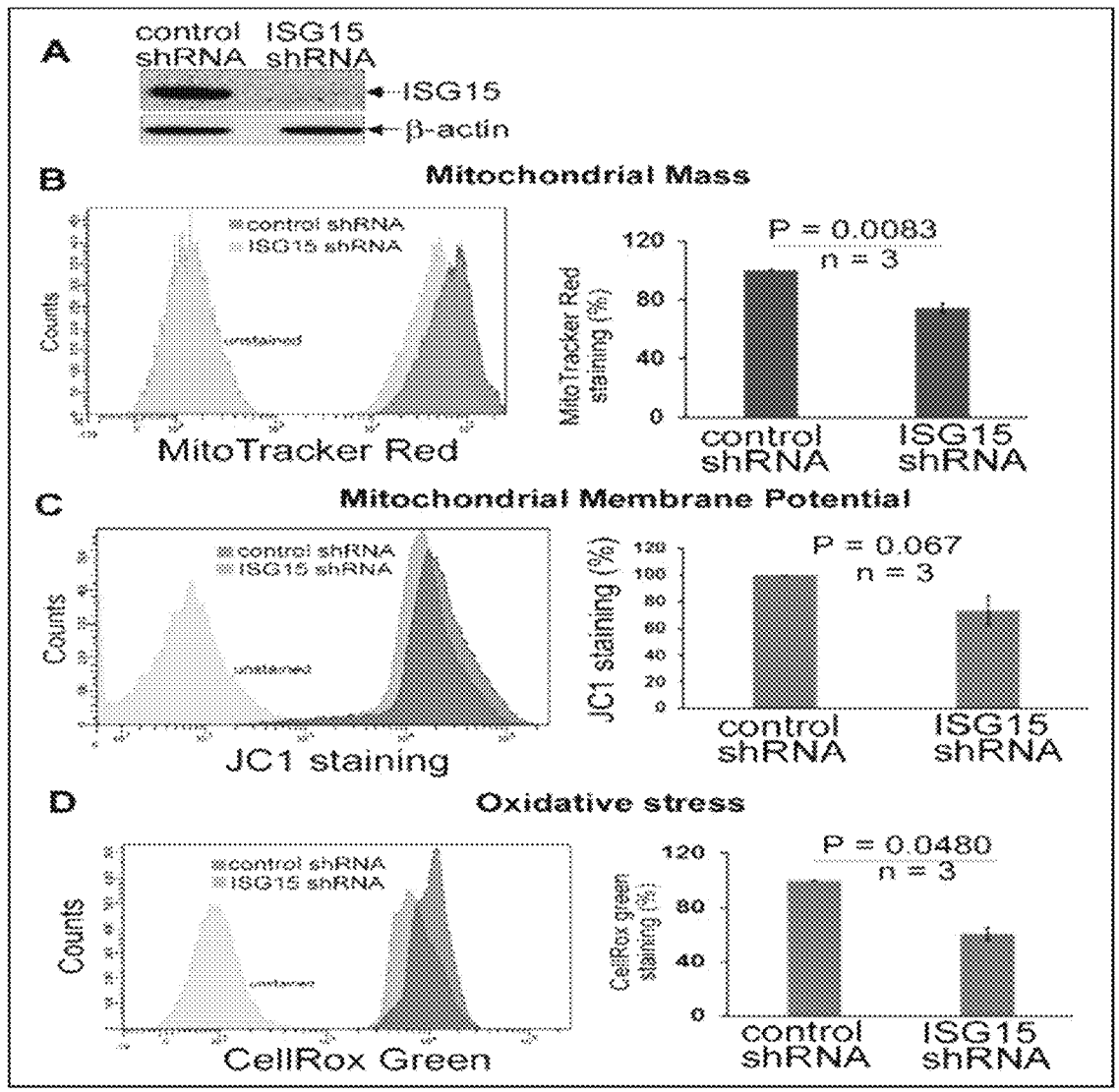
FIG. 26 shows ISG15 inhibits mitophagy in AT. (A) Protein expression of ISG15 in A-T/LV-control and ISG15 shRNA cells is shown via Western blot. (B) Flow cytometric analysis of mitochondrial mass using MitoTracker Red stain in A-T/LV-control and A-T/LV-ISG15 shRNA cells is shown. (C) Flow cytometric analysis of depolarized mitochondria using JC1 stain in A-T/LV-control and A-T/LV-ISG15 shRNA cells is shown. (D) Flow cytometric analysis of oxidative stress using CellRox Green stain in A-T/LV-control and A-T/LV-ISG15 shRNA cells is shown. Mean values of the median fluorescence intensity from three independent experiments are plotted in the bar graphs shown in Panels A, B, and C. In the bar graphs fluorescence intensity values from A-T/LV control shRNA cells are normalized to 100%, and values from A-T/LV-ISG15 shRNA cells are expressed as percent variations over control. Error bars represent +/−.

Similar to protein turnover, defects in mitophagy have also been identified as a leading cause of neurodegeneration in several neurological disorders (18). Recently, two groups have demonstrated that mitophagy, the turnover of old/abnormal mitochondria via autophagy, is also defective in A-T cells (19,20). However, the molecular mechanism underlying this defect is not yet known. Previous literature demonstrates that a functional ubiquitin pathway is necessary for the initiation of mitophagy (21,22), and we have demonstrated that ISG15 inhibits the ubiquitin-dependent signaling (1,14). These independent observations led us to speculate that a constitutively elevated ISG15 ligation pathway may inhibit the ubiquitin pathway and the initiation of mitophagy in A-T cells. In testing this hypothesis, we find that ISG15 conjugation inhibits Mitofusin 2 (MFN2) protein turnover, a step necessary for the initiation of mitophagy (23), potentially explicating the mitophagy defect previously reported by other groups in A-T cells (19,20). Results of these studies are presented (FIG. 26 and FIG. 32B).

Figure 36:
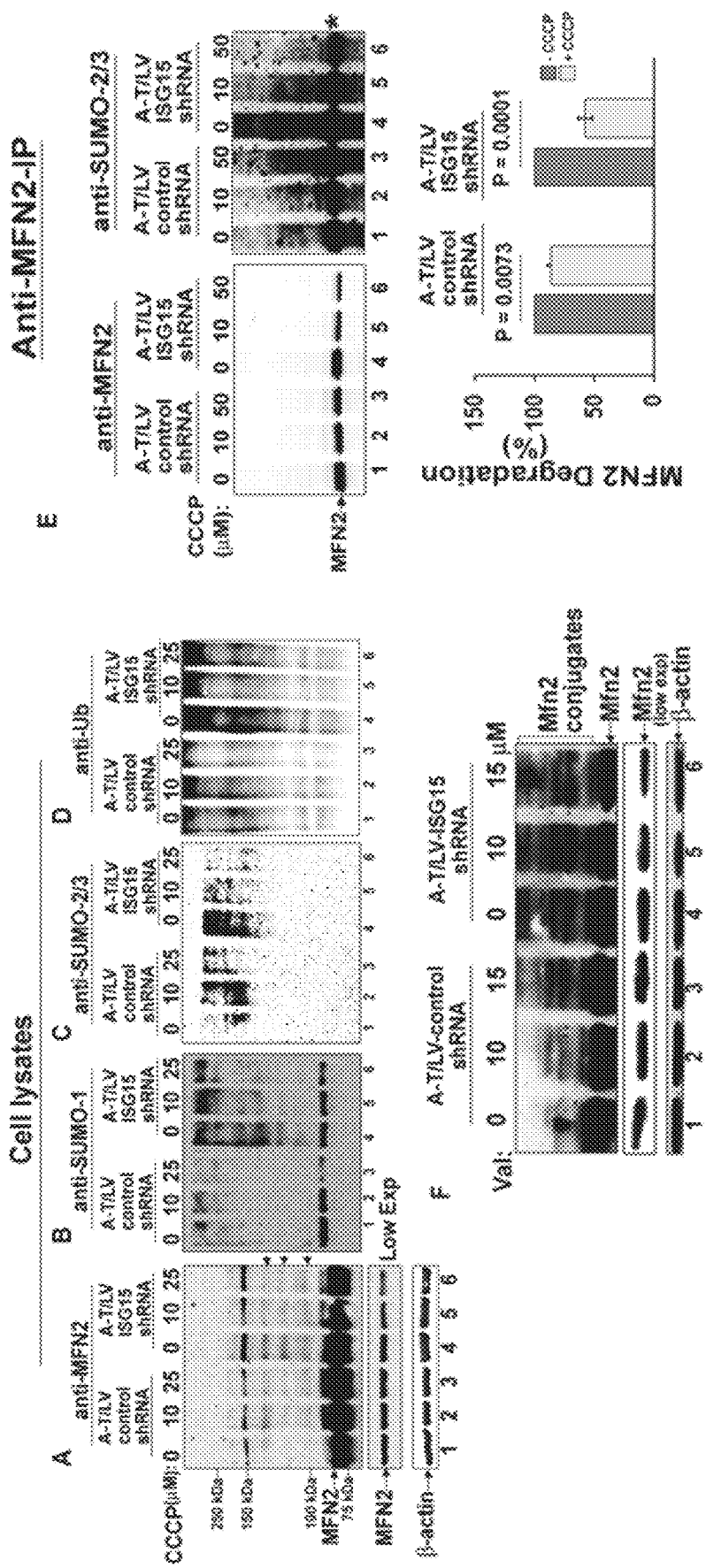

We show evidence of cross-talk between the ubiquitin-like protein SUMO (Small Ubiquitin-like MOdifiers) and ubiquitin pathways in regulating the turnover of mitofusion protein Mitofusin 2 (MFN2) in HEK293 and Ataxia Telangiectasia (A-T) cells. Importantly, we show that ISG15 interferes with this cross-talk in A-T cells (FIGS. 36 and 37). These findings complement our previous findings that topoisomerase 1 is SUMOylated (conjugated to SUMO) prior to its degradation via the proteasome and that ISG15 inhibits this process in cancer cells (24). These two independent findings, which utilize different pathological models, further support a direct role of ISG15 in deregulating ubiquitin-dependent mitophagy.

Our results to date have revealed constitutively elevated ISG15 conjugates may contribute to the A-T pathology (e.g., cerebellar neurodegeneration) by inhibiting the ubiquitin-dependent regulation of protein and mitochondrial turnover. ISG15 is minimally expressed in normal cells but it is constitutively expressed due to the aberrant expression of the IFN pathway in various pathological conditions such as cancer (1,25,26), pathogenic infections (27,28), A-T (5,14), and ALS (Amyotrophic Lateral Sclerosis) (29), the latter another rare neurodegenerative disease (3 to 8 per 100,000 births) that is similar to A-T. Moreover, ISG15 has been identified as a biomarker for neuronal injury, a common occurrence in all neurological disorders (30). Results from our A-T model as well as data utilizing ALS and neuronal injury models indicate that ISG15 can play a common crucial role in the etiology of neurodegeneration. Thus, the constitutively elevated ISG15 ligation pathway inhibits the ubiquitin pathway consequently protein and mitochondrial turnover (mitophagy), and that contributes to neurodegeneration.

Figure 27:
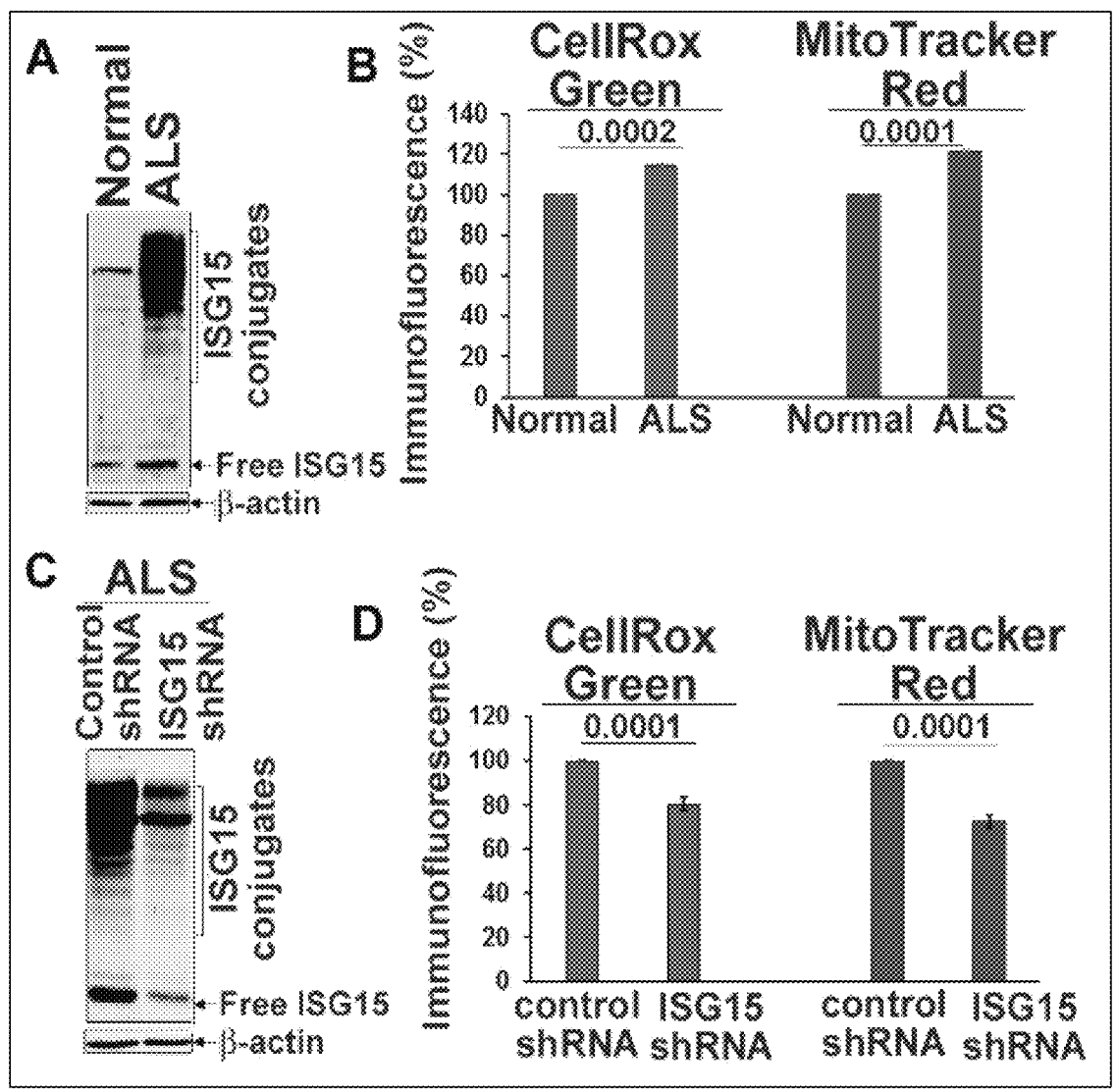
FIG. 27 shows ISG15 inhibits mitophagy in ALS. (A) Protein expression of ISG15 in normal and ALS cells is shown via Western blot. (B) Flow cytometric analysis of oxidative stress using CellRox Green and mitochondrial mass using MitoTracker Red stains in ALS cells are shown. (C) Protein expression of ISG15 in ALS and ISG15-silenced ALS cells is shown via Western blot. (D) Flow cytometric analysis of oxidative stress using CellRox Green and mitochondrial mass using MitoTracker Red stains in ALS and ISG15-silenced ALS cells are shown.
Figure 28:
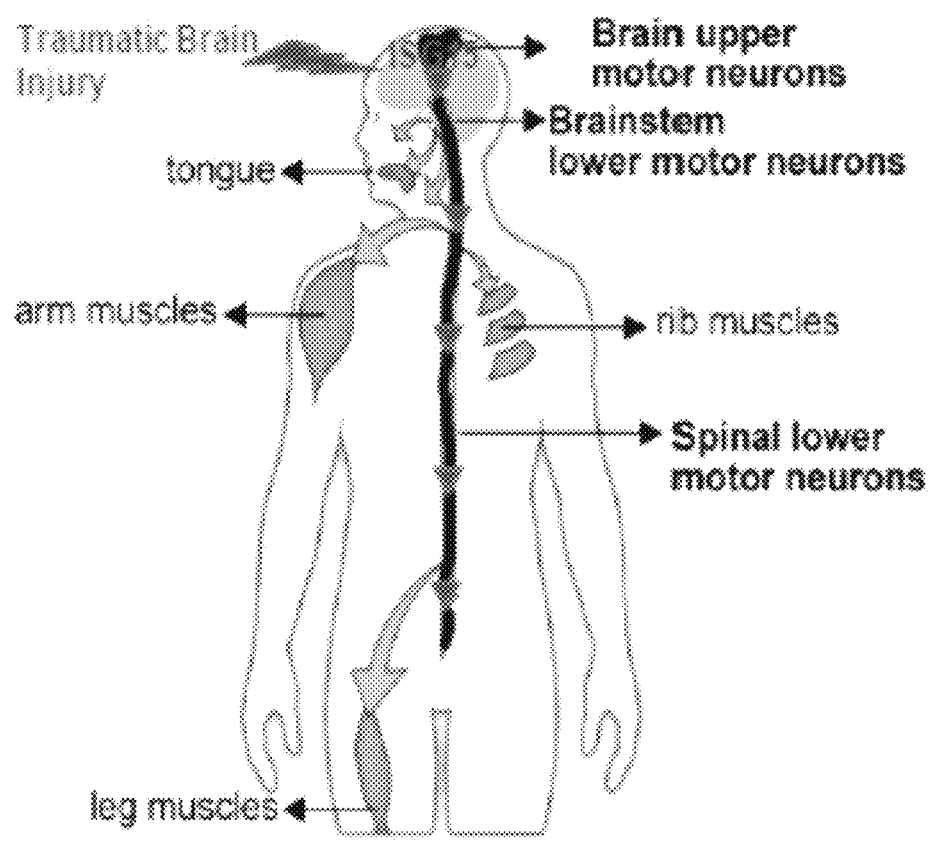
FIG. 28 shows linking of ALS, TBI and ISG15: ISG15 elevation in response to TBI inhibits protein turnover and mitophagy in motor neurons. Accumulation of toxic proteins and abnormal mitochondria, in turn, leads to motor neurodegeneration in ALS.

We have now chosen an ALS model in which ISG15 is also constitutively elevated (29). We have assessed ISG15 expression in several distinct ALS cell lines (Coriell Cell Repository) finding that the ISG15 pathway is indeed elevated in ALS. We have also generated evidence that as in A-T cells, constitutively elevated ISG15 can be causally related to the mitochondrial anomalies in ALS cells (FIG. 27). The goal of this project is to extend these observations and gain a deeper mechanistic understanding of the impact of ISG15 induction on mitophagy using A-T and ALS human neurological disease models. Knowing ISG15 inhibits E3 ubiquitin ligases and the subsequent polyubiquitylation of cellular proteins (1,31-34), and our results that ISG15 interferes with cross-talk between the SUMO and ubiquitin ligation pathways (FIGS. 36 and 37), we will examine whether the constitutively elevated ISG15 ligation pathway inhibits ubiquitin-dependent regulation of mitophagy by inhibiting mitochondrial SUMO/ubiquitin E3 ligases in A-T and ALS.

Statistics show that over six million people in the United States suffer from neurological diseases (35). Unfortunately, there is no cure or preventive medicines available for treating these neurological diseases, as molecular events triggering neurodegeneration are largely unknown. Our current studies will confirm ISG15 proteinopathy as a possible trigger for neurodegeneration in A-T, ALS, and related neurological diseases in which ISG15 is elevated.

Two independent groups have demonstrated that mitophagy is defective in A-T (19,20). However, results from our group and others have revealed that basal autophagy is activated in A-T cells (15,20), leading to the paradox of how autophagy is activated but not mitophagy, a process that is dependent upon autophagy. Our results reveal that ISG15 inhibits ubiquitination of mitophagy proteins, a step necessary for the initiation of mitophagy in A-T cells. Consequently, although autophagy is activated, mitophagy is defective in AT cells. Here, we shall extend these observations.

Mitophagy is defective in several neurological disorders (36,37). Mutations in Parkin (ubiquitin E3 ligase) or Parkin activation by mutations in PINK1 signaling have been implicated in defective mitophagy in Parkinson (38). However, why mitophagy is defective in other neurological diseases where Parkin is functional, is largely unknown. Our studies will potentially reveal a novel ISG15 proteinopathy mechanism underlying defective mitophagy in A-T, ALS, and other related diseases.

Several groups have reported various post-translational modifications (ubiquitin chains of Lys-63 and Lys-48 linkages) of mitophagy proteins (e.g., MFN2) in response to the mitochondrial depolarizing drug CCCP (21). Our studies have revealed for the first time that MFN2 is conjugated to the ubiquitin-like protein SUMO-1, SUMO-2/3, and ubiquitin upon CCCP treatment (FIGS. 36 and 37). Experiments proposed herein will add to the current knowledge of cellular regulation of mitophagy process.

Mitophagy is defective in various human and mouse A-T cell lineages (19,20). However, whether mitophagy is defective in human and mouse A-T neurons, the cell lineage potentially affected in human A-T disease, has not been investigated. Knowing that ISG15 inhibits mitophagy and that ISG15 is elevated in both A-T human and mouse cerebellums (14), such studies are warranted. However, these studies are impractical to conduct in human patients. Also, Atm knockout mice are scarcely available for experimentation due to their embryonic lethality. Therefore, we will establish a unique protocol to generate A-T patient-specific human neural progenitor cells from epithelial-like cells in human urine samples (hUiNPCs) (FIG. 41) as described elsewhere (39,40). We shall then differentiate these hUiNPCs into neurons to study mitophagy. Our results will reveal for the first time whether mitophagy is defective, as in other A-T cell lineages, and whether this defective mitophagy is due to ISG15 overexpression in A-T neurons. This approach has not been employed before in the A-T field. Currently, there are only two "humanized" research brain models (stem cell model) available for A-T (41,42). Hence, such models are highly attractive and can serve as an invaluable resource.

Cellular ISG15 exists in two forms, free and conjugated to cellular proteins (ISGylation) (43). Our studies reveal that ISGylation but not free ISG15, inhibits polyubiquitylation of cellular proteins in A-T cells (14). More recent studies from our lab reveal that ISG15 also inhibits polyubiquitylation of mitochondrial proteins in A-T cells (FIGS. 36 and 37). However, whether ISGylation or free ISG15 inhibit mitochondrial protein degradation during mitophagy is not known. We shall test the impact of ISGylation on polyubiquitylation of mitochondrial proteins using a new ISGylation-deficient A-T cell line that we have made in our lab (FIG. 38).

There is evidence implicating mitochondrial dysfunction as a major event in the pathology of ALS (44,45). However, biochemical evidence for the mechanism(s) underlying defective mitophagy is still lacking. As in A-T cells, ISG15 is also elevated in human as well as mouse models of ALS (29). However, as in A-T cells, whether ISG15 inhibits mitophagy in ALS has not been confirmed. Our results indicate such (FIG. 27). We shall examine the functional impact of ISG15 induction on mitophagy in ALS.

This line of research will lead to clear understanding of whether constitutively elevated ISG15 is an underlying cause of mitochondrial pathology in two distinct neurological syndromes A-T and ALS, and will thus enable us to develop a new "ISG15 theory" to improve current understanding of the neurodegeneration in A-T, ALS, and in related neurological disorders where ISG15 may be elevated.

"As the U.S. population ages, the burden of neurodegenerative disorders, including Alzheimer disease and Parkinson disease, will increase substantially (35). Hence, there is an urgent need to find therapeutic drugs that can slow or stop neurodegeneration in affected subjects. However, for developing such drugs, we urgently need information to determine what causes the trigger for neurodegeneration in these neurological syndromes. Additionally, we need good cellular models that would recapitulate disease phenotypes and assist in drug screening. This research project will establish ISG15 as a therapeutic target to restore, in part, mitochondrial homeostasis and neuronal health in AT and ALS patients. The results from experiments will also generate a clinical and research tool (UiNPCs-derived neurons) that could aid in A-T patient-specific identification of molecular lesions, and therapeutic treatments for A-T, ALS, and other neurological syndromes, as ISG15 is elevated in injured neurons (30), and injury to neurons is common in neurological disorders.

We will develop a cutting-edge unique protocol to generate human A-T patient specific iPSC-derived neurons from renal cells present in the urine samples of A-T patients and normal subjects. Currently, there is no such "Urinary Cell-derived Humanized Neuronal model" for A-T available. This model can be an invaluable resource to study A-T neuropathology in the laboratory setting, and for A-T patient-specific identification of molecular lesions and therapeutic treatments in the clinical setting. Overall, this study will enable us to potentially develop a novel ISG15 mechanism using a unique protocol that will revolutionize current understanding of defective mitophagy in A-T, and pave the way for development of similar protocol(s) to study other neurological disorders, such as ALS, in which ISG15 is also elevated What is the Molecular Mechanism Underlying Defective Mitophagy in Human A-T Cells?

Our studies provide evidence that constitutively elevated ISG15 is an underlying cause of defective mitophagy in A-T cells. However, the precise mechanism by which ISG15 inhibits mitophagy is still unclear.

Initial Studies

Constitutively Elevated ISG15 Inhibits Mitophagy in A-T Cells.

Mitophagy is defective (19,20) and ISG15 is constitutively elevated in A-T cells (5,14). Since mitophagy requires the functional ubiquitin pathway (21) and ISG15 inhibits the ubiquitin pathway (14), we examined whether constitutively elevated ISG15 is an underlying cause of defective mitophagy in A-T cells. To examine the status of mitophagy, we assessed mitochondrial mass (using MitoTracker dye), membrane potential (using JC1 dye), oxidative stress (using Cell Rox stains), and mitochondrial functions (using ATP assay, and Seahorse machine), parameters often deregulated when mitophagy is defective, in A-T and ISG15-silenced A-T cells. We performed immunostaining and flow cytometry assays for these analyses. We present flow cytometry data which is consistent with our immunostaining results. In FIG. 26, Panel A, we show that the ISG15 gene is silenced in ISG15 shRNA expressing (right lane) versus control shRNA expressing (left lane) A-T cells. In Panel B, MitoTracker Red that stains mitochondria in live cells, is decreased, indicating that mitochondrial mass is decreased in ISG15-silenced A-T cells. In depolarized mitochondria, JCI monomers emit a green fluorescence (46,47). Thus, decreased green staining indicate that the number of unhealthy mitochondria are decreased in ISG15-silenced A-T cells (Panel C). Decreased CellRox Green fluorescence indicate that reactive oxygen species (ROS) are decreased in ISG15-silenced A-T cells (Panel D). Together, these results indicate that mitochondrial quality is improved in ISG15-silenced A-T compared to ISG15 overexpressing A-T cells.

ISG15 Inhibits Cellular ATP Levels in A-T Cells.

We measured cellular ATP levels to determine the functional status of mitochondria in A-T cells expressing control or ISG15 shRNAs. Results are shown in FIG. 32B. The restoration of ATP levels indicates ISG15 shRNA has restored the mitochondrial ATP production function in A-T cells. We also assessed mitochondrial functions using Biosciences Seahorse XF24 flux analyzer. Our results reveal that bioenergetic demand, i.e. Oxygen Consumption Rate (OCR), is increased indicating the presence of defective mitochondria in ATM kinase-ablated A-T/LVcontrol shRNA cells. On the other hand, OCR was decreased in ISG15-silenced A-T cells. These results indicate that mitochondrial functions(s) are improved in ISG15-silenced compared to ISG15 overexpressing A-T cells. Results shown in FIG. 26 and FIG. 32B show that defective mitochondria accumulate due to defective mitophagy in A-T cells (19,20). Moreover, we show that defective mitophagy is due to the constitutively elevated expression of ISG15 in A-T cells.

MFN2 is Conjugated to SUMO-1, SUMO-2/3, and Ubiquitin, and ISG15 Attenuates Both SUMOylation and Ubiquitylation in A-T Cells.

ISG15 inhibits the ubiquitin pathway (1,14), and the ubiquitin-mediated degradation of outer mitochondrial membrane proteins (OMNI) (e.g., MFN 1 and 2, among others) is a prerequisite for the initiation of mitophagy (21,48). We speculated that ISG15 may inhibit degradation of OMNI proteins and mitophagy in A-T cells. The mitochondrial depolarizing agent carbonylcyanide m-chlorophenylhydrazone (CCCP) induces ubiquitin mediated degradation of MFN2 prior to mitophagy in cells (21). We therefore assessed the fate of MFN2 in AT/LV-control and A-T/LV-ISG15-silenced cells treated with CCCP. Consistent with the literature reports, we observed a ladder of high molecular weight anti-MFN2 cross-reactive bands above the 86 kDa MFN2 protein band in both ISG15-silenced and ISG15 overexpressing A-T cells (FIG. 36 Panel A) (21,38,49). Although these high molecular weight bands were previously identified as MFN2-ubiquitin conjugates by others (21,38,49), the appearance (doublets) and periodicity of the MFN2 conjugated bands, i.e., 14-17 kDa instead of 8 kDa shifts (see arrows on Panel A) known to result from the conjugation of ubiquitin monomers, caught our attention, as these bands were reminiscent of topoisomerase SUMO-1 (Small Ubiquitin-Like Modifiers 1-2-3) conjugates that we previously observed in cells treated with the anticancer drug camptothecin (24). These past observations prompted us to examine the possibility of the presence of SUMO protein in MFN2 conjugates. We probed the same blot shown in FIG. 36A with the SUMO-1 and SUMO-2/3-specific monoclonal antibodies. Strikingly, the endogenous steady state levels of MFN2-SUMO-1, SUMO-2/3, and ubiquitin cross-reactive bands were remarkably higher in ISG15-silenced compared to the ISG15-overexpressing A-T cells in the absence of any drugs (FIG. 36A-D, compare lanes 1 and 4). Similar to the cell lysate experiment, in the anti-MFN2 immunoprecipitation experiment, levels of MFN2-SUMO-2/3 (FIG. 36E, compare lanes 1 and 4), and MFN2-SUMO-1/Ub-cross-reactive bands were also higher in ISG15-silenced compared to the ISG15-overexpressing A-T cells in the absence of any drugs.

Together, these results indicate that endogenous MFN2 protein is constitutively modified by SUMO and ubiquitin, and these modifications are ablated in ISG15 overexpressing A-T cells. C1b4. ISG15 inhibits CCCP and Valinomycin-induced degradation of MFN2 in A-T cells. We also observed decreased levels of MFN2-SUMO conjugation with increasing doses of CCCP in ISG15-silenced A-T whole cell lysates (FIG. 36A-D, lanes 4-6) and anti-MFN2 immunoprecipitates (FIG. 36E, lanes 4-6). In contrast, there was a modest increase in the level of these MFN2-SUMO/ubiquitin bands under the same drug treatment conditions in ISG15-overexpressing A-T whole-cell lysates (FIG. 36A-D lanes 1-3) and anti-MFN2 immunoprecipitates (FIG. 36E, lanes 1-3). Additionally, a modest decrease (20%) in the free MFN2 level was noted in ISG15-silenced A-T cells treated with CCCP for 24 h in both cell lysates (FIG. 36A, lanes 4-6, see low exposure) and immunoprecipitates (FIG. 36E, left panel, lanes 4-6, and bar graph for quantitation). On the other hand, free MFN2 protein level remained unaffected in CCCP-treated ISG15 overexpressing A-T cells. A similar trend of MFN2-modification and degradation was noted in A-T and ISG15-silenced A-T cells treated with Valinomycin (another mitochondrial depolarizing agent) for 24 h (FIG. 36F). Together, these results indicate that CCCP induces SUMO/ubiquitin conjugation and subsequent degradation of MFN2 in ISG15-silenced A-T cells. This SUMO-ubiquitin modification of MFN2 is defective, and consequently degradation of MFN2 is attenuated in ISG15 overexpressing A-T cells. We do have the evidence that MFN2 degradation is via the proteasome in ISG15-silenced A-T cells. More experimentation however is needed to confirm these observations.

MFN2 is Conjugated to SUMO-1/2/3 and Ubiquitin, and is Degraded in HEK293 Cells Treated with CCCP.

We confirmed CCCP-induced MFN2-SUMO/ubiquitin modification and degradation in "normal" HEK293 cells. Results are shown in FIG. 37. Western blot analysis of cell lysates (Panel A) and anti-MFN2 immunoprecipitates (Panel B) from non-treated and CCCP-treated HEK cells show that CCCP induces conjugation of SUMO-1, SUMO-2/3, and ubiquitin to MFN2 in HEK cells. We have confirmed these results by Mass Spectrophotometry. In HEK cells, CCCP also induced MFN2-SUMO conjugation with a concomitant decrease in MFN2-Ub conjugates and free MFN2 protein in 24 h (FIG. 37). Contrasting reports that showed a robust proteasome mediated degradation of MFN2 in CCCP-treated cells, we consistently found only 20% degradation of MFN2 in CCCP-treated ISG15-silenced A-T (FIG. 36G) and HEK (FIG. 37C) cells. However, CCCP-mediated decrease in MFN2 was proteasome-dependent (FIG. 37D). Together, our results using A-T and HEK293 cells reveal that MFN2 is SUMOylated in response to CCCP treatment. This is the first report demonstrating SUMOylation of MFN2 in response to CCCP-mediated mitophagy induction in cells. More experiments are underway to test the statistical relevance of this data using HEK, A-T, and ISG15-silenced A-T cells.

We conclude that in A-T cells: a) mitophagy is defective due to constitutively elevated ISG15 (FIGS. 26 and 32B); b) MFN2 is SUMOylated in response to CCCP and Valinomycin treatment (FIGS. 36 and 37); c) ISG15 inhibits SUMO and ubiquitin conjugation of MFN2 (FIG. 36); and d) ISG15 inhibits CCCP/Valinomycin-induced degradation of MFN2 (FIGS. 36A and 36F). Experiments are ongoing to test whether these results hold true for MFN1, another mitofusion proteins that are targeted for degradation in response to CCCP treatment. Here, we will investigate the molecular mechanism underlying ISG15-mediated defective mitophagy in A-T cells Does ISGylation Inhibit Mitophagy in A-T Cells?

Rationale: ISG15 exerts its biological effects through conjugating to cellular proteins (6,14,50). Using an ISG15 gene silencing approach we have demonstrated that ISG15 inhibits mitophagy in A-T cells (FIGS. 26 and 32B). However, silencing of the ISG15 gene reduces levels of both free ISG15 as well as ISG15 conjugates (6). Hence, it still remains unclear whether mitophagy defects are due to free ISG15 or ISG15 conjugation in A-T cells. This information is important for two reasons. Previously, we have demonstrated that ISGylation and not free ISG15 inhibits the ubiquitin pathway in A-T cells (14). Second, in our cancer models, we have demonstrated that ISGylation has protumor function while free ISG15 has an antitumor immune boosting function in vivo (50). Corroborating these results, free ISG15 has been identified as an immune cytokine against bacterial/viral infections in human and mice (27,51,52). Since A-T patients are immunocompromised and susceptible to various pathogenic infections (53), we indicate retaining free ISG15 that can boost the immune system and silencing of ISGylation that induces proteinopathy would benefit A-T patients. Therefore, here, we shall test whether ISGylation and/or free ISG15 inhibit mitophagy in A-T fibroblast cells.

ISGylation-Silenced A-T Cells:

To test the role of ISGylation, we have made UbcH8-silenced A-T cells (AT/UbcH8 shRNA cells) in our lab. The UbcH8 enzyme is an ISG15-specific E2 enzyme in the ISG15 conjugation pathway (54,55). Therefore, A-T/UbcH8 shRNA cells are devoid of ISG15 conjugates but continue to express free ISG15 hence, appropriate for understanding the impact of ISG15 conjugates on mitophagy (FIG. 38). A-T cells expressing control shRNA will be used as a control. Using these cells, we shall assess mitochondrial dynamics, properties, and functions using immunostaining and flow cytometry assays that we have established and described in our studies (FIGS. 26 and 32B). Results will reveal whether ISGylation inhibits mitophagy in A-T cells.

Does ISGylation Inhibit Mitophagy in A-T Cells?

Rationale: ISG15 exerts its biological effects through conjugating to cellular proteins (6,14,50). Using an ISG15 gene silencing approach we have demonstrated that ISG15 inhibits mitophagy in A-T cells (FIGS. 26 and 32B). However, silencing of the ISG15 gene reduces levels of both free ISG15 as well as ISG15 conjugates (6). Hence, it still remains unclear whether mitophagy defects are due to free ISG15 or ISG15 conjugation in A-T cells. This information is important for two reasons. We have demonstrated that ISGylation and not free ISG15 inhibits the ubiquitin pathway in A-T cells (14). Second, in our cancer models we have demonstrated that ISGylation has protumor function while free ISG15 has an antitumor immune boosting function in vivo (50). Corroborating these results, free ISG15 has been identified as an immune cytokine against bacterial/viral infections in human and mice (27,51,52). Since A-T patients are immune-compromised and susceptible to various pathogenic infections (53), we indicate retaining free ISG15 that can boost the immune system and silencing of ISGylation that induces proteinopathy would benefit A-T patients. Therefore, in this Aim we shall test whether ISGylation and/or free ISG15 inhibit mitophagy in A-T fibroblast cells.

ISGylation-Silenced A-T Cells:

To test the role of ISGylation, we have made UbcH8-silenced A-T cells (AT/UbcH8 shRNA cells). The UbcH8 enzyme is an ISG15-specific E2 enzyme in the ISG15 conjugation pathway (54,55). Therefore, A-T/UbcH8 shRNA cells are devoid of ISG15 conjugates but continue to express free ISG15 hence, appropriate for understanding the impact of ISG15 conjugates on mitophagy (FIG. 38). A-T cells expressing control shRNA will be used as a control. Using these cells, we shall assess mitochondrial dynamics, properties, and functions using immunostaining and flow cytometry assays that we have established and described (FIGS. 26 and 32B). Results will reveal whether ISGylation inhibits mitophagy in A-T cells.

Rationale: Previously we have demonstrated that topoisomerase 1 is conjugated to SUMO prior to its ubiquitin mediated degradation via the 26S proteasome (24). Several other proteins are similarly conjugated to SUMO-2/3 prior to ubiquitin conjugation by SUMO-targeted Ubiquitin E3 Ligases (STUbLs) for their targeted degradation (56-58). STUbLs bind SUMO chains on SUMOylated substrates through their SUMO-Interacting Motifs (SIM) and conjugates ubiquitin using an internal lysine on SUMO-2/3 (58). Thus, SUMOylation precedes ubiquitylation. We have observed that CCCP-induced MFN2-SUMOylation and ubiquitylation are reduced in ISG15 overexpressing compared to ISG15-silenced A-T cells (FIG. 36B-D). However, whether SUMOylation precedes ubiquitylation or vice versa, and which one of these modifications is defective in A-T are not known.

Knowing that ISG15 inhibits E3 ubiquitin ligases and the subsequent polyubiquitylation of cellular proteins (1,31-34), the constitutively elevated ISG15 ligation pathway inhibits ubiquitin-dependent regulation of mitophagy by inhibiting mitochondrial SUMO/ubiquitin E3 ligases in A-T. To test this, we will first identify ubiquitin/SUMO ligases that modify MFN2 and then test whether ISG15 inhibits these enzymes.

Experimental Design: Identification of Mitochondrial SUMO/Ubiquitin

E3 ligases for MFN2: We shall target three known mitochondrial E3 ligases that regulate mitochondrial dynamics (fusion and fission) by conjugating SUMO (for fission) and ubiquitin to mitochondrial proteins (See FIG. 39). These enzymes include the E3-ubiquitin ligases Parkin (48) and MARCH5 (Membrane associated Ring finger (C3HXC4) (59)5) and SUMO/ubiquitin dual function E3 ligase MULAN/MAPL (Mitochondrial ubiquitin ligase activator of NFκB/mitochondrial-anchored protein ligase)(60-63). All three enzymes are known to target MFN2 for ubiquitin-mediated degradation via the proteasome (48,64,65). Our studies revealed that MFN2 is SUMOylated but the SUMO ligase for MFN2 is not known. To test if these three enzymes are involved in SUMOylation and ubiquitylation of MFN2 in our experiments (FIGS. 36 and 37), we will silence gene expression of these three E3 ligases (one at a time) using siRNAs in ISG15 silenced A-T and HEK cells, since MFN2 modification and degradation is proficient in these cells. Alternatively, we shall use CRISPR/Cas 9 system to silence E3 ligases in HEK cells. All three Parkin, MARCH5, and MULAN CRISPR/Cas9 KO plasmids are commercially available (SantaCruz).

MFN2 modification status will then be assessed in E3-ligase-silenced cell lysates and MFN2-immunoprecipitates using Western analysis and SUMO-2/3-specific antibodies as shown in FIGS. 36 and 37. Contribution of SUMO and ubiquitin to MFN2-mediated degradation will be further confirmed by overexpressing conjugation defective mutants of SUMO and ubiquitin (SUMO/Ub ΔGG) or using A-T/UbcH8 shRNA cells. We shall also examine the fate of other outer mitochondrial proteins such as MFN1, Tom70, VDAC1, Bak, Fis1, and Tom20, which are degraded before mitophagy under these conditions (21). As a negative control, we will assess the levels of intermembrane space protein (cytochrome c), inner membrane protein (Opa1), and matrix proteins (Hsp60, Sod2, F1β), since these mitochondrial proteins remain unaffected during mitophagy (21). Results in E3 ligase-silenced cells are summarized in the following Table:

|  | MFN2-SUMO conjugates | MFN-Ubiquitin conjugates |
|---|---|---|
| PARKIN | No Change* | Decrease |
| MARCH 5 | No Change* | Decrease |
| ** MULAN-Ub-SUMO dual function ligase | Decrease | Decrease |

*If SUMOylation is a prerequisite for ubiquitylation and subsequent MFN2 degradation, the absence of a MFN2-ubiquitin smear and presence of MFN2-SUMO bands, in Parkin or MARCH5-silenced cells will indicate that SUMO is conjugated to MFN2 by a distinct enzyme.
** MULAN compensates for PARKIN function in cells and reduced functions of PINK/Parkin (Ub E3 ligase) and MULAN (SUMO E3 ligase) have been implicated in mitochondrial dysfunction by stabilizing MFN proteins in Parkinson (65). If in our experiments MULAN/MAPL has a SUMO/ubiquitin dual ligase function, this will explain the compensatory function(s) of MULAN and Parkin in Parkinson.

To test whether ISG15 inhibits MFN2-Ub/SUMO E3 ligases: ISG15 could inhibit MFN2-ubiquitin or SUMO E3 ligases by three ways: 1) By competing with ubiquitin to bind ubiquitin-specific E3 ligases (Parkin and MARCH5), or with SUMO to bind SUMO ligase (MULAN/MAPL) thus, forcing these enzymes to add ISG15 instead of Ub/SUMO onto their substrates (e.g., MFN2), as has been demonstrated for several ub/ISG15 bifunctional E3 ligases (e.g., E6AP (66)); 2) By physically interacting and interfering with the functions of ub/SUMO ligases, as in the case of Nedd4 Ub E3 ligase (31); and 3) By conjugating to ub/SUMO E3 ligases, as in the case of Efp E3 ubiquitin ligase (67). To avoid artifacts that may be generated due to simultaneous overexpression of components of the ISG15 pathway (ISG15 E1/E2/E3), we will use A-T cells for these experiments in which the ISG15 pathway is constitutively elevated. The first mechanism mentioned above has since been tested. We did not see any apparent increase in ISG15-MFN2 conjugates and ISGylated proteins in ISG15 overexpressing CCCP-treated A-T cells. Thus, we rule out this possibility.

To test the second possibility, i.e. whether ISG15 physically interacts with Parkin, MARCH5, and MULAN/MAPL E3 ligases, we shall use co-immunopreciptations and pull-down biochemical assays. These assays are widely used in the literature to study protein-protein interactions including studies that tested ISG15 interaction with Nedd4 E2/E3 ligases (31). Also, using this method, physical interactions between Parkin and SUMO-1 have been demonstrated in the literature (68). We shall use UbcH8-silenced A-T cells for these experiments, as these cells are devoid of ISG15 conjugates but continue to express free ISG15 (FIG. 38). Alternatively, we can overexpress free ISG15 in HEK cells. If E3 ligase(s) interacts with ISG15 in these assays, we shall identify the region(s) of E3 ligases that are required for these protein-protein interactions using truncation/deletion analysis (67). Expected results: Positive interactions of ISG15 with Parkin or MARCH5 or MULAN/MAPL, and disruption of this interaction with E3 ligases truncated/deleted in their ISG15 interacting domains, will be taken as an evidence that ISG15 physically interacts and inhibits the functions of E3 ligases therefore MFN2 degradation in A-T cells.

To test the third possibility that ISG15 conjugates to and inhibits the functional activities of E3 ub/SUMO ligases, we shall immunoprecipitate PARKIN, MARCH5, and MULAN from ISG15 overexpressing A-T and UbcH8-silenced A-T (negative control) cell lysates. Immunoprecipitated proteins will then be analyzed by SDSPAGE followed by Western blotting using anti-PARKIN, MARCH5, or MULAN and anti-ISG15 antibodies. If ISG15-E3 conjugates are found, we shall perform in vitro cell free MFN2 ubiquitination assays in the presence of ISG15 or ISGylation conjugation defective proteins (ISG15 ΔGG) and ISG15 conjugating enzymes UBE1L (the E1 for ISG15) and UbcH8 (the E2 for ISG15), to test whether ISG15 conjugation inhibits E3 ligase activity (31). For an in vivo assay, we shall identify lysine residue(s) on these ligases used for ISG15 conjugation (by doing mass-spectrophotometry analysis on immunoprecipitates), mutate this lysine(s), then test the ability of the lysine-mutated E3 ligase to conjugate ubiquitin/SUMO to MFN2 in vivo. Results: If PARKIN, MARCH5, and MULAN/MAPL are ISGylated, anti-ISG15 and/or anti-E3 ligases will crossreact with high molecular weight bands above the free E3 ligase(s) protein bands on the Western blots in cell lysates of A-T/control but not A-T/UbcH8 shRNA (conjugation deficient) cells. Also, inhibition of E3 ligase function will be seen in in vitro ubiquitination assays in the presence of ISG15 and its conjugating enzymes. ISGylation conjugation defective mutant protein (ISG15 ΔGG) is expected to retain E3 ligase function in in vitro assays. Mutation of the lysine residue(s) necessary for ISG15 conjugation on E3 ligases(s) is expected to retain E3 ligase(s) function in A-T cells. Results of these experiments will reveal a molecular mechanism underlying ISG15-mediated defective degradation of MFN2 in A-T cells.

Experimental protocols are standard in the lab, and most A-T/ubiquitin/ISG15 reagents are available already. Regarding mitochondrial SUMO-E3 ligase. Without being bound by theory, MFN2 is a substrate of MULAN/MAPL SUMO ligase. If not, we shall use more robust bioinformatics and molecular biology approach to identify potential SUMO/ubiquitin E3 ligases for MFN2 (69). Without being bound by theory, ISGylation inhibits polyubiquitylation of OMM proteins resulting in inhibition of mitophagy in A-T cells. While ubiquitin conjugation by Parkin to mitochondrial proteins represents a mechanism to target mitochondria for autophagic clearance (48), other mechanism involving the recruitment of Parkin to abnormal mitochondria has been reported. It has been shown that BNIP3L/NIX1 can target Parkin-associated mitochondria for degradation independent of mitochondrial ubiquitylation (70,71). However, we have demonstrated decreased ubiquitylation of mitochondrial proteins and increased number of defective mitochondria (indicating defective mitophagy) in A-T cells overexpressing ISG15 (FIG. 26). These results indicate that ubiquitylation, not BNIP3L/NX1, plays a major role in targeting defective mitochondria for degradation via autophagy in A-T cells overexpressing ISG15.

Ubiquitin linkages: Without being bound by theory, Parkin/MARCH5 conjugates ubiquitin onto substrates through Lys-48-linked ubiquitin chains for the purpose of their proteasomal degradation. However, the majority of the ubiquitin modification by these two enzymes on its substrates that we may observe is not for the purpose of its targeted degradation via proteasome. Instead, these substrates may be conjugated to Lys63-linked polyubiquitin chains, a signal that does not target proteins for degradation (72). In line with this notion, Parkin also conjugates Lys63-linked polyubiquitin chains onto outer mitochondrial membrane proteins (21), and ISG15 can block conjugation of both Lys48- and Lys63-linked ubiquitin chains (1,33,34). Identification of ubiquitin-chains on Parkin/MARCH substrates, and assessment of the fate of these substrates will reveal the function of Parkin/MARCH5/ubiquitin/ISG15 in mitophagy in A-T.

Is Mitophagy Defective in Human A-T Neurons?

Defective mitophagy has been implicated in the neurodegeneration of various neurological syndromes (18,73). Mitophagy is defective in human A-T lymphoblasts and fibroblasts (19,20). Also, ISG15 inhibits mitophagy in A-T fibroblasts (FIG. 26). However, whether mitophagy is defective in A-T neurons, a cell lineage that is principally affected in A-T disease, and whether ISG15 inhibits mitophagy in A-T neurons has not been studied. We demonstrated that ISG15 expression is elevated in the brains of A-T human patients and mice (14). Our results have also revealed that, as in A-T human brains, ISG15 is elevated in cerebellums (14) but minimally expressed in cerebral tissues of Atm$^{-/-}$ mice. Because ISG15 is elevated in both human and mouse brain tissues, a more complete understanding of the functional impact of ISG15 in human or mouse neurons that are devoid of ATM kinase (Atm null) is warranted. However, such studies are obviously impractical to conduct in human patients. Also, Atm knockout mice are scarcely available since pup-yield for homozygots is extremely low due to reduced embryo survivability (74). To circumvent these technical problems, we propose to generate A-T patient specific neurons to study the impact of the ISG15 pathway on mitophagy in A-T. We shall exploit an established approach to reprogram epithelial-like cells from human urine into Neural Progenitor Cells (hUiNPCs) (FIG. 40) (39). We shall then differentiate these hUiNPCs into neurons. Use of urine-derived renal cells to generate UiNPCs as opposed to skin fibroblasts from A-T patients commonly used in literature, is advantageous for several reasons. First, the isolation of urinary cells is simple and does not need invasive procedures. Second, it is a cost-effective method. Third, it can be used to generate UiNPCs from patients of all ages including newborns (e.g., A-T children), as renal cells could be obtained from easily accessible urine samples. Fourth, the entire procedure is quick, which reduces the risk of accumulating genetic mutations in starting renal cells. This is important for A-T, as loss of genomic integrity is a hallmark of the disease Initial Studies.

New data that presented in FIG. 41. We have obtained human de-identified urine samples from normal children, and isolated renal cells as described in (40). As demonstrated in the original paper on UiNPCs (40), these cells show epithelial cell-like morphology (FIG. 41A) and expression of epithelial markers β-catenin and E-cadherin (FIG. 41B). Also, similar to normal cells and tissues, these renal cells minimally express ISG15 (FIG. 41C, lanes 1 and 3). However, the ISG15 pathway is functional and induced in response to IFNβ (FIG. 41C, lanes 2 and 4). These cells also retained a normal karyotype in culture (FIG. 41D).

Experimental Strategy

To Generate hUiNPCs-Derived Neurons from Urine Samples of A-T Patients and Normal Subjects.

We will follow two well-defined protocols described by Zhou et al. (40) and Wang et al. (39) to generate UiNPCs, with some modifications.

Collection and Isolation of Urinary Cells:

Collection and isolation of A-T urine samples will be performed at Children's Hospital of New Orleans as we did for normal subjects (FIG. 10) following the instructions in (40). Without being bound by theory, renal cell colonies from A-T urine samples will be similar to what we have obtained from urine samples of normal children (FIG. 41).

Generation of hUiNPCs:

We shall use ReproRNA™-OKSGM, a non-integrating and self-replicating reprogramming vector for generating hUiPSCs (STEMCELL Technologies, Catalogue #05931). This is a single-stranded RNA replicon vector that contains five reprogramming factors: OCT4, KLF-4, SOX2, GLIS1, and c-MYC, as well as a puromycin-resistance gene. Advantages of using this vector are: a) it is a nonintegrating vector system; b) the vector contains all reprogramming factors (all in one) thus, requiring only a single transfection; c) all the reagents and protocols necessary for generation and maintenance of iPSCs are available from the company; and d) it takes only about 20 days for generating iPSCs. These iPSCs will be directed to differentiate into Neuronal Progenitor Cells (NPCs) using well defined STEMdiffrm Neural System (reagents required for generation, isolation, expansion, and characterization of NPCs), and protocols developed by STEMCELL Technologies. Alternatively, we can also use a protocol for generating iPSCs from renal cells as described in reference 39. Without being bound by theory, rosette-like morphology typical of NPCs will be observed. Some of these colonies will be examined for expression of typical NSC genes such as SOX2, NES (encoding nestin), and Pax 6 by qRT-PCR. Expression of these genes will be taken as evidence of reprogramming of cells toward a neural fate.

Differentiation of hUiNPCs into Neurons:

Degeneration of dopaminergic and GABAergic neurons has been demonstrated in Atm−/− mice and human A-T patients (75). ISG15 is elevated in mid-brain tissues, specifically substantia nigra, obtained from A-T patients (14). We shall therefore generate dopaminergic neuronal precursors from NPCs using the STEMdiff. Neural Induction Medium (Catalog #05835) using an embryoid body protocol. The neuronal precursors generated will be matured using the STEMdiff. Dopaminergic Neuron Maturation Kit (Catalog #08530) to produce a neuronal population containing midbrain dopaminergic neurons. Alternatively, we shall use the protocol developed by Wang et al. described in (39). Without being bound by theory, control and A-T hUiNPCs will differentiate into mature dopaminergic neurons using STEMCELL Technologies (15-30% TH-positive dopaminergic neurons; 90% class III β-tubulin-positive neurons; <10% GFAP-positive astrocytes) or into glutamatergic (37%), GABAergic (15.2%), and dopaminergic (6.5%) neurons, as was demonstrated in the protocol by Wang et al. (39). This procedure will give us an unlimited source of neurons.

Is Mitophagy Defective in A-T Neurons?

We shall assess the structural, functional, and physiological properties of mitochondria in normal and A-T neurons as described in FIG. 26. Without being bound by theory, elevated expression of ISG15, and mitochondrial anomalies in A-T compared to normal neurons will be observed.

Do ISG15 or ISGylation (ISG15 Conjugates) Inhibit Mitophagy in A-T Neurons?

To test the impact of ISG15 or ISGylation on mitophagy, we will downregulate expression of ISG15 or ISG15 conjugates in neurons using lentiviral particles expressing ISG15 or UbcH8 shRNA that we have made in our lab. We shall then assess the structural, functional, and physiological properties of mitochondria in ISG15 or UbcH8-silenced neurons as described herein. Without being bound by theory, silencing of ATM using ATM-specific shRNA in iPSCderived control neurons will be observed indicating the feasibility of the gene silencing approach in neurons (75).

Also, we have successfully used the lentiviral silencing approach in our prior studies. Without being bound by theory, restoration of mitochondrial anomalies will be observed in ISG15/UbcH8-silenced compared to control shRNA expressing A-T neurons.

What is the Molecular Mechanism by which ISG15 Inhibits Mitophagy in A-T Neurons?

Without being bound by theory, constitutively elevated ISG15 ligation pathway inhibits ubiquitin-dependent regulation of mitophagy by inhibiting mitochondrial SUMO/ubiquitin E3 ligases (Parkin, MARCH5, MULAN/MAPL) in A-T neurons using the same set of experiments described herein. Briefly, we shall test whether Parkin and MARCH5 ubiquitin E3 ligases and Mulan/MAPL SUMO E3 ligase target mitophagy proteins for degradation via the 26S proteasome, triggering mitophagy, and whether ISGylation inhibits this process in A-T-ISG15/UbcH8-silenced neurons. Results will reveal whether ISGylation inhibits mitophagy by inhibiting the ubiquitin E3 ligase function in A-T neurons.

We are aware that A-T-specific human iPS cell lines are available in the literature (42). These reported iPSCs are generated from the starter skin fibroblast. We prefer renal cells vs skin fibroblasts as starter cells for two reasons: 1) skin fibroblasts are exposed to higher UV radiation (sunlight) and therefore DNA repair defective fibroblasts such as A-T fibroblasts, are expected to have higher mutations, and 2) skin fibroblasts take more than a month to expand in culture, which may further allow accumulation of undesirable mutations in starting cells. Recently, another iPSC cell line has been generated from blood cells of A-T subjects (41). Without being bound by theory, we will be able to successfully establish a protocol for differentiating human A-T neurons from UiNPCs, and find the role of ISG15/ISGylation in deregulating mitophagy in A-T patient-specific neurons.

Does the ISG15 Conjugation Pathway Inhibits Mitophagy in ALS?

Evidence is building that ALS is also a mitochondrial disease (76-78). Mitochondrial anomalies are noted in ALS mouse models (76-78). Knowing that constitutively elevated ISG15 inhibits mitophagy in A-T cells and that ISG15 is elevated in ALS (29), we asked if mitophagy is defective in ALS due to the elevated ISG15 ligation pathway. Without being bound by theory, defective mitophagy is due to elevated ISG15 conjugation in ALS cells (FIG. 27).

Constitutively Elevated ISG15 Inhibits Mitophagy in ALS:

We assessed ISG15 levels using Western blotting and mitophagy status using Mitotracker Red and CellRox in flow cytometry, in ISG15 overexpressing (FIGS. 27A and B) and ISG15-silenced (FIGS. 27C and D) lymphocytes obtained from a ALS patient (ND14790) and a normal subject (ND00066). As shown in Panel A (FIG. 27), ISG15 is elevated in ALS lymphocytes. Notably, since the first submission, we have screened 13 normal vs 7 ALS cell lines (Coriell Cell Repository) for ISG15 expression finding that ISG15 and its conjugates are indeed elevated in ALS. Also, increased staining with CellRox Green (green bars) and MitoTracker Red (red bars) in ALS lymphocytes compared to the normal lymphocytes indicate that ROS levels and mitochondrial mass/number are increased in ALS lymphocytes. We then silenced the ISG15 gene with lentiviral particles expressing ISG15-specific shRNA in ALS cells (FIG. 27 Panel C). Decreased fluorescence staining of CellRox Green and MitoTracker Red in ALS/ISG15 shRNA cells compared to ALS/control shRNA cells indicate that ROS levels and mitochondrial mass/number are in part restored in ISG15-silenced ALS cells. As in A-T, ISG15 may inhibit mitophagy in ALS. We will investigate the mechanism underlying defective mitophagy in ALS.

Experimental Strategy

Is Mitophagy Defective in ALS Cells?

Studies have revealed that ISG15 is elevated in ALS but not in normal lymphocytes (FIG. 27). We will use these cell lines for assessing the structural, physiological, and functional properties of mitochondria in ALS cells. Because ALS lymphocytes are suspension cells, we will principally use flow cytometry to measure MitoTracker Red, CellROX® Green Reagent, and JC1 staining described in FIG. 26. Alternatively, methods for immunostaining of suspension cells are widely used in the literature. We can use these methods for assessing mitochondrial properties and functions. Without being bound by theory, defects in mitochondrial structural, physiological, and functional properties, and mitophagy will be observed in ISG15 overexpressing (constitutively expressed) ALS but not in normal lymphocytes.

Does ISG15 or ISGylation (ISG15 Conjugates) Inhibit Mitophagy in ALS Cells?

Silencing of ISG15 or UbcH8 using lentiviral particles expressing ISG15 or UbcH8 shRNA will be carried out as described (FIG. 27). ALS cells expressing control shRNA will be used as a control. These cells will be used to assess the structural, physiological, and functional properties of mitochondria as described in FIG. 26. Without being bound by theory, restoration of the structural, physiological, and functional properties of mitochondria will be observed in ISG15-silenced ALS cells. Restoration of the structural, physiological, and functional properties of mitochondria in UbcH8-silenced ALS cells will be taken as an evidence for the role of ISGylation in impairing mitophagy in ALS cells.

What is the Molecular Mechanism by which ISG15 Inhibits Mitophagy in ALS Cells?

The same set of experiments described herein this example will be performed to test whether ISG15/ISGylation inhibits Ub/SUMO E3 ligases-mediated polyubiquitylation of mitochondrial proteins which in turn inhibits mitophagy in ISG15 overexpressing ALS cells. A molecular mechanism underlying ISG15-mediated defective degradation of MFN2 (mitophagy) in ALS cells will be developed.

ISG15 Function in ALS.

ISG15 inhibits the ubiquitin pathway in A-T as well as in non-related cancer cells (1,14). Other groups have validated these results in other cell lineages (79,80). Also, we show that ISG15 inhibits mitophagy in ALS cells. Without being bound by theory, it is highly unlikely that ISG15 which is constitutively elevated in ALS, will have a distinct function in ALS. Inhibition of mitophagy by ISG15 in ALS lymphocytes will be observed.

Use of ALS Lymphocytes Vs Neurons.

Experiments will be conducted using ALS lymphocytes. However, motor neurons are affected in ALS (81). Notably, most work on mitophagy in the field of neurodegeneration has been carried out using diseased fibroblasts, lymphoblasts (19,20), and even nonspecific cells like HeLa cells (21). Our studies and protocols will be extended to ALS motor neurons. The protocol that we will generate for human ATM-deficient neurons from urine samples together with the results herein will form a foundation for this study. Alternatively, ALS-iPSCs are commercially available.

Transient Vs Stable Transfection:

We have generated data demonstrating that transient silencing of ISG15 can restore mitophagy defects in ALS cells. Alternatively, we shall use ALS cells stably expressing ISG15/UbcH8 shRNAs for our experiments. ALS cells that we will use in this study are suspension cells. Hence, to select stable transfectants, we will use a GFP shRNA vector that will allow us to separate ISG15 shRNA expressing stable cells of ALS. Such a vector is commercially available. Specifically, we will use ISG15 shRNA construct in retroviral GFP vector from OriGene (cat #TG319471). Making of lentiviral particles, transduction, and selection of antibiotic resistant ALS/normal cells will be carried out using procedures developed in our lab (82). Alternatively, we shall also screen some ALS adherent fibroblasts (from Coriell Cell Repository) for ISG15 expression, and then use these cells for our studies.

These studies will reveal whether ISGylation inhibits mitophagy by inhibiting the ubiquitin/SUMO E3 ligase functions in ALS cells. These results will show that ISG15 inhibits mitophagy in neurological disorders. The importance of ISG15 will be reinforced in A-T as well as in ALS, to generate novel protocol to generate A-T-specific neurons, and establish ISG15 as a new therapeutic target for A-T, ALS, and related disorders.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed:

1. An in vitro method to diagnose a subject with proteinopathy-induced neurodegeneration, the method comprising:
    a. obtaining a subject sample; and
    b. detecting the level of conjugated Interferon-Stimulated Gene 15 (ISG15) protein in said sample by contacting the subject sample with an anti-ISG15 antibody and detecting binding between ISG15 and the antibody, wherein a significantly increased ISG15 level in the subject as compared with a control sample indicates that the subject has proteinopathy-induced neurodegeneration, and
    c. administering a therapeutic agent to the subject, wherein the therapeutic agent inhibits the expression of a protein selected from the group consisting of ISG15 and UbcH8 (E2-ISG15).

2. The method of claim 1, wherein the sample comprises cerebrospinal fluid, skin fibroblast cells, peripheral blood cells, plasma, blood serum, or a combination thereof.

3. The method of claim 1, further comprising testing the sample for the presence of alphafetoprotein.

4. The method of claim 1 further comprising testing the sample for increased levels of autophagy markers comprising 1A/1B-light chain 3-I (LC3-I), 1A/1B-light chain 3-II (LC3-II), mitochondrial superoxide, mitochondrial mass, or a combination thereof.

5. The method of claim 1, wherein the agent is selected from the group consisting of shRNA and siRNA molecules that are targeted to the nucleic acid molecule encoding ISG15 as in GENBANK Accession No. AY168648 (SEQ ID NO: 1).

6. The method of claim 1, wherein the agent is an shRNA that targets the nucleotides numbered from 232-250 in the nucleic acid molecule encoding ISG15 as in GENBANK Accession No. AY168648 (SEQ ID NO: 1).

7. The method of claim 1, wherein the agent is selected from the group consisting of shRNA and siRNA molecules that are targeted to the nucleic acid molecule encoding UbcH8 as in GENBANK Accession No. AF031141 (SEQ ID NO: 2).

8. The method of claim 1, wherein the agent is an shRNA that targets the nucleotides numbered from 237-255 in the nucleic acid molecule encoding UbcH8 as in GENBANK Accession No. AF031141 (SEQ ID NO: 2).

9. A method of assessing the effectiveness of a course of treatment for a subject suffering from proteinopathy-induced neurodegeneration, the method comprising:
   a. measuring a first level of conjugated ISG15 protein in a sample from the subject at a first time point during the course of treatment with a first therapeutic agent, wherein measuring comprises contacting the sample with an anti-ISG15 antibody and measuring binding between ISG15 and the antibody;
   b. measuring a second level of conjugated ISG15 protein in a sample from the subject in a second time point during the course of treatment with the first therapeutic agent, wherein measuring comprises contacting the sample with an anti-ISG15 antibody and measuring binding between ISG15 and the antibody;
   c. comparing the measurements from steps (a) and (b); wherein if the level from step (a) is greater than the level from step (b), then the treatment with the first therapeutic agent is effective; and wherein if the level from step (b) is equal to or greater than the level from step (a), then the treatment with the first therapeutic agent is not effective; and
   d. if the treatment with the first therapeutic agent is effective, then continuing to administer the first therapeutic agent to the subject, or if the treatment with the first therapeutic agent is not effective, then administering an alternative therapeutic agent to the subject.

10. The method of claim 9 further comprising measuring a first level and a second level of an autophagy or mitophagy marker.

11. The method of claim 10, wherein the marker comprises LC3-I, LC3-II, mitochondrial superoxide, mitochondrial mass, reactive oxygen species (ROS), or a combination thereof.

* * * * *